(12) United States Patent
Liu et al.

(10) Patent No.: US 11,091,460 B2
(45) Date of Patent: Aug. 17, 2021

(54) SYK INHIBITOR AND USE METHOD THEREFOR

(71) Applicant: CHIA TAI TIANQING PHARMACEUTICAL GROUP CO., LTD., Lianyungang (CN)

(72) Inventors: Shilan Liu, Shanghai (CN); Guibai Liang, Shanghai (CN); Hongjian Wang, Shanghai (CN); Ming Zhang, Shanghai (CN); Shuhui Chen, Shanghai (CN)

(73) Assignee: Chia Tai Tianqing Pharmaceutical Group Co., Ltd., Lianyungang (CN)

(*) Notice: Subject to any disclaimer, the term of this patent is extended or adjusted under 35 U.S.C. 154(b) by 0 days.

(21) Appl. No.: 16/619,646

(22) PCT Filed: Jun. 14, 2018

(86) PCT No.: PCT/CN2018/091269
§ 371 (c)(1),
(2) Date: Dec. 5, 2019

(87) PCT Pub. No.: WO2018/228475
PCT Pub. Date: Dec. 20, 2018

(65) Prior Publication Data
US 2020/0199101 A1   Jun. 25, 2020

(30) Foreign Application Priority Data

Jun. 14, 2017 (CN) .................. 201710448438.X

(51) Int. Cl.
| | | |
|---|---|---|
| *C07D 401/10* | (2006.01) | |
| *C07D 401/14* | (2006.01) | |
| *C07D 405/14* | (2006.01) | |
| *C07D 491/107* | (2006.01) | |
| *C07D 403/10* | (2006.01) | |
| *C07D 403/14* | (2006.01) | |
| *C07D 487/08* | (2006.01) | |
| *C07D 417/10* | (2006.01) | |

(52) U.S. Cl.
CPC ......... *C07D 401/10* (2013.01); *C07D 401/14* (2013.01); *C07D 403/10* (2013.01); *C07D 403/14* (2013.01); *C07D 405/14* (2013.01); *C07D 417/10* (2013.01); *C07D 487/08* (2013.01); *C07D 491/107* (2013.01)

(58) Field of Classification Search
CPC .............. C07D 405/14; C07D 491/107; C07D 403/10; C07D 403/14; C07D 487/08; C07D 417/10
USPC .......................................... 514/218
See application file for complete search history.

(56) References Cited

FOREIGN PATENT DOCUMENTS

| | | |
|---|---|---|
| CN | 1784229 A | 6/2006 |
| WO | WO 2010/053757 A1 | 5/2010 |
| WO | WO 2011/112995 A1 | 9/2011 |
| WO | WO 2013/109882 A1 | 7/2013 |
| WO | WO 2014/060113 A1 | 4/2014 |
| WO | WO 2014/093191 A1 | 6/2014 |
| WO | WO 2015/080707 A1 | 6/2015 |
| WO | WO 2016/197897 A1 | 12/2016 |
| WO | WO 2017/001733 A1 | 1/2017 |

OTHER PUBLICATIONS

International Search Report and Written Opinion for International Patent Application No. PCT/CN2018/091269, dated Sep. 12, 2018, with English translation (8 pages).
Written Opinion of International Searching Authority for International Patent Application No. PCT/CN2018/091269, dated Sep. 12, 2018; English translation unavailable (5 pages).
O'Brien, N. et al.; "Synthesis and biological evaluation of substituted 3-anilino-quinolin-2(1H)-ones as PDK1 inhibitors"; Bioorganic & Medicinal Chemistry 22 (2014), pp. 3781-3790 (10 pages).
Extended European Search Report in European Application No. EP 18817720, dated Sep. 29, 2020 (7 pages).

*Primary Examiner* — Tracy Vivlemore
*Assistant Examiner* — Ebenezer O Sackey
(74) *Attorney, Agent, or Firm* — Nixon Peabody LLP

(57) ABSTRACT

Provided are a Syk inhibitor and a use method therefor, and in particular, disclosed are quinolinone represented by formula (I) or quinazoline derivatives or pharmaceutically acceptable salts thereof, a preparation method, a pharmaceutical composition, and uses in preparing a medicament for treatment of Syk receptor related diseases.

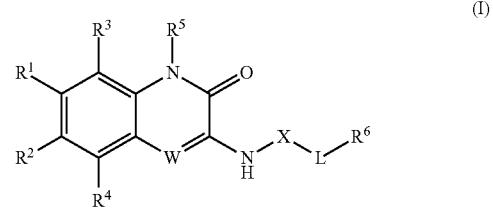

20 Claims, No Drawings

SYK INHIBITOR AND USE METHOD THEREFOR

REFERENCE TO RELATED INVENTIONS

This application claims the benefits of Chinese patent application No. 201710448438.X, filed on Jun. 14, 2017 before the China National Intellectual Property Administration, all the contents of which are incorporated herein by reference in its entirety.

TECHNICAL FIELD

The present application belongs to the field of pharmaceutical chemistry, and specifically relates to a class of Syk inhibitors or pharmaceutically acceptable salts, preparation processes thereof, and pharmaceutical compositions comprising the same.

BACKGROUND

Spleen tyrosine kinase (Syk) is an intracellular tyrosine protein kinase, which belongs to the ZAP70 protein kinase family. Syk plays a key role in the early development of B cells, the development of lymphocytes, and the function of mature B cells. In this process it is involved in a variety of signal transduction pathways and does not need to be activated by phosphorylation of Src kinase.

In addition to being expressed in hematopoietic stem cells universally, Syk is also expressed in non-hematopoietic cells such as epithelial cells, hepatocytes, fibroblasts, nerve cells and breast tissues, and has multiple functions.

Dysfunction of Syk PTK is present in many human diseases, such as allergic reactions, asthma, inflammation and autoimmune diseases, and numerous studies have shown that Syk is an important mediator of acute or chronic inflammation. Syk activation is present in several common B-cell malignancies, such as follicular lymphoma, diffuse large B-cell lymphoma, mantle cell lymphoma and B-cell chronic lymphocytic leukemia, which can be detected antigen-independent phosphorylation of Syk. The researchers found that inhibition of Syk in follicular lymphoma and diffuse large B-cell lymphoma cells can reduce the phosphorylation level of downstream signaling molecules, thereby inhibiting the proliferation and survival of tumor cells. In addition, Syk translocation was found in myelodysplastic syndrome and peripheral T-cell lymphoma, further indicating that the kinase can act as a proto-oncogene.

Thus, inhibition of Syk activity can be used to treat a particular type of cancer, including B cell lymphoma and leukemia.

SUMMARY OF THE INVENTION

The present application provides a compound of formula (I) or a pharmaceutically acceptable salt thereof,

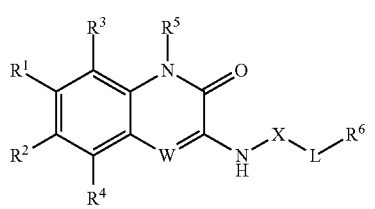

(I)

wherein,

W is $C(R^7)$ or N;

$R^1$ and $R^2$ are each independently selected from H, halogen, amino, hydroxy, cyano, $C_{1-6}$ alkyl, $C_{3-6}$ cycloalkyl, 3-10 membered heterocycloalkyl, 6-12 membered aryl or 5-12 membered heteroaryl, said amino, $C_{1-6}$ alkyl, $C_{3-6}$ cycloalkyl, 3-10 membered heterocycloalkyl, 6-12 membered aryl or 5-12 membered heteroaryl is optionally substituted with $R^8$;

$R^3$, $R^4$ and $R^7$ are each independently selected from H, halogen, amino, hydroxy, cyano, $C_{1-6}$ alkyl, $C_{3-6}$ cycloalkyl or 3-6 membered heterocycloalkyl, said amino, $C_{1-6}$ alkyl, $C_{3-6}$ cycloalkyl or 3-6 membered heterocycloalkyl is optionally substituted with $R^9$;

$R^5$ is selected from H, $C_{1-6}$ alkyl, $C_{3-6}$ cycloalkyl or 3-6 membered heterocycloalkyl, $C_{1-6}$ alkyl C(O), $C_{3-6}$ cycloalkyl C(O) or 3-6 membered heterocycloalkyl C(O), phenyl C(O), 5-6 membered heteroaryl C(O), $C_{1-6}$ alkyl $SO_2$, $C_{3-6}$ cycloalkyl $SO_2$ or 3-6 membered heterocycloalkyl $SO_2$, phenyl $SO_2$ or 5-6 membered heteroaryl $SO_2$, said $C_{1-6}$ alkyl, $C_{3-6}$ cycloalkyl or 3-6 membered heterocycloalkyl, $C_{1-6}$ alkyl C(O), $C_{3-6}$ cycloalkyl C(O) or 3-6 membered heterocycloalkyl C(O), phenyl C(O), 5-6 membered heteroaryl C(O), $C_{1-6}$ alkyl $SO_2$, $C_{3-6}$ cycloalkyl $SO_2$ or 3-6 membered heterocycloalkyl $SO_2$, phenyl $SO_2$ or 5-6 membered heteroaryl $SO_2$ is optionally substituted with $R^9$;

X is selected from 3-12 membered ring with a loss of hydrogen atoms at any two positions, which is optionally substituted with $R^9$;

L is selected from bond, NH, O, S, SO, $SO_2$, C(O), OC(O), C(O)O, C(O)NH, $NHSO_2$, $SO_2NH$, NHC(O)NH or $NHSO_2NH$;

$R^6$ is selected from H, halogen, amino, hydroxy, cyano, $C_{1-6}$ alkyl, $C_{3-10}$cycloalkyl or 3-10 membered heterocycloalkyl, said amino, $C_{1-6}$ alkyl, $C_{3-10}$cycloalkyl or 3-10 membered heterocycloalkyl is optionally substituted with $R^{10}$;

$R^8$ and $R^9$ are each independently selected from halogen, amino, hydroxy, cyano, $C_{1-3}$ alkyl, $C_{1-3}$ alkoxy or COOH;

$R^{10}$ is selected from halogen, amino, hydroxy, cyano, halogenated $C_{1-3}$ alkyl, COOH, =(O), $C_{1-6}$ alkyl, $C_{1-6}$ alkyl $SO_2$, $C_{3-6}$cycloalkyl or 3-10 membered heterocycloalkyl;

and, at least one of $R^1$ and $R^2$ is selected from 6-12 membered aryl or 5-12 membered heteroaryl, said 6-12 membered aryl or 5-12 membered heteroaryl is optionally substituted with $R^8$.

In an embodiment of the compound of formula (I) in the present application, $R^1$ and $R^2$ are each independently selected from H, halogen or 5-12 membered heteroaryl, said 5-12 membered heteroaryl is optionally substituted with $R^8$.

In an embodiment of the compound of formula (I) in the present application, $R^1$ and $R^2$ are each independently selected from H, F, Cl, Br, furanyl, thienyl, pyrrolyl, pyrazolyl, imidazolyl, pyridyl, pyrimidinyl, pyridazinyl, pyrazinyl, thiazolyl, isothiazolyl, oxazolyl, isoxazolyl, tetrazolyl or triazinyl, said furanyl, thienyl, pyrrolyl, pyrazolyl, imidazolyl, pyridyl, pyrimidinyl, pyridazinyl, pyrazinyl, thiazolyl, isothiazolyl, oxazolyl, isoxazolyl, tetrazolyl or triazinyl is optionally substituted with $R^8$.

In an embodiment of the compound of formula (I) in the present application, $R^1$ and $R^2$ are each independently selected from H, F, Cl, thiazolyl, pyrazolyl, imidazolyl or pyridyl, said thiazolyl, pyrazolyl, imidazolyl or pyridyl is optionally substituted with $R^8$.

In an embodiment of the compound of formula (I) in the present application, $R^8$ is selected from amino, methyl, ethyl, propyl or isopropyl.

In an embodiment of the compound of formula (I) in the present application, $R^8$ is selected from amino or methyl.

In an embodiment of the compound of formula (I) in the present application, $R^1$ is selected from H, F,

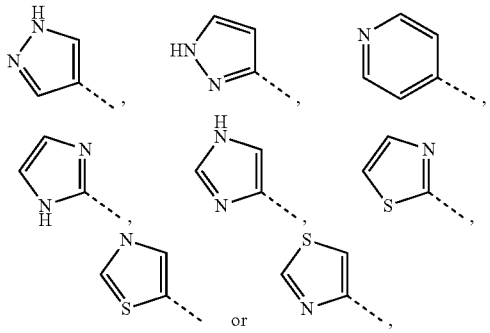

which is optionally substituted with $R^8$.

In an embodiment of the compound of formula (I) in the present application, $R^2$ is selected from H, F,

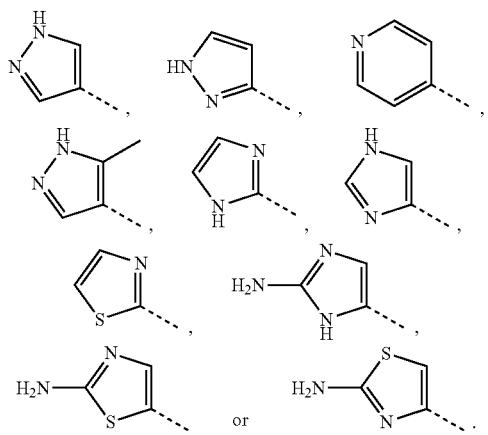

In an embodiment of the compound of formula (I) in the present application, $R^2$ is selected from H, F, Cl or

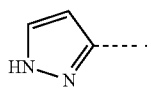

In an embodiment of the compound of formula (I) in the present application, $R^1$ is selected from 5-12 membered heteroaryl; $R^2$ is selected from H or halogen; wherein, $R^1$ is optionally substituted with $R^8$.

In an embodiment of the compound of formula (I) in the present application, $R^1$ is selected from furanyl, thienyl, pyrrolyl, pyrazolyl, imidazolyl, pyridyl, pyrimidinyl, pyridazinyl, pyrazinyl, thiazolyl, isothiazolyl, oxazolyl, isoxazolyl, tetrazolyl or triazinyl; $R^2$ is selected from H, F, Cl or Br; wherein, $R^1$ is optionally substituted with $R^8$.

In an embodiment of the compound of formula (I) in the present application, $R^1$ is selected from thiazolyl, pyrazolyl, imidazolyl or pyridyl; $R^2$ is selected from H, F or Cl; wherein, $R^1$ is optionally substituted with $R^8$.

In an embodiment of the compound of formula (I) in the present application, $R^1$ is selected from

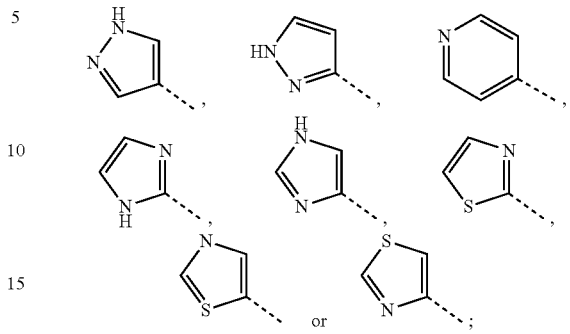

$R^2$ is selected from H, F or Cl; wherein, $R^1$ is optionally substituted with $R^8$.

In an embodiment of the compound of formula (I) in the present application, $R^1$ is selected from

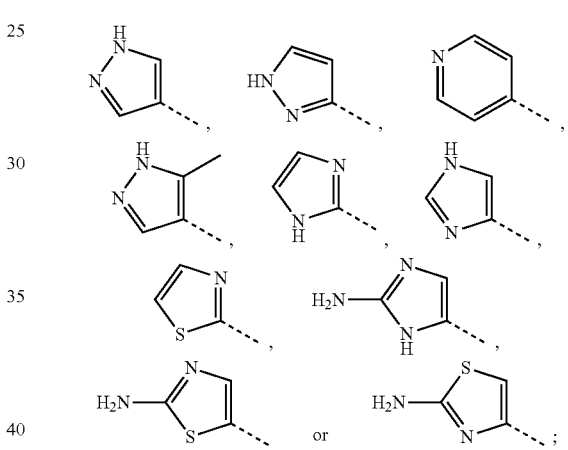

$R^2$ is selected from H, F or Cl.

In an embodiment of the compound of formula (I) in the present application, $R^1$ is selected from H or halogen; $R^2$ is selected from 5-12 membered heteroaryl; wherein, $R^2$ is optionally substituted with $R^8$.

In an embodiment of the compound of formula (I) in the present application, $R^1$ is selected from H, F, Cl or Br; $R^2$ is selected from furanyl, thienyl, pyrrolyl, pyrazolyl, imidazolyl, pyridyl, pyrimidinyl, pyridazinyl, pyrazinyl, thiazolyl, isothiazolyl, oxazolyl, isoxazolyl, tetrazolyl or triazinyl; wherein, $R^2$ is optionally substituted with $R^8$.

In an embodiment of the compound of formula (I) in the present application, $R^1$ is selected from H or F; $R^2$ is selected from pyrazolyl; wherein, $R^2$ is optionally substituted with $R^8$.

In an embodiment of the compound of formula (I) in the present application, $R^1$ is selected from H or F; $R^2$ is selected from

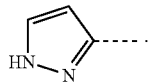

In an embodiment of the compound of formula (I) in the present application, $R^3$, $R^4$ and $R^7$ are each independently selected from H, halogen, $C_{1-6}$ alkyl or $C_{3-6}$ cycloalkyl, said $C_{1-6}$ alkyl or $C_{3-6}$ cycloalkyl is optionally substituted with $R^9$.

In an embodiment of the compound of formula (I) in the present application, $R^3$, $R^4$ and $R^7$ are each independently selected from H or halogen.

In an embodiment of the compound of formula (I) in the present application, $R^3$, $R^4$ and $R^7$ are each independently selected from H, F or Cl.

In an embodiment of the compound of formula (I) in the present application, W is $C(R^7)$, $R^7$ is H, $R^3$ and $R^4$ are each independently selected from H, F or Cl.

In an embodiment of the compound of formula (I) in the present application, W is N, $R^3$ and $R^4$ are each independently selected from H, F or Cl.

In an embodiment of the compound of formula (I) in the present application, $R^5$ is selected from H, $C_{1-6}$ alkyl or $C_{3-6}$ cycloalkyl, said $C_{1-6}$ alkyl or $C_{3-6}$ cycloalkyl is optionally substituted with $R^9$.

In an embodiment of the compound of formula (I) in the present application, $R^5$ is selected from methyl, ethyl, propyl, isopropyl, butyl, isobutyl or tert-butyl, said methyl, ethyl, propyl, isopropyl, butyl, isobutyl or tert-butyl is optionally substituted with $R^9$.

In an embodiment of the compound of formula (I) in the present application, $R^5$ is selected from methyl.

In an embodiment of the compound of formula (I) in the present application, X is selected from phenyl ring or 5-10 membered heteroaryl ring with a loss of hydrogen atoms at any two positions, which is optionally substituted with $R^9$.

In an embodiment of the compound of formula (I) in the present application, X is selected from phenyl ring,

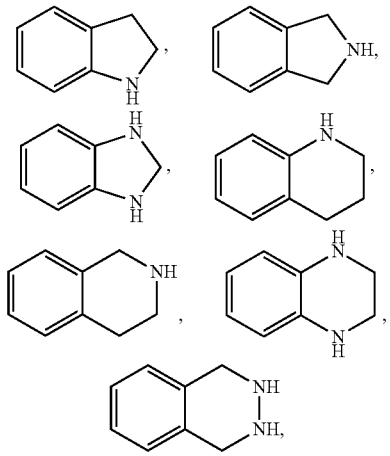

furanyl ring, thienyl ring, pyrrolyl ring, pyrazolyl ring, imidazolyl ring, pyridyl ring, pyrimidinyl ring, pyridazinyl ring, pyrazinyl ring, thiazolyl ring, isothiazolyl ring, oxazolyl ring, isoxazolyl ring, tetrazolyl ring or triazinyl ring with a loss of hydrogen atoms at any two positions, which is optionally substituted with $R^9$.

In an embodiment of the compound of formula (I) in the present application, X is selected from phenyl ring or pyridyl ring with a loss of hydrogen atoms at any two positions, which is optionally substituted with $R^9$.

In an embodiment of the compound of formula (I) in the present application, X is selected from

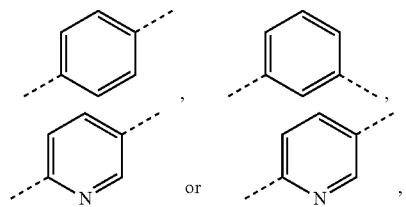

which is optionally substituted with $R^9$.

In an embodiment of the compound of formula (I) in the present application, X is selected from

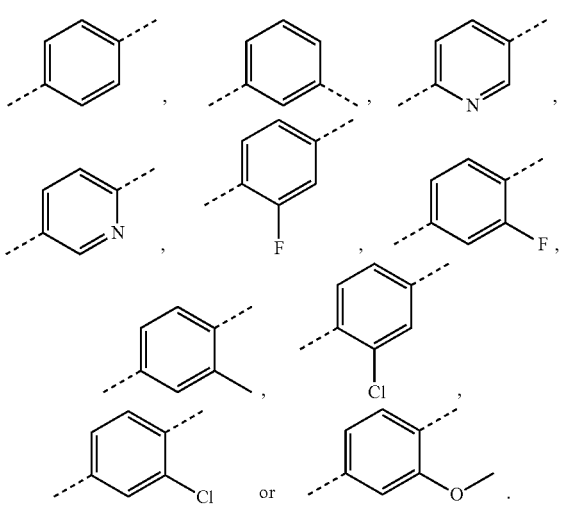

In an embodiment of the compound of formula (I) in the present application, $R^9$ is selected from halogen, $C_{1-3}$ alkyl or $C_{1-3}$ alkoxy.

In an embodiment of the compound of formula (I) in the present application, $R^9$ is selected from F, Cl, methyl or $OCH_3$.

In an embodiment of the compound of formula (I) in the present application, L is selected from bond, NH, O, S, SO, $SO_2$, $NHSO_2$, $SO_2NH$ or $NHSO_2NH$.

In an embodiment of the compound of formula (I) in the present application, L is selected from bond, NH, O, S, SO or $SO_2$.

In an embodiment of the compound of formula (I) in the present application, L is selected from bond, NH or $SO_2$.

In an embodiment of the compound of formula (I) in the present application, $R^6$ is selected from H, amino, $C_{1-6}$ alkyl, $C_{3-6}$cycloalkyl or 3-10 membered heterocycloalkyl, said amino, $C_{1-6}$ alkyl, $C_{3-6}$cycloalkyl or 3-10 membered heterocycloalkyl is optionally substituted with $R^{10}$.

In an embodiment of the compound of formula (I) in the present application, $R^6$ is selected from H, amino, methyl, ethyl, propyl, isopropyl, butyl, isobutyl, tert-butyl, cyclopropyl, cyclobutyl, cyclopentyl, cyclohexyl,

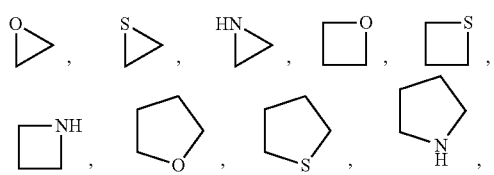

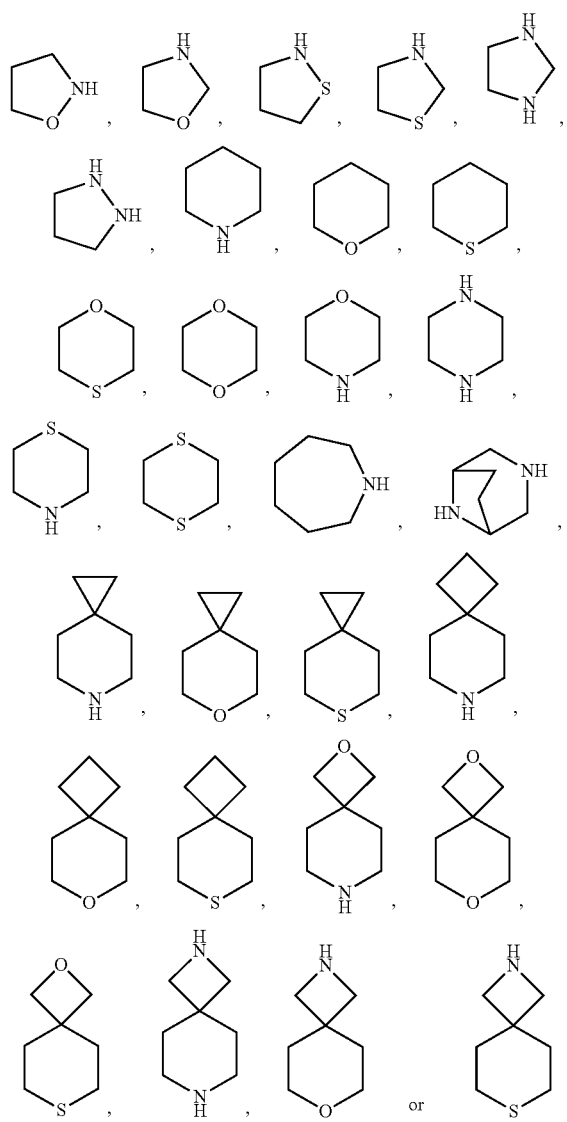

with a loss of one hydrogen atom at any position, said amino, methyl, ethyl, propyl, isopropyl, butyl, isobutyl, tert-butyl, cyclopropyl, cyclobutyl, cyclopentyl, cyclohexyl,

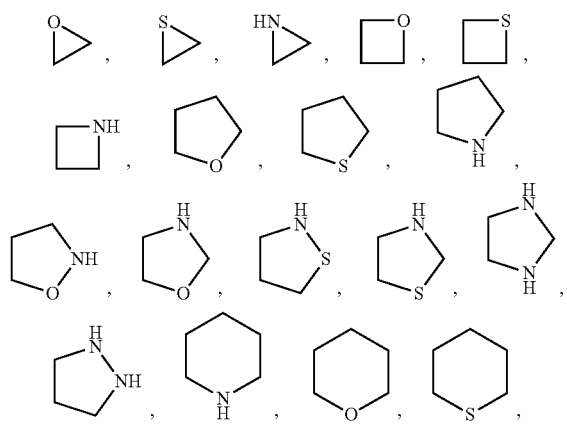

with a loss of one hydrogen atom at any position is optionally substituted with $R^{10}$.

In an embodiment of the compound of formula (I) in the present application, $R^6$ is selected from H, $NH_2$, methyl, isopropyl, cyclobutyl, said $NH_2$, methyl, isopropyl, cyclobutyl, -continued

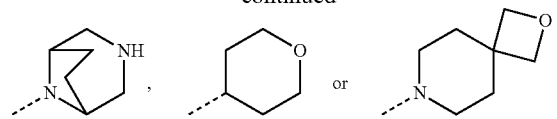

is optionally substituted with $R^{10}$.

In an embodiment of the compound of formula (I) in the present application, $R^6$ is selected from H, $NH_2$, methyl,

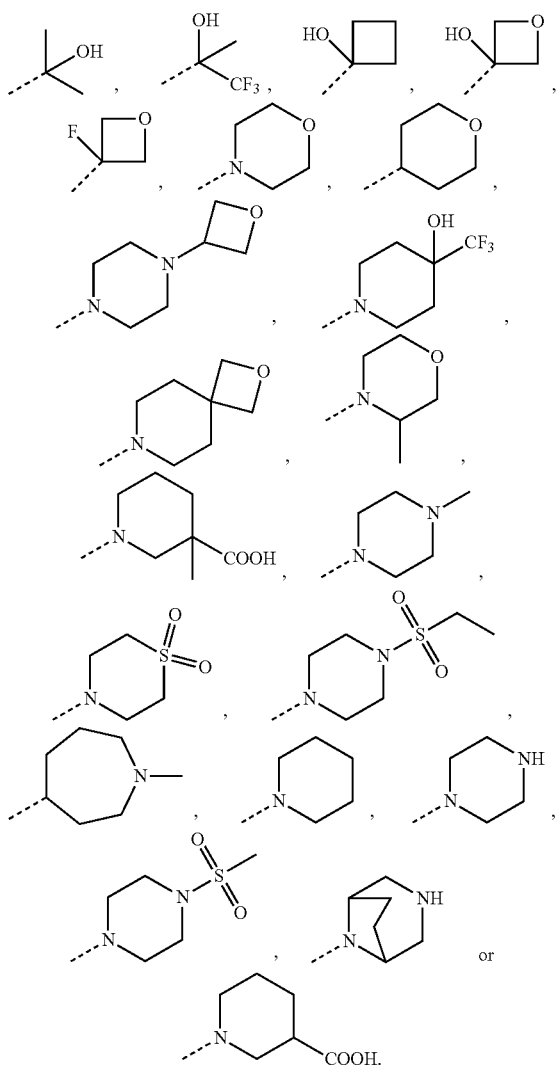

In an embodiment of the compound of formula (I) in the present application, $R^{10}$ is selected from halogen, hydroxy, halogenated $C_{1-3}$ alkyl, COOH, =(O), $C_{1-6}$ alkyl, $C_{1-6}$ alkyl $SO_2$ or 3-10 membered heterocycloalkyl.

In an embodiment of the compound of formula (I) in the present application, $R^{10}$ is selected from F, Cl, Br, OH, monofluoromethyl, difluoromethyl, trifluoromethyl, monofluoroethyl, difluoroethyl, trifluoroethyl, tetrafluoroethyl, pentafluoroethyl, monochlorom ethyl, dichloromethyl, trichlorom ethyl, COOH, =(O), methyl, ethyl, propyl, isopropyl, butyl, isobutyl, tert-butyl, $SO_2CH_3$, $SO_2CH_2CH_3$, $SO_2CH_2CH_2CH_3$, $SO_2CH(CH_3)CH_3$, $SO_2CH_2H_2CH_2CH_3$,

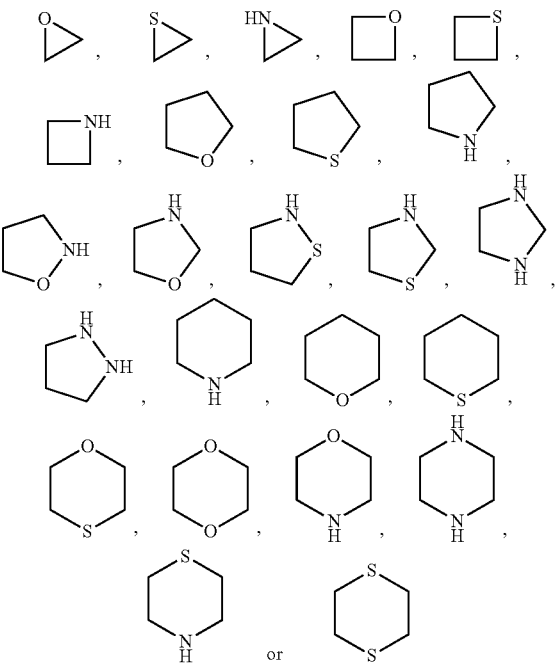

with a loss of one hydrogen atom at any position.

In an embodiment of the compound of formula (I) in the present application, $R^{10}$ is selected from F, OH, trifluoromethyl, COOH, =(O), methyl, $SO_2CH_3$, $SO_2CH_2CH_3$ or

In an embodiment of the compound of formula (I) in the present application, said compound of formula (I) is shown as formula (II),

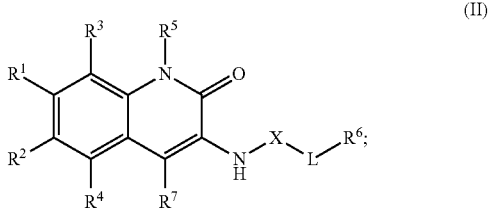

wherein, $R^2$ is selected from 6-12 membered aryl or 5-12 membered heteroaryl, said 6-12 membered aryl or 5-12 membered heteroaryl is optionally substituted with $R^8$;

$R^1$, $R^3$, $R^4$, $R^5$, $R^6$, $R^7$, $R^8$, X and L are as defined in the formula (I).

In an embodiment of the compound of formula (II) in the present application, $R^2$ is selected from pyrazoly, which is optionally substituted with $R^8$.

In an embodiment of the compound of formula (II) in the present application, $R^2$ is selected from

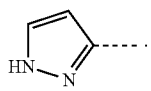

In an embodiment of the compound of formula (I) in the present application, said compound of formula (I) is shown as formula (III),

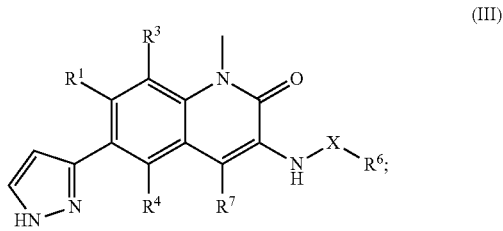

wherein,
$R^1$, $R^3$, $R^4$, $R^6$, $R^7$ and X are as defined in the formula (I).

In an embodiment of the compound of formula (I) in the present application, said compound of formula (I) is shown as formula (IV),

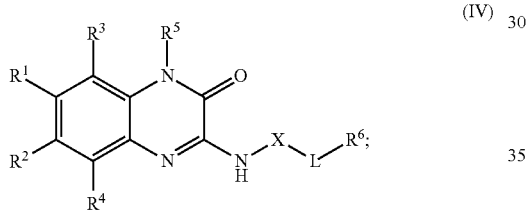

wherein,
$R^1$ is selected from 6-12 membered aryl or 5-12 membered heteroaryl, which is optionally substituted with $R^8$;
$R^2$, $R^3$, $R^4$, $R^5$, $R^6$, $R^8$, X and L are as defined in the formula (I).

In an embodiment of the compound of formula (IV) in the present application, $R^1$ is selected from 5-12 membered heteroaryl, which is optionally substituted with $R^8$.

In an embodiment of the compound of formula (IV) in the present application, $R^1$ is selected from furanyl, thienyl, pyrrolyl, pyrazolyl, imidazolyl, pyridyl, pyrimidinyl, pyridazinyl, pyrazinyl, thiazolyl, isothiazolyl, oxazolyl, isoxazolyl, tetrazolyl or triazinyl, which is optionally substituted with $R^8$.

In an embodiment of the compound of formula (IV) in the present application, $R^1$ is selected from thiazolyl, pyrazolyl, imidazolyl or pyridyl, which is optionally substituted with $R^8$.

In an embodiment of the compound of formula (IV) in the present application, $R^1$ is selected from

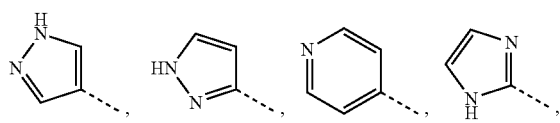

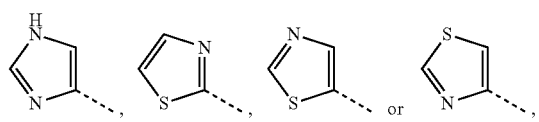

which is optionally substituted with $R^8$.

In an embodiment of the compound of formula (IV) in the present application, $R^1$ is selected from

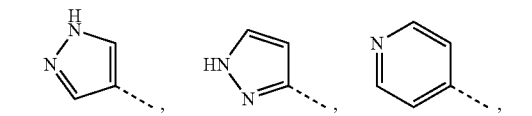

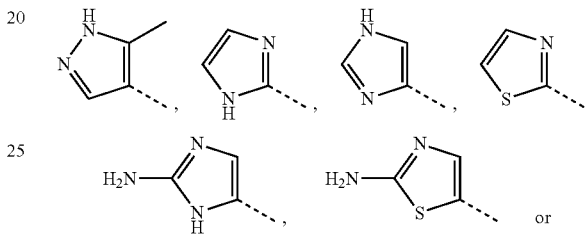

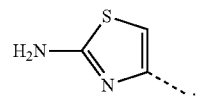

In an embodiment of the compound of formula (I) in the present application, said compound of formula (I) is shown as formula (V),

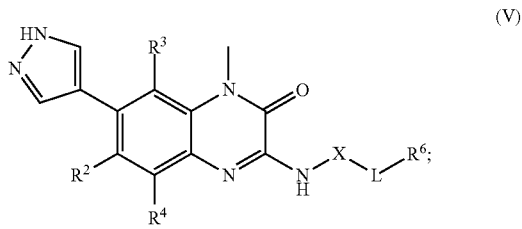

wherein,
$R^2$, $R^3$, $R^4$, $R^6$, X and L are as defined in the formula (I).

In an embodiment of the compound of formula (I) in the present application, said formula (I) is selected from the following compounds:

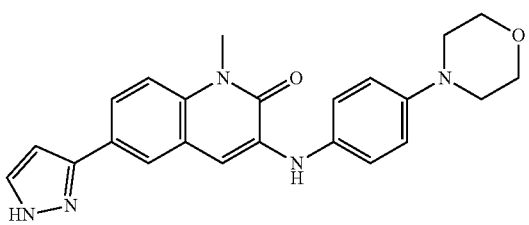

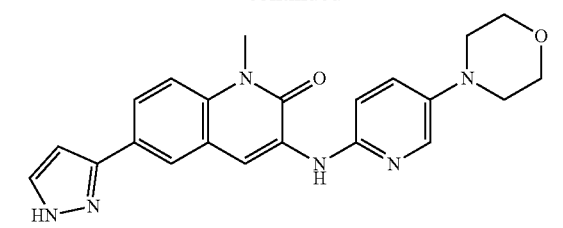
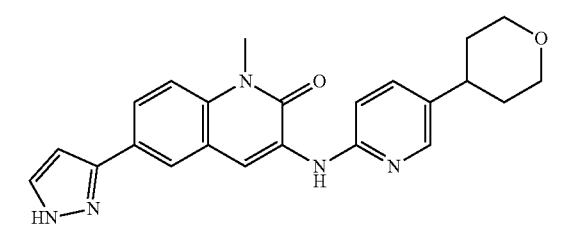
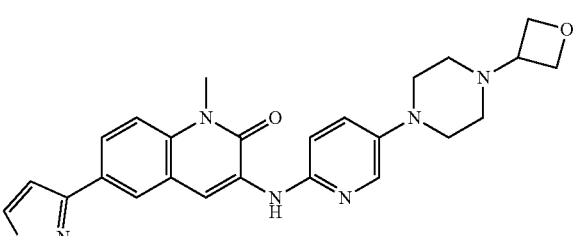
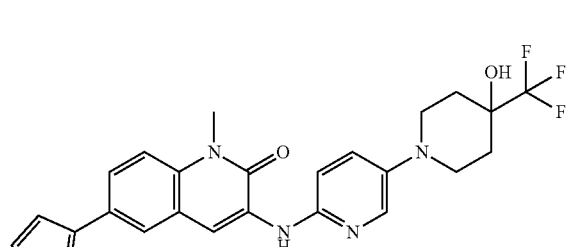
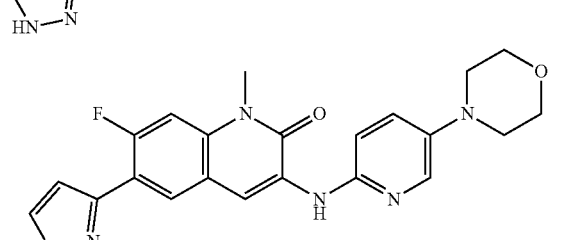
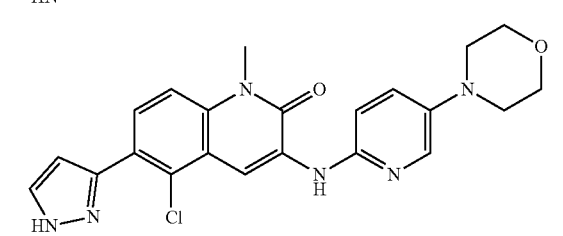
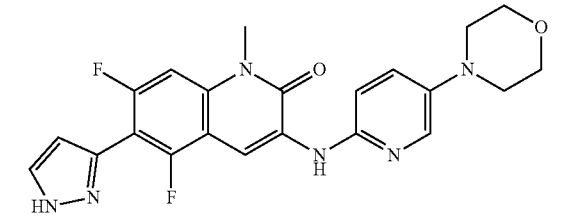
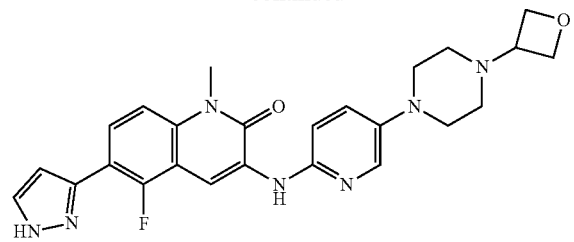
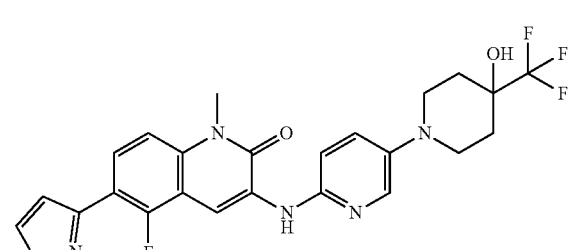
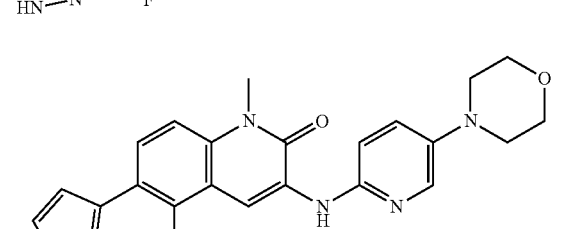
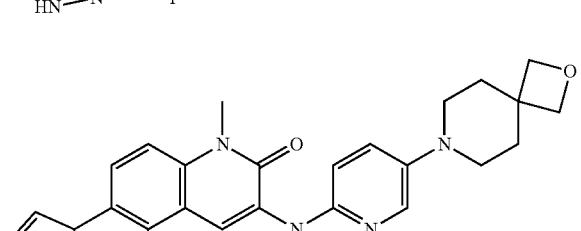
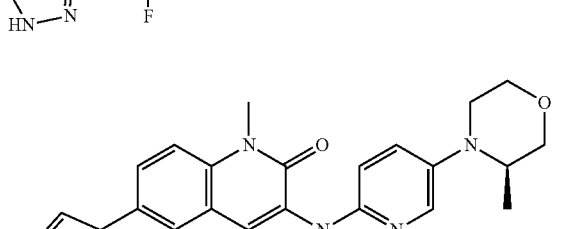
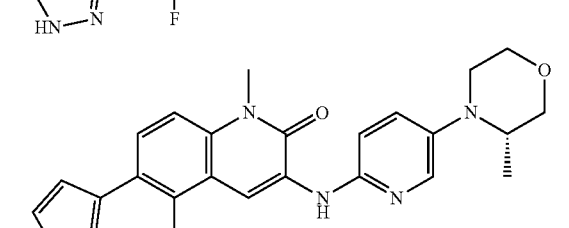
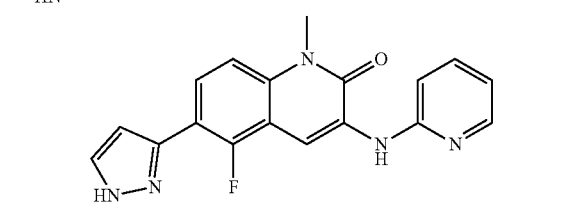

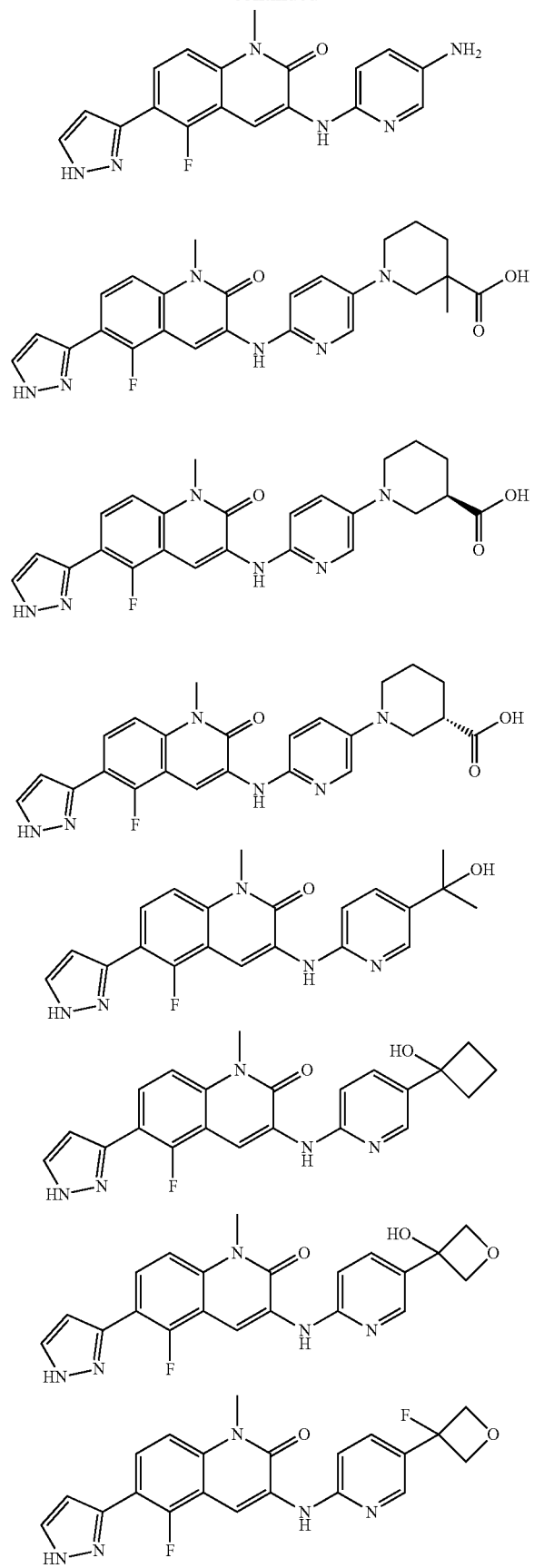

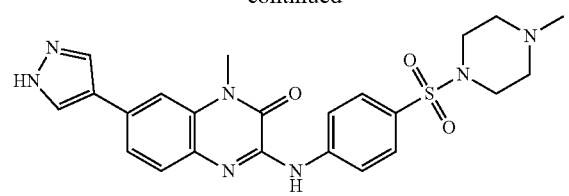
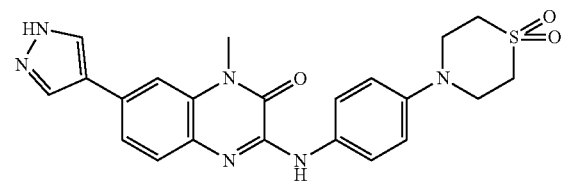
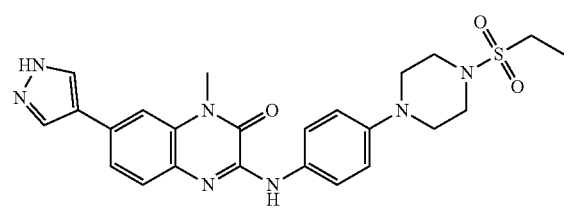
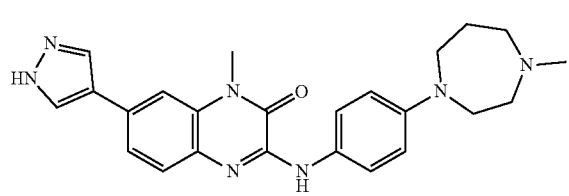
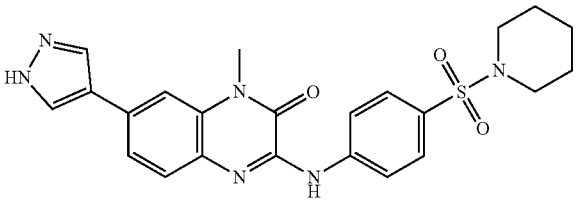
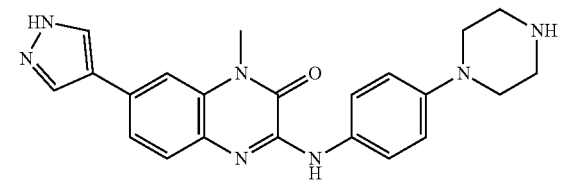
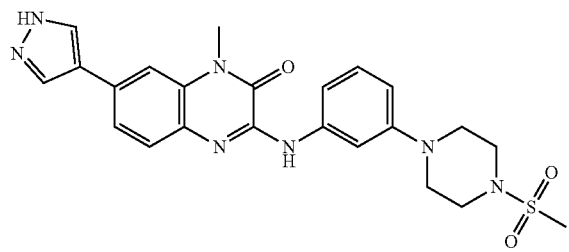
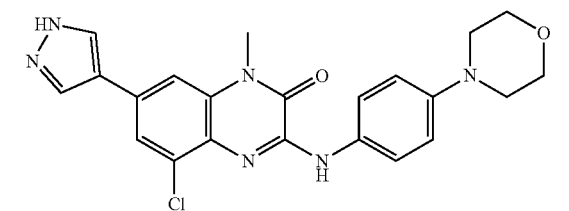
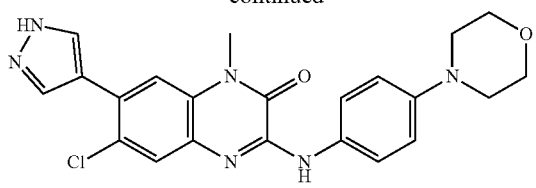
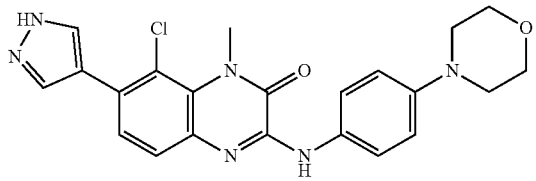
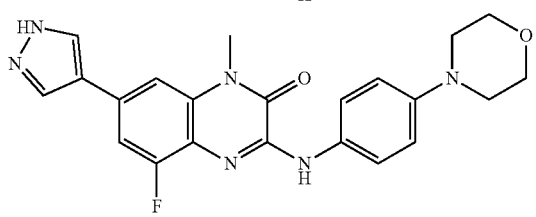
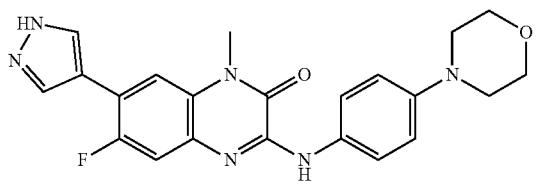
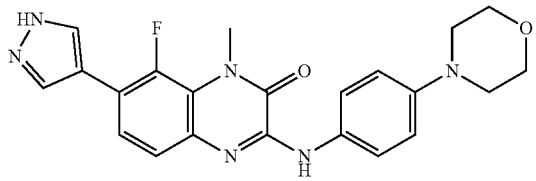
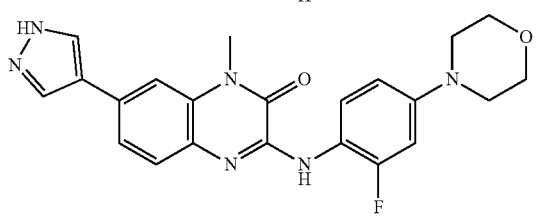
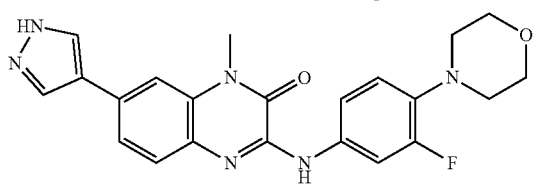
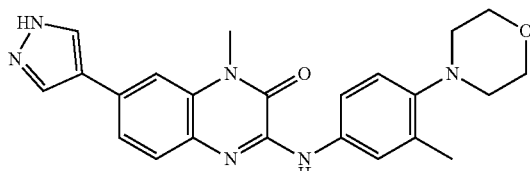
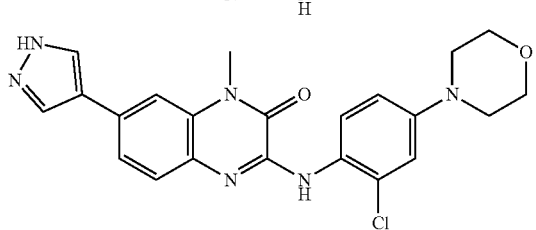

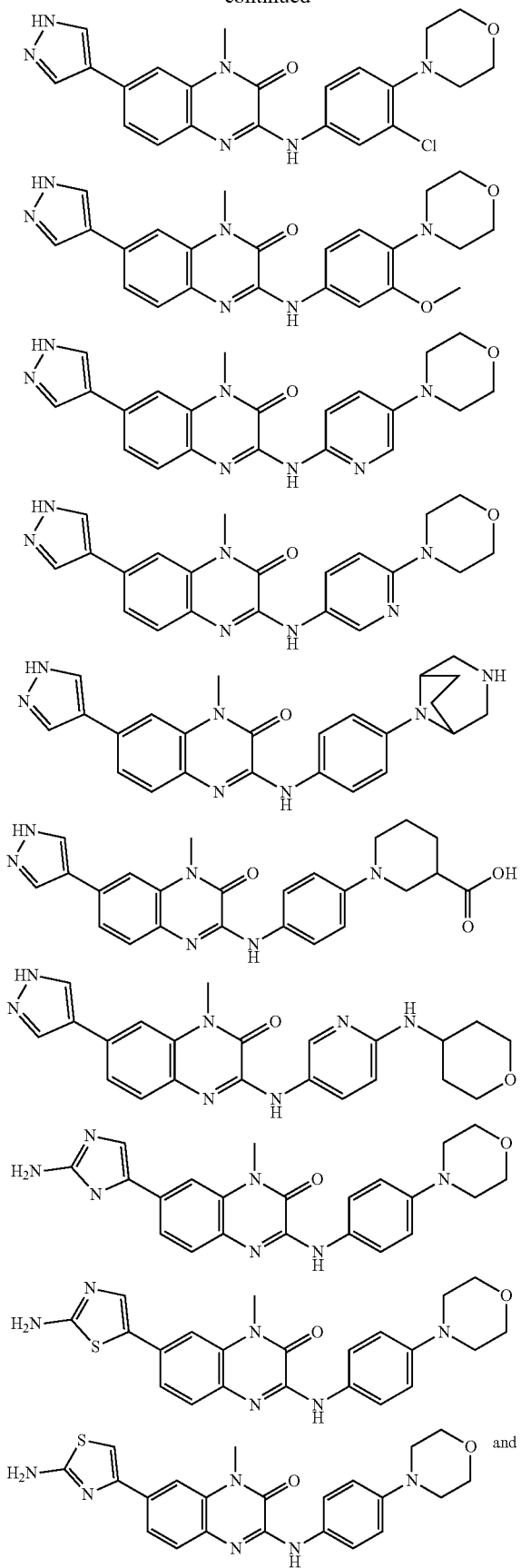

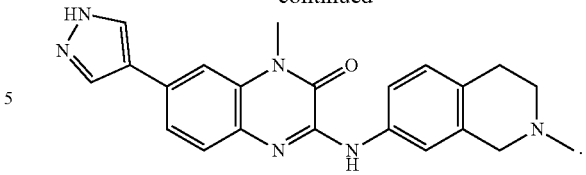

In another aspect, the present application relates to a pharmaceutical composition comprising the compound of formula (I) or a pharmaceutically acceptable salt thereof. In some embodiments, the pharmaceutical composition of the present application further comprises one or more pharmaceutically acceptable excipients.

The pharmaceutical composition of the present invention can be prepared by combining a compound of the present invention or the pharmaceutically acceptable salt thereof with suitable pharmaceutically acceptable excipients.

For example, it can be formulated into solid, semi-solid, liquid or gaseous preparations, such as tablets, pills, capsules, powders, granules, ointments, emulsions, suspensions, solutions, suppositories, injections, inhalants, gels, microspheres, aerosols and the like.

Typical administration routes of the compounds of the present invention or the pharmaceutically acceptable salts thereof, or the pharmaceutical compositions thereof includes, but not limited to, oral, rectal, transmucosal, intestinal administration, or topical, transdermal, inhalation, parenteral, sublingual, intravaginal, intranasal, intraocular, intraperitoneal, intramuscular, subcutaneous, and intravenous administration.

The pharmaceutical composition of the present invention may be manufactured by methods well-known in the art, such as a conventional mixing method, a dissolution method, a granulation method, a method for preparing sugar-coated pills, a grinding method, an emulsification method, a freeze-drying method and the like.

For oral administration, the pharmaceutical composition can be formulated by mixing an active compound with a pharmaceutically acceptable excipient well-known in the art. These excipients can allow the compounds of the present invention to be formulated into tablets, pills, troches, dragees, capsules, liquids, gels, slurries, suspensions and the like, for oral administration to patients. A solid oral composition can be prepared by conventional mixing, filling or tableting methods. For example, it can be obtained by the following methods: mixing the active compound with solid excipients, optionally milling the resultant mixture, adding additional suitable excipients if necessary, and then processing the mixture into granules, to produce tablet cores or dragee cores. Suitable excipients include, but not limited to, adhesives, diluents, disintegrants, lubricants, glidants, sweeteners, flavoring agents or the like.

The pharmaceutical composition can also be suitable for parenteral administration, such as sterile solutions, suspensions or freeze-dried products in a suitable unit dosage form. An appropriate excipient such as a bulking agent, a buffer agent, or surfactant can be used.

The compound of formula (I) or the pharmaceutically acceptable salt thereof in the present invention can be administered by any suitable routes and methods, for example orally or parenterally (e.g., intravenously) administration. The therapeutically effective amount of the compound of formula (I) ranges from about 0.0001 mg/Kg of body weight to 20 mg/Kg of body weight per day, for example from 0.001 mg/Kg of body weight to 10 mg/Kg of body weight per day.

The dosing frequency of the compound of formula (I) depends on needs of individual patients, for example, once or twice every day or more times every day. Administration can be intermittent, for example, where during a period of several days, patients receives a daily dose of the compound of formula (I), and during a period of next several or more days, they do not receive a daily dose of the compound of formula (I).

Another object of the present application is to provide use of the compound of formula (I) or the pharmaceutically acceptable salt thereof, or the above pharmaceutical composition in the preparation of a medicament for treating diseases related to Syk receptors.

Another aspect of the present application provides a method of treating diseases related to Syk receptors, the method comprising administering a therapeutically effective amount of the compound of formula (I) or the pharmaceutically acceptable salt thereof, or the above pharmaceutical composition.

In some embodiments, diseases related to Syk receptors are selected from cancer or inflammatory disease. In some embodiments, diseases related to Syk receptors are selected from B cell lymphoma, Hodgkin's lymphoma, non-Hodgkin's lymphoma, hairy cell leukemia, multiple myeloma, chronic myeloid leukemia, acute myeloid leukemia, chronic lymphocytic leukemia, acute lymphocytic leukemia, rheumatoid arthritis, allergic rhinitis, chronic obstructive pulmonary disease (COPD), adult respiratory distress syndrome (ARDs), allergy-induced inflammatory disease, multiple sclerosis, autoimmune disease, acute inflammatory response, allergic disorder or polycystic kidney.

Definition and Description

Unless otherwise specified, the following terms and phrases as used herein have the following meanings ascribed to them. A particular term or phrase should not be considered to be indefinite or unclear in the absence of a specific definition, but should be interpreted as its ordinary meanings of the art. When a trade name appears herein, it is intended to refer to the corresponding commodity or active ingredient thereof.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salt" refers to the salt of the compound of the present application, which is prepared from the compound with specific substituents found in the present application and a relatively nontoxic acid or base. When the compound of the present invention contains relatively acidic functional groups, the base addition salts thereof can be obtained by contacting the neutral form of such compound with a suitable base. When the compound of the present invention contains relatively basic functional groups, the acid addition salts thereof can be obtained by contacting the neutral form of such compound with a suitable acid. Certain specific compounds of the present application contain basic and acidic functional groups, and thus can be converted to any base or acid addition salts.

Certain compounds of the present application may have asymmetric carbon atoms (optical centers) or double bonds. Racemates, diastereomers, geometric isomers, and individual isomers are all included within the scope of the present application. For example,

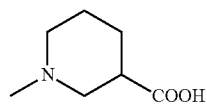

included in structure of the compound can be

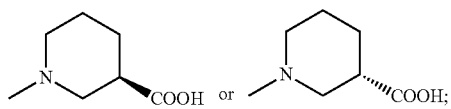

for example,

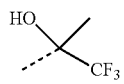

included in the structure of the compound can be

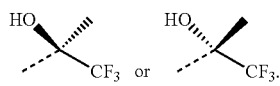

When the compounds described herein contain olefinic double bonds or other geometric asymmetrical centers, unless otherwise specified, they include E, Z geometric isomers. Likewise, all tautomeric forms are included within the scope of the present application, for example,

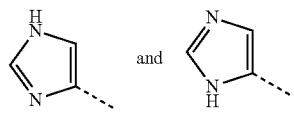

are tautomeric forms.

The compounds of the present application may exist in specific geometric or stereo isomeric forms. All such compounds envisaged by the present application include cis and trans isomers, (−)- and (+)-enantiomers, (R)- and (S)-enantiomers, diastereomers, (D)-isomers, (L)-isomers, and racemic mixtures and other mixtures thereof, such as enantiomers or diastereomers enriched mixtures, all of which fall within the scope of the present application. Other asymmetric carbon atoms may be present in the substituents such as alkyl. All these isomers and their mixtures are included in the scope of the present application.

The optically active (R)- and (S)-isomers as well as the D and L isomers can be prepared by chiral synthesis or chiral reagents or other conventional techniques. If an enantiomer of a certain compound of the present application is desired, it may be prepared by asymmetric synthesis, or by derivatization with a chiral auxiliary, wherein the resulting diastereomeric mixture is separated and the ancillary group is cleaved to provide the pure desired enantiomers. Alternatively, when a molecule contains a basic functional group (such as an amino) or an acidic functional group (such as a carboxyl), it forms a salt of diastereomer with a suitable optically active acid or base, and then a diastereomer resolution is performed by methods well known in the art, followed by recovering to give pure enantiomers. In addition, the separation of the enantiomers and diastereomers is generally accomplished by the use of chromatography adopting a chiral stationary phase, and optionally in combination with chemical derivatization method (e.g., forming carbamates from amines).

The compounds of the present application may contain non-natural proportions of atomic isotopes on one or more atoms which constitute the compound. For example, the compound may be labeled with a radioisotope, such as deuterium ($^2$H), tritium ($^3$H), iodine-125 ($^{125}$I) or C-14 ($^{14}$C). Any isotopic composition transformations of the compounds of the present application, whether are radioactive or not, are included in the scope of the present application.

The term "pharmaceutically acceptable excipients" refers to those excipients that do not cause significant irritation to an organism and do not abrogate the biological activity and properties of the active compound. Suitable excipients are well known to the skilled in the art, such as carbohydrates, waxes, water soluble and/or water swell able polymers, hydrophilic or hydrophobic materials, gelatin, oils, solvents, water, and the like.

The term "effective amount" or "therapeutically effective amount" refers to a sufficient amount of a drug or agent that can achieve the desired effect. The determination of the effective amount varies with each individual, depending on the age and general condition of the subject, as well as the specific active substance. The appropriate effective amount in each case can be determined by the skilled in the art according to routine experiments.

The term "active ingredient", "therapeutic agent", "active substance" or "active agent" refers to a chemical entity that can effectively treat target disorders, diseases or conditions.

The term "optional" or "optionally" means that the subsequently described event or circumstance may or may not occur, and that the description includes instances where said event or circumstance occurs and instances where it does not. For example, ethyl being "optionally" substituted with halogen means that, said ethyl may be unsubstituted (CH$_2$CH$_3$), or monosubstituted (eg, CH$_2$CH$_2$F), polysubstituted (eg, CHFCH$_2$F, CH$_2$CHF$_2$, etc.) or fully substituted (CF$_2$CF$_3$). As to any of the chemical moieties that contain one or more substituents, it is understood by a person skilled in the art that such moieties do not contain any substitution or substitution patterns that are sterically impractical and/or synthetically nonfeasible.

As used herein, C-n refers to that said moiety has m-n carbon atoms. For example, "C$_{3-10}$ cycloalkyl" means that said cycloalkyl group has 3 to 10 carbon atoms. "C$_{0-6}$ alkylene" means that said alkylene group has 0-6 carbon atoms, where the alkylene group has 0 carbon atom, this group is a bond.

The numerical ranges herein refer to include each whole integer within the range. For example, "C$_{1-10}$" means that the group may have 1, 2, 3, 4, 5, 6, 7, 8, 9 or 10 carbon atoms.

The term "substituted" means that any one or more hydrogens on the designated atom is replaced with a substituent provided that the valence of the designated atom is normal and the substitution results in a stable compound.

When the substituent is a ketone group (i.e., =O) (also referred to as oxo), it means that two hydrogen atoms are substituted, and the ketone substitution will not occur on an aromatic group.

When any variable (eg, R) occurs more than one time in constituent or structure of a compound, each definition is independent. Thus, for example, if a group is showed to be substituted with 0-2 R, then said group may optionally be substituted with up to two R, and R at each occurrence is selected independently from the definition of R. In addition, combinations of substituents and/or variables thereof are permissible only if such combinations result in stable compounds.

When one of the variables is selected from a single bond, it means that the two groups to which they are attached are directly linked to each other. For example, when L represents a single bond in A-L-Z, the structure is actually A-Z.

When a substituent is vacant, it means that the substituent does not exist. For example, when X is vacant in A-X, the structure is actually A. When a bond of one substituent can cross-link to two atoms on one ring, this substituent may be bonded to any atom on the ring. When it does not specify through which atom the listed substituent is linked to a compound included but not specifically mentioned in a chemical structure formula, this substituent may be bonded through any of its atoms. The combination of substituents and/or variants thereof is allowable only if such combination will result in stable compounds. For example, the structural unit

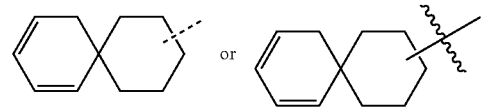

indicates that a substitution may occur at any position on cyclohexyl or cyclohexadiene.

Unless otherwise defined, the term "halogenated" or "halogen" per se or as a part of another substituent denotes a fluorine, chlorine, bromine or iodine atom.

Furthermore, the term "haloalkyl" is intended to include monohaloalkyl and polyhaloalkyl. For example, the term "haloC$_{1-3}$alkyl" is intended to include, but is not limited to, trifluoromethyl, 2,2,2-trifluoroethyl, 3-bromopropyl, etc.

Examples of haloalkyl include, but are not limited to, trifluoromethyl, trichloromethyl, pentafluoroethyl, and pentachloroethyl.

The term "hydroxy" refers to —OH.
The term "cyano" refers to —CN.
The term "amino" refers to —NH$_2$.
The term "alkyl" refers to a straight- or branched-chain saturated aliphatic hydrocarbon group consisting of carbon and hydrogen atoms, such as methyl, ethyl, propyl, butyl, pentyl, hexyl, heptyl, octyl, nonyl, decyl and the like. The specific alkyl includes all isomeric forms thereof, for example, propyl includes —CH$_2$CH$_2$CH$_3$, —CH(CH$_3$)$_2$; for example, butyl includes —CH$_2$CH$_2$CH$_2$CH$_3$, —CH(CH$_3$)(CH$_2$CH$_3$), —C(CH$_3$)$_3$, —CH$_2$CH(CH$_3$)$_2$. The term "C$_{1-8}$ alkyl" refers to an alkyl group having 1-8 carbon atoms. The term "C$_{1-6}$ alkyl" refers to an alkyl group having 1 to 6 carbon atoms. The term "C$_{1-4}$ alkyl" refers to an alkyl group having 1 to 4 carbon atoms. The term "C$_{1-3}$ alkyl" refers to an alkyl group having 1 to 3 carbon atoms.

The term "alkoxy" refers to —O-alkyl.

The term "cycloalkyl" refers to a monocyclic, saturated aliphatic hydrocarbon group consisting solely of carbon and hydrogen atoms, such as $C_{3-10}$ cycloalkyl, preferably $C_{3-6}$ cycloalkyl, such as cyclopropyl, cyclobutyl, cyclopentyl, cyclohexyl and the like.

Unless otherwise specified, the term "hetero" refers to a heteroatom or a heteroatom radical (i.e., a radical containing a heteroatom), including an atom other than carbon (C) and hydrogen (H), and a radical containing these heteroatoms, for example including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and —C(=O)N(H)—, —N(H)—, —C(=NH)—, —S(=O)$_2$N(H)—, or —S(=O)N(H)—.

Unless otherwise specified, a "ring" refers to a substituted or unsubstituted cycloalkyl, heterocycloalkyl, cycloalkenyl, heterocycloalkenyl, cycloalkynyl, heterocycloalkynyl, aryl, or heteroaryl. The ring includes a monocyclic ring, a bicyclic ring, a spiro ring, a fused ring, or a bridged ring. The number of atoms in a ring is typically defined by the number of members in the rings. For example, a "5- to 7-membered ring" refers to 5 to 7 atoms arranged in a circle. Unless otherwise specified, the ring optionally contains 1 to 3 heteroatoms. Thus, a "5- to 7-membered ring" includes, for example, phenyl, pyridine, and piperidine group.

The term "heterocycloalkyl" refers to a cyclic group which is fully saturated and existed as monocyclic ring, bicyclic ring or spiro ring. Unless otherwise specified, the heterocycle is typically a 3 to 10 membered ring containing 1 to 3 heteroatoms independently selected from S, O, and/or N (preferably 1 or 2 heteroatoms). The examples of 3-membered heterocycloalkyl include, but are not limited to oxiranyl, thiiranyl, aziridinyl. The examples of 4-membered heterocycloalkyl include, but are not limited to azetidinyl, oxetanyl, thietanyl. The examples of 5-membered heterocycloalkyl include, but are not limited to tetrahydrofuranyl, tetrahydrothiophenyl, pyrrolidinyl, isoxazolidinyl, oxazolidinyl, isothiazolidinyl, thiazolidinyl, imidazolidinyl, tetrahydropyrazolyl. The examples of 6-membered heterocycloalkyl include, but are not limited to piperidinyl, tetrahydropyranyl, tetrahydrothiopyranyl, morpholinyl, piperazinyl, 1,4-thiazolidine, 1,4-dioxolyl, thiomorpholinyl, 1,3-dithiaalkyl, 1,4-dithiaalkyl.

The examples of 7-membered heterocycloalkyl include, but are not limited to azepanyl, oxepanyl, thiepanyl. The examples of 8-membered heterocycloalkyl include, but are not limited to 3,8-diazabicyclo[3.2.1]octyl. The examples of 9-membered heterocycloalkyl include, but are not limited to 2-oxa-7-azaspiro[3,5]decyl.

The term "aryl" refers to an all-carbon monocyclic or fused polycyclic aromatic ring group which has conjugated π-electron system. For example, aryl can has 6-20 carbon atoms, 6-14 carbon atoms or 6-12 carbon atoms. The non-limiting examples of aryl include, but are not limited to, phenyl, naphthyl, anthracyl and 1,2,3,4-tetrahydronaphthyl.

The term "heteroaryl" refers to a monocyclic or fused polycyclic ring group containing at least one ring atom selected from N, O, S, preferably containing 1, 2 or 3 ring atoms selected from N, O or S, the remaining ring atoms are C, and have at least one aromatic ring. Preferably, heteroaryl has a 4 to 8 members monocyclic, especially 5 to 8 membered monocyclic, or heteroaryl has a 6 to 14 membered fused polycyclic, especially 6 to 10 membered fused polycyclic. The non-limiting examples of heteroaryl include, but are not limited to, pyrrolyl, furyl, thienyl, imidazolyl, oxazolyl, pyrazolyl, pyridyl, pyrimidinyl, pyrazinyl, quinolyl, isoquinolyl, tetrazolyl, triazolyl, triazinyl, benzofuranyl, benzothienyl, indolyl, isoindolyl, etc.

The compounds of the present invention may be prepared by various synthesis methods known to the person skilled in the art, including the specific embodiments listed below, the embodiments formed by combining the specific embodiments with other chemical synthesis methods, and equivalent replacements known to the person skilled in the art, and the preferred embodiments include, but not limited to, the Examples of the present invention.

The chemical reactions in the specific embodiments of the present application are carried out in appropriate solvents that must be suitable for chemical modification of the present application, as well as the reagents and materials needed in such modification. In order to obtain the compounds of the present application, a person skilled in the art sometimes need to modify or select synthesis steps or reaction processes on the basis of the existing embodiments.

It is one important consideration factor for any synthesis scheme in the art to select appropriate protecting groups for the reactive functional groups (such as the amino group in the present application). For example, we can refer to Greene's Protective Groups in Organic Synthesis (4th Ed). Hoboken, N.J.: John Wiley & Sons, Inc. All references cited in the present application are incorporated herein by reference in their entirety.

Synthetic Route Formula A:

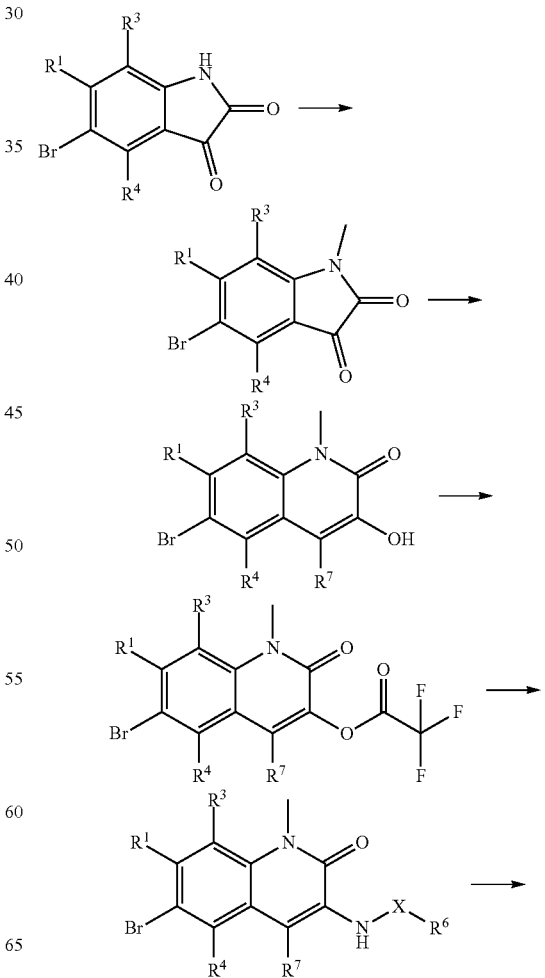

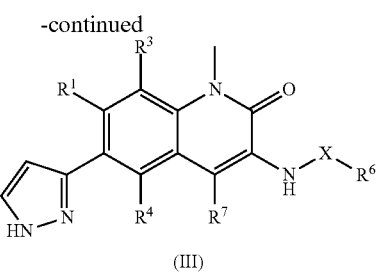

(III)

wherein, the groups are as defined in the formula (III).

Synthetic Route Formula B:

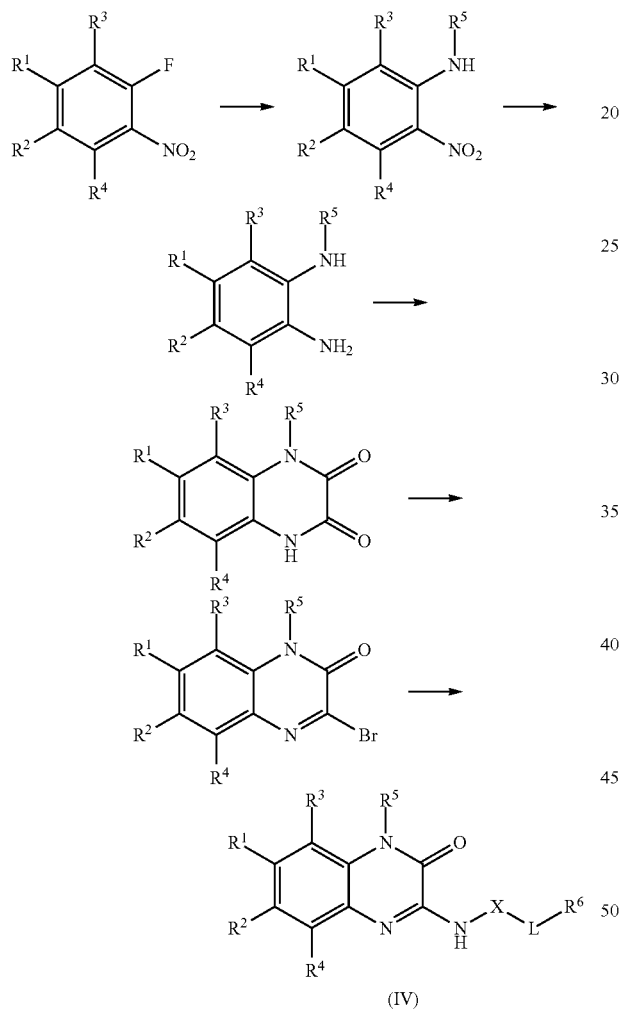

(IV)

wherein, the groups are as defined in the formula (IV).

DETAILED DESCRIPTION

The following specific examples are intended to enable those skilled in the art to clearly understand and practice the present application. They should not be considered as a limitation to the scope of the present application, but are merely exemplary descriptions and typical representations of the present application. Those skilled in the art should understand that: there are other synthetic routes to form the compounds of the present application, and ones provided below are non-limiting examples. Unless otherwise indicated, the temperature is Celsius. Solvents used in the application are commercially available.

The following abbreviations are used in the present application: TMSCHN$_2$ represents trimethylsilylated diazomethane; Tf$_2$O represents trifluoromethanesulfonic anhydride; DMAP represents 4-dimethylaminopyridine; Pd$_2$(dba)$_3$ represents tris(dibenzylideneacetone) di-palladium; Xantphos represents 4,5-bisdiphenylphosphino-9,9-dim ethylxanthene; Pd(dppf)Cl$_2$ represents [1,1'-bis(diphenylphosphino) ferrocene palladium dichloride; NBS represents N-bromosuccinimide; DMF represents N,N-dimethylformamide; DMSO represents dimethyl sulfoxide; DIEA (DIPEA) represents N,N-diisopropylethylamine; Pd(OAc)$_2$ represents palladium acetate; Brettphos represents 2-(dicyclohexylphosphine)-3,6-dim ethoxy-2'-4'-6'-tri-1-propyl-11'-biphenyl; EDTA represents ethylenediaminetetraacetic acid; DTT represents dithiothreitol; TFA represents trifluoroacetic acid; DCM represents dichloromethane; BINAP represents 2,2'-bis-(diphenylphosphino)-1,1'-binaphthyl; DAST represents diethylaminosulfur trifluoride; TLC represents thin layer chromatography; LCMS represents High Performance Liquid Chromatography-Mass Spectrometry; NCS represents N-chloro Succinimide; t-Bu represents tert-butyl; DME represents dim ethyl ether.

Example 1: 1-Methyl-3-((4-morpholinephenyl) amino)-6-(1H-pyrazol-3-yl) quinoline-2(1H)-one

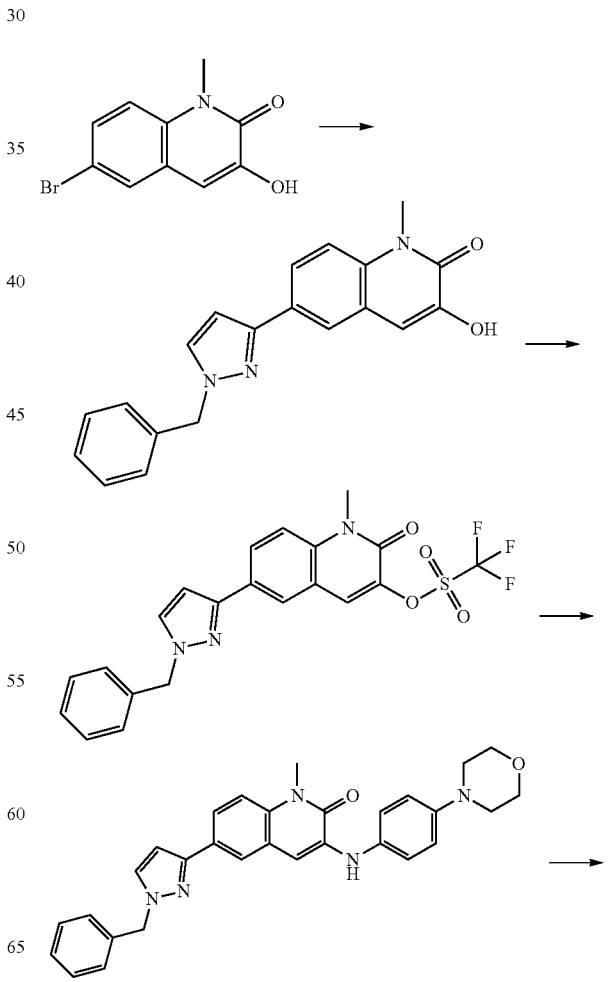

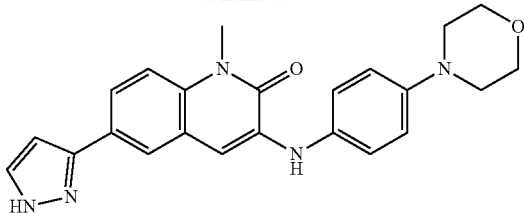

Step A: 6-(1-Benzyl-1H-pyrazol-3-yl)-3-hydroxy-1-methyl-quinoline-2(1H)-one

Under a protection of nitrogen, to a solution of 6-bromo-3-hydroxy-1-methyl-quinolin-2-one (0.6 g, 2.36 mmol), 1-benzyl-3-(4,4,5,5-tetramethyl-1,3,2-dioxaborolan-2-yl) pyrazole (805.2 mg, 2.83 mmol) and potassium carbonate (652.7 mg, 4.72 mmol) in dioxane (4.00 mL) and water (1.00 mL) was added Pd(dppf)Cl$_2$ (172.7 mg, 0.236 mmol). The reaction solution was stirred at 80° C. for 7 hours. The reaction solution was diluted with 40 mL water, and extracted twice with 40 mL dichloromethane. The organic phase was washed with brine, dried over anhydrous sodium sulfate, filtered, and after spin-drying separated by automated column chromatography (dichloromethane/methanol) to give the title compound.

$^1$H NMR (400 MHz, DMSO-d6) δ=9.51 (s, 1H), 7.97 (d, J=2.0 Hz, 1H), 7.90 (d, J=2.4 Hz, 1H), 7.84 (dd, J=2.0, 8.8 Hz, 1H), 7.51-7.45 (m, 1H), 7.39-7.32 (m, 2H), 7.32-7.25 (m, 3H), 7.17 (s, 1H), 6.78 (d, J=2.4 Hz, 1H), 5.39 (s, 2H), 3.71 (s, 3H).

Step B: [6-(1-Benzyl-1H-pyrazol-3-yl)-1-methyl-2-oxo-1,2-dihydro-quinolin-3-yl]trifluoromethanesulfonate To a solution of 6-(1-benzyl-1H-pyrazol-3-yl)-3-hydroxy-1-methyl-quinoline-2(1H)-one (340.00 mg, 1.03 mmol) in chloromethane were added DMAP (125.8 mg, 1.03 mmol), Tf$_2$O (581.2 mg, 2.06 mmol, 0.339 mL) at 0° C., followed by the addition of pyridine (244.4 mg, 3.09 mmol, 0.25 mL). The reaction was stirred at 15° C. for 16 hours. The reaction solution was diluted with 40 mL water, and extracted twice with 40 mL dichloromethane. The organic phase was washed with brine, dried over anhydrous sodium sulfate, filtered, and after spin-drying, separated by automated column chromatography (petroleum ether/tetrahydrofuran=50/50) to give the title compound.

$^1$H NMR (400 MHz, DMSO-d6) δ=8.48 (s, 1H), 8.32 (d, J=2.0 Hz, 1H), 8.16 (dd, J=2.0, 8.8 Hz, 1H), 7.95 (d, J=2.3 Hz, 1H), 7.67 (d, J=9.0 Hz, 1H), 7.39-7.25 (m, 5H), 6.82 (d, J=2.3 Hz, 1H), 5.40 (s, 2H), 3.74 (s, 3H).

Step C: 6-(1-Benzyl-1H-pyrazol-3-yl)-1-methyl-3-((4-morpholinephenyl)amino)quinolin-2(1H)-one To a solution of [6-(1-benzyl-1H-pyrazol-3-yl)-1-methyl-2-oxo-1,2-dihydro-quinolin-3-yl]trifluoromethanesulfonate (150 mg, 323.671 µmol) and 4-morpholine aniline (86.53 mg, 485.51 µmol) in anhydrous dioxane (3 mL) were added cesium carbonate (158.19 mg, 485.51 µmol), Xantphos (37.46 mg, 64.731 µmol) and Pd$_2$(dba)$_3$ (29.64 mg, 32.371 µmol) at 20° C. It was stirred at 100° C. for 7 hours under nitrogen. The reaction solution was diluted with 40 mL water, and extracted twice with 40 mL dichloromethane. The organic phase was washed with brine, dried over anhydrous sodium sulfate, filtered, and after spin-drying, separated by automated column chromatography (petroleum ether/tetrahydrofuran=100%-60/40) to give the title compound.

$^1$H NMR (400 MHz, DMSO-d6) δ=7.90 (dd, J=1.8, 13.2 Hz, 1H), 7.78-7.73 (m, 1H), 7.46 (d, J=8.8 Hz, 1H), 7.39-7.32 (m, 2H), 7.32-7.24 (m, 5H), 7.21 (s, 1H), 6.97 (d, J=8.8 Hz, 2H), 6.77 (d, J=2.4 Hz, 1H), 5.37 (s, 2H), 3.79-3.72 (m, 7H), 3.10-3.04 (m, 1H).

Step D: 1-Methyl-3-((4-morpholinephenyl)amino)-6-(1H-pyrazol-3-yl)quinoline-2(1H)-one To 6-(1-benzyl-1H-pyrazol-3-yl)-1-methyl-3-((4-morpholinephenyl)amino)quinolin-2(1H)-one (30.00 mg, 61.03 µmol) in methanol was added Pd(OH)$_2$ (30.00 mg), and it was stirred at 50° C. under an atmosphere of hydrogen (45 psi) for 16 hours. After the reaction solution was filtered, the filter cake was washed with 30 mL methanol. The filtrate was spin-dried and then purified by preparative HPLC (trifluoroacetic acid system) to give the title compound 1.

$^1$H NMR (400 MHz, DMSO-d6) δ=7.93 (s, 1H), 7.78 (d, J=8.0 Hz, 1H), 7.70 (d, J=2.0 Hz, 1H), 7.50 (d, J=8.8 Hz, 1H), 7.34-7.17 (m, 3H), 7.03 (s, 2H), 6.72 (d, J=2.4 Hz, 1H), 3.77 (s, 7H), 3.12 (s, 4H).

MS-ESI (m/z): 402.2 (M+H)$^+$.

Example 2: 1-Methyl-3-((5-morpholinepyridin-2-yl)amino)-6-(1H-pyrazol-3-yl)quinoline-2(1H)-one

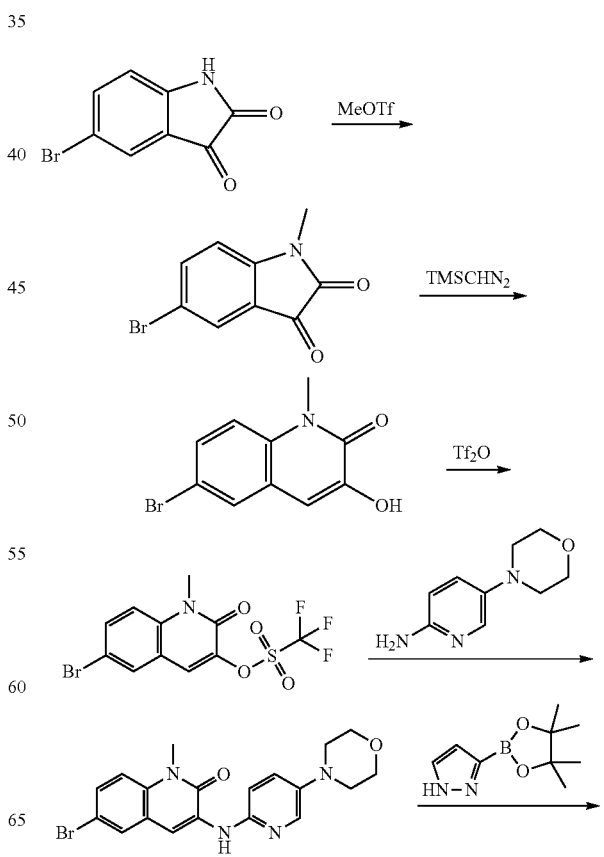

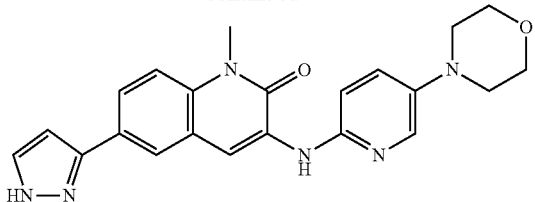

Step A: 5-Bromo-1-methylindolin-2,3-dione

To a solution of 5-bromoindolin-2,3-dione (50.00 g, 221.21 mmol) and cesium carbonate (144.15 g, 442.42 mmol) in acetonitrile (700 mL) was added dropwise methyl trifluoromethanesulfonate (39.93 g, 243.33 mmol) at 0° C. under nitrogen, and it was stirred for one hour at 0° C. The reaction solution was poured into 2 L water and adjusted the pH to 6 with 1 mol/L hydrochloric acid. The precipitated solid was filtered and dried to give the title compound.

1H NMR (400 MHz, DMSO-d6) δ=7.83 (dd, J=2.0, 8.3 Hz, 1H), 7.68 (d, J=2.0 Hz, 1H), 7.11 (d, J=8.5 Hz, 1H), 3.11 (s, 3H).

Step B: 6-Bromo-3-hydroxy-1-methylquinoline-2(1H)-one

Under a protection of nitrogen, to a solution of 5-bromo-1-methyl indolin-2,3-dione (44.00 g, 183.30 mmol) and triethylamine (37.10 g, 366.60 mmol) in ethanol (1 L) was added dropwise TMSCHN$_2$ (2 mol/L, 91.65 mL) at 25° C., and it was stirred at 25° C. for 12 hours. The reaction solution was concentrated to half and filtered. The filter cake was washed with ethyl acetate (100 mL), and dried to give the title compound.

Step C: 6-Bromo-1-methyl-2-oxo-1,2-dihydroquinolin-3-yl trifluoromethanesulfonate Under a protection of nitrogen, trifluoromethanesulfonic anhydride (39.14 g, 138.73 mmol) was added dropwise to a solution of 6-bromo-3-hydroxy-1-methylquinoline-2(1H)-one (23.50 g, 92.49 mmol), pyridine (21.95 g, 277.47 mmol) and DMAP (1.13 g, 9.25 mmol) in dichloromethane (400 mL) at 0° C. It was stirred at 25° C. for 3 hours. The reaction was quenched with 1N hydrochloric acid and adjusted the pH to 6. The organic phase was washed with saturated sodium chloride (500 mL), and dried over anhydrous sodium sulfate. It was then filtered and evaporated to give the title compound.

1H NMR (400 MHz, DMSO-d6) δ=8.38 (s, 1H), 8.15 (d, J=2.3 Hz, 1H), 7.90 (dd, J=2.1, 9.2 Hz, 1H), 7.61 (d, J=9.3 Hz, 1H), 3.72 (s, 3H).

Step D: 6-Bromo-1-methyl-3-((5-morpholinepyridin-2-yl)amino)quinoline-2(1H)-one Under a protection of nitrogen, 6-bromo-1-methyl-2-oxo-1,2-dihydroquinolin-3-yltrifluoromethanesulfonate (28.00 g, 81.95 mmol), 5-morpholinepyridin-2-amino (16.15 g, 90.15 mmol), Pd$_2$(dba)$_3$ (3.75 g, 4.10 mmol), Xantphos (4.74 g, 8.20 mmol) and cesium carbonate (53.40 g, 163.90 mmol) were added into tetrahydrofuran (300 mL). It was stirred at 25° C. for 6 hours. The reaction solution was filtered, and the filtered cake was washed with ethyl acetate (50 mL) and water (200 mL). The solid was dried to give the title compound.

1H NMR (400 MHz, DMSO-d6) δ=8.72 (d, J=11.0 Hz, 2H), 7.97 (d, J=2.8 Hz, 1H), 7.66 (d, J=2.5 Hz, 1H), 7.50 (d, J=9.0 Hz, 1H), 7.41 (ddd, J=2.6, 9.0, 16.9 Hz, 2H), 7.32 (d, J=9.0 Hz, 1H), 3.97-3.67 (m, 7H), 3.13-2.94 (m, 4H).

Step E: 1-Methyl-3-((5-morpholinepyridin-2-yl)amino)-6-(1H-pyrazol-3-yl)quinoline-2(1H)-one Under a protection of nitrogen, to 1,4-dioxane (200 mL) and water (50 mL) were added 6-bromo-1-methyl-3-((5-morpholinepyridin-2-yl)amino)quinoline-2(1H)-one (10.00 g, 24.08 mmol), potassium carbonate (8.32 g, 60.20 mmol), Pd(dppf)Cl$_2$ (7.16 g, 2.41 mmol) and 3-(4,4,5,5-tetramethyl-1,3,2-dioxaborolan-2-yl)-1H-pyrazole (5.61 g, 28.90 mmol). It was stirred at 110° C. for 12 hours. The reaction solution was filtered, and the filtered cake was washed with ethyl acetate (200 mL). The aqueous phase was separated, and the organic phase was dried over anhydrous sodium, concentrated, filtered, and dried to give the title compound 2.

1H NMR (400 MHz, DMSO-d6) δ=13.60-12.56 (m, 1H), 8.86 (s, 1H), 8.63 (br s, 1H), 8.00 (s, 2H), 8.13-7.93 (m, 1H), 7.92-7.68 (m, 1H), 7.53 (br d, J=8.0 Hz, 1H), 7.43 (dd, J=3.0, 9.0 Hz, 1H), 7.32 (d, J=9.0 Hz, 1H), 6.81 (br s, 1H), 3.85-3.70 (m, 7H), 3.18-2.98 (m, 4H).

(ESI) m/z: 403 (M+1)

Example 3: 1-Methyl-6-(1H-pyrazol-3-yl)-((5-)tetrahydro-2H-pyran-4-yl)pyridin-2-yl) amino)quinoline-2(1H)-one

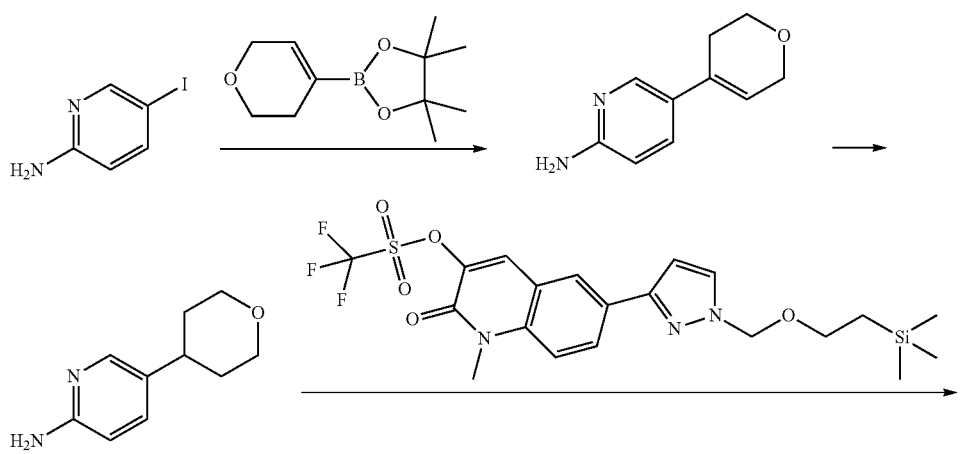

-continued

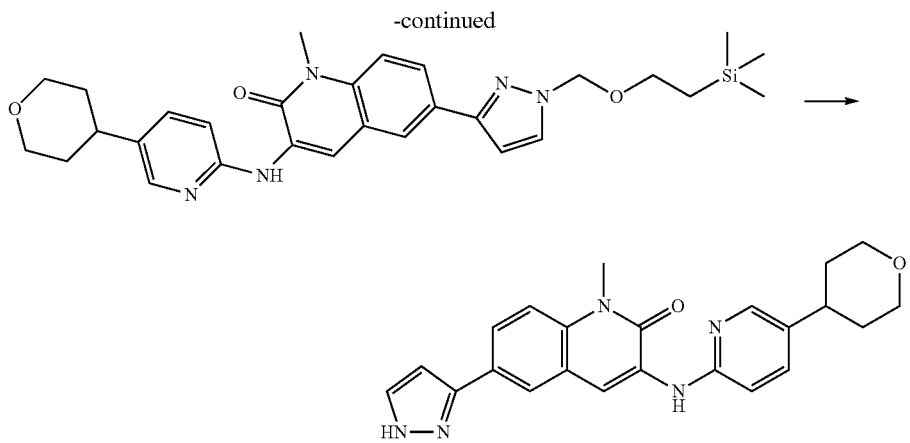

Step A:
5-(3,6-Dihydro-2H-pyran-4-yl)pyridin-2-amine

Under a protection of nitrogen, added 2-(3,6-dihydro-2H-pyran-4-yl)-4,4,5,5-tetramethyl-1,3-2-dioxaborolane (2.29 g, 10.91 mmol), potassium carbonate (3.77 g, 27.27 mmol) and Pd(dppf)Cl$_2$ (332.56 mg, 454.501 μmol) to a solution of 5-iodopyridin-2-amine (2.00 g, 9.09 mmol) in dioxane (32 mL) and water (8 mL), and it was stirred under a protection of nitrogen at 80° C. for 3 hours. The reaction solution was cooled to room temperature, followed by the addition of water (50 mL) into it, and extracted twice with ethyl acetate (50 mL). The organic phase was washed twice with saturated brine (50 mL), dried over anhydrous sodium sulfate, filtered, and spin-dried to yield the residue which was subjected to the column chromatography to give the title compound.

$^1$H NMR (400 MHz, CHLOROFORM-d) δ=8.12 (d, J=2.3 Hz, 1H), 7.49 (dd, J=2.3, 8.5 Hz, 1H), 6.49 (d, J=8.5 Hz, 1H), 6.01-5.94 (m, 1H), 4.58-4.37 (m, 2H), 4.31 (q, J=2.8 Hz, 2H), 3.93 (t, J=5.5 Hz, 2H), 2.51-2.42 (m, 2H).

Step B:
5-(Tetrahydro-2H-pyran-4-yl)pyridin-2-amine

To a solution of 5-(3,6-dihydro-2H-pyran-4-yl)pyridin-2-amine (1.29 g, 7.32 mmol) in ethyl acetate (5 mL) and water was added 10% palladium carbon (0.12 g), and it was replaced three times with hydrogen balloon, and stirred at room temperature for 16 hours. It was then filtered over Celite, rinsed three times with ethyl acetate (50 mL). The filtrate was spin-dried to give the title compound.

1H NMR (400 MHz, CHLOROFORM-d) δ=7.94 (d, J=2.0 Hz, 1H), 7.32 (dd, J=2.3, 8.5 Hz, 1H), 6.49 (d, J=8.3 Hz, 1H), 4.35 (br s, 2H), 4.10-4.02 (m, 2H), 3.51 (dt, J=3.3, 11.2 Hz, 2H), 2.71-2.59 (m, 1H), 1.80-1.71 (m, 4H).

Step C: 1-Methyl-3((5-(tetrahydro-2H-pyran-4-yl)pyridin-2-yl)amino)-6-(1-((2-(triethylsilyl))ethoxy)methyl)-1H-pyrazol-3-yl)quinoline-2(1H)-one Added 5-(tetrahydro-2H-pyran-4-yl)pyridin-2-amine (63.71 mg, 357.441 μmol), cesium carbonate (145.58 mg, 446.81 μmol), Xantphos (34.47 mg, 59.57 μmol) and Pd$_2$(dba)$_3$ (27.28 mg, 29.79 μmol) to a solution of 1-methyl-2-oxo-6-(1-((2-(trimethylsilyl)ethoxy)methyl)-1H-pyrazol-3-yl)-1,2-dihydrolquinolin-3-yl-trifluoromethanesulfonate (150.00 mg, 297.871 μmol) in dioxane (8 mL), and it was stirred under nitrogen at 100° C. for 16 hours. The reaction solution was cooled to room temperature, followed by the addition of water (30 mL) into it, and extracted twice with dichloromethane (30 mL). The organic phase was washed twice with saturated brine (20 mL), dried over anhydrous sodium sulfate, filtered, and spin-dried to yield the residue which was subjected to the column chromatography to give the title compound.

MS-ESI (m/z): 532 (M+H)$^+$

Step D: 1-Methyl-6-(1H-pyrazol-3-yl)-((5-)tetrahydro-2H-pyran-4-yl)pyridin-2-yl) amino)quinoline-2(1H)-one Dissolved 1-methyl-3((5-(tetrahydro-2H-pyran-4-yl)pyridin-2-yl)amino)-6-(1-((2-(trimethylsilyl)ethoxy)methyl)-1H-pyrazol-3-yl)quinolin-2(1H)-one (100.00 mg, 188.07 μmol) in trifluoroacetic acid (4 mL) at room temperature. It was stirred at 95° C. for 3 hours. The reaction solution was cooled to room temperature, spun to dryness, followed by the addition of water (15 mL) into it, and extracted twice with dichloromethane (15 mL). The organic phase was washed twice with saturated brine (20 mL), dried over anhydrous sodium sulfate, filtered, and concentrated under reduced pressure to yield the residue which was separated by preparative HPLC (trifluoroacetic acid) to give the title compound 3.

1H NMR (400 MHz, DMSO-d6) δ=8.99 (br s, 1H), 8.83 (br s, 1H), 8.18 (s, 1H), 8.06 (s, 1H), 7.91 (br d, J=8.5 Hz, 1H), 7.74 (d, J=2.0 Hz, 1H), 7.66 (br d, J=8.8 Hz, 1H), 7.57 (d, J=8.8 Hz, 1H), 7.34 (d, J=8.8 Hz, 1H), 6.81 (d, J=2.3 Hz, 1H), 3.96 (br d, J=10.8 Hz, 2H), 3.79 (s, 3H), 2.81-2.73 (m, 1H), 1.75-1.67 (m, 4H), −0.01-−0.01 (m, 1H).

MS-ESI (m/z): 402 (M+H)+.

Example 4: 1-Methyl-3-[[5-(4-(oxetan-3-yl)piper-azin-1-yl]pyridin-2-yl]amino]-6-(1H-pyrazol-3-yl)quinoline-2(1H)-one $^1$H NMR (400 MHz, DMSO-d$_6$) δ=8.23 (d, J=3.0 Hz, 1H), 8.13 (d, J=9.3 Hz, 1H), 7.44 (dd, J=3.0, 9.3 Hz, 1H), 3.43-3.38 (m, 4H), 2.87-2.76 (m, 4H).

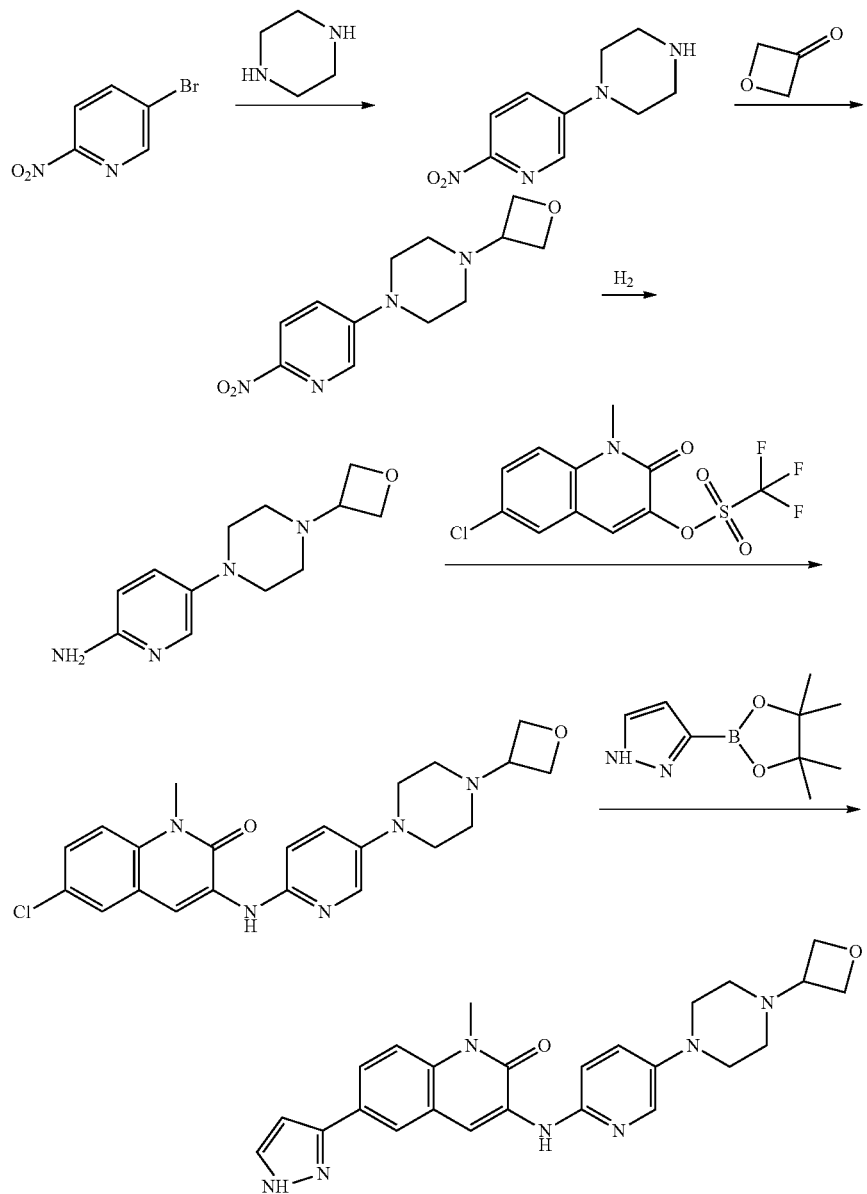

Step A: 1-(6-Nitropyridin-3-yl)piperazine

Under a protection of nitrogen, to a solution of piperazine (2.55 g, 29.56 mmol) and 5-bromo-2-nitro-pyridine (5 g, 24.63 mmol) in acetonitrile (40 mL) were added potassium carbonate (5.11 g, 36.95 mmol) and tetrabutylamine iodide (636.83 mg, 1.72 mmol) and it was stirred at 100° C. for 16 hours. It was immediately filtered at a high temperature, and the filter cake was washed with hot acetonitrile, followed by a precipitating of solid from the filtrate, filtration again. The filter cake was washed with a small portion of cold acetonitrile, then spin-dried to give the title compound.

MS-ESI (m/z): 209 (M+1).

Step B: 1-(6-Nitropyridin-3-yl)-4-(oxetan-3-yl)piperazine

To a solution of zinc chloride (1M, 9.90 mL) and oxetan-3-one (712.92 mg, 9.90 mmol) in methanol (20 mL) was added Example 4A (1.03 g, 4.95 mL), after stirring at 30° C. for 2 hours, and then added slowly sodium cyanoborohydride (621.70 mg, 9.90 mmol) in batches, warming to 50° C. and reacting for 14 hours. It was immediately filtered at a high temperature, and the filter cake was washed with filtrate and methanol (50 mL) separately, then spin-dried to give the title compound.

MS-ESI (m/z): 265 (M+1).

$^1$H NMR (400 MHz, DMSO-d$_6$) δ=8.26 (br d, J=3.0 Hz, 1H), 8.20-8.13 (m, 1H), 7.49 (dd, J=3.0, 9.3 Hz, 1H), 4.60-4.53 (m, 2H), 4.47 (t, J=6.0 Hz, 2H), 3.54-3.49 (m, 4H), 3.16 (d, J=5.3 Hz, 1H), 2.43-2.38 (m, 4H).

Step C: 5-[4-(Oxetan-3-yl)piperazin-1-yl]pyridin-2-amine

A mixture of Example 4B (990 mg, 3.75 mmol) and palladium carbon (100 mg, 10% purity) in methanol (150 mL) was reacted under hydrogen (15 psi) at 50° C. for 16 hours. Then it was filtered with Celite, and the filter cake was washed with methanol (150 mL). The filtrate was spin-dried to give the title compound.

MS-ESI (m/z): 235 (M+1).

$^1$H NMR (400 MHz, DMSO-$d_6$) δ=7.59 (d, J=3.0 Hz, 1H), 7.24-7.10 (m, 1H), 6.40 (d, J=8.8 Hz, 1H), 5.38 (s, 2H), 4.58-4.51 (m, 2H), 4.44 (t, J=6.0 Hz, 2H), 3.45-3.42 (m, 1H), 2.97-2.91 (m, 4H), 2.40-2.34 (m, 4H).

Step D: 6-Chloro-1-methyl-3-[[5-[4-(oxetan-3-yl)piperazin-1-yl]pyridin-2-yl]amino]quinoline-2(1H)-one Under a protection of nitrogen, to a solution of Example 4C (100 mg, 426.801 μmol), (6-chloro-1-methyl-2-oxa-1,2-dihydroquinolin-3-yl)trifluoromethanesulfonate (145.83 mg, 426.80 μmol), cesium carbonate (278.12 mg, 853.60 μmol) in tetrahydrofuran (5 mL) were added Xantphos (49.39 mg, 85.36 μmol), Pd$_2$(dba)$_3$ (39.08 mg, 42.68 μmol). It was stirred at 80° C. for 12 hours. It was then cooled to room temperature, quenched by the addition of water (50 mL), and the aqueous layer was extracted with dichloromethane (50 mL×3). The combined organic layers were washed with saturated brine (100 mL), dried over anhydrous sodium sulfate, filtered and evaporated. The residue was separated and purified by column chromatography to give the title compound.

MS-ESI (m/z): 426.1 (M+1).

Step E: 1-Methyl-3-[[5-(4-(oxetan-3-yl)piperazin-1-yl]pyridin-2-yl]amino]-6-(1H-pyrazol-3-yl)quinoline-2(1H)-one Under a protection of nitrogen, dissolved Example 4D (86 mg, 201.92 μmol), 3-(4,4,5,5-tetramethyl-1,3,2-dioxaborolan-2-yl)-1H-pyrazole (78.36 mg, 403.84 μmol), cesium carbonate (197.37 mg, 605.76 μmol) in dioxane (8 mL), followed by the addition of Brttphos-Pd (32.26 mg, 40.38 μmol), and it was stirred at 110° C. for 15 hours. It was cooled to room temperature, quenched by the addition of water (50 mL), and the aqueous layer was extracted with ethyl acetate (50 mL×3). The combined organic layers were washed with saturated brine (100 mL), dried over anhydrous sodium sulfate, filtered and evaporated. The residue was separated and purified by preparative HPLC (trifluoroacetic acid system) to give the title compound 4.

MS-ESI (m/z): 457.5 (M+H)$^+$.

$^1$H NMR (400 MHz, DMSO-$d_6$) δ=8.85 (s, 1H), 8.77 (s, 1H), 8.06 (d, J=3.0 Hz, 1H), 7.98 (s, 1H), 7.87 (dd, J=2.0, 8.7 Hz, 1H), 7.73 (d, J=2.1 Hz, 1H), 7.58-7.50 (m, 2H), 7.36 (d, J=9.0 Hz, 1H), 6.79 (d, J=2.2 Hz, 1H), 4.82-4.75 (m, 4H), 4.55-4.43 (m, 1H), 3.88-3.83 (m, 9H), 3.31 (br s, 2H).

Example 5: 3-((5-(4-Hydroxy-4-(trifluoromethyl)piperidin-1-yl)piperdin-2-yl)amino)-1-methyl-6-(1H-pyrazole-3-yl)quinoline-2(1H)-one

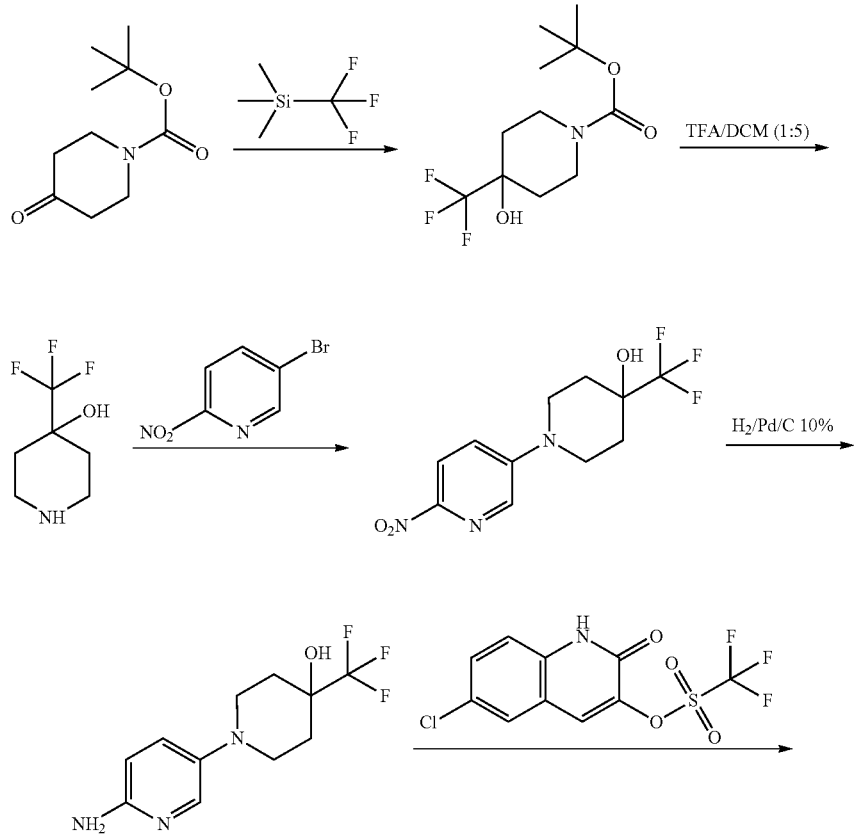

-continued

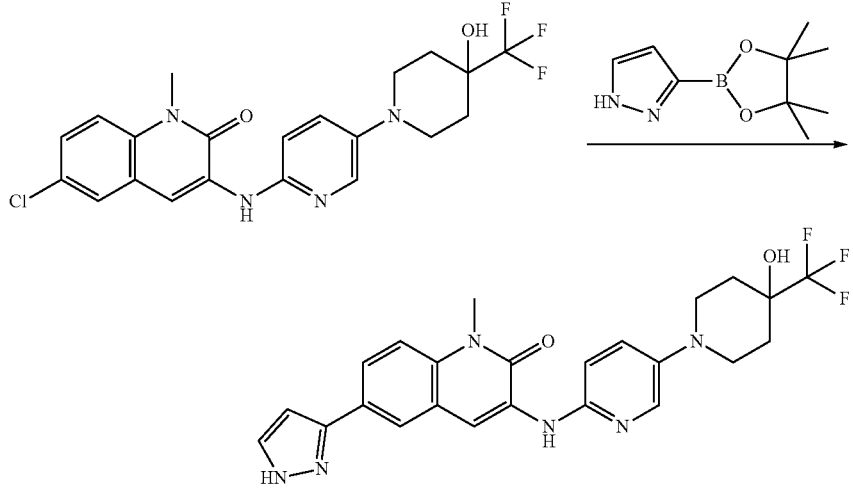

Step A: tert-Butyl 4-hydroxy-4-(trifluoromethyl)piperidine-1-carboxylate

To a solution of tert-butyl 4-carbonylhexahydropyridine-1-carboxylate (1.2 g, 6.02 mmol) in DMF (10 mL) was added dropwise trimethyl(trifluoromethyl)silane (3.85 g, 27.10 mmol) at 0° C. under nitrogen, and after it was stirred at 25° C. for 2 hours, quenched by the addition of water (100 mL), and the aqueous layer was extracted with ethyl acetate (100 mL×3). The combined organic layers were washed with saturated brine (100 mL×2), dried over sodium sulfate, filtered and evaporated to give the title compound.

Step B: 4-(Trifluoromethyl)piperidin-4-ol

Example 5A (1.6 g, 5.94 mmol) in trifluoroacetic acid (2 mL) and dichloromethane (10 mL) was reacted at 25° C. for 12 hours under nitrogen. The reaction mixture was evaporated under reduced pressure to give title compound.

Step C: 1-(6-Nitropyridin-3-yl)-4-(trifluoromethyl)piperidin-4-ol

Under a protection of nitrogen, after a mixture of Example 5B (1.67 g, 5.90 mmol), 5-bromo-2-nitropyridine (1.32 g, 6.49 mmol), potassium carbonate (4.08 g, 29.49 mmol) in DMF (50 mL) was stirred at 100° C. for 10 hours, it was diluted with water (50 mL). The aqueous layer was extracted with ethyl acetate (50 mL×3). After the combined organic layers were washed with brine (50 mL×2), dried over sodium sulfate, filtered and evaporated. The residue was purified by column chromatography to give the title compound.
$^1$H NMR (400 MHz, DMSO-d6) δ=8.29 (d, J=3.0 Hz, 1H), 8.14 (d, J=9.3 Hz, 1H), 7.52 (dd, J=3.0, 9.3 Hz, 1H), 6.18 (s, 1H), 4.10-4.03 (m, 2H), 3.29-3.19 (m, 2H), 1.80-1.72 (m, 4H).

Step D: 1-(6-Aminopyridin-3-yl)-4-(trifluoromethyl)piperidin-4-ol

Under a protection of nitrogen, to a solution of Example 5C (810 mg, 2.78 mmol) in 20 mL methanol, was added 10% wet palladium carbon (81 mg). Then, it was replaced with hydrogen for three times, and stirred for 15 hours at 25° C. under an atmosphere of nitrogen (15 psi). The reaction solution was filtered through Celite and evaporated. The residue was purified by column chromatography to give the title compound.
MS-ESI (m/z): 262 (M+1).

Step E: 6-Chloro-3-[[5-[4-hydroxy-4-(trifluoromethyl)piperidin-1-yl]pyridin-2-yl]amino]-1-methyl-quinoline-2 (1H)-one Under a protection of nitrogen, a mixture of Example 5D (275.24 mg, 1.05 mmol), (6-chloro-1-methyl-2-oxy-3-quinolinyl) trifluoromethanesulfonate (300 mg, 877.99 μmol), Pd$_2$(dba)$_3$ (80.40 mg, 87.80 μmol), cesium carbonate (572.13 mg, 1.76 mmol), Xantphos (76.20 mg, 131.70 μmol) in tetrahydrofuran (10.00 mL) was stirred at 25° C. for 4 hours. It was diluted with water (20 mL) and the aqueous layer was extracted with dichloromethane (20 mL×3). The combined organic layers were washed with brine (20 mL×2), dried over sodium sulfate, filtered and evaporated. The residue was purified by column chromatography to give the title compound.
MS-ESI (m/z): 453 (M+1).
1H NMR (400 MHz, DMSO-d6) δ=8.72 (s, 1H), 8.67 (s, 1H), 8.01 (d, J=2.8 Hz, 1H), 7.65 (d, J=2.0 Hz, 1H), 7.50 (d, J=9.0 Hz, 1H), 7.45 (dd, J=2.8, 9.0 Hz, 1H), 7.41-7.36 (m, 1H), 7.29 (d, J=9.0 Hz, 1H), 6.01 (s, 1H), 3.75 (s, 3H), 3.53 (brd, J=11.8 Hz, 2H), 2.97-2.87 (m, 2H), 1.84-1.71 (m, 4H).

Step F: 3-((5-(4-Hydroxy-4-(trifluoromethyl)piperidin-1-yl)piperdin-2-yl)amino)-1-methyl-6-(1H-pyrazol-3-yl)quinoline-2(1H)-one Under a protection of nitrogen, Example 5E (330 mg, 728.70 μmol), 3-(4,4,5,5-tetramethyl-1,3,2-dioxaborolan-2-yl)-1H-pyrazole (212.10 mg, 1.09 mmol), [2-(2-aminoethyl)phenyl]-chloro-palladium; biscyclohexyl-[3,6-dimethoxy-2-(2,4,6-triisopropylbenzene)phenyl]phosphate (58.21 mg, 72.87 μmol), cesium carbonate (712.28 mg, 2.19 mmol) in dimethyl sulfoxide (8 mL) and water (2 mL), the mixture was stirred at 120° C. for 10 hours. It was diluted with water (30 mL) and the aqueous layer was extracted with dichloromethane (30 mL×3). After the combined organic layers were washed with brine (30 mL×2), dried over sodium sulfate, filtered and evaporated. The residue was purified by column chromatography to give the title compound 5.

MS-ESI (m/z): 485 (M+1).

1H NMR (400 MHz, DMSO-d6) δ=13.41-12.81 (m, 1H), 8.85 (br s, 1H), 8.62 (brs, 1H), 8.02 (brd, J=18.3 Hz, 2H), 7.9-7.74 (m, 1H), 7.62-7.41 (m, 2H), 7.30 (br d, J=8.0 Hz, 1H), 6.80 (br s, 1H), 6.00 (br s, 1H), 3.79 (br s, 3H), 3.52 (brs, 2H), 2.93 (br t, J=11.2 Hz, 2H), 1.90-1.69 (m, 4H).

Example 6: 7-Fluoro-1-methyl-3-((5-morpholinepyridin-2-yl)amino)-6-(1H-pyrazol-3-yl)quinoline-2(1H)-one

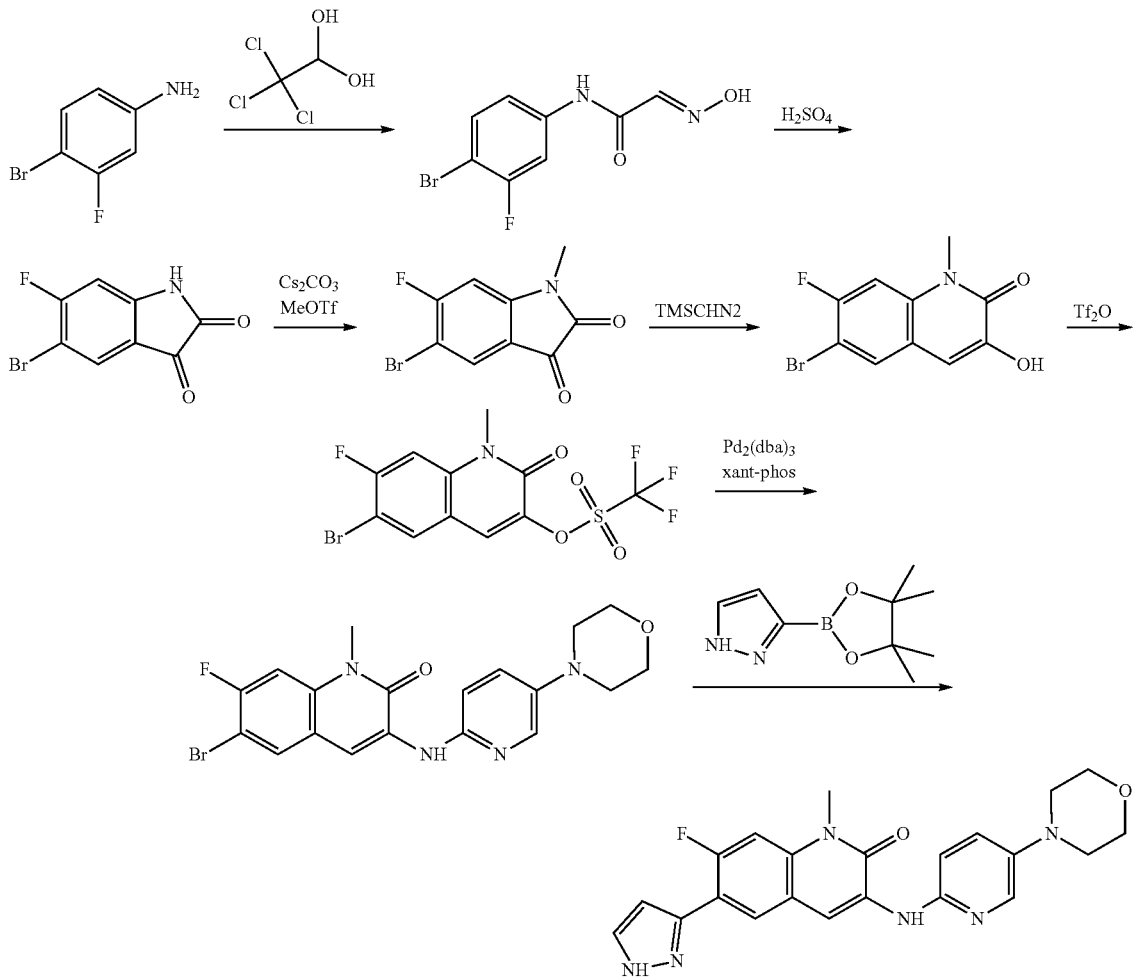

Step A: (E)-N-(4-bromo-3-fluorophenyl)-2-(oximido)acetamide

To a solution of 4-bromo-3-fluoro-aniline (5.00 g, 26.31 mmol) in water (150.00 mL) were added 2,2,2-trichloroethane-1,1-diol (5.66 g, 34.20 mmol), sodium sulfate (8.22 g, 57.88 mmol), hydroxylamine hydrochloride (7.31 g, 105.24 mmol) and hydrochloric acid (2.50 mL). The reaction solution was warmed to 100° C. and stirred for 16 hours. It was then filtered and the filter cake was washed with water (200 mL). The solid was dried to give the title compound.

1H NMR (400 MHz, DMSO-d6) δ=12.30 (s, 1H), 10.50 (s, 1H), 7.83 (dd, J=2.4, 11.4 Hz, 1H), 7.69-7.61 (m, 2H), 7.46 (dd, J=2.0, 8.8 Hz, 1H).

Step B: 5-Bromo-6-fluoroindolin-2,3-dione (E)-N-(4-bromo-3-fluorophenyl)-2-(oximido)acetamide (2.00 g, 7.66 mmol) was dissolved in sulfuric acid (10.00 mL), and the reaction solution was warmed to 80° C. and stirred for one hour. The reaction solution was poured into water (50 mL). The precipitated solid was filtered and dried to give the title compound.

1H NMR (400 MHz, DMSO-d6) δ=11.30 (s, 1H), 7.99-7.75 (m, 1H), 6.94 (d, J=8.8 Hz, 1H).

Step C: 5-Bromo-6-fluoro-1-methylindolin-2,3-dione

Under a protection of nitrogen, to a solution of 5-bromo-6-fluoroindolin-2,3-dione (800.00 mg, 3.28 mmol) in acetonitrile (20.00 mL) were added caesium carbonate (2.14 g, 6.56 mmol) and methyl trifluoromethanesulfonate (645.59 mg, 3.94 mmol) at 0° C. It was stirred for 2 hours at 0° C., quenched with water (100 mL), and extracted three times with ethyl acetate (30 mL). The organic phase was washed with saturated brine (100 mL), dried over anhydrous sodium sulfate. Filtration and evaporation gave the title compound.

Step D: 6-Bromo-7-fluoro-3-hydroxy-1-methylquinoline-2(1H)-one

Under a protection of nitrogen, to a solution of 5-bromo-6-fluoro-1-methylindolin-2,3-dione (800 mg, 3.10 mmol) and triethylamine (627.44 mg, 6.20 mmol) in ethanol (30 mL), was added dropwise TMSCHN$_2$ (2 mol/L, 1.86 mL) at 0° C., and it was stirred at 25° C. for 16 hours.

The reaction solution was concentrated to give the title compound.

MS-ESI (m/z): 272 (M+H)$^+$

Step E: 6-Bromo-7-fluoro-1-methyl-2-oxo-1,2-dihydroquinolin-3-yl-trifluoromethanesulfonate Trifluoromethanesulfonic anhydride (1.87 g, 6.62 mmol) was added dropwise to 6-bromo-7-fluoro-3-hydroxy-1-methylquinoline-2(1H)-one (1.2 g, 4.41 mmol), pyridine (697.76 mg, 8.82 mmol) and DMAP (538.85 mg, 4.41 mmol) in dichloromethane (20 mL) at 0° C. under nitrogen. It was stirred at 25° C. for 16 hours. The reaction was quenched with 1N hydrochloric acid and the pH was adjusted to 6. The resultant was extracted three times with dichloromethane (50 mL). The combined organic layers were washed with saturated sodium chloride (100 mL) and dried over anhydrous sodium sulfate. After filtration and evaporation, the residue was purified by column chromatography on silica gel to give the title compound.

1H NMR (400 MHz, CHLOROFORM-d) δ=7.85 (d, J=7.0 Hz, 1H), 7.63 (s, 1H), 7.19 (d, J=10.0 Hz, 1H), 3.76 (s, 3H).

Step F: 6-Bromo-7-fluoro-1-methyl-3-((5-morpholinepyridin-2-yl)amino)quinoline-2(1H)-one Under a protection of nitrogen, added 6-bromo-7-fluoro-1-methyl-2-oxo-1,2-dihydroquinolin-3-yl-trifluoromethanesulfonate (300 mg, 0.742 mmol), 5-morpholine pyridin-2-amino (146.35 mg, 816.57 μmol), Pd$_2$(dba)$_3$ (67.98 mg, 74.23 μmol), Xantphos (85.91 mg, 148.47 μmol) and cesium carbonate (483.74 mg, 1.48 mmol) to tetrahydrofuran (10 mL). It was stirred at 25° C. for 12 hours. The reaction solution was filtered, and the filter cake was washed with ethyl acetate (20 mL) and water (50 mL). The title compound was obtained after drying.

1H NMR (400 MHz, CHLOROFORM-d) δ=8.72 (s, 1H), 8.03 (d, J=2.8 Hz, 1H), 7.87 (s, 1H), 7.78 (d, J=7.3 Hz, 1H), 7.30 (brd, J=3.0 Hz, 1H), 7.12 (d, J=10.5 Hz, 1H), 6.83 (d, J=9.0 Hz, 1H), 3.97-3.87 (m, 4H), 3.80 (s, 3H), 3.22-3.07 (m, 4H).

Step G: 7-Fluoro-1-methyl-3-((5-morpholinepyridin-2-yl)amino)-6-(1H-pyrazol-3-yl)quinoline-2(1H)-one Under a protection of nitrogen, added 6-bromo-7-fluoro-1-methyl-3-((5-morpholinepyridine-2-yl)amino)quinoline-2(1H)-one (50 mg, 115.4 μmol), potassium carbonate (31.9 mg, 230.8 μmol), Pd(dppf)Cl$_2$ (8.44 mg, 11.54 μmol) and 3-(4,4,5,5-tetramethyl-1,3,2-dioxaborolan-2-yl)-1AA-pyrazole (33.59 mg, 173.1 μmol) to 1,4-dioxane (4 mL) and water (1 mL). It was stirred at 100° C. for 8 hours. The reaction solution was filtered, and the filtrate was concentrated.

The residue was separated by preparative HPLC to give the title compound 6.

1H NMR (400 MHz, DMSO-d6) δ=8.80 (s, 1H), 8.71 (br s, 1H), 8.11 (d, J=8.0 Hz, 1H), 7.96 (d, J=2.8 Hz, 1H), 7.79 (d, J=1.8 Hz, 1H), 7.54-7.43 (m, 2H), 7.32 (d, J=9.0 Hz, 1H), 6.68 (dd, J=2.3, 3.5 Hz, 1H), 3.80-3.71 (m, 7H), 3.13-3.04 (m, 4H).

(ESI) m/z: 421 (M+1)

Example 7: 5-Chloro-1-methyl-3-((5-morpholinepyridin-2-yl)amino)-6-(1H-pyrazol-3-yl)quinoline-2(1H)-one

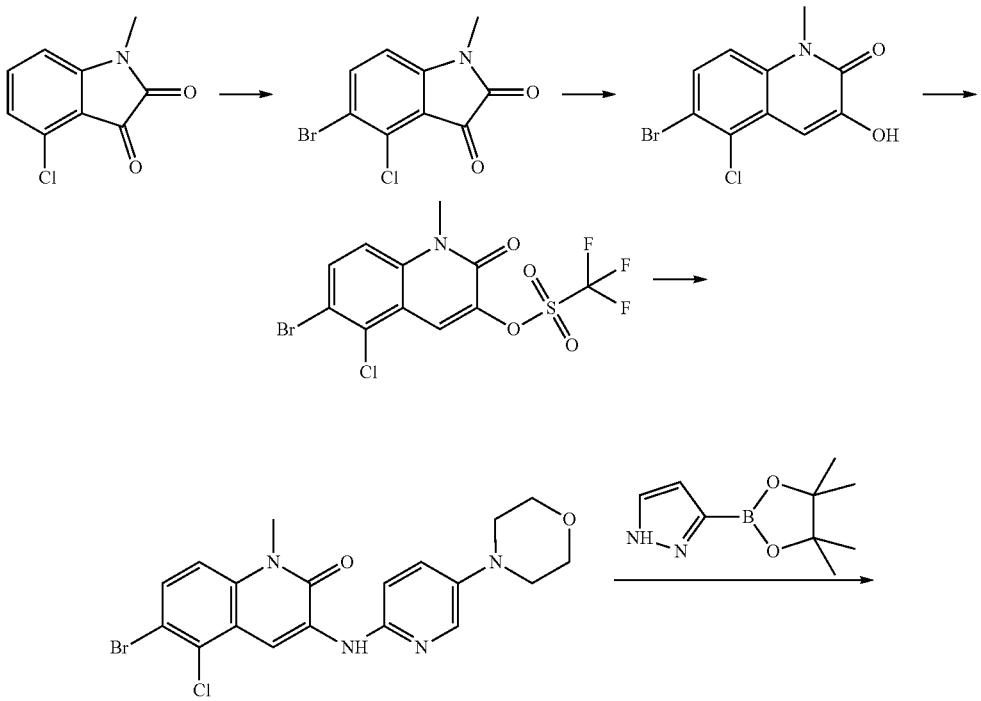

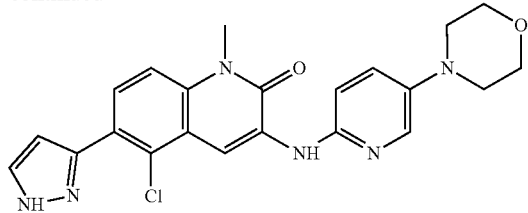

Step A: 5-Bromo-4-chloro-1-methylindolin-2,3-dione

At 25° C., NBS (181.54 mg, 1.02 mmol) was added to 4-chloro-1-methyl indolin-2,3-dione (200 mg, 1.02 mmol) in acetonitrile (7 mL) and water (7 mL). It was stirred for 12 hours, followed by the filtration of the reaction solution, and the filter cake was dried to give the title compound.

1H NMR (400 MHz, DMSO-d6) δ=8.02 (d, J=8.5 Hz, 1H), 7.10 (d, J=8.5 Hz, 1H), 3.14 (s, 3H).

Step B: 6-Bromo-5-chloro-3-hydroxy-1-methylquinoline-2(1H)-one

Under a protection of nitrogen, to a solution of 5-bromo-4-chloro-1-methylindolin-2,3-dione (500 mg, 1.82 mmol) and triethylamine (368.63 mg, 3.64 mmol) in ethanol (15 mL), was added dropwise TMSCHN$_2$ (2 mol/L, 1.09 mL) at 25° C., and it was stirred at 25° C. for 12 hours.

The reaction solution was concentrated to give the crude title compound, which was used directly for the next step reaction.

Step C: 6-Bromo-5-chloro-1-methyl-2-oxo-1,2-dihydroquinolin-3-yl-trifluoromethanesulfonate Trifluoromethanesulfonic anhydride (1.03 g, 3.65 mmol) was added dropwise to 6-bromo-5-chloro-3-hydroxy-1-methylquinoline-2(1H)-one (700 mg, 2.43 mmol), pyridine (576.64 mg, 7.29 mmol) and DMAP (29.69 mg, 0.243 mmol) in dichloromethane (20 mL) at 0° C. under nitrogen. It was stirred at 25° C. for 3 hours. The reaction was quenched with 1N hydrochloric acid and the pH was adjusted to 6. The resultant was extracted three times with dichloromethane (100 mL). The combined the organic phases were washed with saturated sodium chloride (150 mL), and dried over anhydrous sodium sulfate. After filtration and evaporation, the residue was purified by column chromatography on silica gel to give the title compound.

1H NMR (400 MHz, DMSO-d6) δ=8.46 (s, 1H), 8.09 (d, J=9.3 Hz, 1H), 7.63 (d, J=9.3 Hz, 1H), 3.75 (s, 3H).

Step D: 6-Bromo-5-chloro-1-methyl-3-((5-morpholinepyridin-2-yl)amino)quinoline-2(1H)-one Under a protection of nitrogen, to tetrahydrofuran (10 mL) were added 6-bromo-5-chloro-1-methyl-2-oxo-1,2-dihydroquinolin-3-yl-trifluoromethanesulfonate (250 mg, 0.594 mmol), 5-morpholinepyridin-2-amino (127.83 mg, 713.28 μmol), Pd$_2$(dba)$_3$ (54.43 mg, 59.44 μmol), Xantphos (51.59 mg, 89.16 μmol) and cesium carbonate (387.33 mg, 1.19 mmol). It was stirred at 25° C. for 3 hours. The reaction solution was concentrated, and slurried with ethyl acetate (20 mL). It was then filtered and dried to give the title compound.

1H NMR (400 MHz, DMSO-d6) δ=9.27 (s, 1H), 8.93 (s, 1H), 8.01 (d, J=2.5 Hz, 1H), 7.69 (d, J=9.0 Hz, 1H), 7.46 (br d, J=8.8 Hz, 2H), 7.42-7.33 (m, 1H), 3.80-3.72 (m, 7H), 3.10 (br s, 4H).

Step E: 5-Chloro-1-methyl-3-((5-morpholinepyridin-2-yl)amino)-6-(1H-pyrazol-3-yl)quinoline-2(1H)-one Under a protection of nitrogen, to 1,4-dioxane (4 mL) and water (1 ml_), were added 6-bromo-5-chloro-1-methyl-3-((5-morphinpyridin-2-yl) amino)quinoline-2(1H)-one (150 mg, 333.53 μmol), potassium carbonate (138.29 mg, 1.0 mmol), Pd(dppf)Cl$_2$ (24.4 mg, 33.3 μmol) and 3-(4,4,5,5-tetramethyl-1,3,2-dioxaborolan-2-yl)-1H-pyrazole (97.08 mg, 500.3 μmol). It was stirred at 110° C. for 8 hours. The reaction solution was filtered, and the filtered cake was washed with ethyl acetate (30 mL). The filtrate was concentrated and the residue was separated by high-liquid chromatography preparation to give the title compound 7.

1H NMR (400 MHz, DMSO-d6) δ=9.35 (s, 1H), 8.88 (s, 1H), 8.00 (d, J=2.8 Hz, 1H), 7.80 (d, J=2.0 Hz, 1H), 7.74 (d, J=8.8 Hz, 1H), 7.58 (d, J=8.8 Hz, 1H), 7.48 (dd, J=3.0, 9.0 Hz, 1H), 7.37 (d, J=9.0 Hz, 1H), 6.77 (d, J=2.3 Hz, 1H), 3.82 (s, 3H), 3.78-3.73 (m, 4H), 3.14-3.08 (m, 1H), 3.39-2.90 (m, 4H).

(ESI) m/z: 437 (M+1).

Example 8: 5,7-Difluoro-1-methyl-3-((5-morpholinopyridin-2-yl)amino)-6-(1H-pyrazol-3-yl)quinoline-2(1H)-one

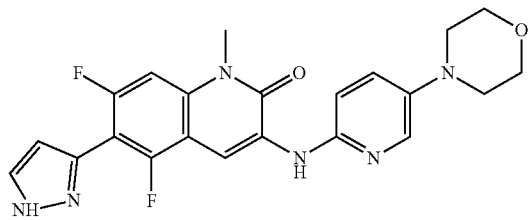 [SMILES: Cn1c(=O)c(Nc2ccc(N3CCOCC3)cn2)cc2c(F)c(-c3cc[nH]n3)c(F)cc21]

The preparation method of Example 8 could refer to the preparation method of Example 6, prepared by using 4-bromo-3,5-difluoroaniline.

1H NMR (400 MHz, DMSO-d6) δ=8.98 (s, 1H), 8.80 (s, 1H), 7.99 (d, J=3.0 Hz, 1H), 7.84 (br s, 1H), 7.47-7.39 (m, 2H), 7.37-7.32 (m, 1H), 7.24-6.95 (m, 1H), 6.62 (s, 1H), 3.77 (s, 3H), 3.75 (brd, J=5.5 Hz, 4H), 3.12-3.06 (m, 4H).

Example 9: 5-Fluoro-1-methyl-3-((5-(4-(oxetan-3-yl)piperazin-1-yl)pyridin-2-yl)amino)-6-(1H-pyrazol-3-yl)quinoline-2(1H)-one

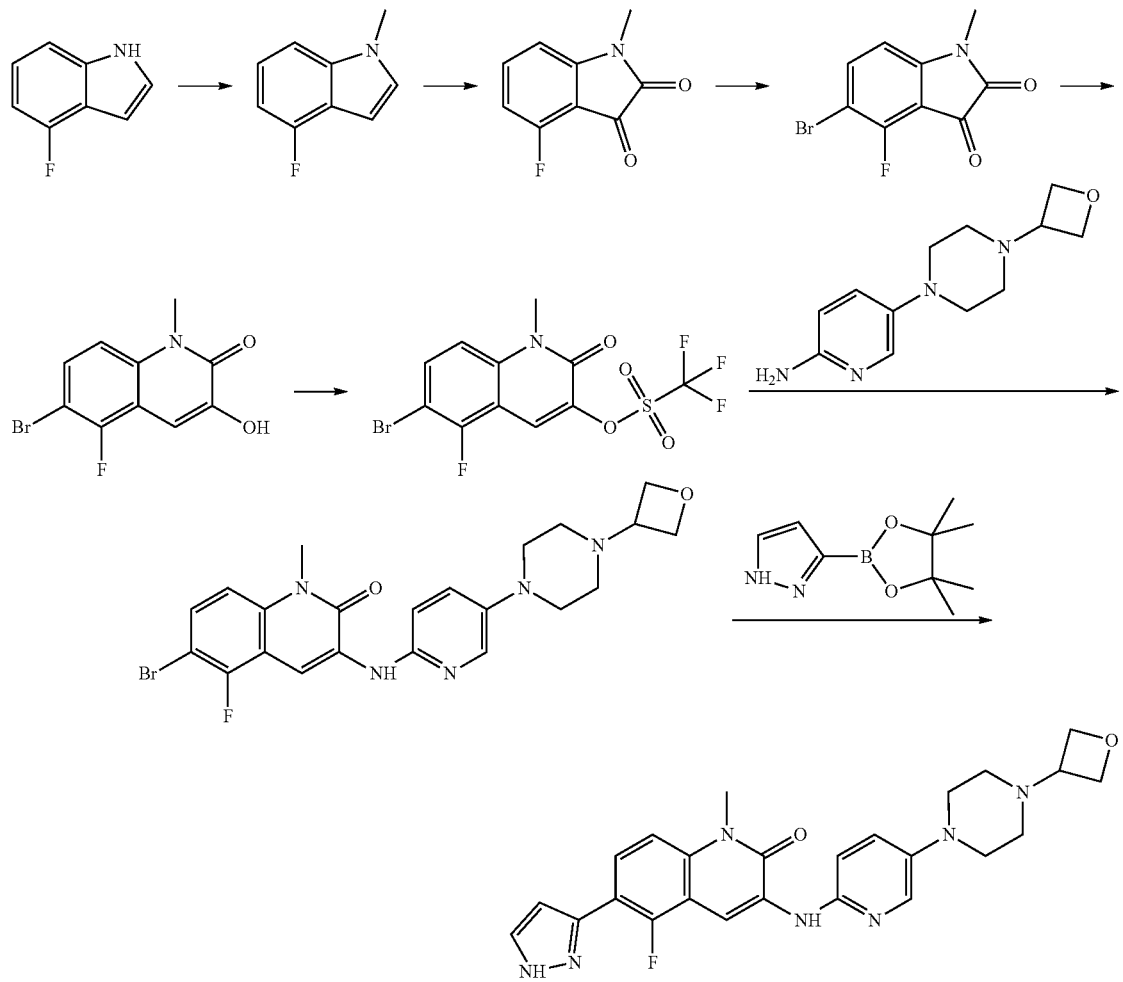

Step A: 4-Fluoro-1-methyl-1H-indole

Under a protection of nitrogen, to a solution of 4-fluoro-1H-indole (59.00 g, 436.59 mmol) in tetrahydrofuran (600 mL), was added sodium hydride (19.24 g, 480.99 mmol, 60% purity) at 0° C. and after it was stirred for 30 minutes, methyl trifluoromethanesulfonate (93.14 g, 567.57 mmol, 62.09 mL) was added. It was continually stirred at 15° C. for 2 hours. The reaction solution was quenched with saturated ammonium chloride (1 L), and extracted three times with ethyl acetate (500 mL). The organic phase was washed with saturated brine (1 L) and dried over anhydrous sodium sulfate. After filtration and concentration, the residue was subjected to column chromatography to give the title compound.

1H NMR (400 MHz, CHLOROFORM-d) δ=7.22-7.08 (m, 2H), 7.03 (br d, J=3.0 Hz, 1H), 6.86-6.73 (m, 1H), 6.58 (d, J=2.5 Hz, 1H), 3.81 (s, 3H).

Step B: 4-Fluoro-1-methylindolin-2,3-dione

Under a protection of nitrogen, to a solution of 4-fluoro-1-methyl-1H-indole (55.00 g, 368.72 mmol) in dimethyl sulfoxide (400 mL), was added NBS (65.63 g, 368.72 mmol), and it was stirred at 20° C. for 1 hour. After adding another batch of NBS (65.63 g, 368.72 mmol), the reaction solution was warmed to 60° C. and continually stirred for 10 hours. The reaction solution was poured into water (6 L) and filtered. The filter cake was dissolved in acetone (2 L), and the insoluble material was filtered, then washing the filter cake with acetone (500 mL). After the filtrate was concentrated, the residue was subjected to column chromatography to give the title compound.

1H NMR (400 MHz, DMSO-d6) δ=7.72 (dt, J=5.8, 8.2 Hz, 1H), 6.99 (d, J=7.8 Hz, 1H), 6.93 (t, J=8.8 Hz, 1H), 3.15 (s, 3H).

Step C: 5-Bromo-4-fluoro-1-methylindolin-2,3-dione

To 4-fluoro-1-methylindolin-2,3-dione (31.0 g, 173.04 mmol) in acetonitrile (300 mL) and water (600 mL) was added NBS (40.04 g, 224.95 mmol)) under nitrogen. It was stirred at 15° C. for 16 hours. The reaction solution was filtered, and the filter cake was washed with water (300 mL), and the title compound was obtained after drying.

1H NMR (400 MHz, DMSO-d6) δ=7.99 (dd, J=7.3, 8.3 Hz, 1H), 6.98 (d, J=8.5 Hz, 1H), 3.14 (s, 3H).

Step D: 6-Bromo-5-fluoro-3-hydroxy-1-methylquinoline-2(1H)-one

Under a protection of nitrogen, to a solution of 5-bromo-4-fluoro-1-methylindolin-2,3-dione (32.00 g, 124.01 mmol) and triethylamine (25.1 g, 248.02 mmol) in ethanol (300 mL) was added dropwise TMSCHN$_2$ (2 mol/L, 65.11 mL) at 0° C., and it was stirred at 0-15° C. for 1 hour.

The reaction solution was concentrated and the residue was slurried with ethyl acetate (500 mL). After filtration, the filter cake was dried to give the title compound.

1H NMR (400 MHz, DMSO-d6) δ=10.17 (br s, 1H), 7.65 (dd, J=7.5, 9.0 Hz, 1H), 7.30 (d, J=9.0 Hz, 1H), 7.11 (s, 1H), 3.69 (s, 3H).

Step E: 6-Bromo-5-fluoro-1-methyl-2-oxo-1,2-dihydroquinolin-3-yl trifluoromethanesulfonate Trifluoromethanesulfonic anhydride (13.48 g, 47.78 mmol) was added dropwise into 6-bromo-5-fluoro-3-hydroxy-1-methylquinoline-2(1H)-one (10.0 g, 36.76 m mol), pyridine (8.72 g, 110.27 mmol) and DMAP (449.04 mg, 3.68 mmol) in dichloromethane (200 mL) at 0° C. under nitrogen. It was stirred at 15° C. for 1 hour. The reaction solution was quenched with water (300 mL) and the pH was adjusted to 5 with 1N hydrochloric acid. The organic phase was washed with saturated sodium chloride (250 mL), and dried over anhydrous sodium sulfate. Filtration and evaporation gave the title compound.

1H NMR (400 MHz, CHLOROFORM-d) δ=7.93 (s, 1H), 7.82-7.75 (m, 1H), 7.11 (d, J=9.0 Hz, 1H), 3.79 (s, 3H).

Step F: 6-Bromo-5-fluoro-1-methyl-3-((5-(4-(oxetan-3-yl)piperazin-1-yl)pyridin-2-yl)amino)quinoline-2(1H)-one Under a protection of nitrogen, to tetrahydrofuran (200 mL) were added 6-bromo-5-fluoro-1-methyl-2-oxo-1,2-dihydroquinolin-3-yl-trifluoromethanesulfonate (10.00 g, 24.74 mmol), 5-(4-(oxetan-3-yl)piperazin-1-yl)pyridine-2-amino (6.38 g, 27.21 mmol), Pd$_2$(dba)$_3$ (2.27 g, 2.47 mmol), Xantphos (2.15 g, 3.71 mmol) and cesium carbonate (16.12 g, 49.48 mmol). It was stirred at 50° C. for 16 hours. The reaction solution was poured into water (200 mL), filtration, and the filter cake was slurried with ethyl acetate (100 mL). After filtration, the solid was dried to give the title compound.

1H NMR (400 MHz, DMSO-d6) δ=9.07-8.76 (m, 2H), 8.00 (brd, J=2.3 Hz, 1H), 7.68-7.40 (m, 2H), 7.32 (br dd, J=9.0, 13.3 Hz, 2H), 4.71-4.39 (m, 4H), 3.75 (s, 3H), 3.52-3.39 (m, 1H), 3.14 (br s, 4H), 2.42 (br s, 4H).

Step G: 5-Fluoro-1-methyl-3-((5-(4-(oxetan-3-yl)piperazin-1-yl)pyridin-2-yl)amino)-6-(1H-pyrazol-3-yl)quinoline-2(1H)-one Under a protection of nitrogen, to 1,4-dioxane (160 mL) and water (40 mL), were added 6-bromo-5-fluoro-1-methyl-3-((5-(4-(oxygenbutyl-3-yl) piperazin-1-yl)pyridin-2-yl)amino)quinolin-2(1H)-one (9.00 g, 18.43 mmol), potassium carbonate (6.37 g, 46.07 mmol), Pd(dppf)Cl$_2$ (1.08 g, 1.47 mmol) and 3-(4,4,5,5-tetramethyl-1,3,2-dioxaborolan-2-yl)-1 AA-pyrazole (5.36 g, 27.64 mmol). It was stirred at 110° C. for 16 hours. After the reaction solution was cooled down, a solid was precipitated and it was filtered. The filter cake was washed with water (200 mL) ethyl acetate (100 mL). The filter cake was dried to give the title compound 9.

1H NMR (400 MHz, DMSO-d6) δ=13.08 (br s, 1H), 9.04 (br s, 1H), 8.78 (br s, 1H), 8.16-7.70 (m, 3H), 7.57-7.23 (m, 3H), 6.73 (brs, 1H), 4.74-4.37 (m, 4H), 3.79 (br s, 3H), 3.56 (br s, 2H), 3.14 (br s, 3H), 2.42 (br s, 4H).

Example 10: 5-Fluoro-3-[[5-[4-hydroxy-4-(trifluoromethyl)piperidin-1-yl]pyridin-2-yl]amino]-1-methyl-6-(1H-pyrazol-3-yl)quinoline-2(1H)-one

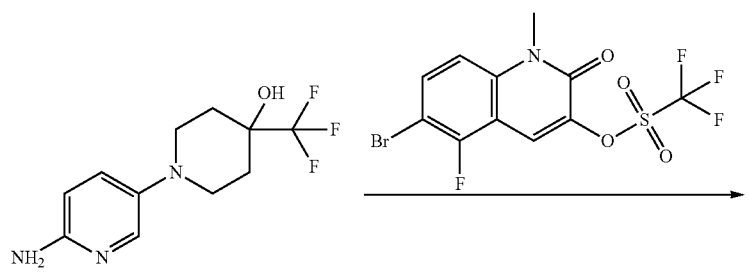

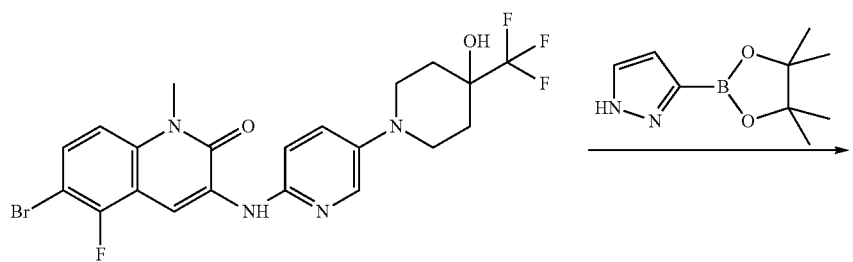

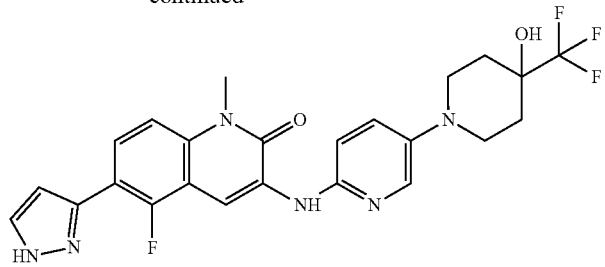

Step A: 6-Bromo-5-fluoro-3-[[5-[4-hydroxy-4-(trifluoromethyl)piperidin-1-yl]pyridin-2-yl]amino]-1-methyl-quinoline-2(1H)-one Under a protection of nitrogen, (6-bromo-5-fluoro-1-methyl-2-oxo-3-quinolyl)trifluoromethanesulfonate (220 mg, 544.38 µmol), 1-(6-amino-3)-nitrophenyl)-4-(trifluoromethyl)piperidin-4-ol (213.32 mg, 544.38 µmol), Pd$_2$(dba)$_3$ (49.85 mg, 54.44 µmol), Xantphos (47.25 mg, 81.66 µmol) and cesium carbonate (354.74 mg, 1.09 mmol) in tetrahydrofuran (10 mL), the mixture was reacted at 25° C. for 2 hours, and quenched by the addition of water (20 mL). The aqueous layer was extracted with dichloromethane (20 mL×2). The combined organic layers were washed with saturated brine (20 mL×2), dried over sodium sulfate, filtered and evaporated. The residue was purified by column chromatography to give the title compound.
LCMS (ESI) m/z: 515 (M+1).

Step B: 5-Fluoro-3-[[5-[4-hydroxy-4-(trifluoromethyl)piperidin-1-yl]pyridin-2-yl]amino]-1-methyl-6-(1H-pyrazol-3-yl)quinoline-2(1H)-one Under a protection of nitrogen, a mixture of Example 10A (220 mg, 426.94 µmol), 5-(4,4,5,5-tetramethyl 1,3,2-dioxaborolan-2-yl)-1H-pyridine (124.27 mg, 640.41 µmol), Pd(dppf)Cl$_2$ (31.24 mg, 42.69 µmol), potassium carbonate (177.02 mg, 1.28 mmol) in dioxane (8 mL) and water (2 mL) was reacted at 120° C. for 10 hours. After cooling to room temperature, it was diluted with water (20 mL), and the aqueous layer was extracted with dichloromethane (20 mL×3). After the combined organic layers were washed with brine (20 mL×3), dried over sodium sulfate, filtered and evaporated. The residue was purified by column chromatography to give the title compound 10.
LCMS (ESI) m/z: 503 (M+1)$^+$
1H NMR (400 MHz, DMSO-d6) δ=13.38-13.04 (m, 1H), 9.04 (s, 1H), 8.86-8.72 (m, 1H), 8.06 (d, J=2.8 Hz, 1H), 7.96 (brt, J=8.3 Hz, 1H), 7.87 (br s, 1H), 7.46 (dd, J=2.8, 9.0 Hz, 1H), 7.40 (br d, J=9.0 Hz, 1H), 7.32 (d, J=9.0 Hz, 1H), 6.73 (br s, 1H), 6.00 (s, 1H), 3.79 (s, 3H), 3.63-3.50 (m, 4H), 2.93 (br t, J=11.2 Hz, 2H), 1.86-1.77 (m, 2H).

Example 11: 5-Fluoro-1-methyl-3-((5-morpholinopyridin-2-yl)amino)-6-(1H-pyrazol-3-yl)quinoline-2(1H)-one

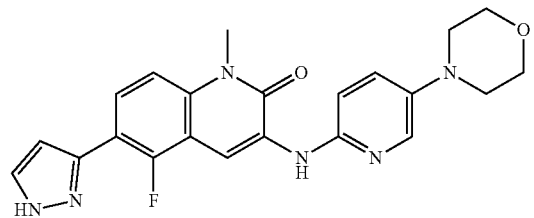 [SMILES: Cn1c(=O)c(Nc2ccc(N3CCOCC3)cn2)cc2c(F)c(-c3cc[nH]n3)ccc21]

The preparation method of Example 11 could be obtained by referring to the preparation method of Example 10.
1H NMR (400 MHz, DMSO-d6) δ=9.01 (s, 1H), 8.85 (br s, 1H), 8.01 (d, J=3.0 Hz, 1H), 7.93 (t, J=8.4 Hz, 1H), 7.81 (d, J=2.0 Hz, 1H), 7.47 (br d, J=9.0 Hz, 1H), 7.42 (d, J=8.8 Hz, 1H), 7.35 (d, J=9.0 Hz, 1H), 6.73 (dd, J=2.3, 3.5 Hz, 1H), 3.79 (s, 3H), 3.77-3.74 (m, 4H), 3.13-3.06 (m, 4H).
MS-ESI (m/z): 421 (M+H)

Example 12: 5-Fluoro-1-methyl-3-[[5-(2-oxazole-7-azaspiro[3.5]nonane-7-yl)pyridin-2-yl]amino]-6-(1H-pyrazol-3)quinoline-2(1H)-one

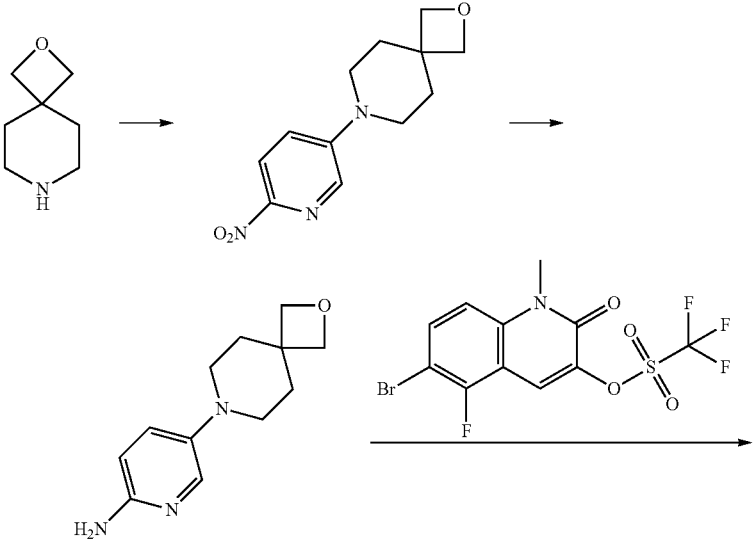

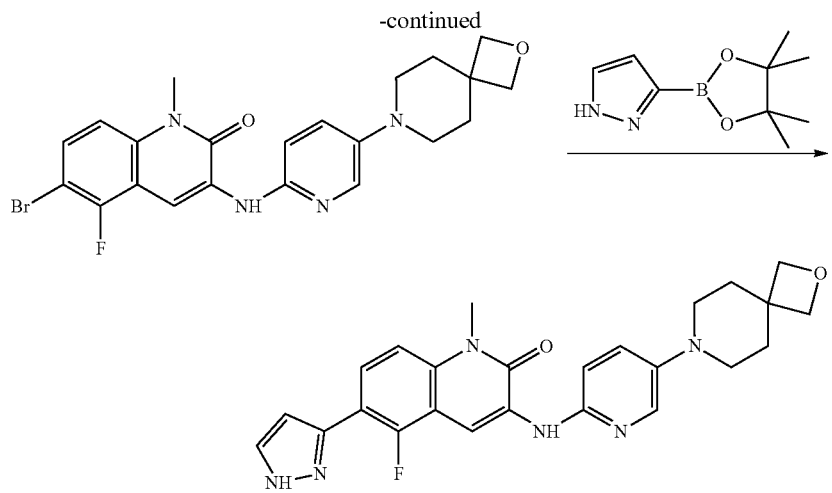

Step A: 7-(6-Nitro-3-pyridine)-2-oxazole-7-azaspiro[3.5]nonane

To a solution of 2-oxa-7-azaspiro[3.5]nonane oxalate (1.00, 4.60 mmol) and potassium carbonate (1.91 g, 13.80 mmol) in dimethyl sulfoxide (15 mL) was added 5-bromo-2-nitro-pyridine (1.12 g, 5.52 mmol), protected by nitrogen, and after it was stirred at 100° C. for 14 hours, cooled to room temperature, and quenched by the addition of water (50 mL). The aqueous layer was extracted with dichloromethane (50 mL×3). The combined organic layers were dried over sodium sulfate, filtered and evaporated. The residue was purified by column chromatography to give the title compound.

LCMS (ESI) m/z: 250 (M+1).

1H NMR (400 MHz, CHLOROFORM-d) δ=8.15-8.11 (m, 2H), 7.21 (dd, J=3.1, 9.2 Hz, 1H), 4.50 (s, 4H), 3.44-3.38 (m, 4H), 2.06-2.00 (m, 4H).

Step B: 5-(2-Oxazole-7-azaspiro[3.5]nonane-7-yl)pyridin-2-amine

A mixture of Example 12A (1 g, 4.01 mmol) and Raney Nickel (34.35 mg, 401.00 μmol) in methanol (110 mL) was reacted under hydrogen (15 psi) at 30° C. for 15 hours. Then the mixture was filtered through Celite, the filter cake was washed with methanol (200 mL), and the filtrate was spin-dried to give the title compound.

LCMS (ESI) m/z: 219.9 (M+1).

1H NMR (400 MHz, DMSO-d6) δ=7.59 (d, J=2.8 Hz, 1H), 7.14 (dd, J=3.0, 8.8 Hz, 1H), 6.37 (d, J=8.8 Hz, 1H), 5.38 (s, 2H), 4.31 (s, 4H), 2.86-2.74 (m, 4H), 1.96-1.80 (m, 4H).

Step C: 6-Bromo-5-fluoro-1-methyl-3-[[5-(2-oxazole-7-azaspiro[3.5]nonane-7-yl)-2-pyridyl]amino]quinoline-2(1H)-one Under a protection of nitrogen, to a mixture of Example 12B (97.67 mg, 445.40 μmol), (6-bromo-5-fluoro-1-methyl-2-oxa-3-quinoline) trifluoromethanesulfonate (150.00 mg, 371.17 μmol), cesium carbonate (241.87 mg, 742.34 μmol) in tetrahydrofuran (5 mL) were added Xantphos (42.95 mg, 74.23 μmol), Pd$_2$(dba)$_3$ (33.99 mg, 37.12 μmol). After stirring at 80° C. for 4 hours, the reaction solution was filtered through a filter paper, and the filter cake was washed three times with a filtrate, and finally, the filter cake was dried to give the title compound.

LCMS (ESI) m/z: 473/475 (M/M+2).

1H NMR (400 MHz, DMSO-d6) δ=8.91 (s, 1H), 8.87 (s, 1H), 7.99 (d, J=2.5 Hz, 1H), 7.59 (t, J=8.3 Hz, 1H), 7.43 (dd, J=3.1, 9.2 Hz, 1H), 7.35-7.29 (m, 2H), 4.34 (s, 4H), 3.75 (s, 3H), 3.07-3.01 (m, 4H), 1.94-1.86 (m, 4H).

Step D: 5-Fluoro-1-methyl-3-[[5-(2-oxazole-7-azaspiro[3.5]nonane-7-yl)pyridin-2-yl]amino]-6-(1H-pyrazol-3)quinoline-2(1H)-one Under a protection of nitrogen, Example 12C, 3-(4,4,5,5-tetramethyl-1,3,2-dioxaborolan-2-yl)-1H-pyrazole (131.18 mg, 676.04 μmol), potassium carbonate (140.15 mg, 1.01 mmol) were dissolved in a solution of dioxane (4 mL) and water (1 ml_), followed by the addition of Pd(dppf)Cl$_2$ (24.73 mg, 33.80 μmol) and it was stirred at 110° C. for 12 hours. Then it was cooled to room temperature, and quenched by the addition of water (50 mL). The aqueous layer was extracted with ethyl acetate (50 mL×4). The combined organic layers were washed with saturated brine (100 mL), dried over anhydrous sodium sulfate, filtered and evaporated. The residue was added into dimethyl sulfoxide (10 mL) and trifluoroacetic acid (0.15 mL), then poured into the stirring water (30 mL), filtration, and the filter cake was washed with ethyl acetate (20 mL), and finally recrystallized with dichloromethane (20 mL) and methanol (20 mL) at 50° C. to give the title compound 12.

MS-ESI (m/z): 461 (M+H)$^+$

1H NMR (400 MHz, DMSO-d6) δ=9.43 (br s, 1H), 9.08-8.98 (m, 1H), 8.84-8.70 (m, 1H), 8.26-8.11 (m, 1H), 8.05-7.92 (m, 2H), 7.58-7.50 (m, 1H), 7.41 (d, J=8.8 Hz, 1H), 6.84 (br s, 1H), 4.40 (s, 3H), 3.76 (s, 3H), 3.58-3.44 (m, 5H), 2.26 (br s, 3H), 1.96-1.83 (m, 1H).

Example 13: (R) 5-fluoro-1-methyl-3-((5-(3-methyl-morpholine)pyridin-2-yl)amino)-6-(1H-pyrazol-3-yl)quinoline-2(1H)-one

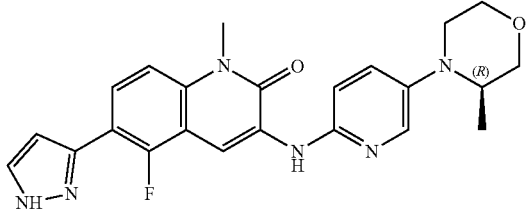

The preparation method of Example 13 could be obtained by referring to the preparation method of Example 12, and preparing with (3R)-3-methylmorpholine.

MS-ESI (m/z): 435 (M+H)+.

1H NMR (400 MHz, METHANOL-d4) δ=8.20 (dd, J=2.6, 9.9 Hz, 1H), 7.97 (d, J=2.8 Hz, 1H), 7.88 (t, J=8.4 Hz, 1H), 7.82 (d, J=2.3 Hz, 1H), 7.48 (d, J=9.8 Hz, 1H), 7.42 (d, J=9.0 Hz, 1H), 7.32 (s, 1H), 6.78 (t, J=2.6 Hz, 1H), 4.22 (br d, J=7.5 Hz, 1H), 4.10 (dd, J=3.6, 11.4 Hz, 1H), 3.92-3.75 (m, 1H), 3.94-3.75 (m, 5H), 3.75-3.65 (m, 1H), 3.62-3.51 (m, 1H), 1.43 (d, J=6.8 Hz, 3H).

Example 14: (S) 5-fluoro-1-methyl-3-((5-(3-methyl-morpholine)pyridin-2-yl)amino)-6-(1H-pyrazol-3-yl)quinoline-2(1H)-one

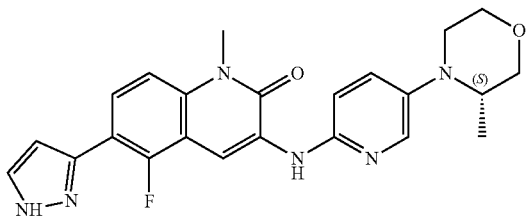

The preparation method of Example 14 could be obtained by referring to the preparation method of Example 12, and preparing with (3S)-3-methylmorpholine.

1H NMR (400 MHz, METHANOL-d4) δ=8.20 (dd, J=2.6, 9.9 Hz, 1H), 7.97 (d, J=2.8 Hz, 1H), 7.88 (t, J=8.4 Hz, 1H), 7.82 (d, J=2.3 Hz, 1H), 7.48 (d, J=9.8 Hz, 1H), 7.42 (d, J=9.0 Hz, 1H), 7.32 (s, 1H), 6.78 (t, J=2.6 Hz, 1H), 4.22 (brd, J=7.5 Hz, 1H), 4.10 (dd, J=3.6, 11.4 Hz, 1H), 3.92-3.75 (m, 1H), 3.94-3.75 (m, 5H), 3.75-3.65 (m, 1H), 3.62-3.51 (m, 1H), 1.43 (d, J=6.8 Hz, 3H).

MS-ESI (m/z): 435 (M+H)+

Example 15: 5-Fluoro-1-methyl-6-(1H-pyrazol-3-yl)-3-(pyridin-2-amine)-quinoline-2(1H)-one

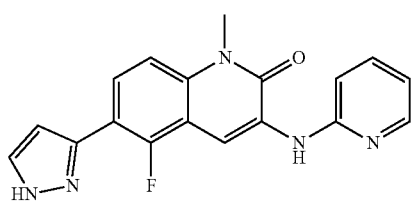 [SMILES: Cn1c(=O)c(Nc2ccccn2)cc2c(F)c(-c3cc[nH]n3)ccc21]

The preparation method of Example 15 could be prepared by referring to the preparation method of Example 12.

1H NMR (400 MHz, DMSO-d6) δ=13.09 (br s, 1H), 9.18 (s, 1H), 8.98 (br s, 1H), 8.38-8.31 (m, 1H), 8.01 (br s, 1H), 7.87 (brs, 1H), 7.71-7.62 (m, 1H), 7.47-7.37 (m, 2H), 6.95-6.88 (m, 1H), 6.75 (br d, J=2.0 Hz, 1H), 3.80 (s, 3H).

MS-ESI (m/z): 336.0 (M+H)+.

Example 16: 3-((5-Aminopyridin-2-yl)amino)-5-fluoro-1-methyl-6-(1H-pyrazol-3-yl)quinoline-2(1H)-one

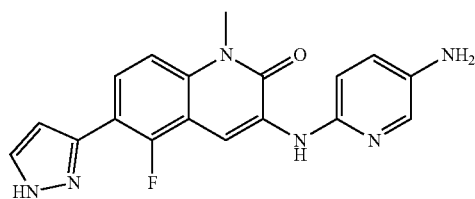 [SMILES: Cn1c(=O)c(Nc2ccc(N)cn2)cc2c(F)c(-c3cc[nH]n3)ccc21]

The preparation method of Example 16 could be prepared by referring to the preparation method of Example 12.

1H NMR (400 MHz, DMSO-d6) δ=8.98 (d, J=7.5 Hz, 2H), 8.09 (s, 1H), 7.96 (t, J=8.5 Hz, 1H), 7.83 (s, 1H), 7.44 (d, J=9.0 Hz, 1H), 7.42-7.37 (m, 2H), 6.74 (br s, 1H), 3.80 (s, 3H).

MS-ESI (m/z): 350.9 (M+H)+.

Example 17: 1-(6-((5-Fluoro-1-methyl-2-oxo-6-(1H-pyrazol-3-yl)-1,2-dihydroquinolin-3-yl)amine)pyridine-3-yl)-3-pipecoline-3-carboxylic acid

The preparation method of Example 17 could be prepared by referring to the preparation method of Example 12.

1H NMR (400 MHz, DMSO-d6) δ=8.99 (s, 1H), 8.86 (br s, 1H), 7.99 (br s, 1H), 7.97-7.92 (m, 1H), 7.83 (s, 1H), 7.43 (br d, J=8.8 Hz, 2H), 7.38-7.31 (m, 1H), 6.74 (br s, 1H), 3.80 (s, 3H), 3.71-3.70 (m, 1H), 3.31 (brd, J=11.8 Hz, 1H), 2.65 (brd, J=16.1 Hz, 1H), 2.05 (brd, J=13.1 Hz, 1H), 1.76-1.63 (m, 2H), 1.33-1.22 (m, 1H), 1.17 (s, 3H).

MS-ESI (m/z): 477.2 (M+H)+.

Example 18: (3R)-1-[6-[[5-fluoro-1-methyl-2-oxa-6-(1H-pyrazol-3-yl)-1,2-dihydroquinolin-3-yl)amino]pyridin-3-yl]piperidine-3-carboxylic acid

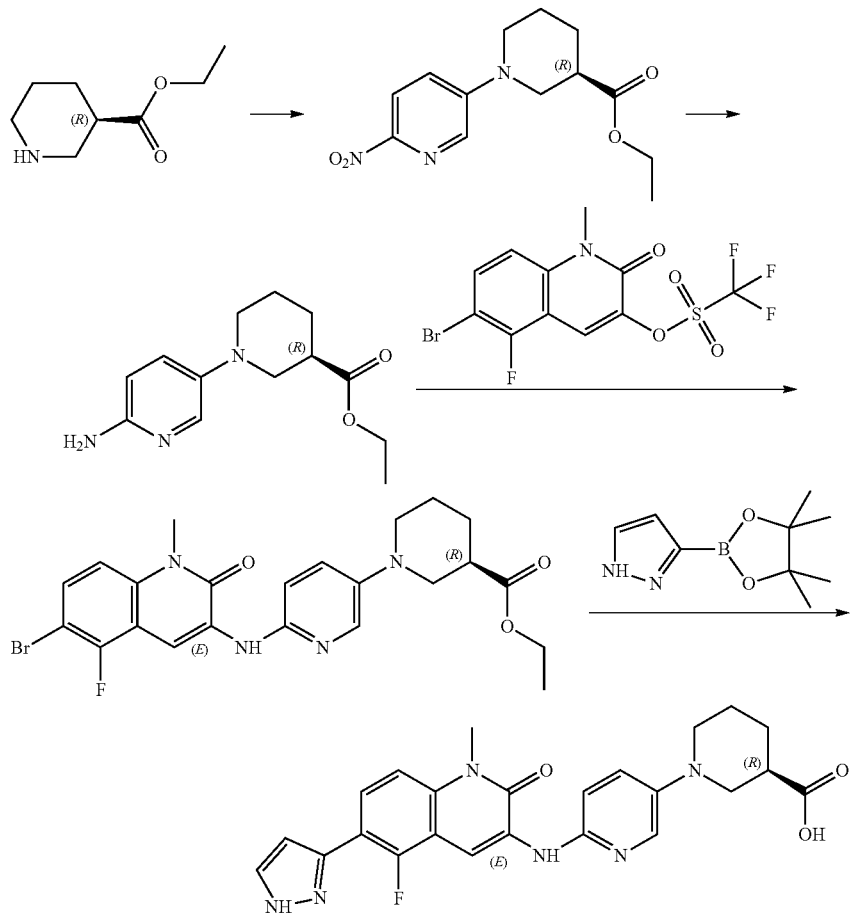

Step A: Ethyl (3R)-1-(6-nitropyridin-3-yl)piperidine-3-carboxylate

To a solution of Ethyl (3R)-piperidine-3-carboxylate (1.00 g, 6.36 mmol) and potassium carbonate (2.64 g, 19.08 mmol) in dimethyl sulfoxide (10 mL) was added 5-bromo-2-nitro-pyridine (1.32 g, 6.49 mmol), and after it was stirred at 85° C. for 14 hours, cooled to room temperature, and quenched by the addition of water (50 mL). The aqueous layer was extracted with ethyl acetate (50 mL×5). The combined organic layers were washed with saturated brine (100 mL×2), dried over anhydrous sodium sulfate, filtered and evaporated. The residue was purified by column chromatography to give the title compound.

LCMS (ESI) m/z: 280.1 (M+1).

$^1$H NMR (400 MHz, CHLOROFORM-d) δ=8.17-8.13 (m, 2H), 7.24 (dd, J=3.0, 9.0 Hz, 1H), 4.18 (q, J=7.3 Hz, 2H), 3.88 (dd, J=3.8, 13.3 Hz, 1H), 3.74-3.66 (m, 1H), 3.48 (dd, J=9.0, 13.3 Hz, 1H), 3.23 (ddd, J=3.3, 9.8, 13.1 Hz, 1H), 2.72-2.61 (m, 1H), 2.14-2.05 (m, 1H), 1.94-1.83 (m, 2H), 1.76-1.67 (m, 1H), 1.29-1.25 (m, 3H).

Step B: Ethyl (3R)-1-(6-aminopyridin-3-yl)piperidine-3-carboxylate

A mixture of Example 18A (1 g, 3.58 mmol) and Raney nickel (30.67 mg) in methanol (50 mL) was reacted under hydrogen (15 psi) at 23° C. for 15 hours. Then the mixture was filtered through Celite, the filter cake was washed with methanol (200 mL), and the filtrate was spin-dried to give the title compound.

LCMS (ESI) m/z: 250.1 (M+1).

$^1$H NMR (400 MHz, CHLOROFORM-d) δ=7.79 (br s, 1H), 7.20 (dd, J=2.4, 8.7 Hz, 1H), 6.48 (d, 0.7=8.8 Hz, 1H), 4.19-4.14 (m, 2H), 3.72 (s, 1H), 3.44 (br d, J=9.5 Hz, 1H), 3.22 (br d, 0.7=11.5 Hz, 1H), 2.97-2.87 (m, 1H), 2.76-2.67 (m, 2H), 2.05-1.96 (m, 1H), 1.69-1.58 (m, 2H), 1.28 (t, J=7.2 Hz, 3H).

Step C: Ethyl (3R)-1-[6-bromo-5-fluoro-1-methyl-2-oxa-1,2-dihydroquinolin-3-yl)]amino]pyridin-3-yl]piperidine-3-carboxylate Under a protection of nitrogen, to a mixture of Example 18B (200 mg, 802.21 µmol), (6-bromo-5-fluoro-1-methyl-2-oxa-3-quinoline) trifluoromethanesulfonate (356.62 mg, 882.43 µmol), cesium carbonate (392.07 mg, 1.2 mmol) in tetrahydrofuran (15 mL) were added Xantphos (69.63 mg, 120.33 µmol), Pd$_2$(dba)$_3$ (73.46 mg, 80.22 µmol), and it was stirred at 15° C. for 16 hours. The resultant was quenched by the addition of water (50 mL), and the aqueous layer was extracted with ethyl acetate (50 mL×3). The combined organic layers were washed with saturated brine (100 mL), and evaporated. The residue was subjected to column chromatography to give the title compound.

LCMS (ESI) m/z: 503/505.0 (M/M+2).

$^1$H NMR (400 MHz, DMSO-d$_6$) δ=8.90 (s, 1H), 8.86 (s, 1H), 7.98 (d, 0.7=2.8 Hz, 1H), 7.57 (dd, 0.7=7.7, 8.9 Hz,

1H), 7.45-7.37 (m, 1H), 7.35-7.26 (m, 2H), 4.09 (q, 0.7=7.2 Hz, 2H), 3.74 (s, 3H), 3.61-3.52 (m, 1H), 2.97 (dd, 0.7=9.5, 11.8 Hz, 1H), 2.86-2.76 (m, 1H), 2.74-2.61 (m, 1H), 1.95-1.68 (m, 3H), 1.67-1.54 (m, 2H), 1.24-1.14 (m, 3H).

Step D: (3R)-1-[6-[[5-fluoro-1-methyl-2-oxa-6-(1H-pyrazol-3-yl)-1,2-dihydroquinolin-3-yl)amino]pyridin-3-yl]piperidine-3-carboxylic acid Under a protection of nitrogen, dissolved Example 1C (350 mg, 695.33 μmol), 3-(4,4,5,5-tetramethyl-1,3,2-dioxaborolan-2-yl)-1H-pyrozole (148.41 mg, 764.86 μmol), cesium carbonate (453.10 mg, 1.39 mmol) in a solution of dioxane (8 mL) and water (2 mL), followed by the addition of Pd(dppf)Cl$_2$ (50.88 mg, 69.53 μmol), and it was stirred at 110° C. for 12 hours. The reaction solution was cooled to room temperature, and spun to dryness. The residue was purified by column chromatography, and finally by chiral resolution, to give the title compound 18 with an ee value of 98.06%.

$^1$H NMR (400 MHz, DMSO-d$_6$) δ=9.04 (s, 1H), 8.78 (s, 1H), 8.00 (d, 0.7=2.8 Hz, 1H), 7.92 (br t, 0.7=8.2 Hz, 1H), 7.81 (br s, 1H), 7.45-7.38 (m, 2H), 7.36-7.29 (m, 1H), 6.73 (dd, 0.7=2.1, 3.6 Hz, 1H), 3.79 (s, 3H), 3.57 (br d, 0.7=8.8 Hz, 1H), 3.17 (d, 0.7=4.3 Hz, 1H), 2.99-2.87 (m, 1H), 2.79 (br t, 0.7=9.4 Hz, 1H), 2.56 (brd, J=9.5 Hz, 1H), 1.90 (brd, 0.7=8.5 Hz, 1H), 1.79-1.71 (m, 1H), 1.66-1.51 (m, 2H).

MS-ESI (m/z): 463.1 (M+H)$^+$.

Example 19: (3S)-1-[6-[[5-fluoro-1-methyl-2-oxa-6-(1H-pyrazol-3-yl)-1,2-dihydroquinolin-3-yl)amine] pyridin-3-yl]piperidine-3-carboxylic acid

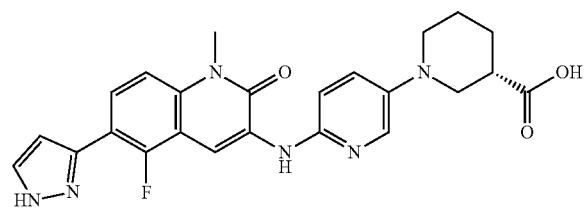 [SMILES: Cn1c(=O)c(Nc2ccc(N3CCC[C@H](C(=O)O)C3)cn2)cc2c(F)c(-c3cc[nH]n3)ccc21]

Prepared by referring to the method of Example 18, with the starting material of (3S)-piperidine-3-carboxylate.

1H NMR (400 MHz, DMSO-d6) δ=9.05 (s, 1H), 8.78 (s, 1H), 8.01 (d, J=2.8 Hz, 1H), 7.93 (brt, J=8.4 Hz, 1H), 7.82 (brs, 1H), 7.46-7.38 (m, 2H), 7.32 (d, J=9.0 Hz, 1H), 7.35-7.27 (m, 1H), 6.74 (dd, J=2.1, 3.8 Hz, 1H), 4.35 (brs, 1H), 3.80 (s, 3H), 3.77 (brd, J=6.1 Hz, 1H), 3.57 (brd, J=11.2 Hz, 1H), 2.97-2.88 (m, 1H), 2.79 (brt, J=9.4 Hz, 1H), 2.62-2.54 (m, 1H), 1.91 (brd, J=8.9 Hz, 1H), 1.74 (brd, J=3.4 Hz, 1H), 1.67-1.51 (m, 2H).

MS-ESI (m/z): 463.1 (M+H)$^+$.

Example 20: 5-Fluoro-3-[[5-(2-hydroxypropan-2-yl) pyridin-2-yl]amino]-1-methyl-6-(1H-pyridin-3-yl) quinoline-2(1H)-one

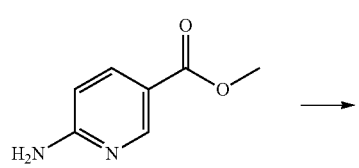

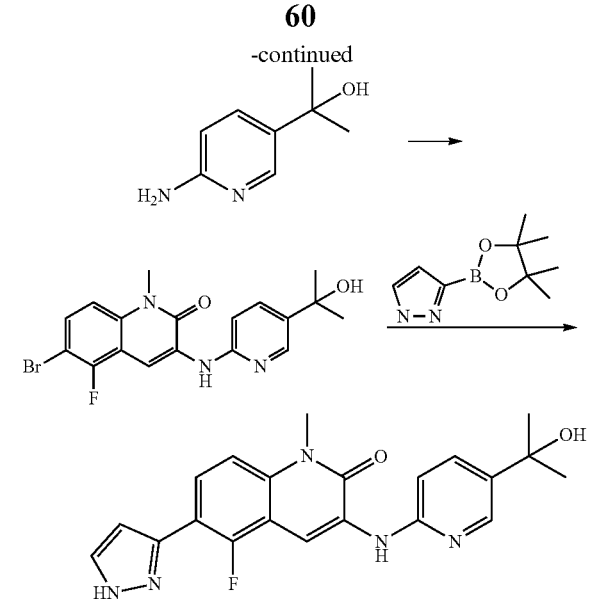

Step A: 2-(6-Amino-3-pyridine)propan-2-ol

To a solution of methyl 6-aminopyridine-3-carboxylate (3.2 g, 21.03 mmol) in tetrahydrofuran (300 mL) was added dropwise methyl magnesium chloride (70.10 mL, 3 mol), at 0° C. under nitrogen, and after it was stirred for 15 hours at 25° C., and quenched by the addition of water (50 mL). The aqueous layer was extracted with ethyl acetate (50 mL×2). The combined organic layers were washed with saturated brine (50 mL×2), then dried over sodium sulfate, filtered and evaporated to give the title compound.

LCMS (ESI) m/z: 153 (M+1).

$^1$H NMR (400 MHz, DMSO-d6) δ=7.96 (d, J=2.3 Hz, 1H), 7.45 (dd, J=2.5, 8.5 Hz, 1H), 6.39 (d, J=8.5 Hz, 1H), 5.74 (br s, 2H), 4.85 (s, 1H), 1.36 (s, 6H).

Step B: 6-Bromo-5-fluoro-3-[[5-(2-hydroxypropan-2-yl)pyridin-2-yl]amino]-1-m ethyl-quinolin-2-one A mixture of Example 20A (400 mg, 2.63 mmol), (6-bromo-5-fluoro-1-methyl-2-oxo-3-quinoline) trifluoromethanesulfonate (1.12 g, 2.76 mmol), Pd$_2$(dba)$_3$ (240.68 mg, 0.263 mmol), Xantphos (228.12 mg, 0.3945 mmol) and cesium carbonate (1.71 g, 5.26 mmol) in tetrahydrofuran (40 mL) was reacted at 25° C. for 15 hours. After cooling to room temperature, it was diluted with water (30 mL), and the aqueous layer was extracted with ethyl acetate (30 mL×3). The combined organic layers were washed with brine (30 mL×3), dried over sodium sulfate, filtered and evaporated. The residue was purified by column chromatography to give the title compound.

LCMS (ESI) m/z: 406 (M+1)

1H NMR (400 MHz, DMSO-d6) δ=9.05 (s, 1H), 9.00 (s, 1H), 8.41 (d, J=2.5 Hz, 1H), 7.74 (dd, J=2.4, 8.7 Hz, 1H), 7.63 (dd, J=7.5, 9.0 Hz, 1H), 7.37-7.31 (m, 2H), 5.08 (s, 1H), 3.76 (s, 3H), 1.45 (s, 6H).

Step C: 5-Fluoro-3-[[5-(2-hydroxypropan-2-yl)pyridin-2-yl]amino]-1-methyl-6-(1H-pyridin-3-yl)quinoline-2(1H)-one Under a protection of nitrogen, after a mixture of Example 20B (100 mg, 0.24615 mmol), 3-(4,4,5,5-tetramethyl-1,3,2- dioxaborolan-2-yl)-1 hydrogen-pyrazole (52.54 mg, 0.27077 mmol), Pd(dppf)Cl$_2$ (18.01 mg, 0.02462 mmol), potassium carbonate (102.06 mg, 0.73845 mmol) in dioxane (2 mL) and water (0.5 mL) was stirred for 15 hours at 100° C., the aqueous layer was diluted with water (20 mL) and extracted with dichloromethane (20 mL×3). After the combined organic layers were washed with brine (20 mL×2), dried over sodium sulphate, filtered and evaporated. The residue was purified by preparative HPLC (trifluoroacetic acid system) to give the title compound 20.

LCMS (ESI) m/z: 394 (M+1)

1H NMR (400 MHz, DMSO-d6) δ=13.12 (br s, 1H), 9.17 (s, 1H), 8.92 (s, 1H), 8.42 (d, J=1.8 Hz, 1H), 7.96 (br t, J=8.4 Hz, 1H), 7.82 (br s, 1H), 7.74 (dd, J=2.3, 8.8 Hz, 1H), 7.43 (d, J=9.0 Hz, 1H), 7.34 (d, J=8.8 Hz, 1H), 6.74 (br s, 1H), 5.08 (s, 1H), 3.80 (s, 3H), 1.46 (s, 6H).

Example 21: 5-Fluoro-3-[5-(1-hydroxycyclobutyl)pyridin-2-yl]-1-methyl-6-(1H-pyrazol-3-yl)quinoline-2(1H)-one

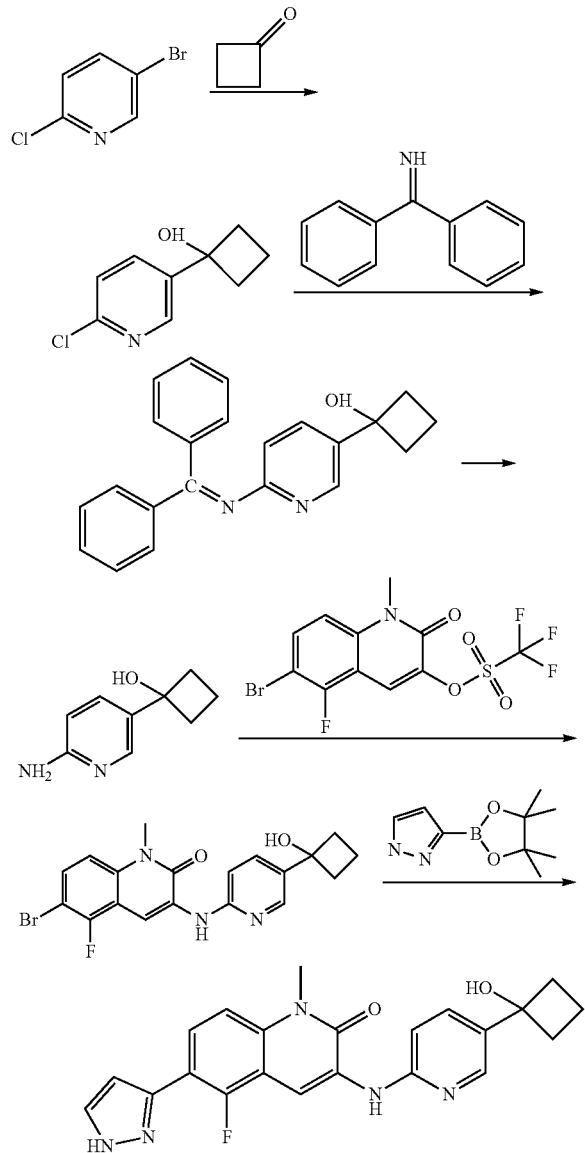

Step A: 1-(6-Chloro-3-pyridine)cyclobutanol

To a solution of 5-bromo-2-chloro-pyridine (10 g, 51.96 mmol) in tetrahydrofuran (100 mL) was added dropwise slowly isopropylmagnesium chloride lithium chloride complex (1.3M, 59.95 mL) at −10° C. under nitrogen, and it was stirred at this temperature for 1 hour, then cyclobutanone (4.01 g, 57.16 mmol) was added dropwise slowly at −10-0° C., stirring for 2 hours in this temperature range, and finally stirring at 0° C. for 2 hours. It was quenched by the addition of a saturated solution of ammonium chloride (100 mL), and the aqueous layer was extracted with ethyl acetate (50 mL×4). The combined organic layers were washed with saturated brine (100 mL×2), dried over anhydrous sodium sulfate, filtered and evaporated. The residue was purified by column chromatography to give the title compound.

LCMS (ESI) m/z: 184.0 (M+1).

$^1$H NMR (400 MHz, CHLOROFORM-d) δ=8.51 (d, J=2.5 Hz, 1H), 7.80 (dd, J=2.6, 8.4 Hz, 1H), 7.32 (d, 0.7=8.3 Hz, 1H), 2.58-2.49 (m, 2H), 2.48-2.37 (m, 3H), 2.13-2.02 (m, 1H), 1.81-1.69 (m, 1H).

Step B: 1-(6((Diphenylmethylene)amine)pyridin-3-yl)cyclobutanol

Under a protection of nitrogen, to a solution of Example 21A (1 g, 5.45 mmol), benzophenone imine (1.48 g, 8.18 mmol) and cesium carbonate (3.55 g, 10.90 mmol) in dioxane (25 mL) were added BINAP (339.36 mg, 545 µmol) and Pd$_2$(dba)$_3$ (249.53 mg, 272.5 µmol), and it was stirred at 100° C. for 12 hours. After cooling to room temperature, it was diluted with water (50 mL), and the aqueous layer was extracted with ethyl acetate (50 mL×4). The combined organic layers were washed with saturated brine (100 mL), dried over anhydrous sodium sulfate, filtered and evaporated. The residue was separated and purified by column chromatography to give the title compound.

LCMS (ESI) m/z: 329.2 (M+1).

$^1$H NMR (400 MHz, CHLOROFORM-d) δ=8.46 (d, 0.7=2.0 Hz, 1H), 7.80 (brd, 0.7=7.5 Hz, 2H), 7.59 (dd, 0.7=2.5, 8.3 Hz, 1H), 7.53-7.47 (m, 1H), 7.45-7.38 (m, 2H), 7.27 (s, 3H), 7.18 (br d, 0.7=6.8 Hz, 2H), 6.58 (d, 0.7=8.3 Hz, 1H), 2.56-2.45 (m, 2H), 2.41-2.30 (m, 2H), 2.04-2.00 (m, 1H), 1.72-1.63 (m, 1H).

Step C: 1-(6-Amine-3-pyridine)cyclobutanol

To a solution of Example 21B (820 mg, 2.5 mmol) and potassium acetate (490.7 mg, 5 mmol) in methanol (10 mL) was added hydroxylamine hydrochloride (347.45 mg, 5 mmol), and after it was stirred at 17° C. for 1 hour, filtered. The filter cake was washed with methanol (5 mL), and the filtrate was evaporated. The residue was separated and purified by column chromatography, to give the title compound.

LCMS (ESI) m/z: 164.9 (M+1).

$^1$H NMR (400 MHz, DMSO-d$_6$) δ=7.99 (d, 0.7=2.3 Hz, 1H), 7.44 (dd, 0.7=2.5, 8.5 Hz, 1H), 6.41 (d, 0.7=8.5 Hz, 1H), 5.74 (s, 2H), 5.28 (br s, 1H), 2.36-2.26 (m, 2H), 2.23-2.13 (m, 2H), 1.87-1.76 (m, 1H), 1.57-1.45 (m, 1H).

Step D: 6-Bromo-5-fluoro-3-((5-(1-hydroxycyclobutyl)pyridin-2-yl)amine)-1-methylquinolin-2(1H)-one Under a protection of nitrogen, to a solution of Example 21C (250 mg, 1.52 mmol) and cesium carbonate (990.49 mg, 3.04 mmol) in tetrahydrofuran (10 mL) were added Xantphos (131.93 mg, 228 μmol) and Pd$_2$(dba)$_3$ (139.19 mg, 152 μmol), and after it was stirred at 15° C. for 12 hours, filtered. The filter cake was washed with methanol (20 mL) and dichloromethane (20 mL) respectively, and the filtrate was evaporated. The residue was separated and purified by column chromatography, to give the title compound.

LCMS (ESI) m/z: 418 (M+1).

$^1$H NMR (400 MHz, DMSO-d$_6$) δ=9.06 (d, 0.7=9.0 Hz, 2H), 8.44 (d, 0.7=2.3 Hz, 1H), 7.75 (dd, 0.7=2.5, 8.5 Hz, 1H), 7.63 (dd, 0.7=7.8, 8.8 Hz, 1H), 7.40 (d, 0.7=8.5 Hz, 1H), 7.33 (d, 0.7=9.3 Hz, 1H), 5.56 (s, 1H), 3.76 (s, 3H), 2.42 (dt, 0.7=4.3, 8.4 Hz, 2H), 2.34-2.22 (m, 2H), 1.94-1.82 (m, 1H), 1.69-1.56 (m, 1H).

Step E: 5-Fluoro-3-[5-(1-hydroxycyclobutyl)pyridin-2-yl]-1-methyl-6-(1H-pyrazol-3-yl)quinoline-2(1H)-one Under a protection of nitrogen, dissolved Example 21D (340 mg, 812.89 μmol), 3-(4,4,5,5-tetramethyl-1,3,2-dioxaborolan-2-yl)-1H-pyrazole (394.33 mg, 2.03 mmol), potassium carbonate (337.04 mg, 2.44 mmol) in a solution of dioxane (10 mL) and water (2.5 mL), then added Pd(dppf)Cl$_2$ (59.48 mg, 81.29 μmol)), and it was stirred at 110° C. for 15 hours; after cooling to room temperature, added additional 3-(4,4,5,5-tetramethyl-1,3,2-dioxaborolan-2-yl)-1H-pyrazole (394.33 mg, 2.03 mmol) and Pd (dppf)Cl$_2$ (59.48 mg, 81.29 μmol), stirring continually at 110° C. for 15 hours under nitrogen. After cooling to room temperature, the reaction solution was filtered, and the filter cake was washed with ethyl acetate (100 mL), and the filtrate was diluted with water (50 mL). The aqueous layer was extracted with ethyl acetate (50 mL×5). The combined organic layers were washed with saturated brine (100 mL), dried over anhydrous sodium sulfate, filtered and evaporated. The residue was separated by preparative HPLC (trifluoroacetic acid) to give title compound 21.

MS-ESI (m/z): 406 (M+H)$^+$ $^1$H NMR (400 MHz, DMSO-d$_6$) δ=9.17 (s, 1H), 9.00 (s, 1H), 8.44 (d, 0.7=1.8 Hz, 1H), 7.97 (br t, 0.7=8.4 Hz, 1H), 7.82 (br s, 1H), 7.76 (dd, 0.7=2.3, 8.8 Hz, 1H), 7.41 (br dd, 0.7=8.7, 20.0 Hz, 2H), 6.74 (br s, 1H), 3.80 (s, 3H), 2.36-2.20 (m, 4H), 1.94-1.85 (m, 1H), 1.70-1.58 (m, 1H), 1.23 (br s, 1H), 1.30-1.18 (m, 1H).

Example 22: 5-Fluoro-3-[[5-(3-hydroxyoxetan-3-yl) pyridin-2-yl]amino]-1-methyl-6-(1H-pyrazol-3-yl) quinoline-2(1H)-one

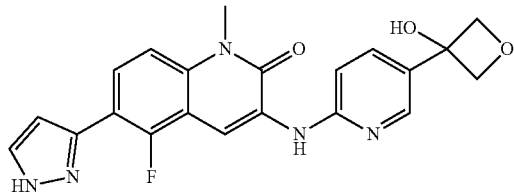 [SMILES: Cn1c(=O)c(Nc2ccc(C3(O)COC3)cn2)cc2c(F)c(-c3cc[nH]n3)ccc21]

The preparation method of Example 22 could be obtained by referring to the preparation method of Example 21, prepared by using the starting material oxetanone.

LCMS (ESI) m/z: 408 (M+1).

$^1$H NMR (400 MHz, DMSO-d6) δ=9.19 (s, 1H), 9.08 (s, 1H), 8.53 (d, J=2.0 Hz, 1H), 7.97 (t, J=8.4 Hz, 1H), 7.87-7.79 (m, 2H), 7.45 (dd, J=3.5, 8.8 Hz, 2H), 6.74 (br s, 1H), 4.76 (s, 4H), 3.81 (s, 3H).

Example 23: 5-Fluoro-3-[[5-(3-fluorooxetan-3-yl) pyridin-2-yl]amino]-1-methyl-6-(1H-pyrazol-3-yl) quinoline-2(1H)-one

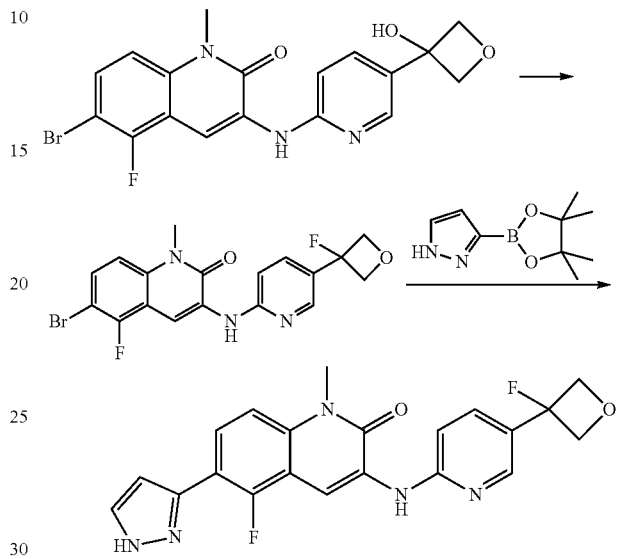

Step A: 6-Bromo-5-fluoro-3-[[5-(3-fluorooxetan-3-yl)pyridin-2-yl]amino]-1-methyl-quinoline-2(1H)-one To 6-bromo-5-fluoro-3-[[5-(3-hydroxyoxetan-3-yl)-2-nitrophenyl]amino]-1-methyl-quinolin-2-one (150 mg, 356.95 μmol) in dichloromethane (5 mL) was added dropwise DAST (103.56 mg, 642.50 μmol) at −10° C. under nitrogen, and the mixture was reacted at −50° C. for 1 hour, then quenched by the addition of water (20 mL). The aqueous layer was extracted with dichloromethane (20 mL×2). The combined organic layers were washed with saturated brine (20 mL×2), dried over anhydrous sodium sulfate, filtered and evaporated. The residue was purified by column chromatography to give the title compound 23A.

LCMS (ESI) m/z: 422 (M+1).

$^1$H NMR (400 MHz, CHLOROFORM-d) δ=9.10 (s, 1H), 8.60 (s, 1H), 8.24 (s, 1H), 7.74 (dd, J=2.3, 8.8 Hz, 1H), 7.51 (dd, J=7.3, 9.0 Hz, 1H), 7.09-6.90 (m, 2H), 5.22-5.09 (m, 2H), 4.98-4.85 (m, 2H), 3.84 (s, 3H).

Step B: 5-Fluoro-3-[[5-(3-fluorooxetan-3-yl)pyridin-2-yl]amino]-1-methyl-6-(1H-pyrazol-3-yl)quinoline-2(1H)-one A mixture of Example 23A (130 mg, 307.89 μmol), 3-(4,4,5,5-tetramethyl 1,3,2-dioxaborolan-2-yl)-1H-pyridine (89.61 mg, 461.84 μmol), Pd(dppf)Cl$_2$ (22.53 mg, 30.79 μmol), potassium fluoride (53.66 mg, 926.68 μmol) in dioxane (4 mL) was reacted at 100° C. under nitrogen for 15 hours. After cooling to room temperature, it was quenched by water (20 mL), and the aqueous layer was extracted with dichloromethane (20 mL×3). The combined organic layers were washed with brine (20 mL×3), dried over sodium sulfate, filtered and evaporated. The residue was purified by preparative HPLC to give the title compound 23.

LCMS (ESI) m/z: 410 (M+1)

1H NMR (400 MHz, DMSO-d6) δ=9.30-9.10 (m, 2H), 8.59-8.47 (m, 1H), 7.98 (brt, J=8.4 Hz, 1H), 7.90-7.77 (m, 2H), 7.58-7.40 (m, 2H), 6.74 (brs, 1H), 5.08-4.91 (m, 2H), 4.76 (s, 2H), 3.80 (s, 3H).

Example 24, 25: 5-Fluoro-1-methyl-6-(1H-pyrazol-3-yl)-3-((5-(1,1,1-trifluoro-2-hydroxypropan-2-yl)pyridine-2-yl)amino)quinoline-2(1H)-one

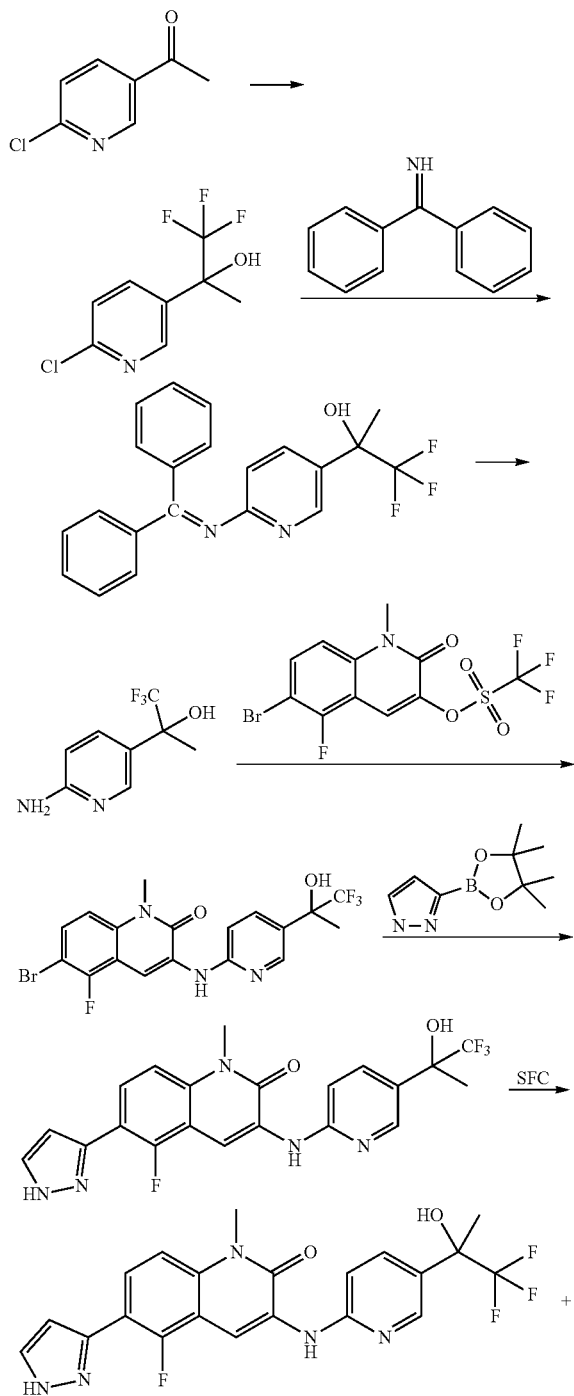

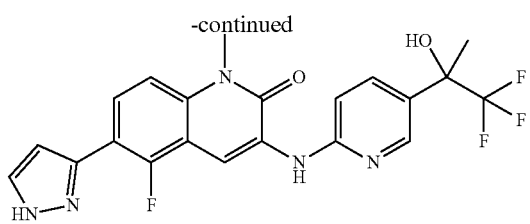

Step A: 2-(6-Chloropyridin-3-yl)-1,1,1-trifluoromethyl-propan-2-ol

To 2-(6-chloro-3-nitrophenyl)-1,1,1-trifluoromethyl-propan-2-ol (5 g, 32.14 mmol) and cesium carbonate (12.57 g, 38.56 mmol) in DMF (80 mL) was added dropwise trifluoromethyltrimethylsilane (20.56 g, 144.62 mmol) at 0° C., and the mixture was reacted at 16° C. for 2 hours, then quenched by the addition of water (100 mL), and the aqueous layer was extracted with ethyl acetate (100 mL×2). The combined organic layers were washed with saturated brine (100 mL×2), dried over sodium sulfate, filtered and evaporated. The residue was purified by column chromatography to give the title compound.

1H NMR (400 MHz, CHLOROFORM-d) δ=8.49 (d, J=2.5 Hz, 1H), 7.84 (dd, J=2.4, 8.4 Hz, 1H), 7.29 (d, J=8.3 Hz, 1H), 3.58 (s, 1H), 1.74 (s, 3H).

Step B: 2-[6-(Diphenylmethyleneamino)pyridin-3-yl]-1,1,1-trifluoromethyl-propan-2-ol Under a protection of nitrogen, a mixture of Example 24A (5.5 g, 24.38 mmol), benzophenone imine (6.63 g, 36.57 mmol), Pd$_2$(dba)$_3$ (2.23 g, 2.44 mmol), BINAP (2.28 g, 3.66 mmol) and cesium carbonate (15.89 g, 48.76 mmol) in dioxane (100 mL), was reacted at 100° C. for 16 hours. After cooling to room temperature, it was diluted with water (100 mL), and the aqueous layer was extracted with ethyl acetate (100 mL×3). The combined organic layers were washed with brine (100 mL×3), dried over sodium sulfate, filtered and evaporated. The residue was purified by column chromatography to give the title compound.

Step C: 2-(6-Aminopyridin-3-yl)-1,1,1-trifluoromethyl-propan-2-ol

Under a protection of nitrogen, 24B (8 g, 21.60 mmol) and potassium acetate (4.24 g, 43.20 mmol), hydroxylamine hydrochloride (3 g, 43.20 mmol) in methanol (100 mL), the mixture was reacted at 16° C. for 2 hours, and the reaction solution was filtered. The filter cake was washed with methanol (100 mL). The filtrate was evaporated, and the residue was purified by column chromatography to give the title compound.

LCMS (ESI) m/z: 207 (M+1).

1H NMR (400 MHz, CHLOROFORM-d) δ=8.15 (s, 1H), 7.67 (br d, J=8.5 Hz, 1H), 6.52 (d, J=8.8 Hz, 1H), 5.22 (br s, 1H), 4.13 (brd, J=7.5 Hz, 2H), 1.75 (s, 3H).

Step D: 6-Bromo-5-fluoro-1-methyl-3-((5-(1,1,1-trifluoro-2-hydroxypropan-2-yl) pyridin-2-yl)amino)quinoline-2(1H)-one Under a protection of nitrogen, to tetrahydrofuran (100 mL) were added 6-bromo-5-fluoro-1-methyl-2-oxo-1,2-1,2-dihydroquinolin-3-yl-trifluoro methanesulfonate (3.0 g, 7.42 mmol), 2-(6-aminopyridin-3-yl)-1,1,1-trifluoropropan-2-ol (1.53 g, 7.42 mmol), Pd$_2$(dba)$_3$ (679.77 mg, 742.33 μmol), Xantphos (644.29 mg, 1.11 mmol) and cesium carbonate (4.84 g, 14.85 mmol). It was stirred at 30° C. for 16 hours. The reaction solution was quenched with water (200 mL), and extracted three times with dichloromethane (100 mL×3). The organic phase was washed with brine (200 mL), and dried over sodium sulfate. After filtration and concentration, the residue was slurried with ethyl acetate (50 mL). The title compound was obtained after filtrating and drying.

1H NMR (400 MHz, CHLOROFORM-d) δ=9.12 (s, 1H), 8.60 (s, 1H), 8.21 (s, 1H), 7.83 (brd, J=9.0 Hz, 1H), 7.67-7.44 (m, 1H), 7.06 (d, J=9.0 Hz, 1H), 6.89 (d, J=8.8 Hz, 1H), 3.85 (s, 3H), 2.42 (s, 1H), 1.85 (s, 3H).

Step E: 5-Fluoro-1-methyl-6-(1H-pyrazol-3-yl)-3-((5-(1,1,1-trifluoro-2-hydroxypropan-2-yl)pyridine-2-yl)amino)quinoline-2(1H)-one Under a protection of nitrogen, to 1,4-dioxane (40 mL) and water (10 mL) were added 6-bromo-5-fluoro-1-methyl-3-((5-(1,1,1-trifluoro-2-hydroxypropan-2-yl)pyridin-2-yl)amino)quinolin-2(1H)-one (1.8 g, 3.91 mmol), potassium carbonate (1.62 g, 11.73 mmol), Pd(dppf)Cl$_2$ (286.18 mg, 391 μmol) and 3-(4,4,5,5-tetramethyl-1,3,2-dioxaborolan-2-yl)-1AA-pyrazole (1.14 g, 5.87 mmol). It was stirred at 100° C. for 16 hours. The reaction was quenched with water (200 mL) and dichloromethane (150 mL). After the organic phase separated, the aqueous phase was extracted with dichloromethane (150 mL). The organic phases were combined, and dried over anhydrous sodium sulfate. The resultant was filtered and concentrated, and the residue was slurried with dichloromethane (60 mL). The title compound was obtained after filtrating and drying.

1H NMR (400 MHz, DMSO-d6) δ=9.21 (s, 1H), 9.13 (s, 1H), 8.52 (d, J=1.8 Hz, 1H), 7.99 (brt, J=8.5 Hz, 1H), 7.90-7.77 (m, 2H), 7.45 (d, J=9.0 Hz, 2H), 6.75 (br s, 1H), 3.81 (s, 3H), 1.73 (s, 3H).

Step F: 5-Fluoro-1-methyl-6-(1H-pyrazol-3-yl)-3-((5-(1,1,1-trifluoro-2-hydroxypropan-2-yl)pyridine-2-yl)amino)quinoline-2(1H)-one 5-Fluoro-1-methyl-6-(1H-pyrazol-3-yl)-3-((5-(1,1,1-trifluoro-2-hydroxypropan-2-yl)pyridine-2-yl)amino)quinoline-2(1H)-one (0.95 g, 2.12 mmol) was subjected to chiral resolution (column: Chiralpak AD-3 50*4.6 mm I.D., Sum mobile phase: 40% ethanol (0.05% diethanolamine) in carbon dioxide flow rate: 4 mL/min, column temperature: 40° C.) to give peak 1 (0.990 min, 99% ee) as compound 24, peak 2 (1.601 min, 97% ee) as compound 25.

Compound 24: 1H NMR (400 MHz, DMSO-d6) δ=13.56-12.88 (m, 1H), 9.21 (s, 1H), 9.13 (brs, 1H), 8.53 (s, 1H), 8.03 (brs, 1H), 7.9-7.80 (m, 2H), 7.45 (br d, J=8.5 Hz, 2H), 6.75 (br s, 1H), 6.68 (s, 1H), 3.81 (s, 3H), 1.73 (s, 3H). Compound 25:1 H NMR (400 MHz, DMSO-d6) δ=13.10 (br s, 1H), 9.20 (d, J=4.3 Hz, 1H), 9.13 (brs, 1H), 8.52 (brs, 1H), 8.10-7.76 (m, 3H), 7.44 (br dd, J=4.5, 8.5 Hz, 2H), 6.74 (br s, 1H), 6.67 (d, J=4.3 Hz, 1H), 3.80 (d, J=4.3 Hz, 3H), 1.73 (br d, J=4.0 Hz, 3H).

(ESI) m/z: 448.1 (M+1).

Example 26: 1-Methyl-3-((4-morpholinephenyl)amino)-7-(1H-pyrazol-4-yl)quinoxaline-2(1H)-one

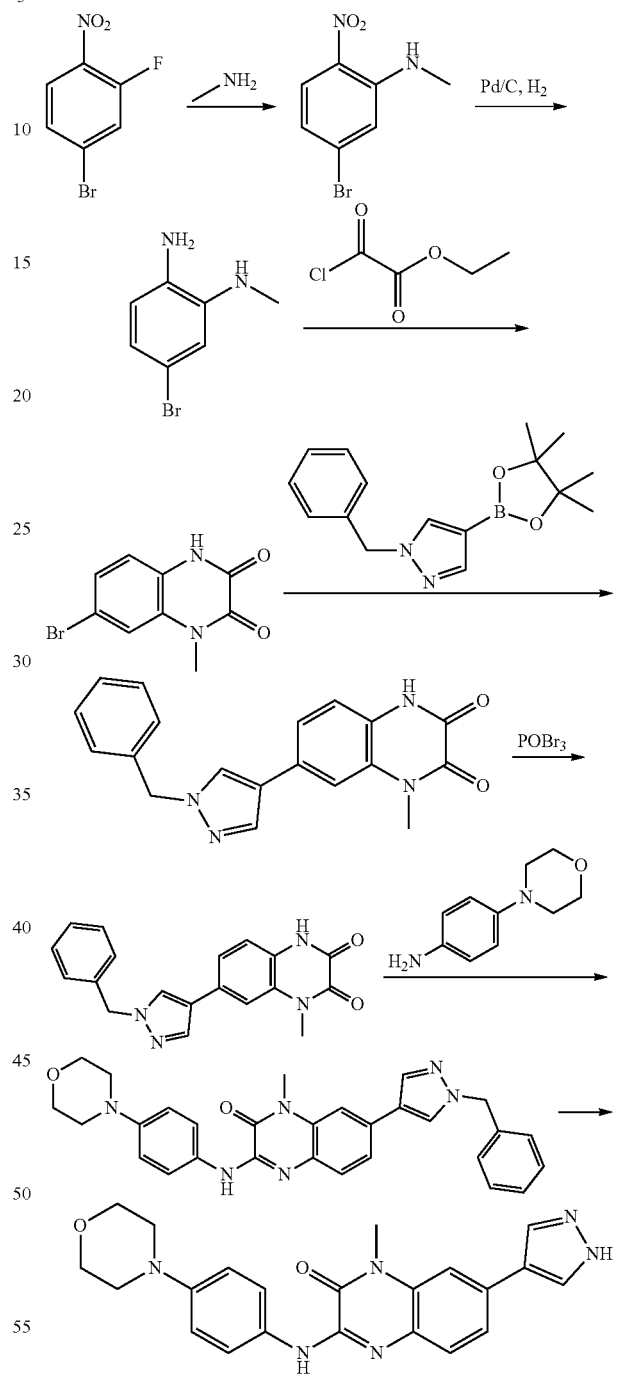

Step A: 5-Bromo-N-methyl-2-nitroaniline

Under a protection of nitrogen, to a solution of 4-bromo-2-fluoro-1-nitroaniline (15.0 g, 68.18 mmol) and potassium carbonate (11.31 g, 81.82 mmol) in DMF (250 mL) was added dropwise methylamine in tetrahydrofuran (2M, 68.18 mL) at 25° C., and it was stirred at 25° C. for 18 hours. The reaction solution was poured into 500 mL water, and it was stirred for 10 minutes. The precipitated solid was filtered and dried to give the title compound.

1H NMR (400 MHz, CHLOROFORM-d) δ=8.03 (d, J=9.4 Hz, 2H), 7.01 (s, 1H), 6.77 (dd, J=1.8, 9.2 Hz, 1H), 3.02 (d, J=5.1 Hz, 3H).

Step B: 5-Bromo-N¹-methylbenzene-1,2-diamine

Under a protection of nitrogen, to a solution of 5-bromo-N-methyl-2-nitroaniline (9.0 g, 38.95 mmol) in tetrahydrofuran (300 mL) was added Raney Nickel (1.67 g). The reaction solution was replaced several times with hydrogen, and then reacted at 50 Psi at 25° C. for 5 hours. The reaction solution was filtered, and the filtrate was concentrated to give the title compound.

1H NMR (400 MHz, CHLOROFORM-d) δ=6.79 (dd, J=2.1, 8.2 Hz, 1H), 6.75 (d, J=2.0 Hz, 1H), 6.59 (d, J=8.0 Hz, 1H), 2.87 (s, 3H).

Step C: 7-Bromo-1-methylquinoxaline-2,3(1H,4H)-dione

Under a protection of nitrogen, to 5-bromo-N-1-methylbenzene-1,2-diamine (7.7 g, 38.3 mmol) and triethylamine (9.69 g, 95.75 mmol) in 1,2-dichloroethane (80 mL) was added oxalyl chloride monoethyl ester (6.27 g, 45.96 mmol) at 0° C. It was stirred at 25° C. for 2 hours. The temperature was raised to 60° C. for stirring for 3 hours.

The reaction solution was filtered, and the filter cake was washed twice with water (20 mL). The filter cake was dried to give the title compound.

1H NMR (400 MHz, DMSO-d6) δ=12.07 (br. s., 1H), 7.51 (d, J=1.2 Hz, 1H), 7.33 (dd, J=1.6, 8.2 Hz, 1H), 7.07 (d, J=8.6 Hz, 1H), 3.47 (s, 3H).

Step D: 7-(1-Benzyl-1H-pyrazol-4-yl)-1-methylquinoxaline-2,3(1H,4H)-dione

Under a protection of nitrogen, added 7-bromo-1-methylquinoxaline-2,3(1H,4H)-dione (1.00 g, 3.92 mmol), 1-benzyl-4-(4,4,5,5-tetramethyl-1,3,2-dioxaborolan-2-yl)pyrazole (1.23 g, 4.31 mmol), potassium carbonate (1.08 g, 7.84 mmol) and Pd(dppf)Cl₂ (286.86 mg, 392.05 µmol) to DMF (10 mL), dioxane (10 mL) and water (5 mL). It was stirred at 100° C. for 5 hours. The reaction solution was quenched with water (100 mL), and the precipitated solid was filtered. The filter cake was subjected to column chromatography to give the title compound.

1H NMR (400 MHz, DMSO-d6) δ=12.01 (s, 1H), 8.35 (s, 1H), 8.00 (s, 1H), 7.50 (s, 1H), 7.44-7.24 (m, 6H), 7.14 (d, J=8.2 Hz, 1H), 5.35 (s, 2H), 3.57 (s, 3H).

Step E: 7-(1-Benzyl-1H-pyrazol-4-yl)-3-bromo-1-methylquinoxaline-2(1H)-one

To 7-(1-benzyl-1H-pyrazol-4-yl)-1-methylquinoxaline-2,3(1H,4H)-dione (500 mg, 1.5 mmol) and triethylamine (152.23 mg, 1.50 mmol) in 1,2-dichloroethane was added phosphorusoxy bromide (1.29 g, 4.5 mmol) at 0° C. under nitrogen. It was stirred at 80° C. for 5 hours. The reaction was quenched with saturated sodium bicarbonate (100 mL), and extracted twice with dichloromethane (100 mL). The organic phase was dried over anhydrous sodium sulfate, and the concentrated residue was subjected to column chromatography to give the title compound.

1H NMR (400 MHz, DMSO-d6) δ=8.55 (s, 1H), 8.16 (s, 1H), 7.76-7.66 (m, 2H), 7.62 (d, J=8.2 Hz, 1H), 7.43-7.08 (m, 5H), 5.35 (s, 2H), 3.69 (s, 3H).

Step F: 7-(1-Benzyl-1H-pyrazol-4-yl)-1-methyl-3-((4-morpholinephenyl)amino)quinoxaline-2(1H)-one Under a protection of nitrogen, added 7-(1-benzyl-1H-pyrazol-4-yl)-3-bromo-1-methylquinoxaline-2(1H)-one (220.0 mg, 556.61 µmol), 4-morpholine aniline (128.97 mg, 723.59 µmol), cesium carbonate (362.71 mg, 1.50 mmol) and [2-(2-aminoethyl)phenyl]-chloride-palladium; di-tert-butyl-[2-(2,4,6-triisopropylpheny)phenyl]phosphate (38.22 mg, 55.66 µmol) to 1,4-dioxane (10 mL). It was stirred at 70° C. for 3 hours. The reaction solution was quenched with water (40 mL), and extracted twice with dichloromethane (50 mL). The organic phase was dried over anhydrous sodium sulfate, and the concentrated residue was prepared and separated by high performance liquid chromatography to give the title compound.

1H NMR (400 MHz, DMSO-d6) δ=9.25 (s, 1H), 8.39 (s, 1H), 8.03 (s, 1H), 7.97 (d, J=8.6 Hz, 2H), 7.56 (s, 1H), 7.51-7.40 (m, 2H), 7.38-7.23 (m, 4H), 6.93 (d, J=9.0 Hz, 2H), 5.34 (s, 2H), 3.72 (br. s., 7H), 3.06 (br. s., 4H).

Step G: 1-Methyl-3-((4-morpholinephenyl)amino)-7-(1H-pyrazol-4-yl) quinoxaline-2(1H)-one To a solution of 7-(1-benzyl-1H-pyrazol-4-yl)-1-methyl-3-((4-morpholinephenyl)amino)quinoxaline-2(1H)-one (40.0 mg, 81.21 µmol) in DMSO (2 mL) was added potassium tert-butoxide (63.79 mg, 568.45 µmol). It was stirred at 25° C. for 18 hours. The reaction solution was directly prepared and separated by high performance liquid chromatography (trifluoroacetic acid additive) to give the title compound 26.

1H NMR (400 MHz, DMSO-d6) δ=9.31 (br. s., 1H), 8.17 (s, 2H), 7.99 (d, J=8.6 Hz, 2H), 7.60 (s, 1H), 7.56-7.49 (m, 1H), 7.45 (d, J=8.2 Hz, 1H), 6.98 (d, J=8.2 Hz, 2H), 3.73 (br. s., 8H), 3.09 (br. s., 3H).

Example 27: 1-Methyl-3-((4-morpholinephenyl)amino)-7-(1H-pyrazol-3-yl) quinoxaline-2(1H)-one

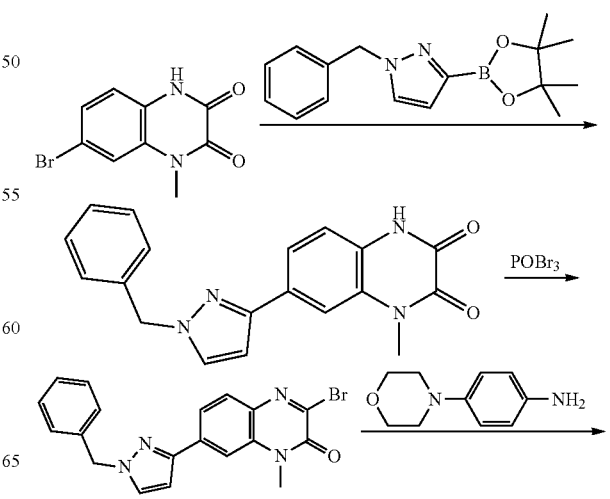

-continued

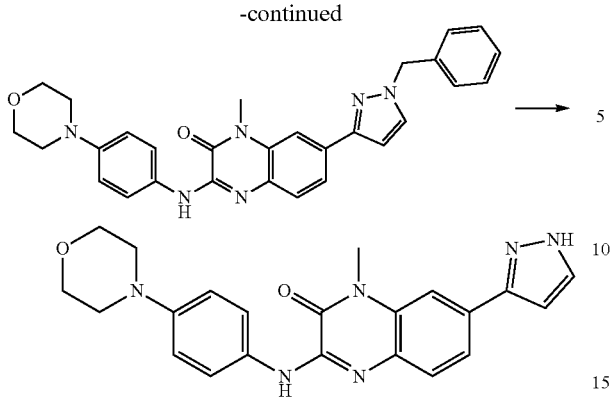

Step A: 7-(1-Benzyl-1H-pyrazol-3-yl)-1-methylquinoxaline-2,3(1H,4H)-dione

Under a protection of nitrogen, to DMF (10 mL), dioxane (10 mL) and water (5 mL), was added 7-bromo-1-methylquinoxaline-2,3(1H,4H)-dione (1.00 g, 3.92 mmol), 1-benzyl-3-(4,4,5,5-tetramethyl-1,3,2-dioxaborolan-2-yl) pyrazole (1.45 g, 5.10 mmol), potassium carbonate (1.08 g, 7.84 mmol) and Pd(dppf)Cl$_2$ (286.86 mg, 392.0 µmol). It was stirred at 100° C. for 5 hours. The reaction solution was quenched with water (100 mL), and the precipitated solid was filtered. The filter cake was subjected to column chromatography to give the title compound.

1H NMR (400 MHz, DMSO-d6) δ=12.05 (br. s., 1H), 7.87 (br. s., 1H), 7.65-7.55 (m, 2H), 7.35-7.11 (m, 6H), 6.81 (br. s., 1H), 5.36 (s, 2H), 3.54 (s, 3H).

Step B: 7-(1-Benzyl-1H-pyrazol-3-yl)-3-bromo-1-methylquinoxaline-2(1H)-one

To 7-(1-benzyl-1H-pyrazol-3-yl)-1-methylquinoxaline-2,3(1H,4H)-dione (700 mg, 2.11 mmol) and triethylamine (213.51 mg, 2.11 mmol) in 1,2-dichloroethane (20 mL) was added phosphorusoxy bromide (1.81 g, 6.33 mmol) at 0° C. under nitrogen. It was stirred at 80° C. for 5 hours. The reaction solution was quenched with saturated sodium bicarbonate (100 mL), and extracted twice with dichloromethane (100 mL). The organic phase was dried over anhydrous sodium sulfate, and the residue after concentrating was subjected to column chromatography to give the title compound.

1H NMR (400 MHz, DMSO-d6) δ=7.94 (d, J=2.3 Hz, 1H), 7.87-7.79 (m, 2H), 7.78-7.74 (m, 1H), 7.38-7.21 (m, 5H), 7.02 (d, J=2.3 Hz, 1H), 5.40 (s, 2H), 3.70 (s, 3H).

Step C: 7-(1-Benzyl-1H-pyrazol-3-yl)-1-methyl-3-((4-morpholinephenyl)amino)quinoxaline-2(1H)-one Under a protection of nitrogen, to 1,4-dioxane (10 mL) were added 7-(1-benzyl-1H-pyrazol-3-yl)-3-bromo-1-methylquinoxaline-2(1H)-one (300.0 mg, 759.01 µmol), 4-morpholine aniline (175.86 mg, 986.71 µmol), cesium carbonate (494.60 mg, 1.52 mmol) and [2-(2-aminoethyl)phenyl]-chloro-palladium; di-tert-butyl-[2-(2,4,6-triisopropylphenyl)phenyl]phosphate (52.12 mg, 75.9 µmol). It was stirred at 70° C. for 3 hours. The reaction solution was quenched with water (40 mL), and extracted twice with dichloromethane (50 mL). The organic phase was dried over anhydrous sodium sulfate, and the residue after concentrating was subjected to column chromatography to give the title compound.

1H NMR (400 MHz, DMSO-d6) δ=9.36 (s, 1H), 8.01 (d, J=9.0 Hz, 2H), 7.93 (d, J=2.3 Hz, 1H), 7.77-7.69 (m, 2H), 7.50 (d, J=8.3 Hz, 1H), 7.40-7.26 (m, 5H), 6.97 (d, J=9.0 Hz, 2H), 6.90 (d, J=2.3 Hz, 1H), 5.42 (s, 2H), 3.80-3.71 (m, 7H), 3.12-3.06 (m, 4H).

Step D: 1-Methyl-3-((4-morpholinephenyl)amino)-7-(1H-pyrazol-3-yl)quinoxaline-2(1H)-one To a solution of 7-(1-benzyl-1H-pyrazol-3-yl)-1-methyl-3-((4-morpholinephenyl)amino)quinoxaline-2(1H)-one (100.0 mg, 203.02 µmol) in DMSO (5 mL) was added potassium tert-butoxide (159.47 mg, 1.42 mmol). It was stirred at 25° C. for 18 hours. After the reaction solution was concentrated, the residue was prepared and separated by high performance liquid chromatography (trifluoroacetic acid additive) to give the title compound 27.

1H NMR (400 MHz, DMSO-d6) δ=3.13 (br. s., 4H), 3.48-3.64 (m, 7H), 6.82 (br. s., 1H), 7.03 (br. s., 2H), 7.50 (br. s., 1H), 7.61-7.85 (m, 3H), 8.00 (d, J=7.83 Hz, 2H), 9.45 (br. s., 1H).

Example 28: 1-Methyl-3-((4-morpholinephenyl)amino)-7-(pyridin-4-yl)quinoxaline-2(1H)-one

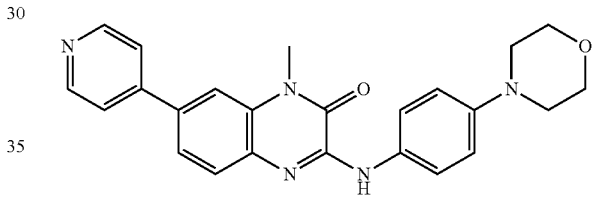

The preparation of Example 28 could be obtained by referring to the preparation method of Example 27.

1H NMR (400 MHz, CHLOROFORM-d) δ=8.93 (d, J=6.3 Hz, 1H), 8.64 (s, 1H), 8.09 (d, J=6.0 Hz, 2H), 8.00 (d, J=9.0 Hz, 2H), 7.87 (d, J=8.5 Hz, 1H), 7.73 (d, J=9.8 Hz, 1H), 7.60 (s, 1H), 7.25 (d, J=9.0 Hz, 2H), 4.05-4.00 (m, 4H), 3.92 (s, 3H), 3.38-3.32 (m, 4H).

MS-ESI (m/z): 414 (M+H)$^+$.

Example 29: 1-Methyl-7-(5-methyl-1H-pyrazol-4-yl)-3-((4-morpholinephenyl)amino)quinoxaline-2(1H)-one

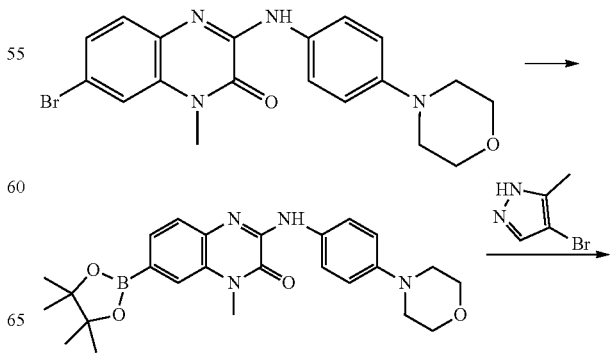

-continued

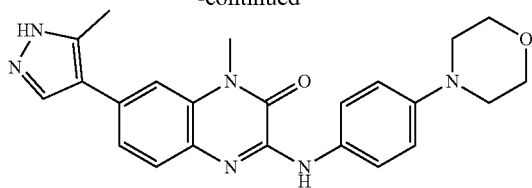

Step A: 1-Methyl-3-((4-morpholinephenyl)amino)-7-(4,4,5,5-tetramethyl-1,3,2-dioxaborolan-2-yl)qinoxaline-2(1H)-one Under a protection of nitrogen, to 7-bromo-1-methyl-3-((4-morpholinephenyl)amino)quinoxaline-2(1H)-one (2.00 g, 4.82 mmol) in DMF (30 mL) were added Bis(pinacolato)diboron (1.84 g, 7.23 mmol), sodium acetate (1.19 g, 14.46 mmol) and Pd(dppf)Cl$_2$ (352.68 mg, 482 µmol). It was stirred at 100° C. for 5 hours. The reaction solution was quenched with water (100 mL), and extracted three times with ethyl acetate (30 mL). The organic phases were combined and washed with saturated brine (100 mL). Filtration, and after concentrating, the residue was subjected to column chromatography to give the title compound.

1H NMR (400 MHz, CHLOROFORM-d) δ=8.41 (s, 1H), 7.86 (d, J=8.8 Hz, 2H), 7.72 (d, J=8.0 Hz, 1H), 7.67 (s, 1H), 7.65-7.60 (m, 1H), 6.95 (d, J=9.0 Hz, 2H), 3.92-3.85 (m, 4H), 3.83-3.79 (m, 3H), 3.18-3.10 (m, 4H), 1.40-1.33 (m, 12H).

Step B: 1-Methyl-7-(5-methyl-1H-pyrazol-4-yl)-3-((4-morpholinephenyl)amino)quinoxaline-2(1H)-one Under a protection of nitrogen, 1-methyl-3-((4-morpholinephenyl)amino)-7-(4,4,5,5-tetramethyl-1,3,2-dioxahexrolane-2-yl)quinoxaline-2(1H)-one, 5-methyl-1H-pyrazole (41.79 mg, 259.55 µmol), potassium carbonate (89.68 mg, 648.87 mmol) and Pd(dppf)Cl$_2$ (15.83 mg, 21.63 µmol). It was stirred at 80° C. for 5 hours. The reaction solution was filtered, and after the filtrate was concentrated, the residue was prepared and separated by high performance liquid chromatography to give the title compound 29.

1H NMR (400 MHz, DMSO-d6) δ=9.43 (br. s., 1H), 8.17-7.86 (m, 3H), 7.62-7.31 (m, 3H), 7.05 (br. s., 2H), 3.90-3.63 (m, 7H), 3.15 (br. s., 4H) 2.44 (br. s., 3H).

MS-ESI (m/z): 417 (M+H)$^+$

The preparations of Examples 30-32 could be prepared by referring to the preparation method of Example 29:

| Title compound | Compound | Name |
|---|---|---|
| Example 30 | | 7-(1H-imidazol-2-yl)-1-methyl-3-((4-morpholinephenyl)amino)quinoxaline-2(1H)-one |
| | 1H NMR (400MHz, DMSO-d6) δ = 9.66 (br. s., 1H), 8.14 (br. s., 1H), 8.00 (d, J = 8.0 Hz, 2H), 7.91 (d, J = 8.0 Hz, 1H), 7.79 (br. s., 2H), 7.63 (d, J = 8.0 Hz, 1H), 6.96 (d, J = 7.5 Hz, 2H), 3.74 (br. s., 7H), 3.09 (br. s., 4H).<br>MS-ESI (m/z): 403 (M + H)$^+$ | |
| Example 31 | | 7-(1H-imidazol-4-yl)-1-methyl-3-((4-morpholinephenyl)amino)quinoxaline-2(1H)-one |
| | 1H NMR (400MHz, DMSO-d6) δ = 9.52 (s, 1H), 9.23 (s, 1H), 8.26 (s, 1H), 8.00 (d, J = 8.6 Hz, 2H), 7.85 (s, 1H), 7.70 (d, J = 8.4 Hz, 1H), 7.57 (d, J = 8.2 Hz, 1H), 7.04-6.91 (m, 2H), 3.82-3.68 (m, 6H), 3.09 (br. s., 4H).<br>MS-ESI (m/z): 403 (M + H)$^+$ | |
| Example 32 | | 1-Methyl-3-((4-morpholinephenyl)amino)-7-(thiazol-2-yl)quinoxaline-2(1H)-one |
| | 1H NMR (400MHz, CHLOROFORM-d) δ = 8.45 (br. s., 1H), 7.89 (dd, J = 7.5, 15.9 Hz, 4H), 7.74 (d, J = 7.8 Hz, 1H), 7.63 (d, J = 8.2 Hz, 1H), 7.32 (br. s., 1H), 7.13 (d, J = 7.8 Hz, 2H), 3.92 (br. s., 4H), 3.79 (br. s., 3H), 3.23 (br. s., 4H). | |

Example 33: 1-Methyl-3((4-(4-methylpiperazin-1-yl)phenyl)amino)-7-(1H-pyrazol-4-yl) quinoxaline-2(1H)-one

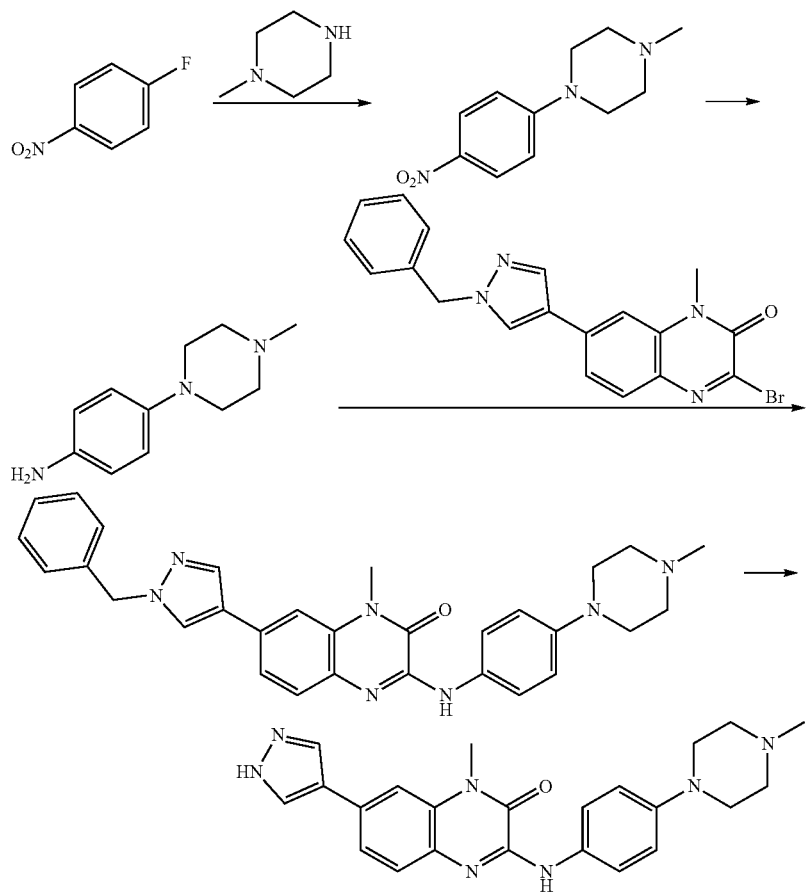

Step A: 1-Methyl-4-(4-nitrophenyl)piperazine

Added potassium carbonate (10.77 g, 77.96 mmol) to a solution of 1-fluoro-4-nitrobenzene (10.00 g, 70.87 mmol) in dimethylsulfoxide (25 mL), and it was stirred at room temperature for half an hour. Further, 1-methylpiperazine (7.17 g, 71.58 mmol) was added dropwise to the reaction solution, and it was stirred at room temperature for 16 hours. Water (300 mL) was added to the reaction solution, with a solid precipitated, then filtered, and spin-dried to give the title compound.

1H NMR (400 MHz, DMSO-d6): δ=8.04 (d, J=9.3 Hz, 2H), 7.02 (d, J=9.3 Hz, 2H), 3.46-3.41 (m, 4H), 2.44-2.39 (m, 4H), 2.21 (s, 3H).

Step B: 4-(4-Methylpiperazin-1-yl)aniline

To a solution of 1-methyl-4-(4-nitrophenyl)piperazine (5.00 g, 22.60 mmol) in ethyl acetate (80 mL) was added 10% palladiumcarbon (2.00 g), and it was replaced three times with a hydrogen balloon, stirred at room temperature for 16 hours. It was filtered over Celite, rinsed five times with dichloromethane and methanol (200 mL), and spin-dried to give the title compound.

1H NMR (400 MHz, DMSO-d6): δ=6.67 (d, J=8.8 Hz, 2H), 6.48 (d, J=8.6 Hz, 2H), 4.54 (s, 2H), 2.93-2.80 (m, 4H), 2.46-2.36 (m, 4H), 2.19 (s, 3H).

Step C: 7-(1-Phenyl-1H-pyrazol-4-yl)-1-methyl-3((4-(4-m ethylpiperazin-1-yl)phenyl)amino)quinoxaline-2(1H)-one 4-(4-Methylpiperazin-1-yl)amine (48.39 mg, 253.00 μmol) and DIEA (98.09 mg, 759.00 μmol) were added to a solution of 7-(1-phenyl pyrazol-4-yl)-3-bromo-1-methyl-quinoxalin-2-one (100.00 mg, 253.00 μmol) in isopropanol (3 mL), and it was stirred under nitrogen for 16 hours at 115° C. The reaction solution was cooled to room temperature, with a solid precipitated, then filtered. The filter cake was rinsed with ethanol (5 mL), and then spin-dried to give the title compound.

1H NMR (400 MHz, DMSO-d6) δ=9.26 (s, 1H), 8.41 (s, 1H), 8.06 (s, 1H), 7.97 (d, J=8.8 Hz, 2H), 7.58 (s, 1H), 7.50-7.43 (m, 2H), 7.37-7.28 (m, 5H), 6.94 (d, J=8.8 Hz, 2H), 5.36 (s, 2H), 3.74 (s, 3H), 3.10 (br. s., 4H), 2.46 (br. s., 4H), 2.22 (s, 3H).

Step D: 1-Methyl-3((4-(4-methylpiperazin-1-yl) phenyl)amino)-7-(1H-pyrazol-4-yl) quinoxaline-2(1H)-one A solution of potassium tert-butoxide in tetrahydrofuran (1M, 71.02 mg, 632.88 μmol) was added to a solution of 7-(1-phenyl-1H-pyrazol-4-yl)-1-methyl-3((4-(4-methylpiperazin-1-yl)phenyl)amino)quinoxaline-2(1H)-one (40.00 mg, 79.11 μmol) in dimethyl sulfoxide (3 mL) at room temperature. It was replaced three times with oxygen balloon at room temperature and stirred for another 16 hours. Water (15 mL) was added to the reaction solution and extracted twice with ethyl acetate (15 mL). The organic phase was washed twice with saturated brine (20 mL), dried over anhydrous sodium sulfate, and filtered. The residue which was obtained by concentrating under reduced pressure was prepared and separated (trifluoroacetic acid) to give the title compound 33.

1H NMR (400 MHz, DMSO-d6) δ=9.35 (s, 1H), 8.20 (s, 2H), 8.04 (d, J=9.0 Hz, 2H), 7.62 (s, 1H), 7.56-7.51 (m, 1H), 7.45 (d, J=8.4 Hz, 1H), 7.02 (d, J=8.8 Hz, 2H), 3.81 (d, J=13.2 Hz, 2H), 3.76 (s, 3H), 3.53 (d, J=11.7 Hz, 2H), 3.18 (d, J=10.8 Hz, 2H), 2.97-2.86 (m, 5H).

MS-ESI (m/z): 416 (M+H)+.

Example 34: 1-Methyl-3-((4-((4-methylpiperazin-1-yl)sulfonyl)phenyl)amino)-7-(1H-pyrazol-4-yl)quinoxaline-2(1H)-one 1H NMR (400 MHz, DMSO-d6): δ=8.44 (d, J=8.8 Hz, 2H), 8.00 (d, J=8.8 Hz, 2H), 2.96 (br. s, 4H), 2.36 (t, J=4.4 Hz, 4H), 2.13 (s, 3H).

Step B: 4-((4-Methylpiperazin-1-yl)sulfonyl)aniline

To a solution of 1-methyl-4-((4-nitrophenyl)sulfonyl)piperazine (3.70 g, 12.97 mmol) in methanol (50.00 mL) was added Pd/C (800 mg). The reaction solution was stirred under a hydrogen balloon (15 Psi) at 15° C. for 2 hours. The reaction solution was filtered, and the filtrate was concentrated to give the title compound.

1H NMR (400 MHz, DMSO-d6): δ=7.33 (d, J=8.5 Hz, 2H), 6.64 (d, J=8.5 Hz, 2H), 6.08 (s, 2H), 2.78 (br. s., 4H), 2.34 (br. s., 4H), 2.13 (s, 3H).

Step C: 7-(1-Benzyl-1 AA-pyrazol-4-yl)-1-methyl-3-((4-((4-methylpiperazin-1-yl)sulfonyl)phenyl)amino))quinoxaline-2(1H)-one The preparation of the step C in Example 34 could be referring to the preparation method of the step C in Example 33.

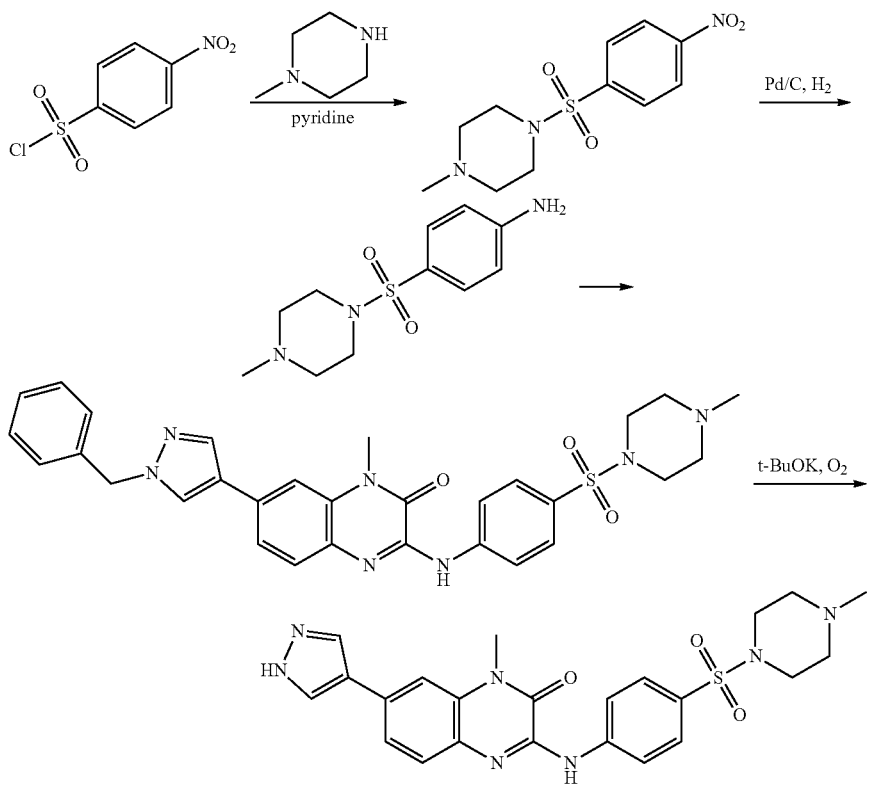

Step A: 1-Methyl-4-((4-nitrophenyl)sulfonyl)piperazine

At 0° C., to 1-methylpiperazine (4.52 g, 45.12 mmol) in pyridine (40 mL) was added a solution of 4-nitrobenzenesulfonyl chloride (10.00 g, 45.12 mmol) in pyridine (20 mL_). The reaction solution was stirred at 0-20° C. for 2 hours. Quenched with water (200 mL), and the precipitated solid was filtered. The filter cake was recrystallized from dichloromethane/methanol (22 mL, 10/1) to give the title compound.

1H NMR (400 MHz, DMSO-d6) δ=9.95 (s, 1H), 8.51-8.42 (m, 2H), 8.10 (s, 1H), 7.73-7.63 (m, 3H), 7.59 (d, J=2.6 Hz, 2H), 7.42-7.24 (m, 5H), 5.38 (s, 2H), 3.77 (s, 3H), 2.88 (br. s., 4H), 2.36 (br. s., 4H), 2.13 (s, 3H).

Step D: 1-Methyl-3-((4-((4-methylpiperazin-1-yl)sulfonyl)phenyl)amino)-7-(1H-pyrazol-4-yl)quinoxaline-2(1H)-one The preparation of the step D in Example 34 could be referring to the preparation method of the step D in Example 33.

1H NMR (400 MHz, DMSO-d6) δ=10.02 (s, 1H), 9.45-9.34 (m, 1H), 8.51 (d, J=8.8 Hz, 2H), 8.24 (br. s., 2H), 7.76 (d, J=8.4 Hz, 2H), 7.69 (s, 1H), 7.64-7.56 (m, 2H), 3.79 (s, 5H), 3.16 (br. s., 6H), 2.79 (s, 3H).
MS-ESI (m/z): 480.2 (M+H)+.

Example 35: 3-((4-(1,1-Dioxothiomorpholine)phenyl)amino)-1-methyl-7-(1H-pyrazol-4-yl)quinoxaline-2(1H)-one

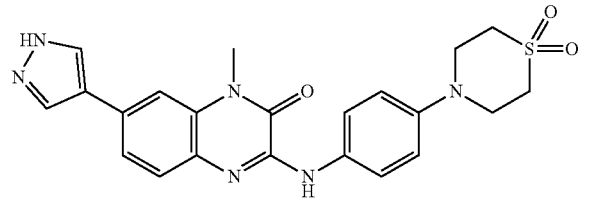 [SMILES: Cn1c(=O)c(Nc2ccc(N3CCS(=O)(=O)CC3)cc2)nc2ccc(-c3cn[nH]c3)cc21]

The preparation of Example 35 could be obtained by referring to the preparation method of Example 33.
1H NMR (400 MHz, DMSO-d6) δ=12.97 (br s, 1H), 9.33 (s, 1H), 8.32 (s, 1H), 8.04 (br d, J=9.0 Hz, 3H), 7.61 (d, J=1.3 Hz, 1H), 7.56-7.51 (m, 1H), 7.47-7.43 (m, 1H), 7.05 (d, J=9.3 Hz, 2H), 3.75 (s, 7H), 3.14 (br s, 4H).
LCMS (ESI) m/z: 451 (M+1).

Example 36: 3-((4-(4-(Ethylsulfonyl)piperazin-1-yl)phenyl)amino)-1-methyl-7-(1H-pyrazol-4-yl)quinoxaline-2(1H)-one

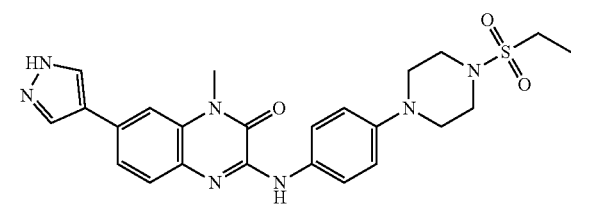 [SMILES: CCS(=O)(=O)N1CCN(c2ccc(Nc3nc4ccc(-c5cn[nH]c5)cc4n(C)c3=O)cc2)CC1]

The preparation of Example 36 could be obtained by referring to the preparation method of Example 33.
1H NMR (400 MHz, DMSO-d6) δ=9.35 (s, 1H), 8.20 (s, 2H), 8.01 (d, J=8.8 Hz, 2H), 7.61 (s, 1H), 7.54 (d, J=8.0 Hz, 1H), 7.46 (d, J=8.0 Hz, 1H), 7.01 (d, J=8.0 Hz, 2H), 3.75 (s, 3H), 3.33 (brs, 4H), 3.19 (brs, 4H), 3.10-3.22 (m, 2H), 1.22-1.26 (m, 3H).
LCMS (ESI) m/z: 494.1 (M+1).

Example 37: 1-Methyl-3-((4-(4-methyl-1,4-diazepan-1-yl)phenyl)amino)-7-(1H-pyrazol-4-yl)quinoxaline-2(1H)-one

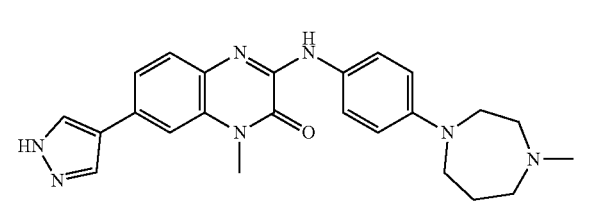 [SMILES: CN1CCCN(c2ccc(Nc3nc4ccc(-c5cn[nH]c5)cc4n(C)c3=O)cc2)CC1]

The preparation of Example 37 could be obtained by referring to the preparation method of Example 33.
1H NMR (400 MHz, DMSO-d6) δ=9.35 (s, 1H), 8.20 (s, 2H), 8.04 (d, J=9.0 Hz, 2H), 7.62 (s, 1H), 7.56-7.51 (m, 1H), 7.45 (d, J=8.4 Hz, 1H), 7.02 (d, J=8.8 Hz, 2H), 3.80 (br, 5H), 3.52-3.65 (m, 4H), 3.32-3.39 (m, 2H), 2.95 (s, 3H), 2.25-2.29 (m, 2H).
MS-ESI (m/z): 429 (M+H)+.

Example 38: 1-Methyl-3-((4-(piperidin-1-ylsulfonyl)phenyl)amino)-7-(1H-pyrazol-4-yl)quinoxaline-2(1H)-one

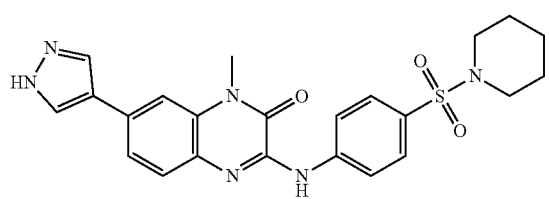 [SMILES: Cn1c(=O)c(Nc2ccc(S(=O)(=O)N3CCCCC3)cc2)nc2ccc(-c3cn[nH]c3)cc21]

The preparation of Example 38 could be obtained by referring to the preparation method of Example 34.
1H NMR (400 MHz, DMSO-d6) δ=9.93 (s, 2H), 8.45 (d, J=8.6 Hz, 2H), 8.24 (br. s., 1H), 7.74-7.53 (m, 5H), 3.78 (s, 3H), 2.87 (br. s., 4H), 1.54 (br. s., 4H), 1.35 (br. s., 2H).

Example 39: 1-Methyl-3-((4-(piperazin-1-yl)phenyl)amino)-7-(1H-pyrazol-4-yl)quinoxaline-2(1H)-one

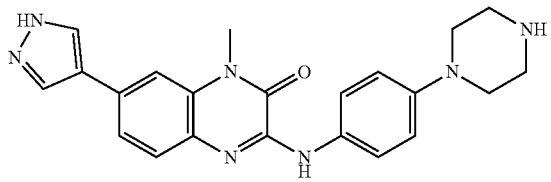 [SMILES: Cn1c(=O)c(Nc2ccc(N3CCNCC3)cc2)nc2ccc(-c3cn[nH]c3)cc21]

The preparation of Example 39 could be obtained by referring to the preparation method of Example 33.
1H NMR (400 MHz, DMSO-d6) δ=9.35 (s, 1H), 8.76 (s, 2H), 8.20 (s, 2H), 8.03 (d, J=8.8 Hz, 2H), 7.62 (s, 1H), 7.54 (d, J=8.4 Hz, 1H), 7.45 (d, J=8.0 Hz, 1H), 7.01 (d, J=8.8 Hz, 2H), 3.75 (s, 3H), 3.28 (d, J=16.0 Hz, 8H).
LCMS (ESI) m/z: 402.1 (M+1).

Example 40: 1-Methyl-3-((3-(4-(methylsulfonyl)piperazin-1-yl)phenyl)amino)-7-(1H-pyrazol-4-yl)quinoxaline-2(1H)-one

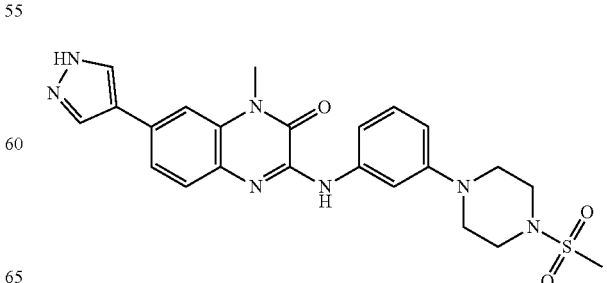

The preparation of Example 40 could be obtained by referring to the preparation method of Example 33.

1H NMR (400 MHz, DMSO-d6) δ=12.99 (br. s., 1H), 9.28 (br. s., 1H), 8.34 (br. s., 1H), 8.07 (br. s., 1H), 7.87 (br. s., 1H), 7.70 (d, J=7.7 Hz, 1H), 7.64 (br. s., 1H), 7.54 (br. s., 2H), 7.21 (t, J=8.0 Hz, 1H), 6.69 (d, J=7.5 Hz, 1H), 3.76 (s, 3H), 3.33 (s, 8H), 2.94 (s, 3H).

Example 41: 5-Chloro-1-methyl-3-((4-morpholine-phenyl)amino)-7-(1H-pyrazol-4-yl)quinoxaline-2 (1H)-one

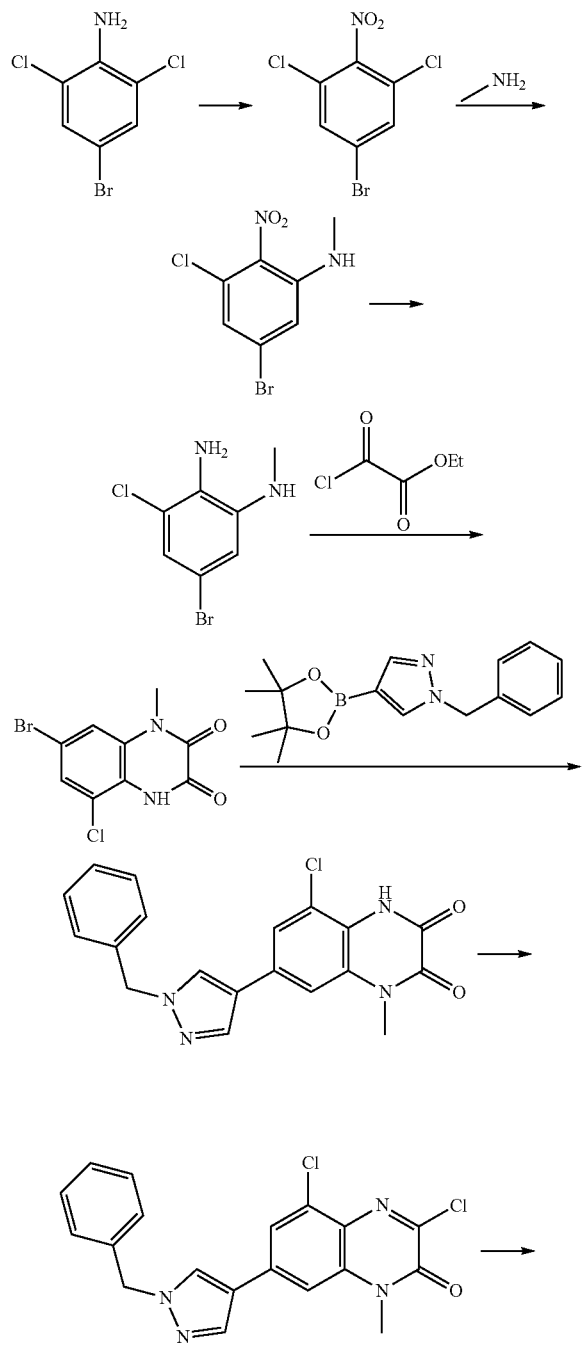

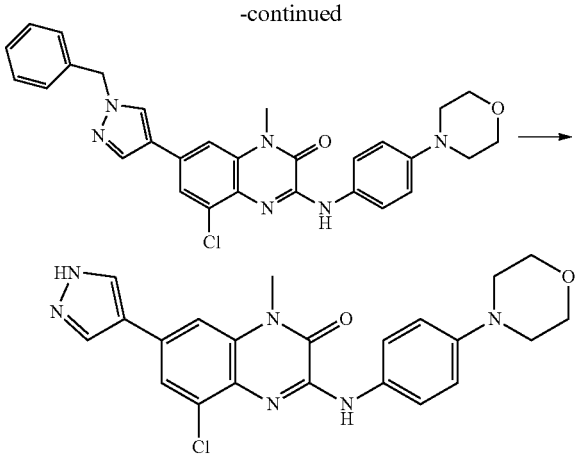

Step A: 5-Bromo-1,3-dichloro-2-nitrobenzene

To a solution of 4-bromo-2,6-dichloro-aniline (10 g, 41.51 mmol) in dichloroethane (250 mL) was added 80% m-chloroperoxybenzoic acid (35.82 g, 166 mmol) in portions at 20° C., and after it was stirred at room temperature for one hour, heated to 70° C. for reacting for 8 hours. TLC showed that the raw materials were reacted completely. Cooling down, and after it was quenched by slowly adding a saturated aqueous solution of sodium thiosulfate (350 mL) to the reaction solution, extracted by adding 280 mL dichloromethane. The organic phase was washed with 2M aqueous sodium hydroxide solution (150 mL) and saturated brine, dried over anhydrous sodium sulfate, filtered, and spin-dried to give the title compound 5-bromo-1,3-dichloro-2-nitrobenzene.

Step B: 5-Bromo-3-chloro-N-methyl-2-nitrobenzene

At 0° C., to a solution of 5-bromo-1,3-dichloro-2-nitrobenzene (6 g, 22.15 mmol) in DMF (150 mL) was added triethylamine (3.07 mL, 22.15 mmol) and methylamine solution (2M, 22.15 mL, 44.3 mmol) separately, and after stirring at room temperature for one hour it was heated to 50° C. for 6 hours.

TLC showed that the raw materials were reacted completely. Cooling down, and the reaction solution was extracted by adding water (100 mL) and ethyl acetate (150 mL). The organic phase was washed with saturated brine, dried over anhydrous sodium sulfate, filtered, and spin-dried to give the title compound 5-bromo-3-chloro-N-methyl-2-nitrobenzene.

Step C: 5-Bromo-3-chloro-N1-toluene-1,2-diamine

To a solution of 5-bromo-3-chloro-N-methyl-2-nitrobenzene (2.5 g, 22.15 mmol) in ethanol (50 mL) and water (50 mL) were added iron powder (3.16 g, 56.5 mmol) and acetic acid (0.56 g, 9.42 mmol) in portions, and after it was stirred at room temperature for one hour, heated to 60° C. for 4 hours. TLC showed that the raw materials were reacted completely. Cooling down, filtration, and the filtrate was extracted three times by adding ethyl acetate (150 mL). The organic phase was washed with saturated brine, dried over anhydrous sodium sulfate, filtered, and spin-dried to give the title compound 5-bromo-3-chloro-N1-toluene-1,2-diamine.

Step D: 7-Bromo-5-chloro-1-methylquinoxaline-2,3 (1H,4H)-dione

To a solution of 5-bromo-3-chloro-N1-toluene-1,2-diamine (1.2 g, 5.1 mmol) in 1,2-dichloroethane (130.00 mL) were added triethylamine (0.52 g, 5.1 mmol) and ethyl-2-chloro-2-oxoacetate (1.04 g, 7.65 mmol) at 0° C. After stirring at 15° C. for 12 hours, TLC showed that the raw materials were reacted completely. The reaction solution was concentrated and washed twice with ethyl acetate (20 mL) to give 7-bromo-5-chloro-1-methylquinoxaline-2,3 (1H, 4H)-dione.

1H NMR (DMSO-d6, 400 MHz): d=11.56 (br. s., 1H), 7.55 (dd, J=12.3, 1.8 Hz, 2H), 3.50 ppm (s, 3H).

Step E: 7-(1-Benzyl-1H-pyrazol-4-yl)-5-chloro-1-methylquinoxaline-2,3(1H, 4H)-dione To a solution of 7-bromo-5-chloro-1-methylquinoxaline-2,3(1H,4H)-dione (3.50 g, 12.09 mmol) and 1-benzyl-4-(4,4,5,5-tetramethyl-1,3,2-dioxaborolan-2-yl)pyrazole (3.78 g, 13.3 mmol) in DMF (20 mL), dioxane (20.00 mL) and water (10.00 mL) were added Pd(dppf)Cl$_2$ (0.88 mg, 1.21 mmol) and potassium carbonate (5.01 g, 36.27 mmol). After stirring at 100° C. for 2 hours, TLC showed that the raw materials were reacted completely. After the reaction solution was concentrated, dichloromethane (100 mL) and water (50 mL) were added. The aqueous phase was extracted three times with 100 mL dichloromethane. The organic phase was washed with saturated brine, dried over anhydrous sodium sulfate, and filtered. After spin-drying, 7-(1-benzyl-1H-pyrazol-4-yl)-5-chloro-1-methylquinoxaline-2,3(1H,4H)-dione was obtained by silica gel column chromatography.

1H NMR (CHLOROFORM-d, 400 MHz): d=9.12 (br. s., 1H), 7.82 (s, 1H), 7.67 (s, 1H), 7.34-7.44 (m, 4H), 7.29-7.32 (m, 2H), 7.18 (d, J=1.5 Hz, 1H), 5.37 (s, 2H), 3.71 ppm (s, 3H).

Step F: 7-(1-Benzyl-1H-pyrazol-4-yl)-3,5-dichloro-1-methylquinoxaline-2(1H)-one To a solution of 7-(1-benzyl-1H-pyrazol-4-yl)-5-chloro-1-methylquinoxaline-2,3(1H,4H)-dione (1.2 g, 3.27 mmol) in toluene (35.00 mL) were added N,N-dimethylethylenediamine (0.43 g, 3.27 mmol) and phosphorus oxychloride (1 g, 6.54 mmol) at 0° C. After stirring at 100° C. for 3 hours, TLC showed that the raw materials were reacted completely. Cooling to 0° C., and after the reaction solution was quenched by slowly adding a saturated aqueous solution of sodium hydrogencarbonate (200 mL), it was extracted by adding dichloromethane (120 mL). The organic phase was washed with saturated brine, dried over anhydrous sodium sulfate, and filtered. After spin-drying, the target compound 7-(1-benzyl-1H-pyrazol-4-yl)-3,5-dichloro-1-methylquinoxaline-2(1H)-one was obtained.

1H NMR (CHLOROFORM-d, 400 MHz): d=7.90 (s, 1H), 7.74 (s, 1H), 7.55 (d, J=1.3 Hz, 1H), 7.34-7.44 (m, 3H), 7.30 (d, J=6.5 Hz, 2H), 7.23 (d, J=1.3 Hz, 1H), 5.38 (s, 2H), 3.79 ppm (s, 3H).

Step G: 7-(1-Benzyl-1H-pyrazol-4-yl)-5-chloro-1-methyl-3-((4-morpholinephenyl) amino)quinoxaline-2(1H)-one At 20° C. a solution of 7-(1-benzyl-1H-pyrazol-4-yl)-3,5-dichloro-1-methylquinoxaline-2(1H)-one (700.00 mg, 1.82 mmol) and 4-morpholine aniline (647 mg, 3.63 mmol) in acetonitrile (5.00 mL) was stirred. The reaction solution was stirred at 100° C. for 4 hours. After the reaction solution was concentrated, it was extracted three times by adding 1M hydrochloric acid (50 mL) and dichloromethane DCM (50 mL) separately. The organic phase was washed with saturated brine, dried over anhydrous sodium sulfate, and filtered. After spin-drying, the target compound 7-(1-benzyl-1H-pyrazol-4-yl)-5-chloro-1-methyl-3-((4-morpholinephenyl)amino)quinoxaline-2(1H)-one was obtained.

MS-ESI (m/z): 527.0 (M+H).

Step H: 5-Chloro-1-methyl-3-((4-morpholinephenyl) amino)-7-(1H-pyrazol-4-yl)quinoxaline-2(1H)-one To a solution of 7-(1-benzyl-1H-pyrazol-4-yl)-5-chloro-1-methyl-3-((4-morpholinephenyl) amino)quinoxaline-2(1H)-one (100.00 mg, 189.75 μmol) in DMSO (5.00 mL) was added a solution of potassium t-butoxide in THF (127.75 mg, 1.14 mmol) at 20° C. and it was stirred for one hour in oxygen. LCMS showed that the raw materials were reacted completely. After the reaction solution was concentrated, it was poured into 10 mL water, and extracted three times with 15 mL ethyl acetate. The organic phase was washed with saturated brine, dried over anhydrous sodium sulfate, and after spin-drying it was prepared and separated (trifluoroacetic acid system) to give 5-chloro-1-methyl-3-((4-morpholinephenyl)amino)-7-(1H-pyrazol-4-yl)quinoxaline-2(1H)-one (Compound 41).

1H NMR (DMSO-d6, 400 MHz): d=9.89 (br. s., 1H), 8.44 (d, J=8.0 Hz, 2H), 8.33 (s, 2H), 7.80 (s, 1H), 7.63 (br. s., 3H), 4.02 (br. s., 4H), 3.76 (s, 3H), 3.48 ppm (br. s., 4H).

MS-ESI (m/z): 437.1 (M+H).

Example 42: 6-Chloro-1-methyl-3-((4-morpholinephenyl)amino)-7-(1H-pyrazol-4-yl)quinoxaline-2 (1H)-one

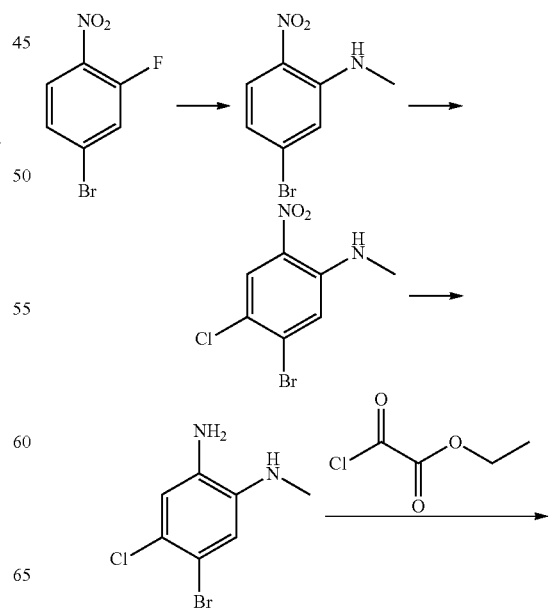

85

-continued

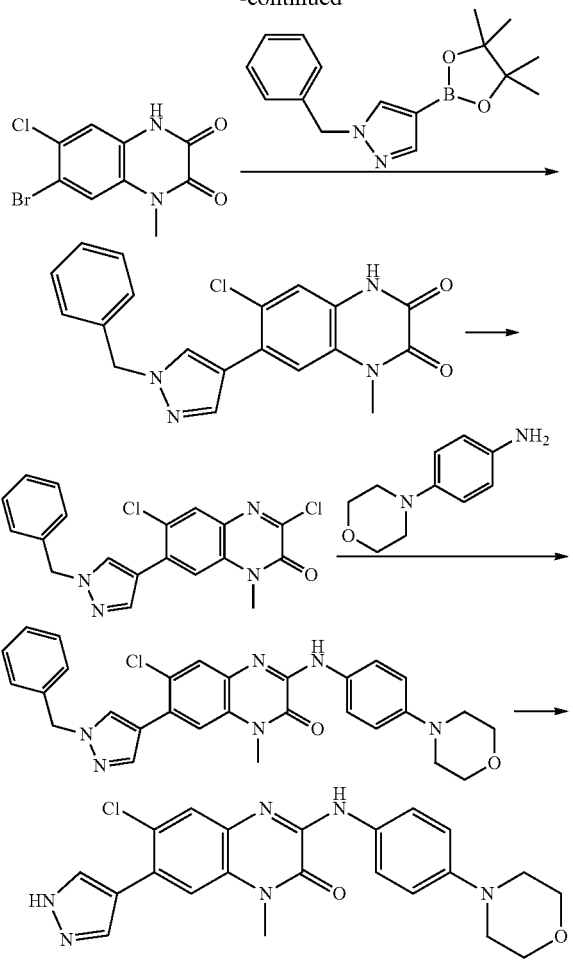

Step A: 5-Bromo-N-methyl 2-nitroaniline

To a solution of 5-bromo-N-methyl 2-nitroaniline (30 g, 136.36 mmol), potassium carbonate (28.27 g, 204.54 mmol) in DMF (500 mL) was added dropwise a solution of methylamine in tetrahydrofuran (2M, 81.82 mL) at 0° C. under nitrogen, and after stirring at 25° C. for 2 hours, the reaction solution was poured into ice water (1000 mL), with stirring for 10 minutes, filtration, and the filter cake was washed with water (50 mL×2) to provide the title compound.

1H NMR (400 MHz, CHLOROFORM-d) δ=8.03 (d, J=9.0 Hz, 2H), 7.01 (d, J=1.3 Hz, 1H), 6.77 (dd, J=1.7, 9.2 Hz, 1H), 3.02 (d, J=5.1 Hz, 3H).

Step B: 5-Bromo-4-chloro-N-methyl-2-nitroaniline

At 25° C., Example 42A (20 g, 86.56 mmol), NCS (11.79 g, 88.29 mmol) in DMF (300 mL), it was reacted at 40° C. for 18 hours, and the aqueous layer was diluted with water (500 mL) then extracted with ethyl acetate (500 mL×2). After the combined organic layers were washed with brine (1000 mL), dried over sodium sulfate, filtered and evaporated. The residue was purified by column chromatography to give the title compound.

1H NMR (400 MHz, CHLOROFORM-d) δ=7.94 (br. s., 1H), 7.26 (s, 1H), 7.15 (s, 1H), 3.02 (d, J=5.1 Hz, 3H).

86

Step C: 5-Bromo-4-chloro-N1-methylbenzene-1,2-diamine

To a solution of Example 42B (4 g, 15.07 mmol) in ethanol (80 mL) were added zinc powder (4.93 g, 75.33 mmol) and amine formate (4.75 g, 75.33 mmol) at 25° C. under nitrogen, after it was stirred at 50° C. for 2 hours, the reaction solution was filtered, and the filter cake was washed with dichloromethane (100 mL). The filtrate was washed with water (50 mL). The organic layer was washed with saturated brine (100 mL), then dried over sodium sulfate, filtered and evaporated to provide the title compound.

1H NMR (400 MHz, CHLOROFORM-d) δ=6.78 (s, 2H), 3.40-3.30 (m, 2H), 2.83 (s, 3H).

Step D: 7-Bromo-6-chloro-1-methylquinoxaline-2,3 (1H,4H)-dione

At 0° C., to Example 42O (3.4 g, 14.44 mmol), triethylamine (3.65 g, 36.10 mmol) in 1,2-dichloroethane (60 mL) was added dropwise ethyl 2-chloro-2-oxo-acetate (2.37 g, 17.33 mmol), and it was reacted at 25° C. for 2 hours. After a white solid is formed, it is reacted at 60° C. for 3 hours. The reaction solution was filtered, and the filter cake was washed with water (50×2 mL), then evaporated under reduced pressure to give the title compound.

1H NMR (400 MHz, DMSO-d6) δ=12.08 (br. s., 1H), 7.66 (s, 1H), 7.26 (s, 1H), 3.46 (s, 3H).

Step E: 7-(1-Benzyl-1H-pyrazol-4-yl)-6-chloro-1-methylquinoxaline-2,3(1H, 4H)-dione Under a protection of nitrogen, Example 42D (1 g, 3.45 mmol), 1-benzyl-4-(4,4,5,5-tetramethyl 1,3,2-dioxaborolan-2-yl) pyrazole (1.08 g, 3.8 mmol), Pd(dppf)Cl₂ (282.08 mg, 345.41 μmol), potassium carbonate (954.79 mg, 6.91 mmol) in DMF (15.00 mL), dioxane (15.00 mL) and water (5.00 mL), the mixture was stirred at 100° C. for 5 hours. It was cooled to room temperature, diluted with water (100 mL), and filtered. The filter cake was purified by column chromatography to give the title compound.

1H NMR (400 MHz, DMSO-d6) δ=1 2.06 (s, 1H), 8.36 (s, 1H), 7.95 (s, 1H), 7.43 (s, 1H), 7.38-7.26 (m, 5H), 7.22 (s, 1H), 5.38 (s, 2H), 3.53 (s, 3H).

Step F: 7-(1-Benzyl-1H-pyrazol-4-yl)-3,6-dichloro-1-methylquinoxaline-2(1H)-one To a solution of Example 42E (900 mg, 2.45 mmol) and DIEA (265.98 mg, 2.06 mmol) in toluene (9 mL) was added phosphorus oxychloride (589.78 g, 3.85 mmol) at 0° C. under nitrogen, and after it was stirred at 110° C. for 2 hours, the reaction solution was poured slowly into an aqueous solution of sodium hydrogencarbonate (50 mL), with stirring for 10 minutes, and extracted with dichloromethane (50 mL×2). The organic layer was washed with saturated brine (100 mL), then dried over sodium sulphate, filtered and evaporated, and purified by column chromatography to give the title compound.

1H NMR (400 MHz, DMSO-d6) δ=8.56 (s, 1H), 8.12 (s, 1H), 7.92 (s, 1H), 7.69 (s, 1H), 7.39-7.33 (m, 2H), 7.33-7.26 (m, 3H), 5.41 (s, 2H), 3.69 (s, 3H).

Step G: 7-(1-Benzyl-1H-pyrazol-4-yl)-6-chloro-1-methyl-3-((4-morpholinephenyl) amino)quinoxaline-2(1H)-one Under a protection of nitrogen, Example 42F (100 mg, 259.57 μmol), 4-morpholine aniline (92.53 mg, 519.1 μmol)

in acetonitrile (2 mL), the mixture was reacted at 80° C. for 18 hours, and the reaction solution was evaporated under reduced pressure. The residue was purified by column chromatography to give the title compound.

1H NMR (400 MHz, DMSO-d6) δ=9.47 (s, 1H), 8.41 (s, 1H), 8.03-7.91 (m, 3H), 7.53 (d, J=11.2 Hz, 2H), 7.41-7.22 (m, 5H), 6.94 (d, J=9.0 Hz, 2H), 5.40 (s, 2H), 3.79-3.66 (m, 7H), 3.11-3.02 (m, 4H).

Step H: 6-Chloro-1-methyl-3-((4-morpholinephenyl)amino)-7-(1H-pyrazol-4-yl)quinoxaline-2(1H)-one Under a protection of nitrogen, Example 42G (80 mg, 151.80 μmol), t-BuOK (1M, 1.06 mL), DMSO (1.00 mL), and the mixture was stirred at 25° C. for 4 hours. The reaction solution was diluted by pouring it into ice water (10 mL), with stirring for 10 minutes, and it was adjusted to pH 8 with 1M hydrochloric acid. Extraction with dichloromethane (10 mL×2), and the organic layer was washed with saturated brine (20 mL), then dried over sodium sulfate, filtered and evaporated. The residue was purified by preparative HPLC to give the title compound 42.

LCMS (ESI) m/z: 437.1 (M+1).

1H NMR (400 MHz, DMSO-d6) δ=9.48 (s, 1H), 8.10 (s, 2H), 7.98 (d, J=8.8 Hz, 2H), 7.51 (d, J=13.5 Hz, 2H), 6.96 (d, J=8.8 Hz, 2H), 3.73 (br. s., 4H), 3.69 (s, 3H), 3.08 (br. s., 4H).

Example 43: 8-Chloro-1-methyl-3-((4-morpholinephenyl)amino)-7-(1H-pyrazol-4-yl)quinoxaline-2(1H)-one

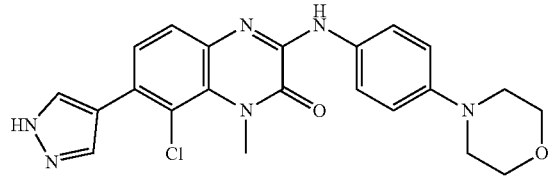 [SMILES: Cn1c(=O)c(Nc2ccc(N3CCOCC3)cc2)nc2ccc(-c3cn[nH]c3)c(Cl)c21]

The preparation of Example 43 could be obtained by referring to the preparation method of Example 42.

1H NMR (400 MHz, DMSO-d6) δ=9.53 (s, 1H), 8.06-7.94 (m, 4H), 7.43 (s, 2H), 7.01 (d, J=9.0 Hz, 2H), 3.90 (s, 3H), 3.76 (d, J=4.8 Hz, 4H), 3.15-3.10 (m, 4H).

LCMS (ESI) m/z: 437.1 (M+1).

Example 44: 5-Fluoro-1-methyl-3-((4-morpholinephenyl)amino)-7-(1H-pyrazol-4-yl)quinoline-2(1H)-one

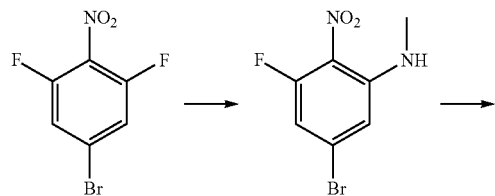

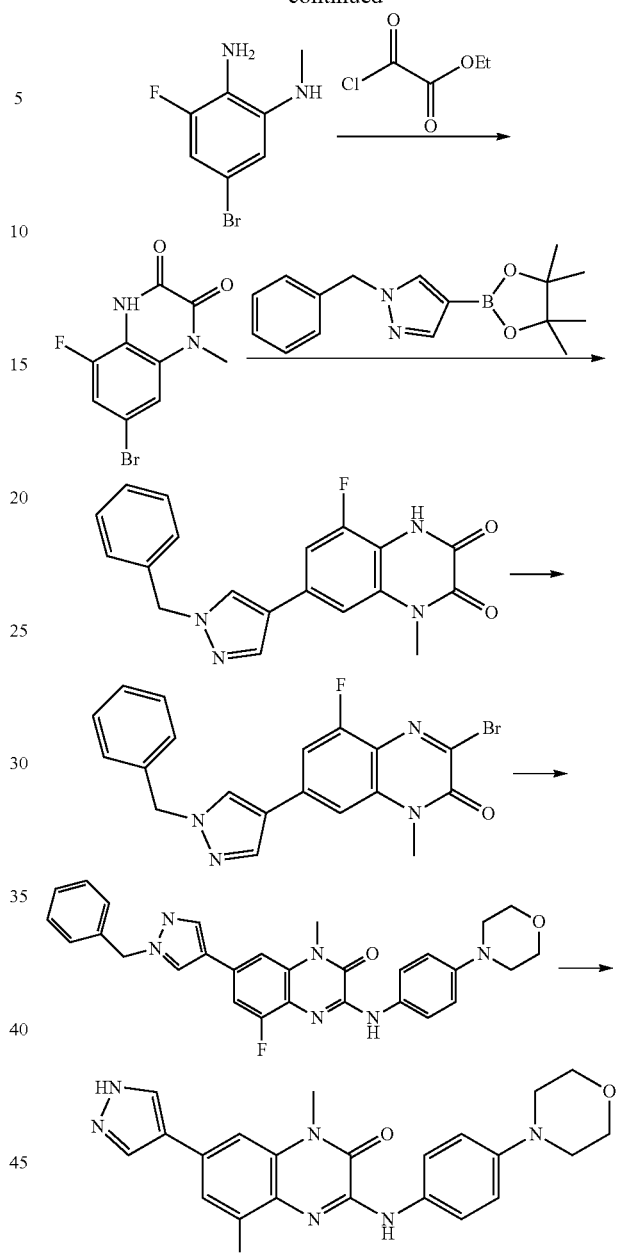

Step A: 5-Bromo-3-fluoro-N-methyl-2-nitrobenzene

Added Methylamine (21.01 mL, 2.0 mol/L) to a solution of 5-bromo-1,3-difluoro-2-nitrobenzene (10.00 g, 42.02 mmol) in DMF (100.00 mL) at 0° C. The reaction solution was stirred at 0° C. to room temperature for 16 hours. The reaction solution was poured into water (500.00 mL) and extracted twice with ethyl acetate (500.00 mL). The organic phase was washed twice with saturated brine (500 mL), dried over anhydrous sodium sulfate. The residue which obtained by spin-drying under reduced pressure was separated by column chromatography to give the title compound.

1H NMR (400 MHz, DMSO-d6) δ=7.56 (d, J=4.3 Hz, 1H), 6.93-6.85 (m, 2H), 2.86 (d, J=5.0 Hz, 3H).

Step B: 5-Bromo-3-fluoro-N1-methylbenzene-1,2-diamine

Added iron powder (11.17 g, 199.98 mmol) and acetic acid (2.00 g, 33.33 mmol) into a solution of 5-bromo-3-fluoro-N-methyl-2-nitrobenzene (8.30 g, 33.33 mmol) in ethanol (80 mL) and water (80 mL), and it was stirred at 60° C. for 3 hours. The reaction solution was filtered, and the filtrate was concentrated, then extracted three times with ethyl acetate (80.00 mL). The organic phase was washed twice with saturated brine (80 mL), dried over anhydrous sodium sulfate, with a solid precipitated, and filtered. The solid was spin-dried to give the title compound.

1H NMR (400 MHz, DMSO-d6) δ=6.69-6.47 (m, 1H), 6.36-6.18 (m, 1H), 5.27 (br. s., 1H), 4.54 (br. s., 2H), 2.78-2.61 (m, 3H).

Step C: 7-Bromo-5-fluoro-1-methylquinoxaline-2,3(1H,4H)-dione

At 0° C., under nitrogen, added dropwise ethyl oxalyl monochloride (4.36 g, 31.96 mmol) to a solution of 5-bromo-3-fluoro-N1-methylbenzene-1,2 diamine (7.00 g, 31.96 mmol) and triethylamine (8.08 g, 79.89 mmol) in 1,2-dichloroethane (70.00 mL), and it was reacted at room temperature for 2 hours, with a white solid precipitated, and then it was heated to 60° C. for stirring for 3 hours. The reaction solution was cooled to room temperature, and filtered. The filter cake was washed twice with water (40 mL), and the residue which was obtained by spin-drying of the filter cake was slurried with ethyl acetate to give the title compound.

Step D: 7-(1-Benzyl-1H-pyrazol-4-yl)-5-fluoro-1-methylquinoxaline-2,3(1H, 4H)-dione Under a protection of nitrogen, at room temperature, added 1-benzyl-4-benacol borate pyrazole (1.04 g, 3.66 mmol), potassium carbonate (1.01 g, 7.32 mmol) and Pd(dppf)Cl₂ (267.96 mg, 366.22 mmol, 1.01 mL) to a solution of 7-bromo-5-fluoro-1-methylquinoxaline-2,3(1H, 4H)-dione (1.00 g, 3.66 mmol) in dioxane (30 mL) and water (6 mL), and it was stirred at 100° C. for 4 hours under nitrogen. The reaction solution was cooled to room temperature, followed by the addition of water (100 mL) into it, and extracted twice with dichloromethane (100 mL). The organic phase was washed twice with saturated brine (100 mL), dried over anhydrous sodium sulfate, filtered, and spun to dryness. It was slurried with ethyl acetate to give the title compound.

1H NMR (400 MHz, DMSO-d6) δ=8.30 (s, 1H), 7.95 (s, 1H), 7.38-7.25 (m, 5H), 7.19-7.10 (m, 2H), 5.33 (s, 2H), 3.61-3.52 (m, 3H).

Step E: 7-(1-Benzyl-1H-pyrazol-4-yl)-3-bromo-5-fluoro-1-methylquinoxaline-2(1H)-one At 0° C., added phosphorusoxybromide (368.23 mg, 1.28 mmol) dropwise to a solution of 7-(1-benzyl-1H-pyrazol-4-yl)-5-fluoro-1-methylquinoxaline-2,3(1H, 4H)-dione (300.00 mg, 856.29 mol) and DIEA (88.53 g, 685.03 mol) in toluene (8 mL), and it was stirred at 110° C. for 1.5 hours under nitrogen. The reaction solution was filtered with Celite, followed by the addition of water (10 mL) into the filtrate, and extracted three times with ethyl acetate (10 mL). The organic phase was washed twice with saturated brine, dried over anhydrous sodium sulfate, filtered, and spin-dried to give the title compound.

1H NMR (400 MHz, CHLOROFORM-d) δ=8.62 (s, 1H), 8.23 (s, 1H), 7.62 (d, J=7.3 Hz, 1H), 7.56 (s, 1H), 7.37-7.29 (m, 5H), 5.42-5.33 (m, 2H), 3.70 (s, 3H).

Step F: 7-(1-Benzyl-1H-pyrazol-4-yl)-5-fluoro-1-methyl-3-((4-morpholinephenyl) amino)quinoxaline-2(1H)-one At room temperature, dissolved 7-(1-benzyl-1H-pyrazol-4-yl)-3-bromo-5-fluoro-1-methylquinoxaline-2(1H)-one (100 mg, 241.99 mmol) in toluene (5 mL), then added 4-morpholine aniline (51.76 mg, 290.39 μmol), cesium carbonate (236.54 mg, 725.97 μmol), Xphos (23.07 mg, 48.40 μmol) and Pd₂(dba)₃ (22.16 mg, 24.20 μmol) under nitrogen. It was stirred at 100° C. for 4 hours under nitrogen. The reaction solution was cooled to room temperature, followed by the addition of water (15 mL) into it, and extracted twice with dichloroethane (15 mL). The organic phase was washed twice with saturated brine (20 mL), dried over anhydrous sodium sulfate, and filtered. The residue which was obtained by concentrating under reduced pressure was separated by column chromatography to give the title compound.

1H NMR (400 MHz, DMSO-d6) δ=9.48 (d, J=6.8 Hz, 1H), 8.47 (d, J=6.8 Hz, 1H), 8.12-8.03 (m, 3H), 7.48-7.27 (m, 6H), 6.96 (br. s., 2H), 5.36 (d, J=6.0 Hz, 2H), 3.73 (d, J=6.5 Hz, 7H), 3.08 (br. s., 4H).

Step G: 5-Fluoro-1-methyl-3-((4-morpholinephenyl)amino)-7-(1H-pyrazol-4-yl)quinoxaline-2(1H)-one At room temperature, dissolved 7-(1-benzyl-1H-pyrazol-4-yl)-5-fluoro-1-methyl-3-((4-morpholinephenyl) amino) quinoxaline-2(1H)-one (30 mg, 58.76 μmol) in dimethyl sulfoxide (3 mL), and then added potassium t-butoxide (2 mol, 235.04 μL) under nitrogen.

Further, it was replaced three times with an oxygen balloon. It was stirred at 35° C. for 3 hours under oxygen. The reaction solution was slowly added dropwise into water (15 mL), and it was extracted twice with ethyl acetate (15 mL). The organic phase was washed twice with saturated brine (20 mL), dried over anhydrous sodium sulfate, and filtered. The residue which was obtained by concentrating under reduced pressure was prepared and separated (trifluoroacetic acid) to give the title compound 44.

1H NMR (400 MHz, DMSO-d6) δ=9.49 (br. s., 1H), 8.24 (s, 2H), 8.08 (d, J=8.5 Hz, 2H), 7.55-7.45 (m, 2H), 7.10-6.92 (m, 2H), 3.74 (br. s., 7H), 3.12 (br. s., 4H).

MS-ESI (m/z): 421 (M+H)⁺.

Example 45: 6-Fluoro-1-methyl-3-((4-morpholinephenyl)amino)-7-(1H-pyrazol-4-yl)quinoxaline-2(1H)-one

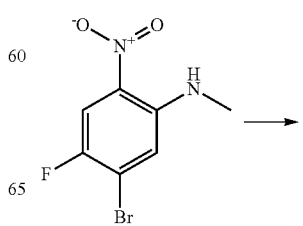

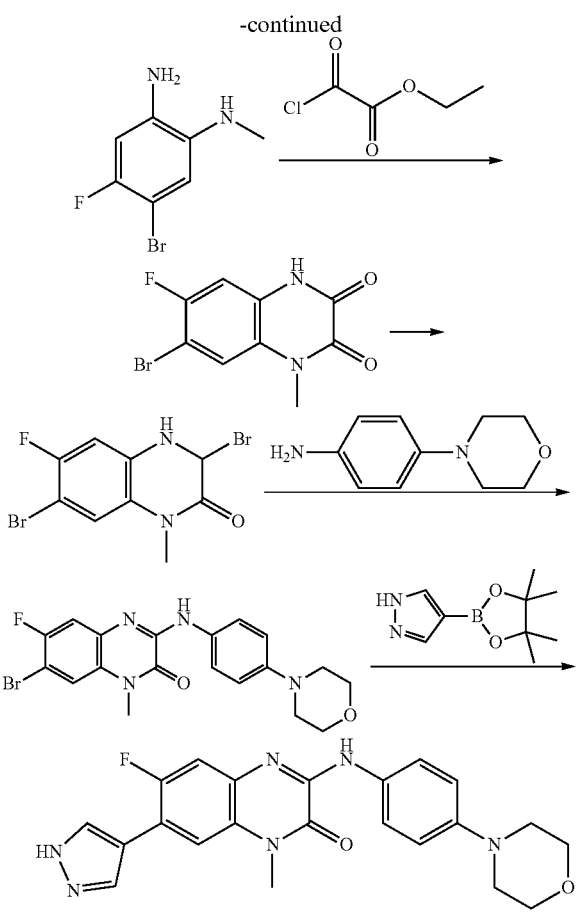

Step A:
5-Bromo-4-fluoro-N1-methyl-benzene-1,2-diamine

At 0° C. under nitrogen, to a solution of 4-bromo-5-fluoro-N2-methyl-benzene-1,2-diamine (6 g, 24.09 mmol) in ethanol (120 mL) were added zinc powder (7.88 g, 120.45 mmol) and amine formate (7.6 g, 120.45 mmol), and after it was stirred at 50° C. for 2 hours, the reaction solution was filtered. The filter cake was washed with dichloromethane (500 mL), and the filtrate was washed with water (200 mL). The organic layer was washed with saturated brine (500 mL), then dried over sodium sulfate, filtered and evaporated to provide the title compound.

Step B: 7-Bromo-6-fluoro-1-methylquinoxaline-2,3(1H,4H)-dione

At 0° C., to Example 45A (4.65 g, 21.23 mmol), triethylamine (5.37 g, 53.08 mmol) in 1,2-dichloroethane (120 mL) was added dropwise ethyl 2-chloro-2-oxo-acetate (3.48 g, 25.48 mmol), and it was reacted at 25° C. for 2 hours. After a white solid was formed, it was reacted at 60° C. for 2 hours. The reaction solution was filtered, and the filter cake was washed with water (50×2 mL), and then evaporated under reduced pressure to give the title compound.

LCMS (ESI) m/z: 273 (M+1).

1H NMR (400 MHz, DMSO-d6) δ=12.14 (s, 1H), 7.65 (d, J=6.3 Hz, 1H), 7.06 (d, J=9.0 Hz, 1H), 3.48 (s, 3H).

Step C: 3,7-Dibromo-6-fluoro-1-methyl-3,4-dihydroquinoxaline-2(1H)-one

Under a protection of nitrogen, after a mixture of Example 45B (2.4 g, 8.79 mmol), triethylamine (1.33 g, 13.18 mmol), phosphorusoxy bromide (7.56 g, 26.37 mmol) in 1,2-dichloroethane (50 mL) was stirred at 90° C. for 6 hours, the reaction mixture was poured slowly into the cold sodium hydrogencarbonate (300 mL), with stirring for 10 minutes, and the mixture was filtered. The filter cake was spin-dried under reduced pressure to give the title compound.

LCMS (ESI) m/z: 337 (M+1).

1H NMR (400 MHz, DMSO-d6) δ=8.01 (d, J=6.3 Hz, 1H), 7.89 (d, J=8.8 Hz, 1H), 3.65 (s, 3H).

Step D: 7-Bromo-6-fluoro-1-methyl-3-((4-morpholinephenyl)amino)quinoxaline-2(1H)-one Under a protection of nitrogen, a solution of Example 45C (1.95 g, 5.80 mmol), sodium acetate (1.43 g, 17.41 mmol), 4-morpholine aniline (1.24 g, 6.97 mmol) in isopropyl alcohol (30 mL), the mixture was reacted at 100° C. for 12 hours. The mixture was cooled to room temperature, and filtered to give the title compound.

1H NMR (400 MHz, DMSO-d6) δ=9.56 (s, 1H), 7.96 (br d, J=8.8 Hz, 2H), 7.73 (br d, J=6.0 Hz, 1H), 7.41 (br d, J=9.8 Hz, 1H), 6.94 (br d, J=8.8 Hz, 2H), 3.74 (br s, 4H), 3.67 (s, 3H), 3.08 (br s, 4H).

Step E: 6-Fluoro-1-methyl-3-((4-morpholinephenyl)amino)-7-(1H-pyrazol-4-yl)quinoxaline-2(1H)-one Under a protection of nitrogen, Example 45D (2.3 g, 5.31 mmol), 4-(4,4,5,5-tetramethyl 1,3,2-dioxaborolan-2-yl)-1H-pyrazole (1.55 g, 7.96 mmol), Pd(dppf)Cl₂ (388.43 mg, 530.85 μmol), potassium carbonate (2.2 mg, 15.93 mmol) in dioxane (40.00 mL) and water (10.00 mL), the mixture was stirred at 120° C. for 10 hours. It was cooled to room temperature, and the aqueous layer was diluted with water (100 mL) and extracted with dichloromethane (100 mL×3). After the combined organic layers were washed with brine (100 mL×2), dried over sodium sulfate, filtered and evaporated. The residue was purified by column chromatography to give the title compound 45.

1H NMR (400 MHz, DMSO-d6) δ=13.12 (br s, 1H), 9.40 (s, 1H), 8.27 (br s, 1H), 8.07 (br s, 1H), 7.97 (br d, J=9.0 Hz, 2H), 7.65 (d, J=7.0 Hz, 1H), 7.31 (d, J=12.0 Hz, 1H), 6.95 (br d, J=8.8 Hz, 2H), 3.75 (s, 7H), 3.10-3.06 (m, 4H). LCMS (ESI) m/z: 421 (M+1).

Example 46: 8-Fluoro-1-methyl-3-((4-morpholinephenyl)amino)-7-(1H-pyrazol-4-yl)quinoxaline-2(1H)-one

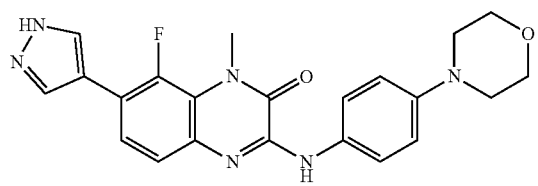 [SMILES: Cn1c(=O)c(Nc2ccc(N3CCOCC3)cc2)nc2ccc(-c3cn[nH]c3)c(F)c21]

The preparation of Example 46 could be obtained by referring to the preparation method of Example 44.

1H NMR (400 MHz, DMSO-d6) δ=9.48 (br. s., 1H), 8.08 (br. s., 2H), 8.00 (d, J=7.6 Hz, 2H), 7.58 (br. s., 1H), 7.30 (d, J=8.0 Hz, 1H), 7.01 (d, J=5.8 Hz, 2H), 3.90 (d, J=7.6 Hz, 7H), 3.13 (br. s., 4H).

MS-ESI (m/z): 421 (M+H)+.

Example 47: 3-((2-Fluoro-4-morpholinephenyl)amino)-1-methyl-7-(1H-pyrazol-4-yl)quinoxaline-2(1H)-one

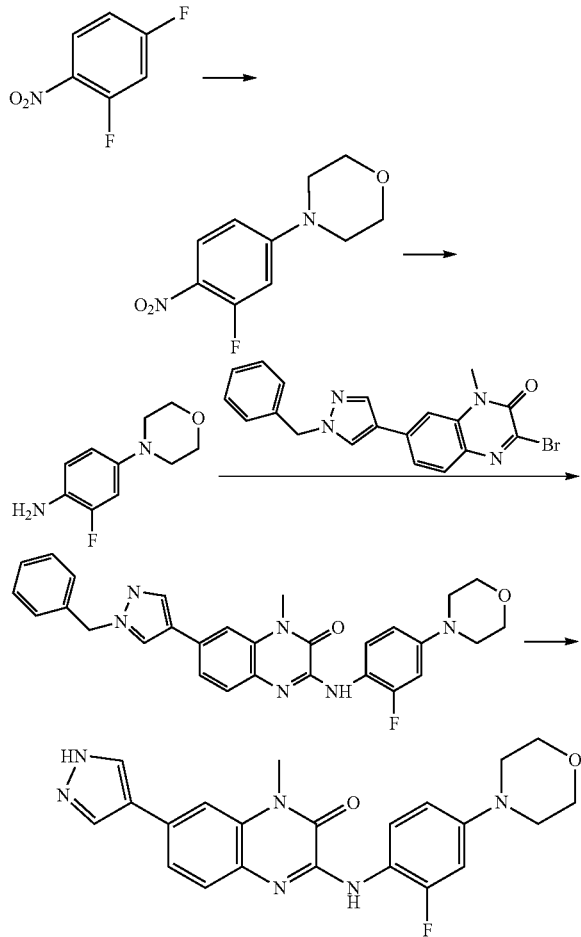

Step A: 4-(3-Fluoro-4-nitrophenyl)morpholine

Added potassium carbonate (9.87 g, 71.43 mmol) and morpholine (2.49 g, 28.57 mmol) to a solution of 2,4-difluoro-1-nitro-benzene (5.00 g, 31.43 mmol) in DMF (50 mL), and it was stirred at 80° C. for 2.5 hours. Further, added 1-methylpiperazine (7.17 g, 71.58 mmol) dropwise to the reaction solution, stirring at room temperature for 16 hours. The reaction solution was diluted with ethyl acetate (200 mL), washed three times with saturated brine (150 mL), dried over anhydrous sodium sulfate, filtered, and spin-dried to yield the residue, which was separated by column to give the title compound.

1H NMR (400 MHz, DMSO-d6) δ=8.02 (t, J=9.3 Hz, 1H), 6.96 (dd, J=2.5, 16.1 Hz, 1H), 6.87 (dd, J=2.5, 9.5 Hz, 1H), 3.76-3.68 (m, 4H), 3.48-3.41 (m, 4H).

Step B: 2-Fluoro-4-morpholine aniline

To a solution of 4-(3-fluoro-4-nitrophenyl)morpholine (1.00 g, 4.42 mmol) in methanol (20 mL) was added palladium carbon (517.41 mg, 486.20 μmol), and it was replaced three times with a hydrogen balloon and then stirred at room temperature for 3 hours. It was filtered with Celite and spin-dried to give the title compound.

1H NMR (400 MHz, DMSO-d6) δ=6.73-6.63 (m, 2H), 6.54 (dd, J=1.9, 8.4 Hz, 1H), 4.58 (s, 2H), 3.74-3.65 (m, 4H), 2.97-2.85 (m, 4H).

Step C: 7-(1-phenyl-1H-pyrazol-4-yl)-3-((2-fluoro-4-morpholinephenyl)amino)-1-methylquinoxaline-2(1H)-one Under a protection of nitrogen, to a solution of 7-(1-phenylpyrazol-4-yl)-3-bromo-1-methyl-quinoxalin-2-one (100.00 mg, 253.00 μmol) in dioxane (3 mL) were added 2-fluoro-4-morpholine-aniline (99.29 mg, 506.00 μmol), cesium carbonate (247.30 mg, 759.00 μmol), Xantphos (14.64 mg, 25.30 μmol) and Pd(OAc)2 (11.36 mg, 50.60 μmol)), and it was stirred under nitrogen for 16 hours at 110° C. The reaction solution was cooled to room temperature, filtered through Celite and spin-dried to give a residue. The residue was separated by column to give the title compound.

ES-ESI (m/z): 511 (M+H)+

Step D: 3-((2-Fuoro-4-morpholinephenyl)amino)-1-methyl-7-(1H-pyrazol-4-yl)quinoxaline-2(1H)-one At room temperature, added potassium tert-butoxide (1 mol, 1.65 mL) to a solution of 7-(1-phenyl-1H-pyrazol-4-yl)-3-((2-fluoro-4-morpholinephenyl)amino)-1-methylquinoxaline-2(1H)-one (120.00 mg, 235.04 μmol) in dimethyl sulfoxide (3 mL). It was replaced three times with an oxygen balloon at 35° C. and stirred for another 16 hours. A saturated aqueous ammonium chloride solution (50 mL) was added into the reaction solution which was extracted four times with dichloromethane to isopropyl alcohol (10:1) (50 mL). The residue which was obtained by concentrating under reduced pressure was prepared and separated (trifluoroacetic acid) to give the title compound 47.

1H NMR (400 MHz, DMSO-d6) δ=8.75 (s, 1H), 8.21 (s, 2H), 8.11 (t, J=9.0 Hz, 1H), 7.65 (s, 1H), 7.55 (d, J=8.5 Hz, 1H), 7.43 (d, J=8.0 Hz, 1H), 6.95 (dd, J=2.0, 14.1 Hz, 1H), 6.84 (d, J=8.5 Hz, 1H), 3.77-3.74 (m, 7H), 3.17-3.13 (m, 4H).

MS-ESI (m/z): 421.1 (M+H).

Example 48: 3-((3-Fluoro-4-morpholinephenyl)amino)-1-methyl-7-(1H-pyrazol-4-yl)quinoxaline-2(1H)-one

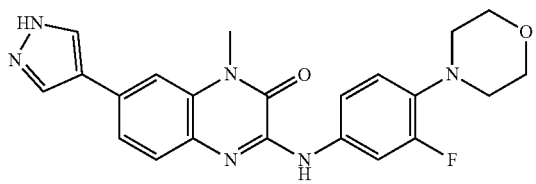 [SMILES: Cn1c(=O)c(Nc2ccc(N3CCOCC3)c(F)c2)nc2ccc(-c3cn[nH]c3)cc21]

The preparation of Example 48 could be obtained by referring to the preparation method of Example 47.

1H NMR (400 MHz, DMSO-d6) δ=9.52 (br. s., 1H), 8.18 (br. s., 2H), 8.09 (d, J=15.2 Hz, 1H), 7.86 (d, J=8.2 Hz, 1H), 7.60 (br. s., 1H), 7.54-7.46 (m, 2H), 7.00 (t, J=9.3 Hz, 2H), 3.72 (br. s., 7H), 2.94 (br. s., 4H).

MS-ESI (m/z): 421.2 (M+H).

Example 49: 1-Methyl-3-((3-fluoro-4-morpholine-phenyl)amino)-7-(1H-pyrazol-4-yl)quinoxaline-2(1H)-one

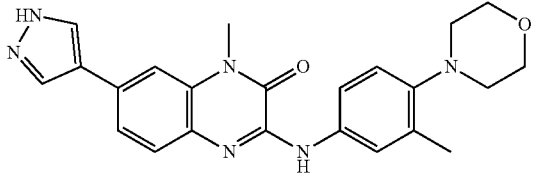

The preparation of Example 49 could be obtained by referring to the preparation method of Example 47.

1HNMR (400 MHz, DMSO-d6) δ=9.25 (s, 1H), 8.19 (s, 2H), 7.95 (d, J=8.6 Hz, 1H), 7.88 (br. s., 1H), 7.60 (s, 1H), 7.56-7.50 (m, 1H), 7.50-7.45 (m, 1H), 7.03 (d, J=8.6 Hz, 1H), 3.74 (s, 7H), 2.82 (br. s., 4H), 2.28 (s, 3H).

MS-ESI (m/z): 417.1 (M+H)⁺.

Example 50: 3-((3-Chloro-4-morpholinephenyl)amino)-1-methyl-7-(1H-pyrazol-4-yl)quinoxaline-2(1H)-one

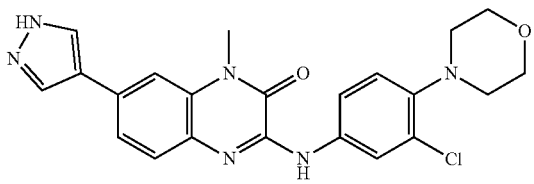

The preparation of Example 50 could be obtained by referring to the preparation method of Example 47.

1HNMR (400 MHz, DMSO-d6) δ=9.77-9.42 (m, 1H), 8.54-7.93 (m, 4H), 7.78-7.40 (m, 3H), 7.21 (br. s., 1H), 3.79 (br. s., 7H), 2.98 (br. s., 4H).

MS-ESI (m/z): 437.0 (M+H)⁺.

Example 51: 3-((3-Methoxy-4-morpholinephenyl)amino)-1-methyl-7-(1H-pyrazol-4-yl)quinoxaline-2(1H)one

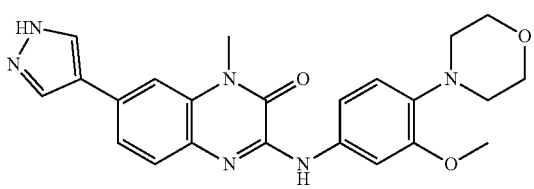 [SMILES: COc1cc(Nc2nc3ccc(-c4cn[nH]c4)cc3n(C)c2=O)ccc1N1CCOCC1]

The preparation of Example 51 could be obtained by referring to the preparation method of Example 47.

1H NMR (400 MHz, DMSO-d6) δ=13.03 (br. s., 1H), 9.36 (br. s., 1H), 8.46-7.45 (m, 7H), 6.90 (br. s., 1H), 4.04-3.63 (m, 10H), 2.97 (br. s., 4H).

MS-ESI (m/z): 433.1 (M+H)⁺.

Example 52: 1-Methyl-3-((5-morpholinepyridin-2-yl)amino)-7-(1H-pyrazol-4-yl)quinoxaline-2(1H)one

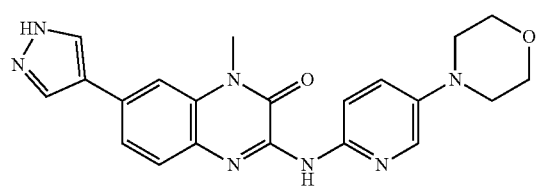

The preparation of Example 52 could be obtained by referring to the preparation method of Example 47.

1H NMR (400 MHz, DMSO-d6) δ=10.93 (br. s., 1H), 8.27 (s, 2H), 8.16-8.12 (m, 1H), 8.06-8.02 (m, 2H), 7.87 (d, J=8.5 Hz, 1H), 7.72-7.65 (m, 2H), 7.32-7.01 (m, 1H), 3.81-3.76 (m, 7H), 3.19 (br. s., 4H).

MS-ESI (m/z): 404.1 (M+H)⁺.

Example 53: 1-Methyl-3-((6-morpholinepyridin-3-yl)amino)-7-(1H-pyrazol-4-yl) quinoxaline-2(1H)one

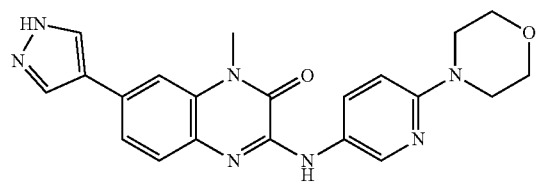 [SMILES: Cn1c(=O)c(Nc2ccc(N3CCOCC3)nc2)nc2ccc(-c3cn[nH]c3)cc21]

The preparation of Example 53 could be obtained by referring to the preparation method of Example 47, using different amines.

1H NMR (400 MHz, METHANOL-d4) δ=9.43-9.35 (m, 1H), 8.32 (d, J=9.0 Hz, 1H), 8.10 (br. s., 2H), 7.59-7.49 (m, 3H), 7.44-7.37 (m, 1H), 3.91-3.85 (m, 4H), 3.79 (s, 3H), 3.63 (d, J=4.5 Hz, 4H).

MS-ESI (m/z): 404.1 (M+H)⁺.

Example 54: 3-[4-(3,8-Diazabicyclo[3.2.1]octane-8-yl)aniline]-1-methyl-7-(1H-pyrazol-4-yl)quinoxaline-2(1H)-one

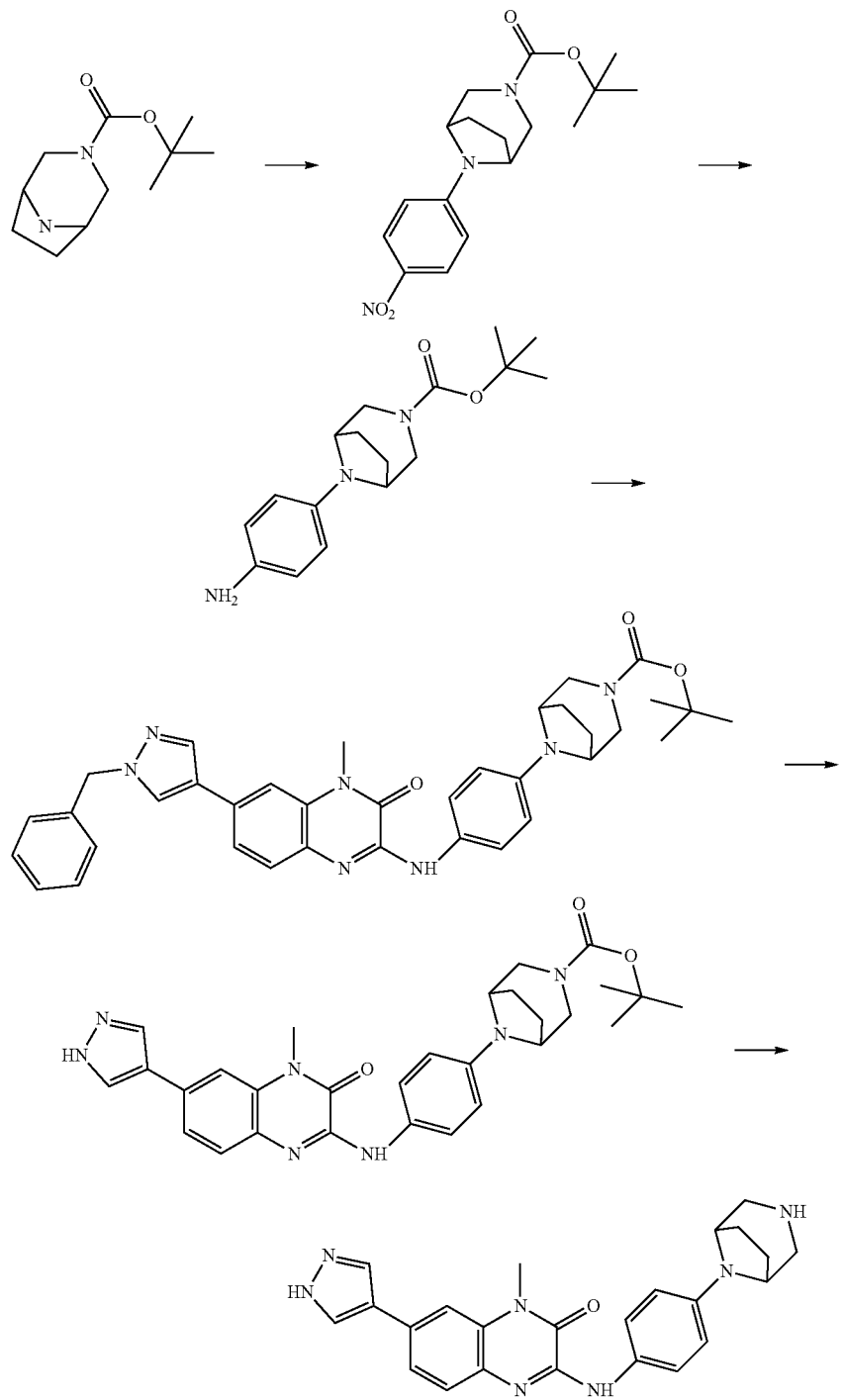

Step A: tert-Butyl-8-(4-nitrophenyl)-3,8-diazabicyclo[3.2.1]octane-3-carboxylate To a solution of tert-butyl-3,8-diazabicyclo[3.2.1]octane-3-carboxylate (399.0 mg, 1.88 mmol) in DMF (4.00 mL) were added potassium carbonate (742.19 mg, 5.37 mmol) and 1-fluoro-4-nitrobenzene (252.57 mg, 1.79 mmol). It was stirred at 80° C. for 36 hours. After the reaction was cooled down, 20 mL water was added, and after the solid was precipitated, filtration gave the title compound.

1H NMR (400 MHz, CHLOROFORM-d) δ=8.14 (d, J=9.2 Hz, 2H), 6.71 (d, J=9.2 Hz, 2H), 4.33 (d, J=19.2 Hz, 2H), 3.92-3.62 (m, 2H), 3.30-3.05 (m, 2H), 2.08 (br. s., 2H), 1.93 (dd, J=7.2, 14.2 Hz, 2H), 1.45 (s, 9H).

Step B: tert-Butyl-8-(4-aminophenyl)-3,8-diazabicyclo[3.2.1]octane-3-carboxylate To a solution of tert-butyl-8-(4-nitrophenyl)-3,8-diazabicyclo[3.2.1]octane-3-carboxylate (400.00 mg, 1.20 mmol) in methanol (50.00 mL) was added Pd/C (200.00 mg, 1.20 mmol). It was stirred in an atmosphere of hydrogen (15 psi) for one hour. After the reaction, removed the catalyst by filtration, and the mother liquid was concentrated to give the title compound.

1H NMR (400 MHz, CHLOROFORM-d) δ=6.72-6.61 (m, 4H), 4.14-3.96 (m, 2H), 3.72 (d, J=12.0 Hz, 1H), 3.58 (d, J=13.2 Hz, 1H), 3.44-3.15 (m, 4H), 2.07-1.91 (m, 2H), 1.88-1.68 (m, 2H), 1.50-1.38 (m, 9H).

Step C: tert-Butyl-8-[4-[[6-(1-benzyl-1H-pyrazol-4-yl)-4-methyl-3-oxo-3,4-dihydroquinoxaline-2-yl]amino]phenyl]-3,8-diazabicyclo[3.2.1]octane-3-carboxylate To a solution of tert-butyl-8-(4-aminophenyl)-3,8-diazabicyclo[3.2.1]octane-3-carboxylate (340.00 mg, 1.12 mmol) in isopropanol were added 7-(1-benzylpyrazol-4-yl)-3-bromo-1-methyl-quinoxalin-2-one (486.95 mg, 1.23 mmol) and DIPEA (217.12 mg, 1.68 mmol), and it was stirred at 100° C. for 12 hours. TLC showed that the raw materials were reacted completely. After the reaction solution was concentrated, it was separated by silica gel column chromatography (petroleum ether/ethyl acetate=10/1-1/1) to give the title compound.

1H NMR (400 MHz, CHLOROFORM-d) δ=8.28 (s, 1H), 7.88 (s, 1H), 7.83 (d, J=9.2 Hz, 2H), 7.68 (s, 1H), 7.60 (d, J=8.4 Hz, 1H), 7.42-7.33 (m, 4H), 7.32-7.28 (m, 3H), 6.93-6.80 (m, 2H), 5.38 (s, 2H), 4.24-4.11 (m, 2H), 3.81-3.78 (m, 3H), 3.75 (d, J=12.4 Hz, 1H), 3.61 (d, J=12.4 Hz, 1H), 3.42-3.17 (m, 2H), 1.85 (dd, J=7.2, 14.8 Hz, 2H), 1.46 (s, 9H).

Step D: tert-Butyl-8-[4-[[4-methyl-3-oxo-6-(1H-pyrazol-4-yl)-3,4-dihydroquinoxalin-2-yl]amino]phenyl]-3,8-diazabicyclo[3.2.1]octane-3-carboxylate To a solution of tert-butyl-8-[4-[[6-(1-benzyl-1H-pyrazol-4-yl)-4-methyl-3-oxo-3,4-dihydroquinoxaline-2-yl]amino]phenyl]-3,8-diazabicyclo[3.2.1]octane-3-carboxylate (380.00 mg, 615.15 μmol) in DMSO (10.00 mL) was added potassium tert-butoxide (345.13 mg, 3.08 mmol), and then the reaction solution was stirred at 20° C. in an atmosphere of O$_2$ (15 psi) for one hour. TLC showed that the raw materials were reacted completely. The reaction solution was poured into 10 mL ice water and extracted three times with 20 mL ethyl acetate. The organic phase was washed with saturated brine, dried over anhydrous sodium sulfate, filtered and concentrated to give the title compound.

Step E: 3-[4-(3,8-Diazabicyclo[3.2.1]octane-8-yl)aniline]-1-methyl-7-(1H-pyrazol-4-yl)quinoxaline-2(1H)-one A solution of tert-butyl-8-[4-[[4-methyl-3-oxo-6-(1H-pyrazol-4-yl)-3,4-dihydroquinoxalin-2-yl]amino]phenyl]-3,8-diazabicyclo[3.2.1]octane-3-carboxylate (300.00 mg, 568.59 μmol) in 4M HCl in methanol (10.00 mL) was stirred at 20° C. for 0.5 hour. TLC showed that the raw materials were reacted completely. The reaction solution was concentrated, then prepared and separated (formic acid system) to give the title compound 54.

1H NMR (400 MHz, DMSO-d6) δ=9.24 (s, 1H), 8.32-8.13 (m, 3H), 7.99 (d, J=8.8 Hz, 1H), 7.61 (s, 1H), 7.55-7.49 (m, 1H), 7.44 (d, J=8.4 Hz, 1H), 6.87 (d, J=8.8 Hz, 2H), 4.24 (br. s., 2H), 3.75 (s, 4H), 3.05 (d, J=12.4 Hz, 2H), 2.75-2.63 (m, 2H), 1.98 (br. s., 3H).

MS-ESI (m/z): 428.2 (M+H)$^+$.

Example 55: 1-(4-((4-methyl-3-oxo-6-(1H-pyrazol-4-yl)-3,4-dihydroquinoxalin-2-yl)amino)phenyl)piperidine-3-carboxylic acid

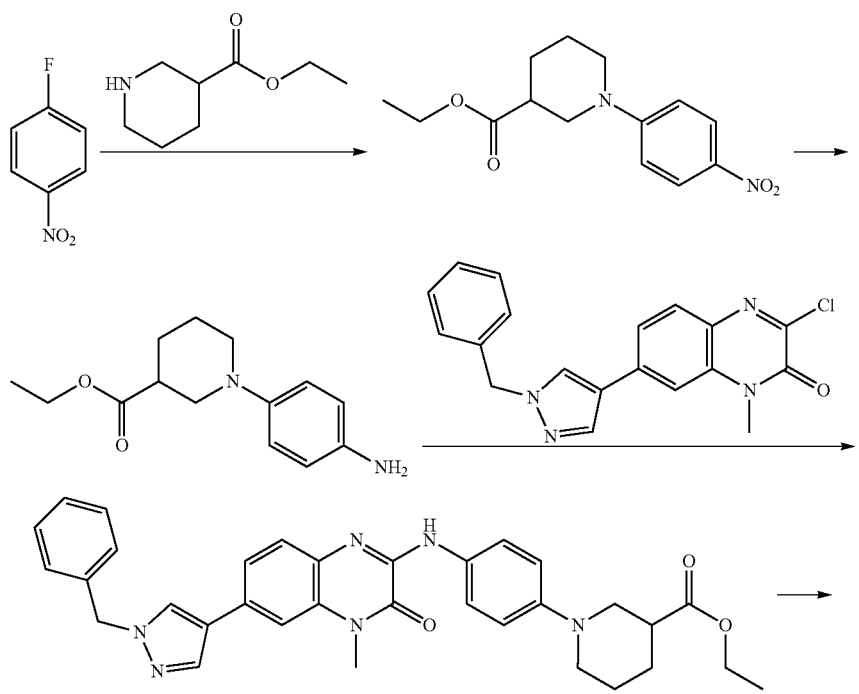

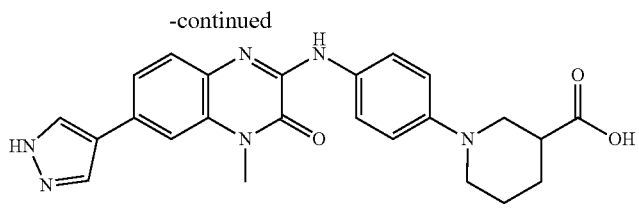

Step A: Ethyl 1-(4-nitrophenyl)piperidine-3-carboxylate

Added triethylamine (7.17 g, 70.88 mmol) and ethyl piperidine-3-carboxylate (5.57 g, 35.44 mmol) to a solution of 1-fluoro-4-nitrobenzene (5.00 g, 35.44 mmol) in THF (100 mL), and it was stirred at 80° C. for 16 hours. The reaction solution was spin-dried, diluted with ethyl acetate (100 mL), washed twice with saturated brine (100 mL), dried over anhydrous sodium sulfate, and filtered. The resulting residue which was obtained by concentrating under reduced pressure was separated by column to give the title compound.

1H NMR (400 MHz, CHLOROFORM-d) δ=8.10 (d, J=9.2 Hz, 2H), 6.83 (d, J=9.2 Hz, 2H), 4.23-4.04 (m, 2H), 3.97-3.84 (m, 1H), 3.77-3.63 (m, 1H), 3.35 (dd, J=9.6, 13.3 Hz, 1H), 3.20-3.04 (m, 1H), 2.68-2.51 (m, 1H), 2.12-2.03 (m, 1H), 1.88-1.75 (m, 2H), 1.70-1.57 (m, 1H), 1.26 (t, J=7.1 Hz, 3H).

Step B: Ethyl 1-(4-aminophenyl)piperidine-3-carboxylate

To a solution of ethyl 1-(4-nitrophenyl)piperidine-3-carboxylate (2.00 g, 7.19 mmol) in methanol (30 mL) was added 10% palladium carbon (0.2 g), and then it was replaced three times with a hydrogen balloon, and stirred at room temperature for 16 hours. It was filtered through Celite, and rinsed three times with dichloromethane and methanol (15 mL). The filtrate was spin-dried to give the title compound.

1H NMR (400 MHz, CHLOROFORM-d) δ=6.84 (d, J=8.6 Hz, 2H), 6.70-6.58 (m, 2H), 4.17 (q, J=7.1 Hz, 2H), 3.51 (d, J=10.4 Hz, 1H), 3.44 (br. s., 2H), 3.29 (d, J=11.7 Hz, 1H), 2.92-2.80 (m, 1H), 2.73-2.56 (m, 2H), 2.05-1.93 (m, 1H), 1.87-1.78 (m, 1H), 1.75-1.57 (m, 2H), 1.28 (t, J=7.2 Hz, 3H).

Step C: Ethyl 1-(4-((6-(1-phenyl-1H-pyrazol-4-yl)-4-methyl-3-oxo-3,4-dihydroquinoxalin-2-yl)amino)phenyl) piperidine-3-carboxylate Added ethyl 1-(4-aminophenyl)piperidine-3-carboxylate (169.89 mg, 684.16 μmol) and DIEA (221.05 mg, 1.17 mmol) to a solution of 7-(1-phenylpyrazol-4-yl)-3-chloro-1-methyl-quinoxalin-2-one (200.00 mg, 570.13 μmol) in isopropanol (6 mL), and it was stirred at 100° C. for 32 hours.

The reaction solution was cooled to room temperature, with a solid precipitated, filtered, and spin-dried to give the title compound.

1H NMR (400 MHz, DMSO-d6) δ=9.27 (s, 1H), 8.42 (s, 1H), 8.06 (s, 1H), 7.97 (d, J=9.0 Hz, 1H), 7.73 (d, J=5.3 Hz, 1H), 7.66 (d, J=7.5 Hz, 1H), 7.58 (s, 1H), 7.53-7.48 (m, 1H), 7.33-7.26 (m, 4H), 6.94 (d, J=8.8 Hz, 2H), 5.38 (d, J=8.8 Hz, 2H), 4.10 (q, J=7.1 Hz, 2H), 3.73 (d, J=5.3 Hz, 3H), 3.58 (d, J=9.5 Hz, 1H), 3.06-2.93 (m, 2H), 2.78 (d, J=9.7 Hz, 2H), 1.89 (br. s., 1H), 1.72 (br. s., 1H), 1.60 (t, J=9.3 Hz, 2H), 1.27-1.15 (m, 3H).

Step D: 1-(4-((4-Methyl-3-oxo-6-(1H-pyrazol-4-yl)-3,4-dihydroquinoxalin-2-yl)amino)phenyl)piperidine-3-carboxylic acid At room temperature, added potassium tert-butoxide (159.54 mg, 1.42 mmol) to a solution of ethyl 1-(4-((6-(1-phenyl-1H-pyrazol-4-yl)-4-methyl-3-oxo-3,4-dihydroquinoxalin-2-yl)amine)phenyl)piperidine-3-carboxylate (100.00 mg, 177.73 μmol) in dimethyl sulfoxide (3 mL). Replaced three times with oxygen balloon at room temperature, and then it was stirred at 40° C. for 3 hours. Water (15 mL) was added to the reaction solution, and extracted twice with ethyl acetate (15 mL). The organic phase was washed twice with saturated brine (20 mL), dried over anhydrous sodium sulfate, and filtered. The resulting residue which was obtained by concentrating under reduced pressure was prepared and separated (trifluoroacetic acid) to give the title compound 55.

1H NMR (400 MHz, DMSO-d6) δ=9.53 (br. s., 1H), 8.21 (s, 2H), 8.13 (d, J=5.5 Hz, 2H), 7.64 (br. s., 1H), 7.59-7.53 (m, 1H), 7.51 (br. s., 1H), 7.36-7.22 (m, 2H), 3.76 (s, 3H), 3.70-3.57 (m, 2H), 3.48 (br. s., 1H), 3.30-3.03 (m, 2H), 2.76 (br. s., 1H), 2.04-1.57 (m, 3H).

MS-ESI (m/z): 445 (M+H)$^+$.

Example 56: 1-Methyl-7-(1H-pyrazol-4-yl)-3-((6-((tetrahydro-2H-pyran-4-yl)amino)pyridin-3-yl)amino)quinoxaline-2(1H)-one

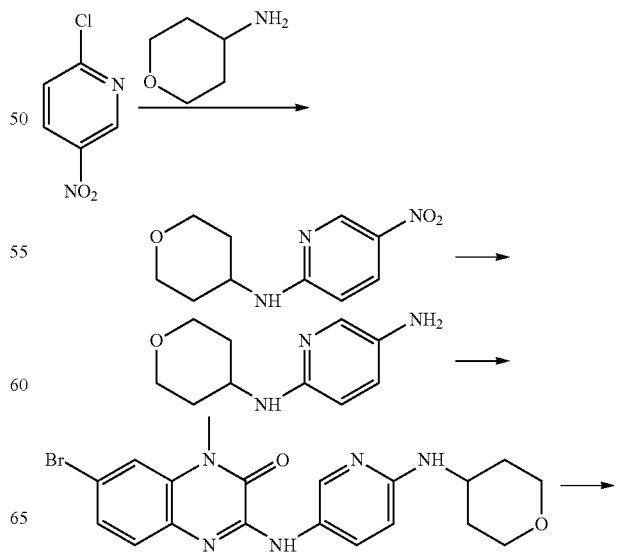

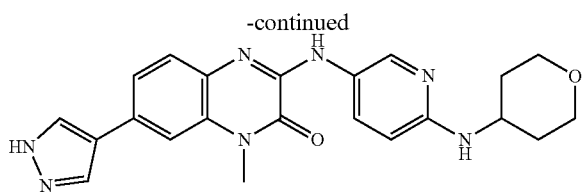

Step A: 5-Nitro-N-(tetrahydro-2H-pyran-4-yl)pyridin-2-amine

Added triethylamine (5.11 g, 50.46 mmol) and tetrahydropyran-4-amine (2.55 g, 25.23 mmol) to a solution of 2-chloro-5-nitro-pyridine (4.00 g, 25.23 mmol) in DME (100 mL), and it was stirred at 80° C. for 16 hours. The reaction solution was spin-dried, diluted with ethyl acetate (100 mL), washed twice with saturated brine (100 mL), dried over anhydrous sodium sulfate, and filtered. The residue which was obtained by concentrating under reduced pressure was separated by column to give the title compound.

1H NMR (400 MHz, DMSO-d6) δ=8.91 (d, J=2.4 Hz, 1H), 8.19-8.00 (m, 2H), 6.56 (d, J=9.0 Hz, 1H), 4.13 (br. s., 1H), 3.87 (d, J=11.2 Hz, 2H), 3.41 (t, J=10.8 Hz, 2H), 1.86 (d, J=12.1 Hz, 2H), 1.57-1.39 (m, 2H).

Step B: N²-(tetrahydro-2H-pyran-4-yl)pyridine-2,5-diamine

To a solution of 5-nitro-N-(tetrahydro-2H-pyran-4-yl)pyridin-2-amine (800.00 mg, 3.58 mmol) in methanol (20 mL) was added 10% palladium carbon (0.2 g), and it was replaced three times with hydrogen, and stirred at room temperature for 3 hours. After being filtered with Celite, the filtrate was spin-dried to give the title compound.

1H NMR (400 MHz, CHLOROFORM-d) δ=7.68 (d, J=2.4 Hz, 1H), 6.94 (dd, J=2.6, 8.6 Hz, 1H), 6.31 (d, J=8.8 Hz, 1H), 3.98 (d, J=11.5 Hz, 3H), 3.81-3.68 (m, 1H), 3.52 (dt, J=1.5, 11.5 Hz, 2H), 3.21 (br. s., 2H), 2.02 (d, J=12.6 Hz, 2H), 1.55-1.39 (m, 2H).

Step C: 7-Bromo-1-methyl-3-((6-((tetrahydro-2H-pyran-4-yl)amino)pyridin-3-yl)amino)quinoxaline-2(1H)-one Added N²-(tetrahydro-2H-pyran-4-yl)pyridine-2,5-diamine (494.59 mg, 2.56 mmol) and DIEA (992.30 mg, 7.68 mmol) to a solution of 7-bromo-3-chloro-1-methylquinoxaline-2(1H)-one (700.00 mg, 2.56 mmol) in isopropanol (15 mL), and it was stirred at 100° C. for 24 hours. The reaction solution was cooled to room temperature, with a solid was precipitated, and filtered. The filter cake was rinsed three times with ethyl acetate (5 mL), and spin-dried to give the title compound.

1H NMR (400 MHz, DMSO-d6) δ=9.39 (br. s., 1H), 8.63 (br. s., 1H), 7.98 (d, J=8.3 Hz, 1H), 7.59 (br. s., 1H), 7.37 (br. s., 2H), 6.55-6.27 (m, 2H), 3.87 (d, J=9.3 Hz, 2H), 3.65 (br. s., 3H), 1.88 (d, J=11.8 Hz, 2H), 1.41 (d, J=9.5 Hz, 2H), 1.03 (d, J=5.8 Hz, 3H).

Step D: 1-Methyl-7-(1H-pyrazol-4-yl) 3-((6-((tetrahydro-2H-pyran-4-yl)amino)pyridin-3-yl)amino)quinoxaline-2(1H)-one Under a protection of nitrogen, added potassium carbonate (192.72 mg, 1.39 mmol), tert-butyl 4-(4,4,5,5-tetramethyl-1,3,2-dioxaborolane (246.00 mg, 836.46 µmol) and Pd(dppf)Cl₂ (51.01 mg, 69.72 µmol) to a mixture solution of 7-bromo-1-methyl-3-((6-((tetrahydro-2H-pyran-4-yl)amino)pyridin-3-yl)amino)quinoxaline-2(1H)-one (300.00 mg, 697.19 µmol) in dioxane (8 mL) and water (2 mL), and it was stirred at 100° C. for 4 hours. The reaction solution was cooled to room temperature, concentrated, followed by the addition of water (20 mL) into it, and filtered to give the residue, which was prepared and separated (trifluoroacetic acid) to give the title compound 56.

1H NMR (400 MHz, DMSO-d6) δ=9.78 (s, 1H), 9.11 (br. s., 1H), 8.35 (d, J=8.3 Hz, 1H), 8.19 (s, 2H), 7.62-7.53 (m, 2H), 7.45 (d, J=8.3 Hz, 1H), 7.03 (d, J=9.5 Hz, 1H), 3.97-3.81 (m, 3H), 3.71 (s, 3H), 3.41 (t, J=11.2 Hz, 2H), 1.92 (d, J=11.5 Hz, 2H), 1.58-1.39 (m, 2H).

MS-ESI (m/z): 418 (M+H)⁺.

Example 57: 7-(2-Amino-1H-imidazol-5-yl)-1-methyl-3-((4-morpholinephenyl)amino)quinoxaline-2(1H)-one

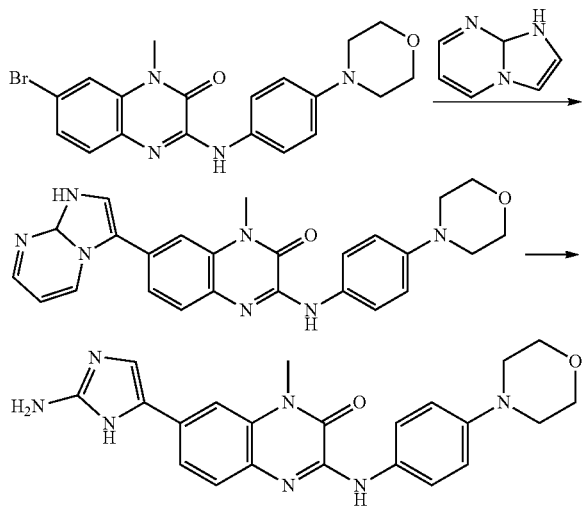

Step A: 7-imidazo[1,2-a]pyrimidin-3-yl-1-methyl-3-((4-morpholinephenyl)amino)quinoxaline-2(1H)-one To 7-bromo-1-methyl-3-((4-morpholinephenyl)amino)quinoxaline-2 (1H)-one (100.00 mg, 240.80 µmol) and imidazo[1,2-a]pyrimidine (57.80 mg, 288.96 µmol, hydrobromide) in dioxane (2.00 mL) were added triphenylphosphine (12.63 mg, 48.16 µmol), palladium acetate (5.41 mg, 24.08 µmol) and cesium carbonate (235.37 mg, 722.40 µmol). The reaction solution was heated and stirred under nitrogen for 17 hours. LCMS showed that it was reacted completely. The reaction solution was filtered over Celite and the filter cake was washed with dichloromethane. The mother liquid was spin-dried and the title compound was obtained by silica gel column chromatography (methanol dichloromethane=0~10%).

MS-ESI (m/z): 456 (M+H)⁺

Step B: 7-(2-Amino-1H-imidazol-5-yl)-1-methyl-3-((4-morpholinephenyl)amino)quinoxaline-2(1H)-one A solution of 7-imidazo[1,2-a]pyrimidin-3-yl-1-methyl-3-((4-morpholinephenyl)amino) quinoxaline-2(1H)-one (40.00 mg, 88.20 μmol) and hydrazine hydrate (1.78 g, 55.54 mmol) in ethanol (3.00 mL) was heated in a tank (105° C.) for 16 hours.

LCMS showed that the raw materials were reacted completely. Spin-dried the reaction solution, followed by the preparation and separation (trifluoroacetic acid system) to give 7-(2-amino-1H-imidazol-5-yl)-1-methyl-3-((4-morphinolinylphenyl)amino) quinoxaline-2(1H)-one (Compound 57).

1H NMR (400 MHz, DMSO-d6) δ=12.83 (br. s., 1H), 12.13 (br. s., 1H), 9.45 (s, 1H), 8.01 (d, J=9.0 Hz, 2H), 7.66 (s, 1H), 7.60 (br. s., 2H), 7.57-7.51 (m, 2H), 6.97 (d, J=9.0 Hz, 2H), 3.78-3.72 (m, 7H), 3.13-3.06 (m, 4H).

MS-ESI (m/z): 418.2 (M+H)+.

Example 58: 7-(2-Aminothiazol-5-yl)-1-methyl-3-((4-morpholinephenyl)amino)quinoxaline-2(1H)-one

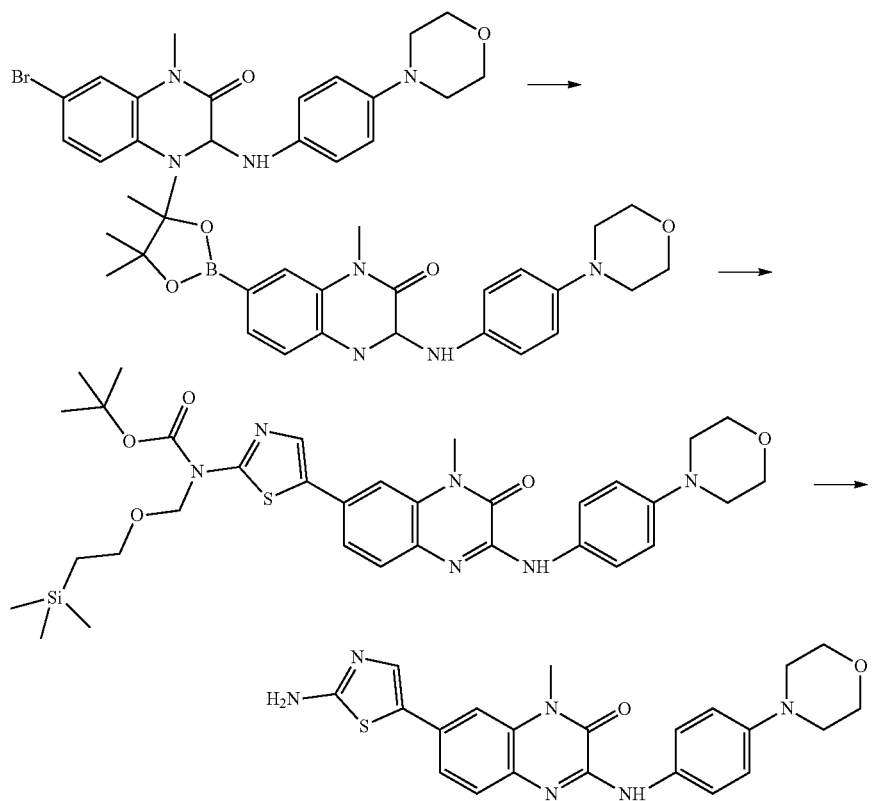

Step A: 1-Methyl-3-((4-morpholinephenyl)amino)-7-(4,4,5,5-tetramethyl-1,3,2-dioxaborolan-2-yl)quinoxaline-2(1H)-one A solution of 7-bromo-1-methyl-3-((4-morpholinephenyl)amino)quinoxaline-2(1H)-one (500.00 mg, 1.20 mmol), 4,4,5,5-tetramethyl-2-(4,4,5,5-tetramethyl-1,3,2-dioxaborolan-2-yl)-1,3,2-dioxaborane (335.20 mg, 1.32 mmol), Pd(dppf)Cl$_2$ (70.24 mg, 96.00 μmol) and potassium acetate (353.30 mg, 3.60 mmol) in dioxane (50.00 mL) was degassed and replaced with nitrogen, reflowing at 110° C. for 1.5 hours under nitrogen, then cooled down, diluted with dichloromethane (100 mL), washed with saturated brine (50 mL three times), dried over anhydrous sodium sulfate, and after concentrating, the title compound was obtained by silica gel column chromatography (12 g, tetrahydrofuran/dichloromethane=0 to 5%).

MS-ESI (m/z): 463 (M+H)+.

Step B: tert-Butyl (5-(4-methyl-2-((4-morpholinephenyl)amino)-3-oxa-3,4-dihydroquinoxalin-6-yl)thiazol-2-yl)((2-(trimethylsilyl)ethoxy)methyl)formate To a solution of tert-butyl N-(5-bromothiazol-2-yl)-N-(2-trimethylsilylethoxymethyl)formate (102.28 mg, 249.81 μmol) and 1-methyl-3-((4-morpholinephenyl)amino)-7-(4,4,5,5-tetramethyl-1,3,2-dioxaborolan-2-yl)quinoxaline-2 (1H)-one (100.00 mg, 166.54 μmol) in DMF (2.00 mL) were added Brettphos palladium procatalyst (26.61 mg, 33.31 μmol) and cesium carbonate (108.52 mg, 333.08 μmol). The mixture was heated and stirred at 90° C. for 5 hours in an atmosphere of nitrogen. It was stirred at 100° C. for 16 hours. LCMS showed that the raw materials were reacted completely. After the mixture was cooled down, diluted with 150 mL dichloromethane, washed with saturated brine, dried over anhydrous sodium sulfate, filtered, and spin-dried, the silica gel column chromatography (tetrahydrofuran/dichloromethane=0~30%) gave the title compound.

MS-ESI (m/z): 665.5 (M+H)+.

Step C: 7-(2-Aminothiazol-5-yl)-1-methyl-3-((4-morpholinephenyl)amino)quinoxaline-2(1H)-one To a solution of tert-butyl (5-(4-methyl-2-((4-morpholinephenyl)amino)-3-oxa-3,4-dihydroquinoxalin-6-yl)thiazol-2-yl)((2-(trimethylsilyl)ethoxy)methyl)carboxylate (133.33 mg, 150.40 μmol) in dichloromethane (20.00 mL)

was added trifluoroacetic acid (6.12 g, 53.67 mmol), and the mixture was stirred at 20° C. for one hour then at 35° C. for four hours. LCMS showed that the raw materials were reacted completely. After spin-drying of dichloromethane, preparation and separation (trifluoroacetic acid system) gave the title compound 58.

1H NMR (400 MHz, DMSO-d6) δ=9.41 (s, 1H), 8.33-8.14 (m, 1H), 8.00 (d, J=9.0 Hz, 2H), 7.74 (s, 1H), 7.47 (d, J=4.0 Hz, 2H), 7.36 (d, J=8.0 Hz, 1H), 6.98 (d, J=9.0 Hz, 2H), 3.78-3.73 (m, 7H), 3.13-3.08 (m, 4H).

MS-ESI (m/z): 435.0 (M+H)+.

Example 59: 7-(2-Aminothiazol-4-yl)-1-methyl-3-((4-morpholinephenyl)amino)quinoxaline-2(1H)-one

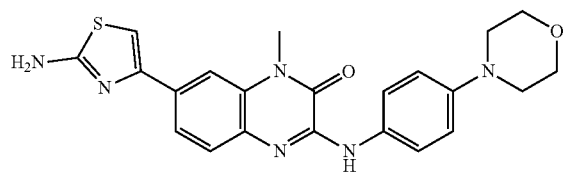 [SMILES: Cn1c(=O)c(Nc2ccc(N3CCOCC3)cc2)nc2ccc(-c3csc(N)n3)cc21]

The preparation of Example 59 could be obtained by referring to the preparation method of Example 58.

1H NMR (400 MHz, DMSO-d6) δ=9.43 (br. s., 1H), 8.02 (d, J=8.0 Hz, 2H), 7.79 (br. s., 1H), 7.71 (d, J=8.0 Hz, 1H), 7.50 (d, J=8.0 Hz, 1H), 7.21 (br. s., 1H), 7.00 (d, J=8.0 Hz, 2H), 3.75 (d, J=13.1 Hz, 9H), 3.12 (br. s., 4H).

MS-ESI (m/z): 435.1 (M+H)+.

Experimental Example 1: In Vitro Test of the Inhibition Effect of the Example Compounds on SYK Kinase 1.1 Experimental Purpose: The interaction between the substrate and the enzyme was detected by homogeneous time-resolved fluorescence (HTRF), and the inhibition effect of the compounds on tyrosine (SYK) kinase was evaluated by an index of the half-cell inhibition concentration (IC50) value of the compounds.

1.2 Experimental Materials:
Tyrosine kinase (Invitrogen, PV3857)
Dithiothreitol (DTT) (Sigma #43815)
Adenosine triphosphate (ATP) (Sigma #A7699)
Magnesium chloride (MgCl2) (Sigma #63020)
Manganese chloride (MnCl2) (Sigma #M1787)
Ethylenediaminetetraacetic acid (EDTA) (Invitrogen #15575-020)
4-Hydroxyethylpiperazine ethanesulfonic acid buffer (HEPES Buffer) (Invitrogen #15630-080)
HTRF® Kin EASE™ Tyrosine Kinase Kit (Cisbio #62TK0PEC, 20000 tests)
Low capacity, 384-well, white polystyrene board (Greiner #784075)
384 Microplate (Greiner #781946)
Centrifuge (Eppendorf #581 OR)
Pipette (Eppendorf)
Pipette (Greiner)
Pipetting gun (Eppendorf)
Multidrop automatic dispenser
POD 810 Plate Assembler Fully Automatic Microplate Pretreatment System
Envision Reader Multi-function Microplate Reader 1.3 Experimental procedures and methods:
a) Compound dilution and board
1) The compound powder was weighed, and was dissolved in a certain amount of dimethyl sulfoxide, with an initial concentration of 10 mM.
2) The compound concentration was diluted to 0.74 mM, and plated using a fully automated microplate pretreatment system, 135 nL per well, the starting concentration of compound was 10 uM, with 11 concentration points, and a 3 fold downgrading dilution.
b) Reaction stage of enzyme and substrate
1) Prepared the test buffer for dilution, diluted the 5×HTRF buffer in the kit to 1×, and added the specified amount of dithiothreitol and magnesium chloride solution for use.
2) The tyrosinase reaction solution was prepared with 1×HTRF buffer, to make a final reaction concentration of tyrosine kinase at 0.0156 ng/μL.
3) A mixture of tyrosine kinase-substrate-biotin/adenosine triphosphate was prepared to control the final substrate concentration to 0.2 uM. Adenosine triphosphate concentration was controlled at 2 uM.
4) Loaded with a Multidrop automatic dispenser, and a mixture of tyrosinase solution and tyrosine kinase-substrate-biotin/adenosine triphosphate was added in an amount of 5 ul per well, and incubated at 23° C. for 1 hour.
c) Detection phase:
1) Added 13.33 mL of ethylenediaminetetraacetic acid solution to the Detection Buffer in the kit, added the specified amount of uranium (Eu)-labeled antibody and streptavidin XL-665, and prepared the detection solution.
2) Loaded with a Multidrop automatic dispenser, and 10 uL of the detection solution per well, incubated at 23° C. for 1 hour. It terminated the reaction of the enzyme and substrate mixture.
3) Reading after centrifugation on a multi-function microplate reader,
d) Data Analysis: Analyzed the data with XL-Fit, and calculated the IC50 value of the compound.

Experimental Example 2: In Vitro Test of the Inhibition Effect of the Example Compounds on AKT Phosphorylation 2.1 Experimental Purpose: Intracellular protein kinase AKT phosphorylation detected by experiment was measured by enzyme-linked immunosorbent assay (ELISA), and the inhibition of the compound on protein kinase AKT phosphorylation was evaluated by an index of the half-cell inhibition concentration (IC50) value of the compound.

2.2 Experimental Materials:
Cell line: Ramos cell line
Cell culture medium (RPMI1640, Invitrogen #22400-105; 10% serum Gibco #10099-141; L-glutamine 1×, Gibco #25030-081)
Experimental medium (without serum, RPM11640, Invitrogen #22400-105; L-glutamine 1×, Gibco #25030)
Lysis buffer (trishydroxymethylaminomethane hydrochloride, Invitrogen15567-1000 ml; sodium chloride, domestic; sodium deoxycholate, Sigma30970-25 G; polyethylene glycol octylphenyl ether, SigmaT9284-100 ml; dodecane sodium sulfonate, SigmaL3771; ethylenediaminetetraacetic acid, Invitrogen15575-038-100 ml; ultrapure water, MilliQ)
Protease inhibitor (Roche, 4693159001-30/BOX)
Phosphatase inhibitor mixture 2 (Sigma, P5726-5 ML)

Phosphatase inhibitor mixture 3 (Sigma, P0044-5 ML)
Goat Anti-Human immunoglobulin M (F(ab')2 Goat Anti-Human IgM) (Jackson Immuno Research-109-006-129)
Phosphorylated AKT assay kit (Phospho-AKT 1/2/3 (ser473)) (TGR Bioscience, EKT002)
10× Hank's balanced salt solution (Gibco #14065-056)
96-well cell plate (Greiner #655090)
Compound V-well dilution plate (Axygen #WITP02280)
$CO_2$ incubator (Thermo #371)
Centrifuge (Eppendorf #581 OR)
Vi-cell cell counter (Beckman Coulter)
Pipette (Eppendorf)
Pipette (Greiner)
Pipetting gun (Eppendorf)
Multi-purpose microplate reader (Envision Reader)

2.3 Experimental procedures and methods:

a) Cell Seeding (Ramos Cells)
  1) The medium was preheated in a 37° C. water bath. Suspended cells and their culture solution were aspirated, centrifuged at 1000 rpm for 5 minutes.
  2) Aspirated the cell culture medium, added 10 mL of pre-warmed medium to the centrifuge tube, blew off the resuspended cells, pipette 1 mL of the cell suspension, and counted with Vi-cell;
  3) The Ramos cells were diluted with a medium to a density of 5×106/mL, and the diluted cells were added to a 96-well cell culture plate (100 μL/well) using a lance. Placed the cell plates in a 37° C., 5% $CO_2$ incubator for overnight.

b) Cell starvation:
  1) After cultured the inoculation cells for overnight, centrifuged at 1000 rpm for 5 minutes on the next day, aspirated the original medium by a lance, added serum-free experimental medium, placed the cell plates in a 37° C., 5% $CO_2$ incubator, and starved for overnight.

c) Compound preparation and dosing:
  1) The compound was diluted with dimethyl sulfoxide to give an initial concentration of 5 mM. A triple gradient dilution was done with compound V dilution plate to make 10 concentration points.
  2) Took another new compound V-well dilution plate, added 198 ul of serum-free experimental medium to each well, and then added 2 ul of the diluted compound above to each well, and mixed with a lance. At this point the compound was diluted 100-fold with an initial concentration of 50 uM.
  3) The prepared compound was added to the cell culture plate at 25 uL per well (100 uL of cell culture medium), and the compound was diluted 5 times, and finally the initial reaction concentration was 10 uM, three-fold gradient, 10 concentration points.
  4) After the drug was added, centrifuged at 1000 rpm for 1 minute, and placed the cell plate in a 37° C., 5% $CO_2$ incubator to allow the compound to act for 1 hour.

d) Stimulating factor stimulation:
  1) Prepared two tubes of 1× balanced salt solution, diluted the 10× balanced salt solution with double distilled water to 1× balanced salt solution, and placed in a 37° C. incubator and a 4° C. refrigerator respectively for use.
  2) Prepared a tube of the lysis mixture and placed in a 4° C. refrigerator for use. The formulation was as follows: 1 tablet of protease inhibitor+100 ul phosphatase inhibitor mixed with 2+100 ul phosphatase inhibitor mixed with 3+10 ml lysate.
  3) Diluted the goat anti-human immunoglobulin M (F(ab')2 Goat Anti-Human IgM) (1.2 mg/ml) to 60 ug/ml with a 1× balanced salt solution preheated at 37° C.
  4) After the cells were treated with the compound for one hour, 25 ul of diluted goat anti-human immunoglobulin M (F(ab') 2 Goat Anti-Human IgM) was added to each well, at which time the concentration of IgM was 10 ug/ml.
  5) Stimulated the cells with IgM for 10 minutes, centrifuged at 4000 rpm for 5 minutes, making the suspended cells deposited on the bottom of a 96-well plate, gently dropped the liquid in the 96-well plate, and removed the remaining liquid with a paper towel. Note: Try not to get rid of suspended cells.
  6) Added 250 ul of pre-cooled (4° C.) 1× balanced salt solution to each well and centrifuged at 4000 rpm for 5 minutes to stop stimulation of the cells by the stimulating factor.

e) Preparation of cell lysate:
  1) Gently poured off the liquid from the 96-well plate, and removed the remaining liquid with a paper towel. Added 100 ul of the lysis mixture to each well, and shaken at 4° C. for 1 hour to lyse the cells. 2) After the cells were lysed for 1 hour, centrifuged at 4000 rpm for 5 minutes at 4° C., and the supernatant was gently aspirated to obtain a cell lysate.

f) Enzyme-Linked Immunosorbent Assay (ELISA) Assay:
  1) Took out the 96-well Elisa plate in the phosphorylated AKT assay kit, equilibrated to room temperature, and added 50 ul of cell lysate to each well.
  2) The capture antibody reagent (Capture Antibody Reagent) and the detection antibody reagent (Detection Antibody Reagent) were mixed 1:1, and then added 50 μl per well to a 96-well Elisa plate. The cell lysate and antibody mixture were shaken for 1 hour at room temperature on a shaker.
  3) The washing solution (1 Ox) in the kit was diluted to 1× with double distilled water, poured off the liquid in the Elisa plate, patted to dryness on the absorbent paper, added 200 μl of 1× washing solution to each well, washed the plate and patted to dryness, and repeated four times.
  4) Diluted 10-acetyl.3,7.dihydroxyphenazine (ADHP) (100×) substrate to 1× with ADHP dilution, added 100 ul per well to 96-well Elisa plates, and shaken for 10 minutes at room temperature on a shaker.
  5) Added 10 ul of stop solution to each well and centrifuged instantaneously. It was shaken for 5 minutes at room temperature on a shaker. Read the values by the Envision Reader multi-function microplate reader.

g) Data analysis: Analyzed the data with XL-Fit, and calculated the IC50 value of the compound.

The results of Experimental Example 1 and Experimental Example 2 are shown in Table 1:

TABLE 1
| Test Sample (Title compound) | Structure | SYK Inhibit SYK kinase IC50 (nM) | Inhibit AKT phosphorylation IC50 (nM) |
| --- | --- | --- | --- |
| Example 1 | 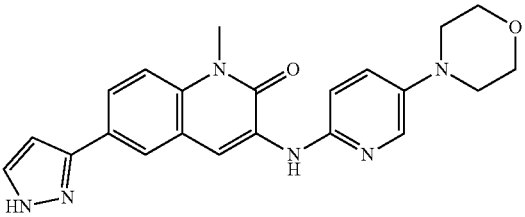 [SMILES: Cn1c(=O)c(Nc2ccc(N3CCOCC3)cc2)cc2cc(-c3cc[nH]n3)ccc21] | 33.8 | 248 |
| Example 2 | 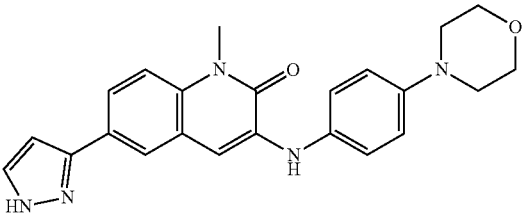 | 203.6 | 750 |
| Example 3 | 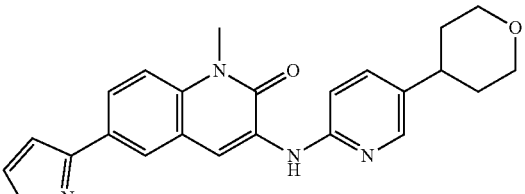 | 40.7 | 323 |
| Example 4 | 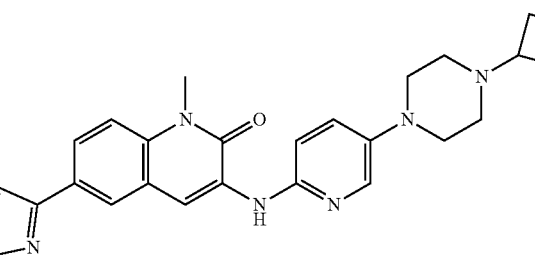 | 34.3 | 585 |
| Example 5 | 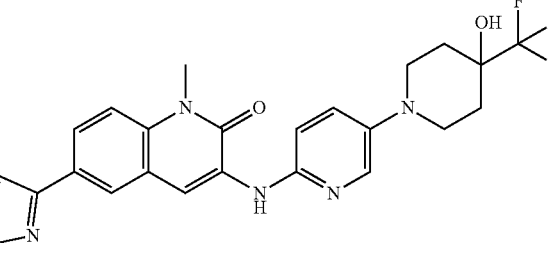 | 58.4 | — |
| Example 6 | 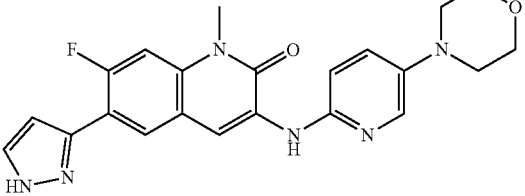 | 21.1 | 446 |

TABLE 1-continued

| Test Sample (Title compound) | Structure | SYK Inhibit SYK kinase IC50 (nM) | Inhibit AKT phosphorylation IC50 (nM) |
|---|---|---|---|
| Example 7 | 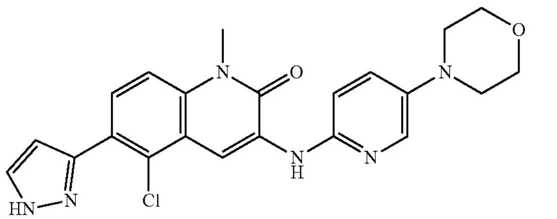 | 10.3 | 211 |
| Example 8 | 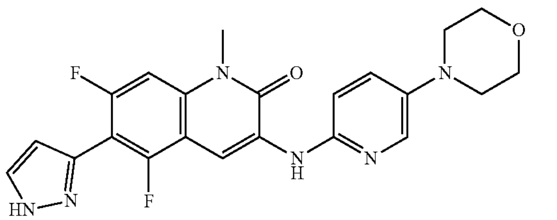 [SMILES: Cn1c(=O)c(Nc2ccc(N3CCOCC3)cn2)cc2cc(-c3cc[nH]n3)c(F)cc21] | 54.6 | 188 |
| Example 9 | 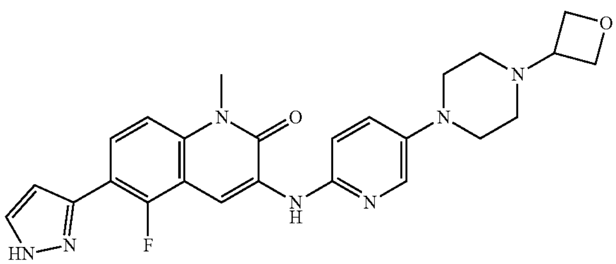 [SMILES: Cn1c(=O)c(Nc2ccc(N3CCN(C4COC4)CC3)cn2)cc2c(F)c(-c3cc[nH]n3)ccc21] | 12 | 170 |
| Example 10 | 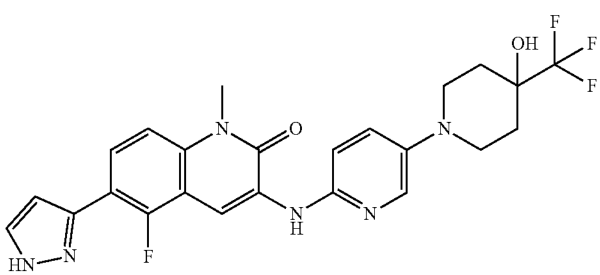 [SMILES: Cn1c(=O)c(Nc2ccc(N3CCC(O)(C(F)(F)F)CC3)cn2)cc2c(F)c(-c3cc[nH]n3)ccc21] | 30 | 343 |
| Example 11 | 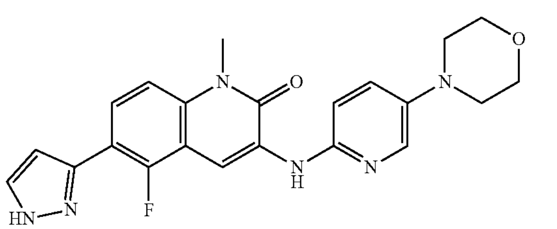 | 15 | 230 |
| Example 12 | 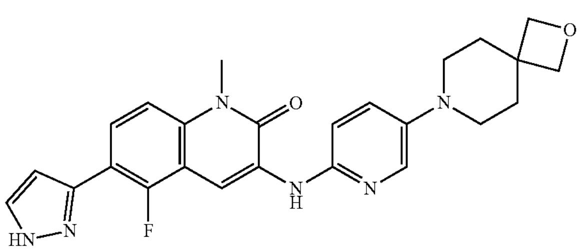 [SMILES: Cn1c(=O)c(Nc2ccc(N3CCC4(CC3)COC4)cn2)cc2c(F)c(-c3cc[nH]n3)ccc21] | 114 | 750 |

TABLE 1-continued
| Test Sample (Title compound) | Structure | SYK Inhibit SYK kinase IC50 (nM) | Inhibit AKT phosphorylation IC50 (nM) |
|---|---|---|---|
| Example 13 | 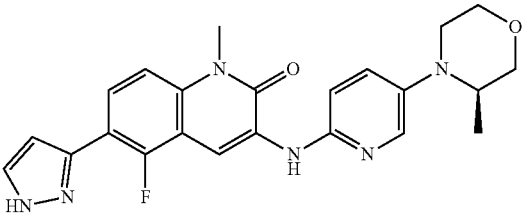 [SMILES: C[C@@H]1COCCN1c1ccc(Nc2cc3c(F)c(-c4cc[nH]n4)ccc3n(C)c2=O)nc1] | 923 | — |
| Example 14 | 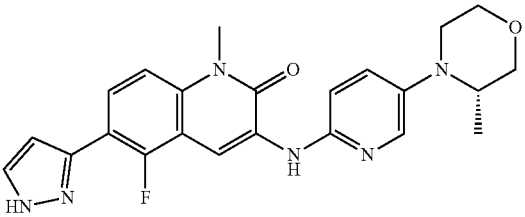 | 237 | — |
| Example 15 | 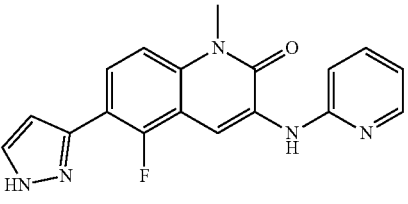 [SMILES: Cn1c(=O)c(Nc2ccccn2)cc2c(F)c(-c3cc[nH]n3)ccc21] | 100.7 | 425 |
| Example 16 | 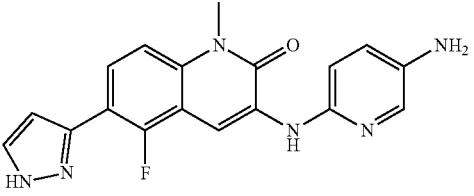 [SMILES: Cn1c(=O)c(Nc2ccc(N)cn2)cc2c(F)c(-c3cc[nH]n3)ccc21] | 47.9 | 197 |
| Example 17 | 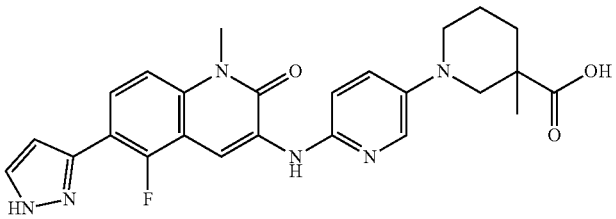 [SMILES: Cn1c(=O)c(Nc2ccc(N3CCCC(C)(C(=O)O)C3)cn2)cc2c(F)c(-c3cc[nH]n3)ccc21] | 24.9 | 255 |
| Example 18 | 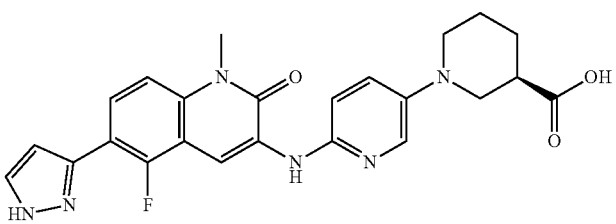 [SMILES: Cn1c(=O)c(Nc2ccc(N3CCC[C@@H](C(=O)O)C3)cn2)cc2c(F)c(-c3cc[nH]n3)ccc21] | 26 | 844 |

TABLE 1-continued
| Test Sample (Title compound) | Structure | SYK Inhibit SYK kinase IC50 (nM) | Inhibit AKT phosphorylation IC50 (nM) |
|---|---|---|---|
| Example 19 | 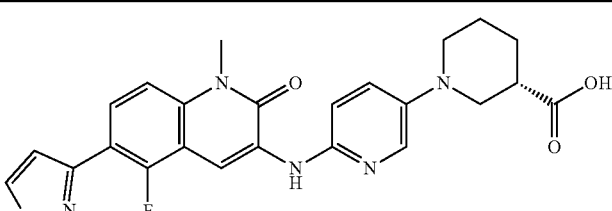 | 14.3 | 388 |
| Example 20 | 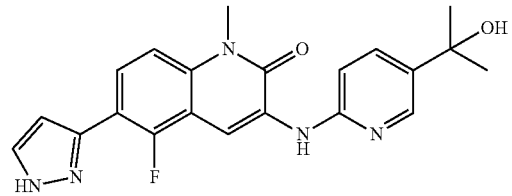 [SMILES: Cn1c(=O)c(Nc2ccc(C(C)(C)O)cn2)cc2c(F)c(-c3cc[nH]n3)ccc21] | 12.7 | 63 |
| Example 21 | 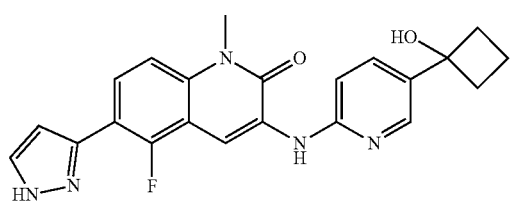 [SMILES: Cn1c(=O)c(Nc2ccc(C3(O)CCC3)cn2)cc2c(F)c(-c3cc[nH]n3)ccc21] | 22 | 200 |
| Example 22 | 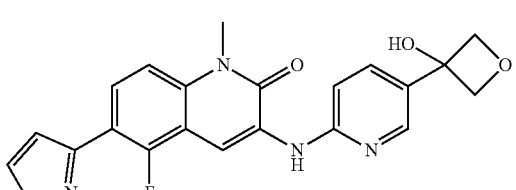 | 38.5 | — |
| Example 23 | 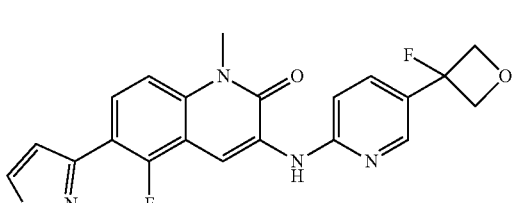 | 26.9 | 169 |
| Example 24 | 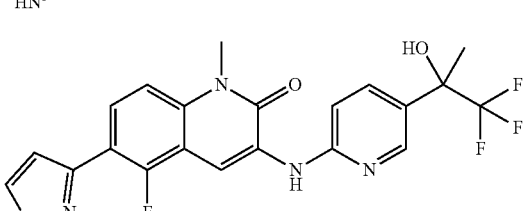 | 12.3 | 175 |
| Example 25 | 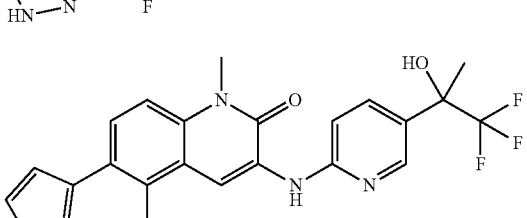 | 8.9 | 121 |

TABLE 1-continued

| Test Sample (Title compound) | Structure | SYK Inhibit SYK kinase IC50 (nM) | Inhibit AKT phosphorylation IC50 (nM) |
|---|---|---|---|
| Example 26 | (structure) | 4.2 | 50 |
| Example 27 | (structure) | 78 | — |
| Example 28 | (structure) | 230 | — |
| Example 29 | (structure) | 61 | 233 |
| Example 30 | (structure) | 461 | — |
| Example 31 | (structure) | 81 | 132 |
| Example 32 | (structure) | 212 | — |

TABLE 1-continued

| Test Sample (Title compound) | Structure | SYK Inhibit SYK kinase IC50 (nM) | Inhibit AKT phosphorylation IC50 (nM) |
|---|---|---|---|
| Example 33 | 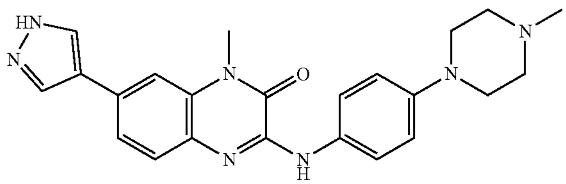 [SMILES: CN1CCN(c2ccc(Nc3nc4ccc(-c5cn[nH]c5)cc4n(C)c3=O)cc2)CC1] | 3.2 | 226 |
| Example 34 | 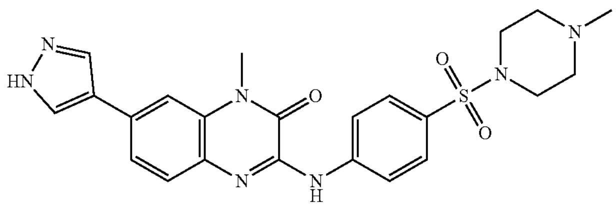 [SMILES: CN1CCN(S(=O)(=O)c2ccc(Nc3nc4ccc(-c5cn[nH]c5)cc4n(C)c3=O)cc2)CC1] | 26.0 | — |
| Example 35 | 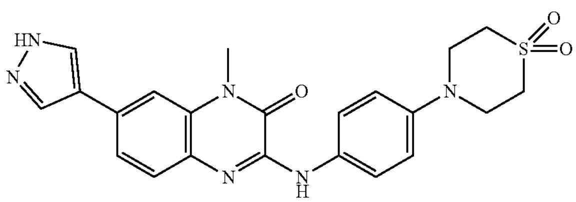 [SMILES: Cn1c(=O)c(Nc2ccc(N3CCS(=O)(=O)CC3)cc2)nc2ccc(-c3cn[nH]c3)cc21] | 5.1 | 52.2 |
| Example 36 | 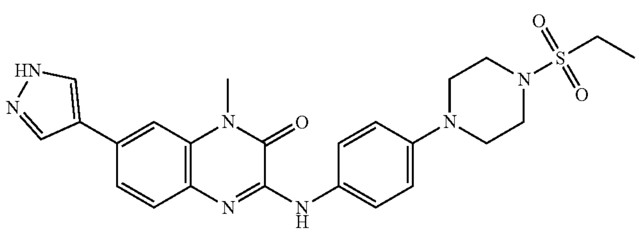 [SMILES: CCS(=O)(=O)N1CCN(c2ccc(Nc3nc4ccc(-c5cn[nH]c5)cc4n(C)c3=O)cc2)CC1] | 6.4 | — |
| Example 37 | 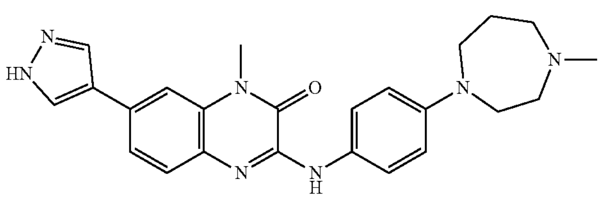 [SMILES: CN1CCCN(c2ccc(Nc3nc4ccc(-c5cn[nH]c5)cc4n(C)c3=O)cc2)CC1] | 10.1 | 261 |
| Example 38 | 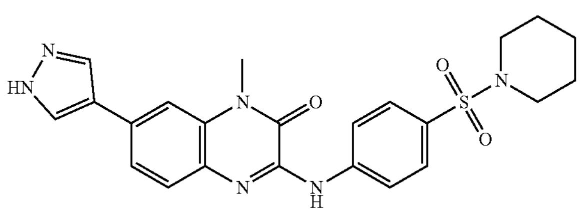 [SMILES: Cn1c(=O)c(Nc2ccc(S(=O)(=O)N3CCCCC3)cc2)nc2ccc(-c3cn[nH]c3)cc21] | 40 | 343 |
| Example 39 | 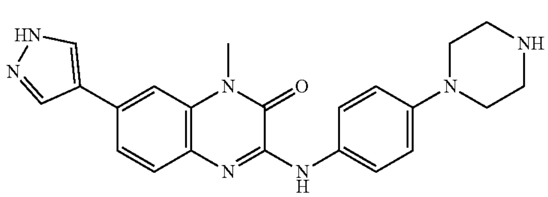 [SMILES: Cn1c(=O)c(Nc2ccc(N3CCNCC3)cc2)nc2ccc(-c3cn[nH]c3)cc21] | 3.6 | 60.1 |

TABLE 1-continued

| Test Sample (Title compound) | Structure | SYK Inhibit SYK kinase IC50 (nM) | Inhibit AKT phosphorylation IC50 (nM) |
|---|---|---|---|
| Example 40 | 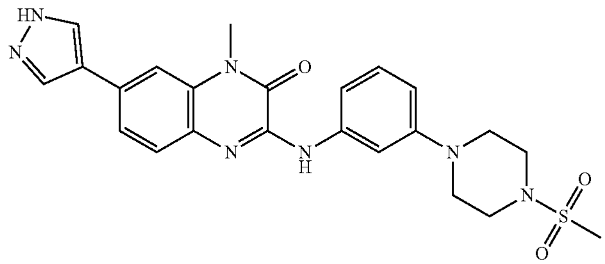 [SMILES: Cn1c(=O)c(Nc2cccc(N3CCN(S(C)(=O)=O)CC3)c2)nc2ccc(-c3cn[nH]c3)cc21] | 163 | — |
| Example 41 | 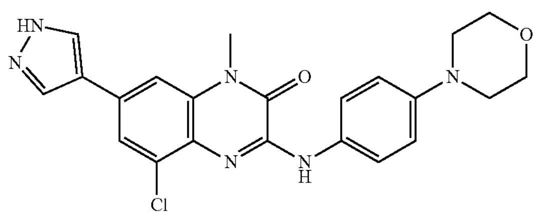 [SMILES: Cn1c(=O)c(Nc2ccc(N3CCOCC3)cc2)nc2c(Cl)cc(-c3cn[nH]c3)cc21] | 4.8 | 98.8 |
| Example 42 | 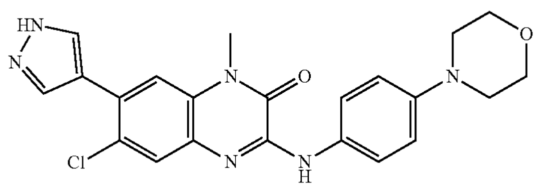 [SMILES: Cn1c(=O)c(Nc2ccc(N3CCOCC3)cc2)nc2cc(Cl)c(-c3cn[nH]c3)cc21] | 30 | — |
| Example 43 | 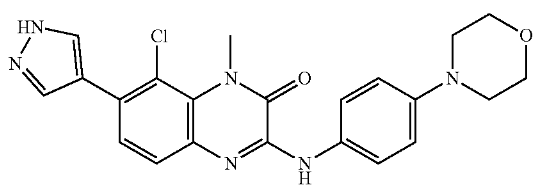 | 116 | — |
| Example 44 | 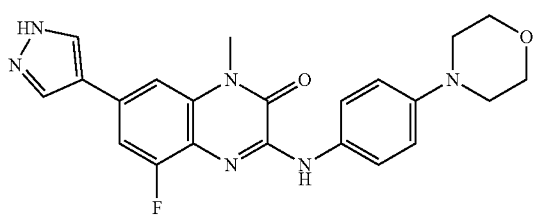 [SMILES: Cn1c(=O)c(Nc2ccc(N3CCOCC3)cc2)nc2c(F)cc(-c3cn[nH]c3)cc21] | 4.4 | 97 |
| Example 45 | 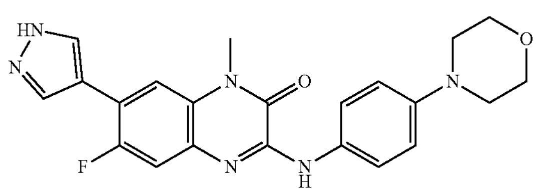 [SMILES: Cn1c(=O)c(Nc2ccc(N3CCOCC3)cc2)nc2cc(F)c(-c3cn[nH]c3)cc21] | 20.2 | 83.3 |
| Example 46 | 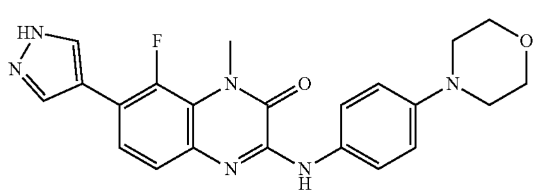 [SMILES: Cn1c(=O)c(Nc2ccc(N3CCOCC3)cc2)nc2ccc(-c3cn[nH]c3)c(F)c21] | 9.5 | 114 |

TABLE 1-continued

| Test Sample (Title compound) | Structure | SYK Inhibit SYK kinase IC50 (nM) | Inhibit AKT phosphorylation IC50 (nM) |
|---|---|---|---|
| Example 47 | 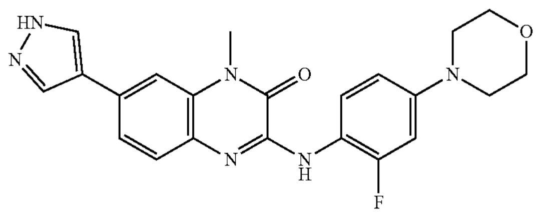 [SMILES: Cn1c(=O)c(Nc2ccc(N3CCOCC3)cc2F)nc2ccc(-c3cn[nH]c3)cc21] | 242 | — |
| Example 48 | 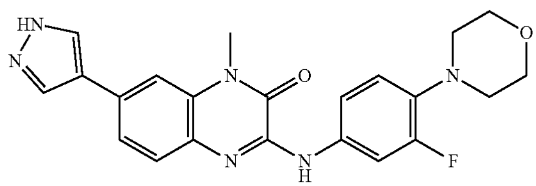 [SMILES: Cn1c(=O)c(Nc2ccc(N3CCOCC3)c(F)c2)nc2ccc(-c3cn[nH]c3)cc21] | 10.5 | 114 |
| Example 49 | 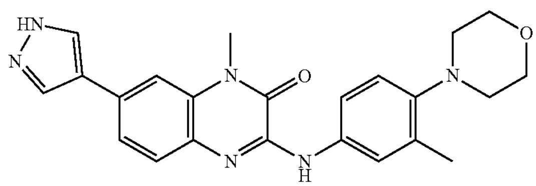 [SMILES: Cc1cc(Nc2nc3ccc(-c4cn[nH]c4)cc3n(C)c2=O)ccc1N1CCOCC1] | 22.5 | — |
| Example 50 | 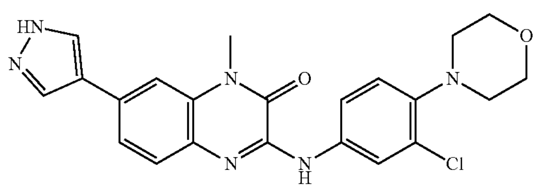 [SMILES: Cn1c(=O)c(Nc2ccc(N3CCOCC3)c(Cl)c2)nc2ccc(-c3cn[nH]c3)cc21] | 49 | — |
| Example 51 | 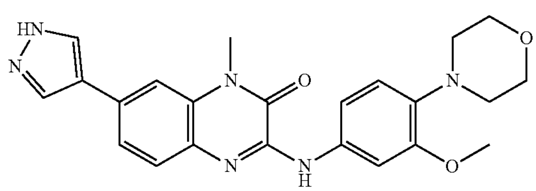 [SMILES: COc1cc(Nc2nc3ccc(-c4cn[nH]c4)cc3n(C)c2=O)ccc1N1CCOCC1] | 12.9 | — |
| Example 52 | 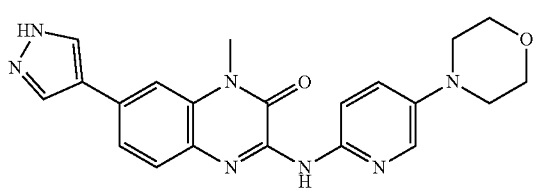 [SMILES: Cn1c(=O)c(Nc2ccc(N3CCOCC3)cn2)nc2ccc(-c3cn[nH]c3)cc21] | 29.7 | — |
| Example 53 | 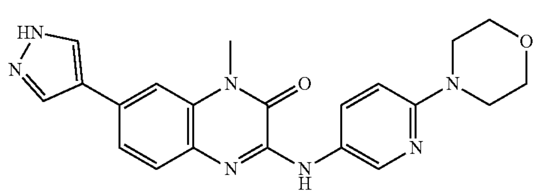 [SMILES: Cn1c(=O)c(Nc2ccc(N3CCOCC3)nc2)nc2ccc(-c3cn[nH]c3)cc21] | 39.3 | — |

TABLE 1-continued
| Test Sample (Title compound) | Structure | SYK Inhibit SYK kinase IC50 (nM) | Inhibit AKT phosphorylation IC50 (nM) |
|---|---|---|---|
| Example 54 | 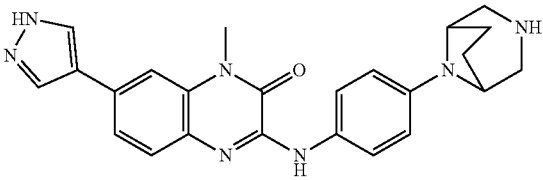 [SMILES: Cn1c(=O)c(Nc2ccc(N3C4CCC3CNC4)cc2)nc2ccc(-c3cn[nH]c3)cc21] | 5.0 | 69 |
| Example 55 | 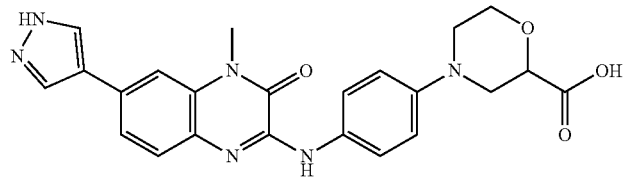 [SMILES: Cn1c(=O)c(Nc2ccc(N3CCOC(C(=O)O)C3)cc2)nc2ccc(-c3cn[nH]c3)cc21] | 4.1 | 116 |
| Example 56 | 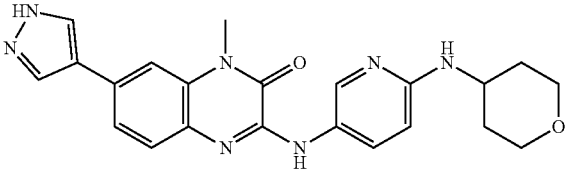 [SMILES: Cn1c(=O)c(Nc2ccc(NC3CCOCC3)nc2)nc2ccc(-c3cn[nH]c3)cc21] | 29.2 | — |
| Example 57 | 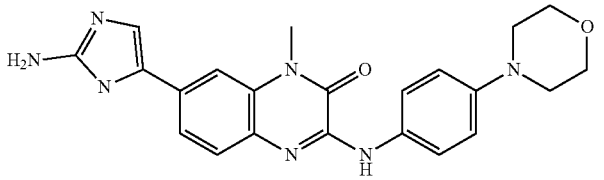 [SMILES: Cn1c(=O)c(Nc2ccc(N3CCOCC3)cc2)nc2ccc(-c3cnc(N)[nH]3)cc21] | 62.9 | — |
| Example 58 | 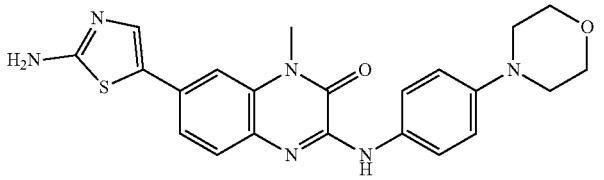 [SMILES: Cn1c(=O)c(Nc2ccc(N3CCOCC3)cc2)nc2ccc(-c3cnc(N)s3)cc21] | 197.3 | — |
| Example 59 | 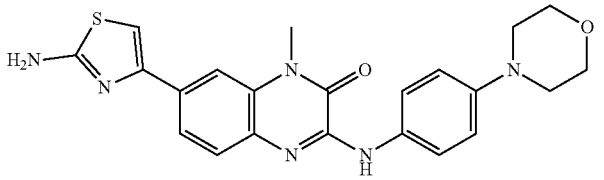 [SMILES: Cn1c(=O)c(Nc2ccc(N3CCOCC3)cc2)nc2ccc(-c3csc(N)n3)cc21] | 46 | 248 |

What is claimed is:

1. A compound of formula (I) or a pharmaceutically acceptable salt thereof,

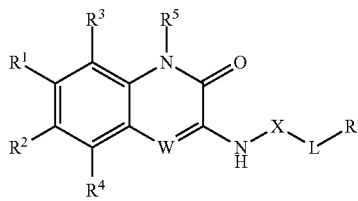

wherein,

W is C(R$^7$) or N;

R$^1$ and R$^2$ are each independently selected from H, halogen, amino, hydroxy, cyano, C$_{1-6}$ alkyl, C$_{3-6}$ cycloalkyl, 3-10 membered heterocycloalkyl, 6-12 membered aryl or 5-12 membered heteroaryl, said amino, C$_{1-6}$ alkyl, C$_{3-6}$ cycloalkyl, 3-10 membered heterocycloalkyl, 6-12 membered aryl or 5-12 membered heteroaryl is optionally substituted with R$^8$;

R$^3$, R$^4$ and R$^7$ are each independently selected from H, halogen, amino, hydroxy, cyano, C$_{1-6}$ alkyl, C$_{3-6}$ cycloalkyl or 3-6 membered heterocycloalkyl, said amino, C$_{1-6}$ alkyl, C$_{3-6}$ cycloalkyl or 3-6 membered heterocycloalkyl is optionally substituted with R$^9$;

R$^5$ is selected from H, C$_{1-6}$ alkyl, C$_{3-6}$ cycloalkyl or 3-6 membered heterocycloalkyl, C$_{1-6}$ alkyl C(O), C$_{3-6}$ cycloalkyl C(O) or 3-6 membered heterocycloalkyl C(O), phenyl C(O), 5-6 membered heteroaryl C(O), C$_{1-6}$ alkyl SO$_2$, C$_{3-6}$ cycloalkyl SO$_2$ or 3-6 membered heterocycloalkyl SO$_2$, phenyl SO$_2$ or 5-6 membered heteroaryl SO$_2$, said C$_{1-6}$ alkyl, C$_{3-6}$ cycloalkyl or 3-6 membered heterocycloalkyl, C$_{1-6}$ alkyl C(O), C$_{3-6}$ cycloalkyl C(O) or 3-6 membered heterocycloalkyl C(O), phenyl C(O), 5-6 membered heteroaryl C(O), C$_{1-6}$ alkyl SO$_2$, C$_{3-6}$ cycloalkyl SO$_2$ or 3-6 membered heterocycloalkyl SO$_2$, phenyl SO$_2$ or 5-6 membered heteroaryl SO$_2$ is optionally substituted with R$^9$;

X is selected from 3-12 membered ring with a loss of hydrogen atoms at any two positions, which is optionally substituted with R$^9$;

L is selected from bond, NH, O, S, SO, SO$_2$, C(O), OC(O), C(O)O, C(O)NH, NHSO$_2$, SO$_2$NH, NHC(O) NH or NHSO$_2$NH;

R$^6$ is selected from H, halogen, amino, hydroxy, cyano, C$_{1-6}$ alkyl, C$_{3-10}$ cycloalkyl or 3-10 membered heterocycloalkyl, said amino, C$_{1-6}$ alkyl, C$_{3-10}$ cycloalkyl or 3-10 membered heterocycloalkyl is optionally substituted with R$^{10}$;

R$^8$ and R$^9$ are each independently selected from halogen, amino, hydroxy, cyano, C$_{1-3}$ alkyl, C$_{1-3}$ alkoxy or COOH;

R$^{10}$ is selected from halogen, amino, hydroxy, cyano, halogenated C$_{1-3}$ alkyl, COOH, =(O), C$_{1-6}$ alkyl, C$_{1-6}$ alkyl SO$_2$, C$_{3-6}$ cycloalkyl or 3-10 membered heterocycloalkyl;

and, at least one of R$^1$ and R$^2$ is selected from 6-12 membered aryl or 5-12 membered heteroaryl, said 6-12 membered aryl or 5-12 membered heteroaryl is optionally substituted with R$^8$.

2. The compound or the pharmaceutically acceptable salt thereof according to claim 1, wherein R$^1$ and R$^2$ are each independently selected from H, F, Cl, Br, furanyl, thienyl, pyrrolyl, pyrazolyl, imidazolyl, pyridyl, pyrimidinyl, pyridazinyl, pyrazinyl, thiazolyl, isothiazolyl, oxazolyl, isoxazolyl, tetrazolyl or triazinyl, said furanyl, thienyl, pyrrolyl, pyrazolyl, imidazolyl, pyridyl, pyrimidinyl, pyridazinyl, pyrazinyl, thiazolyl, isothiazolyl, oxazolyl, isoxazolyl, tetrazolyl or triazinyl is optionally substituted with R$^8$.

3. The compound or the pharmaceutically acceptable salt thereof according to claim 2, wherein R$^1$ is selected from H, F, Cl, Br,

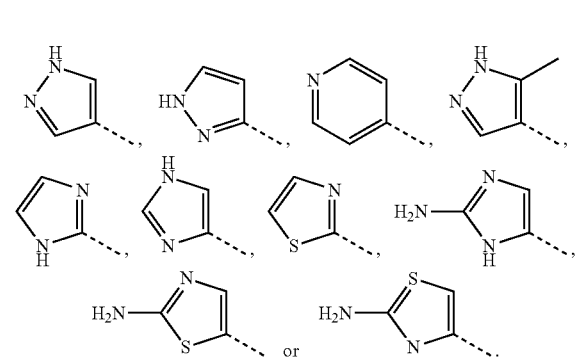

4. The compound or the pharmaceutically acceptable salt thereof according to claim 2, wherein R$^2$ is selected from H, F, Cl, Br or

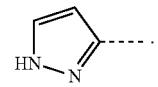

5. The compound or the pharmaceutically acceptable salt thereof according to claim 1, wherein R$^8$ is selected from amino, methyl, ethyl, propyl or isopropyl.

6. The compound or the pharmaceutically acceptable salt thereof according to claim 1, wherein R$^1$ is selected from

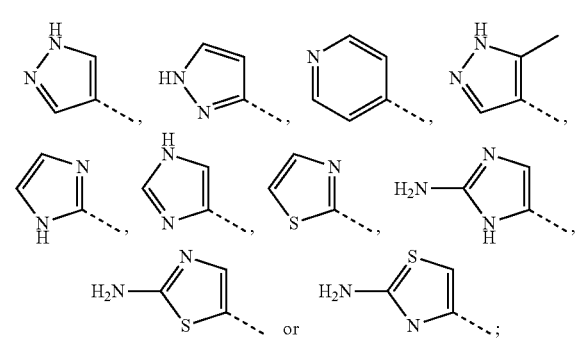

R$^2$ is selected from H, F or Cl.

7. The compound or the pharmaceutically acceptable salt thereof according to claim 1, wherein R$^1$ is selected from H or F; R$^2$ is selected from

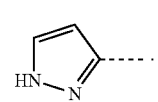

8. The compound or the pharmaceutically acceptable salt thereof according to claim 1, wherein R$^3$, R$^4$ and R$^7$ are each independently selected from H, halogen, $C_{1-6}$ alkyl or $C_{3-6}$ cycloalkyl, said $C_{1-6}$ alkyl or $C_{3-6}$ cycloalkyl is optionally substituted with $R^9$.

9. The compound or the pharmaceutically acceptable salt thereof according to claim 1, wherein $R^5$ is selected from H, methyl, ethyl, propyl, isopropyl, butyl, isobutyl or tert-butyl, said methyl, ethyl, propyl, isopropyl, butyl, isobutyl or tert-butyl is optionally substituted with $R^9$.

10. The compound or the pharmaceutically acceptable salt thereof according to claim 1, wherein X is selected from phenyl ring,

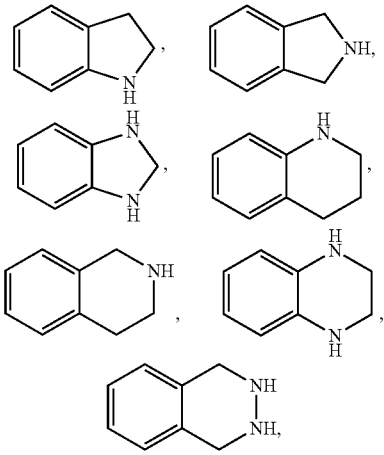

furanyl ring, thienyl ring, pyrrolyl ring, pyrazolyl ring, imidazolyl ring, pyridyl ring, pyrimidinyl ring, pyridazinyl ring, pyrazinyl ring, thiazolyl ring, isothiazolyl ring, oxazolyl ring, isoxazolyl ring, tetrazolyl ring or triazinyl ring with a loss of hydrogen atoms at any two positions, which is optionally substituted with $R^9$.

11. The compound or the pharmaceutically acceptable salt thereof according to claim 10, wherein X is selected from

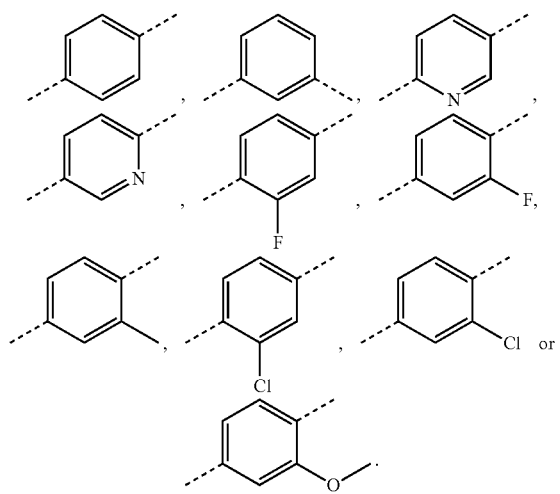

12. The compound or the pharmaceutically acceptable salt thereof according to claim 1, wherein $R^9$ is selected from halogen, $C_{1-3}$ alkyl or $C_{1-3}$ alkoxy.

13. The compound or the pharmaceutically acceptable salt thereof according to claim 1, wherein L is selected from bond, NH or $SO_2$.

14. The compound or the pharmaceutically acceptable salt thereof according to claim 1, wherein $R^6$ is selected from: H, amino, methyl, ethyl, propyl, isopropyl, butyl, isobutyl, tert-butyl, cyclopropyl, cyclobutyl, cyclopentyl, cyclohexyl; or

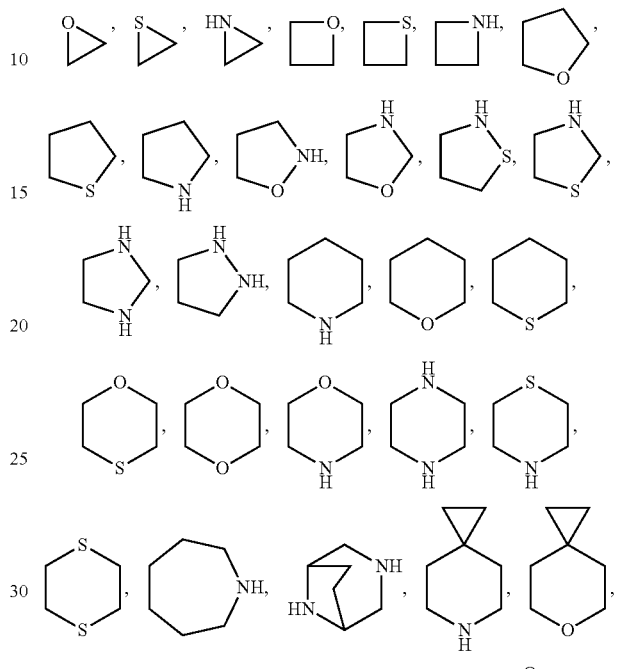

with a loss of one hydrogen atom at any position;
said amino, methyl, ethyl, propyl, isopropyl, butyl, isobutyl, tert-butyl, cyclopropyl, cyclobutyl, cyclopentyl, cyclohexyl,

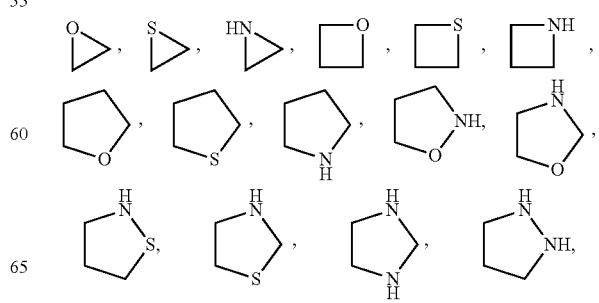

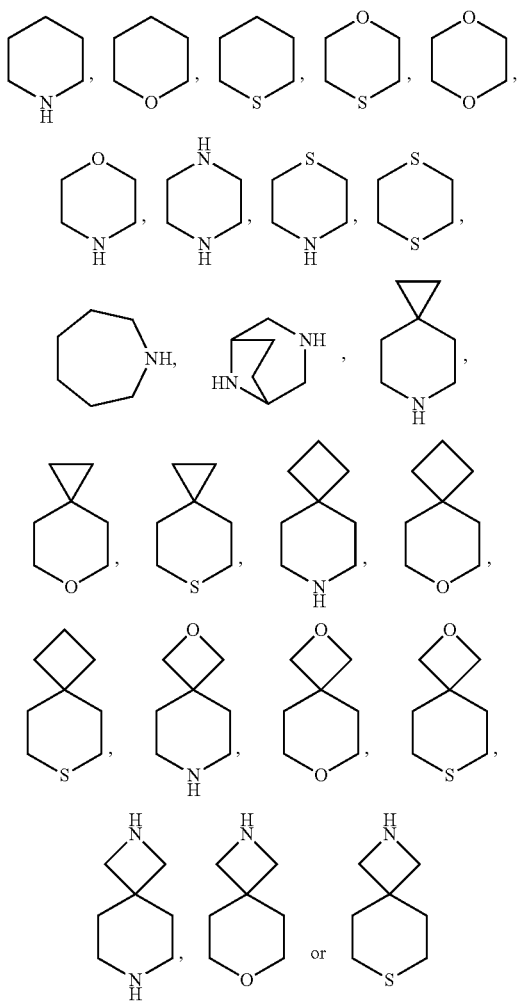

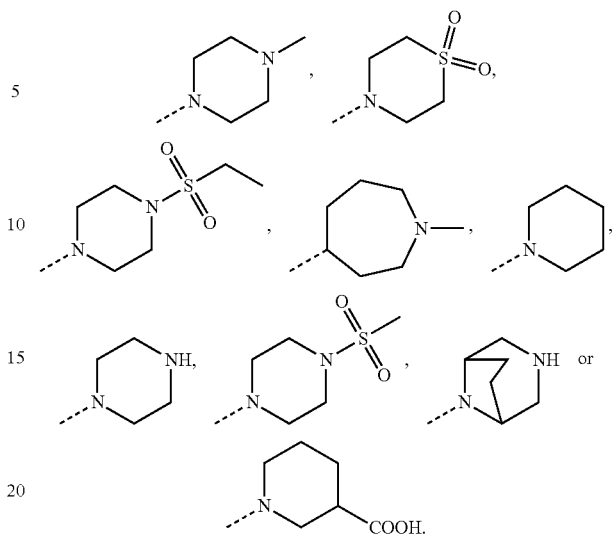

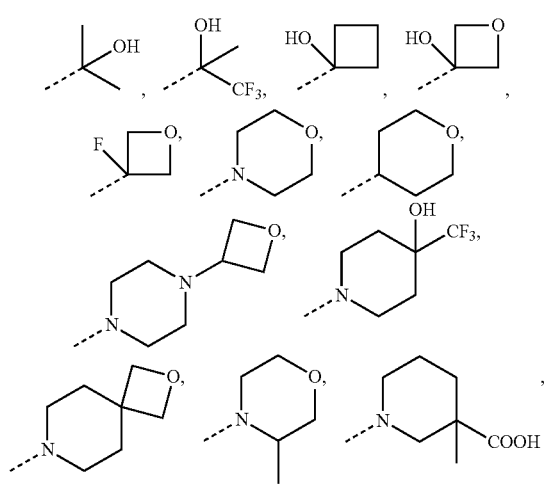

with a loss of one hydrogen atom at any position is optionally substituted with $R^{10}$.

15. The compound or the pharmaceutically acceptable salt thereof according to claim 14, wherein $R^6$ is selected from H, $NH_2$, methyl, 16. The compound or the pharmaceutically acceptable salt thereof according to claim 1, wherein $R^{10}$ is selected from: F, Cl, Br, OH, monofluoromethyl, difluoromethyl, trifluoromethyl, monofluoroethyl, difluoroethyl, trifluoroethyl, tetrafluoroethyl, pentafluoroethyl, monochloromethyl, dichloromethyl, trichloromethyl, COOH, =(O), methyl, ethyl, propyl, isopropyl, butyl, isobutyl, tert-butyl, $SO_2CH_3$, $SO_2CH_2CH_3$, $SO_2CH_2CH_2CH_3$, $SO_2CH(CH_3)CH_3$, $SO_2CH_2CH_2CH_2CH_3$, $SO_2CH(CH_3)CH_2CH_3$, $SO_2CH_2CH(CH_3)_2$, $SO_2C(CH_3)_3$; or

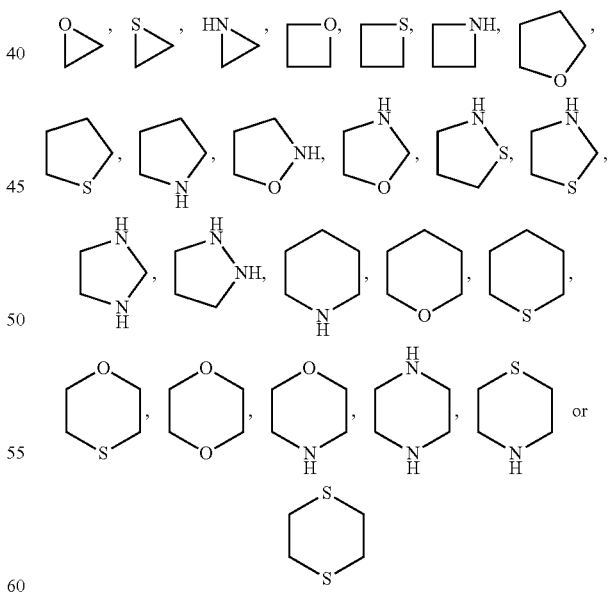

with a loss of one hydrogen atom at any position.

17. The compound or the pharmaceutically acceptable salt thereof according to claim 16, wherein $R^{10}$ is selected from F, OH, trifluoromethyl, COOH, =(O), methyl, $SO_2CH_3$, $SO_2CH_2CH_3$ or

18. The compound or the pharmaceutically acceptable salt thereof according to claim 1, wherein the compound of formula (I) is selected from the following compounds:
-continued
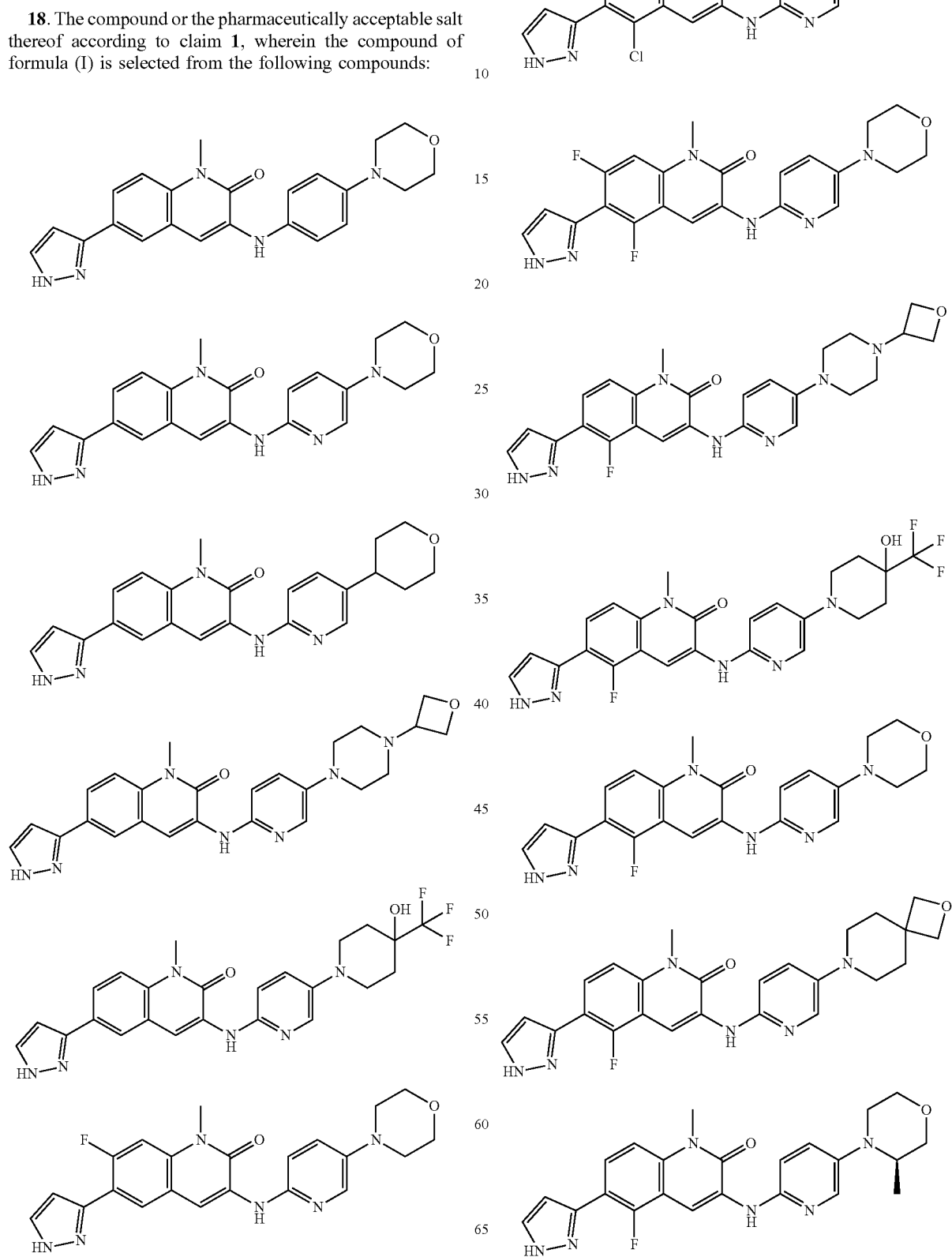

137
-continued
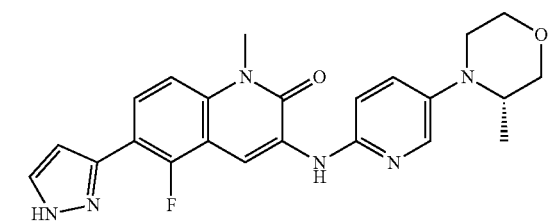
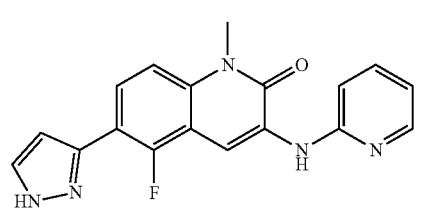
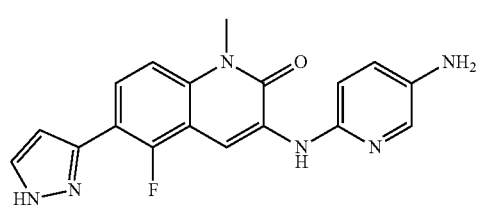
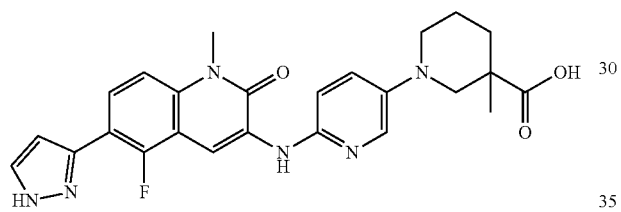
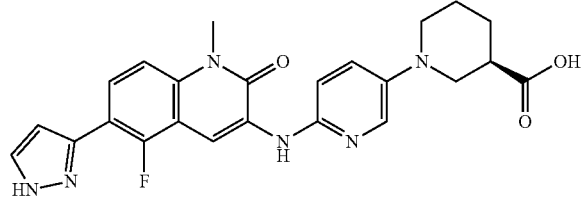
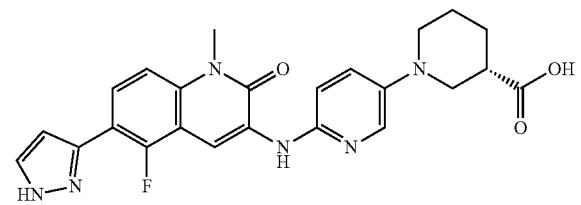
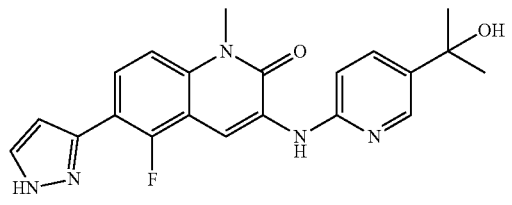
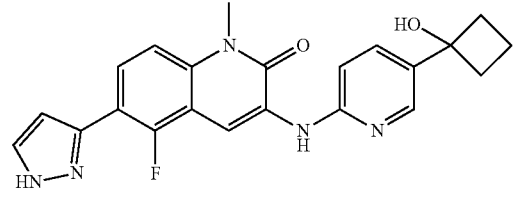
138
-continued
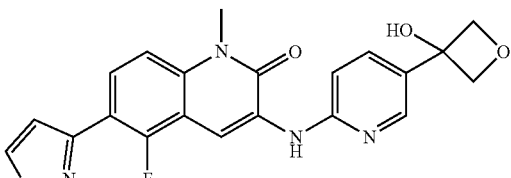
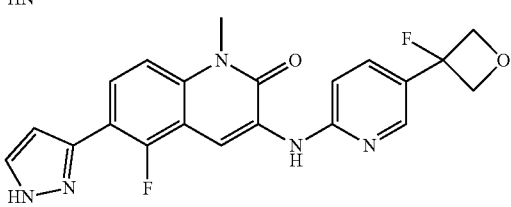
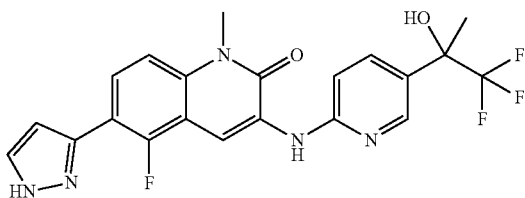
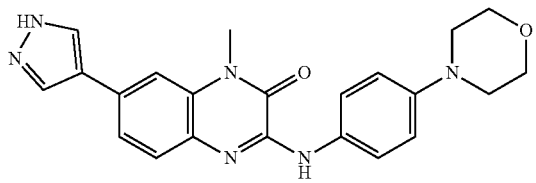
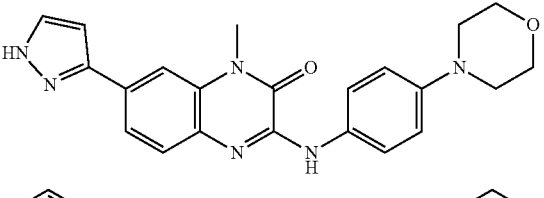
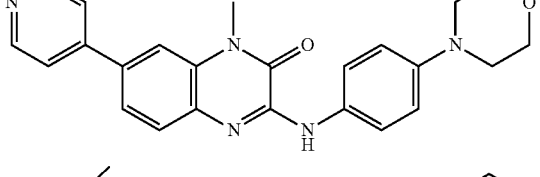
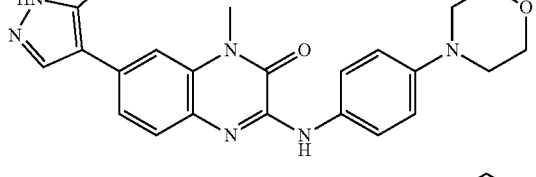
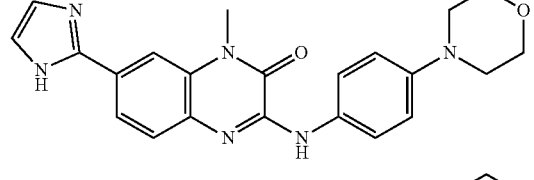
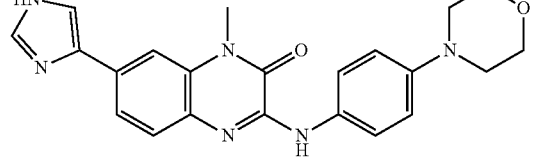

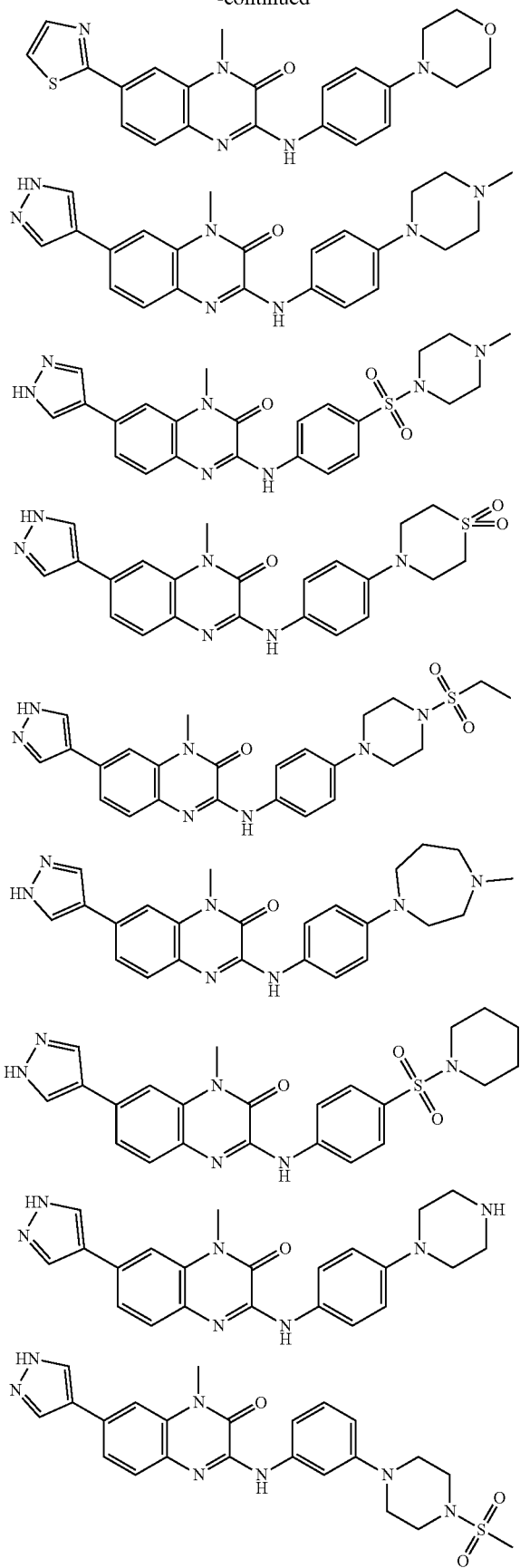
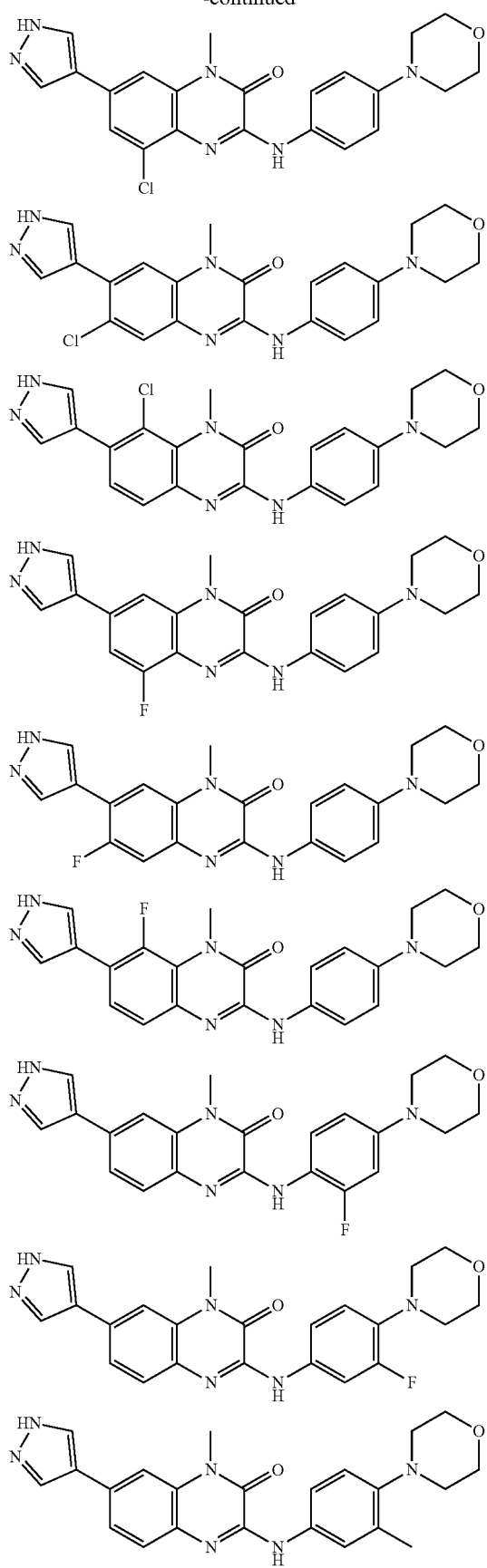

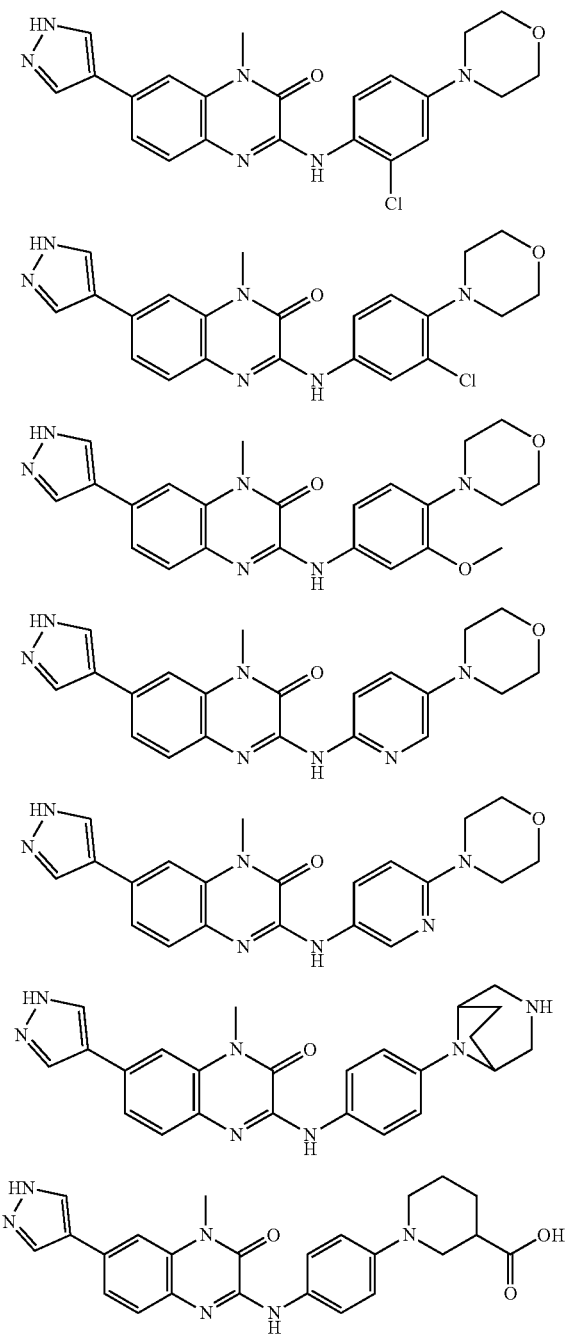
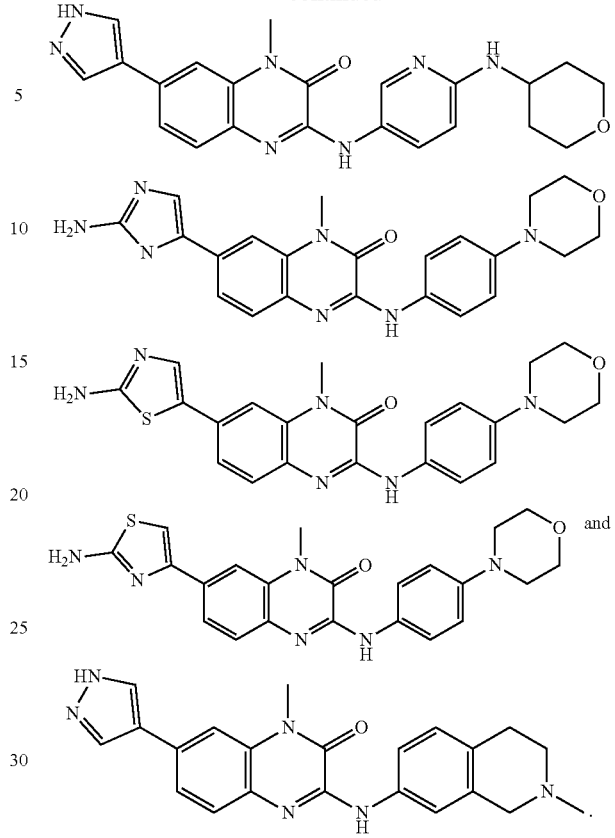

19. A pharmaceutical composition comprising a therapeutically effective amount of the compound or the pharmaceutically acceptable salt thereof according to claim 1, and one or more pharmaceutically acceptable excipients.

20. A method of treating diseases related to Syk receptors consisting of cancers, inflammatory diseases, B cell lymphoma, Hodgkin's lymphoma, non-Hodgkin's lymphoma, hairy cell leukemia, multiple myeloma, chronic myeloid leukemia, acute myeloid leukemia, chronic lymphocytic leukemia, acute lymphocytic leukemia, rheumatoid arthritis, allergic rhinitis, chronic obstructive pulmonary disease (COPD), adult respiratory distress syndrome (ARDs), allergy-induced inflammatory disease, multiple sclerosis, autoimmune disease, acute inflammatory response, allergic disorder and polycystic kidney, comprising administering a therapeutically effective amount of the compound or the pharmaceutically acceptable salt thereof according to claim 1.

* * * * *